(12) United States Patent
Fisher

(10) Patent No.: US 6,472,520 B2
(45) Date of Patent: Oct. 29, 2002

(54) RAT PEG-3 PROMOTER

(75) Inventor: Paul B. Fisher, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/052,753

(22) Filed: Mar. 31, 1998

(65) Prior Publication Data

US 2001/0014734 A1 Aug. 16, 2001

Related U.S. Application Data

(63) Continuation-in-part of application No. PCT/US98/05783, filed on Mar. 20, 1998, which is a continuation-in-part of application No. 08/821,818, filed on Mar. 21, 1997, now Pat. No. 6,146,877.

(51) Int. Cl.$^7$ .................. C07H 21/04; C12N 15/11; C12N 15/63
(52) U.S. Cl. ............. 536/24.1; 536/23.1; 435/320.1
(58) Field of Search ............. 514/44; 536/23.1, 536/24.1; 424/93.1; 435/320.1

(56) References Cited

PUBLICATIONS

Ross et al. Human Gene Therapy, vol. 7, pp. 1781–1790, Sep. 1996.*
Verma et al. Nature, vol. 389, pp. 239–242, Sep. 17, 1996.*
Auzat, Isabelle, Le Bras, Gisele, and Garel, Jean–Renaud, (1994) The cooperativity and allosteric inibition of *Escherichia coli* phosphofructikinase depend on the interaction thereonine–125 and ATP, *Proc. Natl. Acad. Sci. USA*, 91:5242–5251 (Exhibit 1).
Bishop, Michael J., (1991) Molecular themes in oncogenesis. *Cell* 64:235–248 (Exhibit 2).
Boylan, John F., et al. (1990) Role of the ha–ras (Ras$^H$) oncogene in mediating progression of the tumor cell phenotype (Review), *Anti Can Res*, 10:717–724; (Exhibit 3).
Cornelis, Jan J., et al. (1981) Indirect induction of mutagenesis of intact parvovirus H–1 in mammalian cells treated with UV light or with UV–irradiated H–1 or simian virus 40, *Proc. Natl. Acad. Sci. USA*, 78:4480–4484; (Exhibit 4).
Crystal, Ronald G. (1995) Transfer of genes to humans: early lessons and obstacles to success, *Science* 270:404–410 (Exhibit 5).
Fornance, Albert J., Jr., Alamo, I., Jr. and Hollander, M. C. (1988) DNA damage–inducible transcripts in mammalian cells, *Proc. Natl. Acad. Sci.* USA 85:8800–8804 (Exhibit 6).
Jiang, Hongping, Lin, Jian, and Fisher, Paul B. (1994) A molecular definition of terminal cell differentiation in human melanoma cells. *Mol. Cell Different*, 2:(3):221–239 (Exhibit 7).
Jiang H., Su Z.–z., Lin J. J., Goldstein N. I., Young C. S. H. & Fisher P. B. (1996) The melanoma differentiation associated gene mda–7 suppresses cancer cell growth. *Proc. Natl. Acad. Sci. USA* 93:9160–9165 (Exhibit 8).
Knudson, Alfred G., (1993) Antioncogenes and human cancer, *Proc. Natl. Acad. Sci. USA*, 90:10914–10921 (Exhibit 9).
Levine, Arnold J., (1993) The tumor suppressor genes, *Annual Rev. Biochem.*, 62:623–651 (Exhibit 10).
Report and recommendations of the panel to assess the NIH investment in research on gene therapy, Orkin and Motulsky, co–chairs. National Institute of Health (Exhibit 11).
Shen, R., et al. (1995) Identification of the human prostatic carcinoma oncogene PTI–1 by rapid expression cloning and differential RNA display. *Proc. Natl. Acad. of Sci.*, USA 92:6778–6782; (Exhibit 12).
Stull, et al. (1995) Antigene, ribozyme and aptamer nucleic acid drugs: Progress and prospects, *Pharm. Res.*, 12:465–483; (Exhibit 13).
Su, Zao–Zhong, Zhang, Peiquan and Fisher, Paul B., (1990) Enhancement of viral and DNA mediated transformation of cloned rat embryo fibroblast cells by 3–Aminobenzamide, Molecular Carcinogenesis, 3:309–318 (Exhibit 14).
Su, et al. (1997) Subtraction hybridization identifies a transformation progression–associated gene PEG–3 with sequence homology to a growth arrest and DNA damage–inducible gene. *Proc. Natl. Acad. of Sci.*, USA, 94:9125–9130 (Exhibit 15).
Vairapandi, Mariappan, et al. (1996) The differentiation primary response gene MyD118, related to GADD45, encodes for a nuclear protein which interacts with PCNA and p21$^{WAF1/cip1}$, Oncogene 11:2579–2594 (Exhibit 16).
Vogelstein, Bert and Kinzler, Kenneth W., (1993) The multistep nature of cancer. *Trends in Genetics*, 9(4):138–141 (Exhibit 17) and.
Zhan, et al. (1994) The gadd and Myd genes define a novel set of mammalian genes encoding acidic proteins that synergistically suppress cell growth. *Mol. and Cell Biol.* 14:2361–2371 (Exhibit 18).
Kang D., et al., (1998) "Cloning of progression elevated and Proc. progression suppressed genes by reciprocal subtraction RNA display" *Am Assoc Can Res.*, 39:347 Abstract #2368, (Exhibit 1).

* cited by examiner

Primary Examiner—Michael C. Wilson
(74) *Attorney, Agent, or Firm*—Baker Botts LLP

(57) ABSTRACT

This invention provides a vector suitable for introduction into a cell, having: a) an inducible PEG-3 regulatory region; and b) a gene encoding a product that causes or may be induced to cause the death or inhibition of cancer cell growth. In addition, this invention further provides the above-described vectors, wherein the inducible PEG-3 regulatory region is a promoter. This invention further provides the above-described vectors, wherein the gene encodes an inducer of apoptosis. In addition, this invention provides the above-described vectors, wherein the gene is a tumor suppressor gene. In addition, this invention provides the above-described vectors, wherein the gene encodes a viral replication protein. This invention also provides the above-described vectors, wherein the gene encodes a product toxic to cells or an intermediate to a product toxic to cells. In addition, this invention provides the above-described vectors, wherein the gene encodes a product causing enhanced immune recognition of the cell. This invention further provides the above-described vectors, wherein the gene encodes a product causing the cell to express a specific antigen.

10 Claims, 39 Drawing Sheets

```
            1                                                        50
PEG-3    MAPSPRPQHV LHWKEAHSFY LLSPLMGFLS RAWSRLRGPE VSEAWLAETV
GADD34   MAPSPRPQHI LLWRDAHSFH LLSPLMGFLS RAWSRLRVPE APEPWPAETV
MYD116   MAPSPRPQHV LHWRDAHNFY LLSPLMGLLS RAWSRLRGPE VPEAWLAKTV 51                                                       100
PEG-3    AGANQIEADA LLTPPPVSEN HLPLRETEGN GTPEWSKAAQ RLCLDVEAQS
GADD34   TGADQIEADA HPAPPLVPEN HPPQGEAEES GTPEEGKAAQ GPCLDVQANS
MYD116   TGADQIEAAA LLTPTPVSGN LLPHGETEES GSPEQSQAAQ RLCL.VEAES 101                                                       150
PEG-3    SPPKTWGLSD IDEHNGKPGQ DGLREQEVEH TAGLPTLQPL HLQGADKKVG
GADD34   SPPETLGLSD DD....KQGQ DGPREQGRAH TAGLPILLSP GLQSADKSLG
MYD116   SPPETWGLSN VDEYNAKPGQ DDLREKEMER TAGKATLQPA GLQGADKRLG 151                                                       200
PEG-3    EVVAREEGVS ELAYPTSHWE GGPAEDEEDT ETVKKAHQAS AASIAPGYKP
GADD34   EVVAGEEGVT ELAYPTSHWE GCPSEEEEDG ETVKKAFRAS ADS..PGHKS
MYD116   EVVAREEGVA EPAYPTSQLE GGPAENEEDG ETV.KTYQAS AASIAPGYKP 201                                                       250
PEG-3    STSVYCPGEA EHRATEEKGT DNKAEP..... .SGSHSRVWE YHTRERPKQE
GADD34   STSVYCPGEA EHQATEEKQT ENKADPPSSP .SGSHSRAWE YCS....KQE
MYD116   STPVPFLGEA EHQATEEKGT ENKADPSNSP SSGSHSRAWE YYSREKPKQE 251                                                       300
PEG-3    GETKPEQHRA GQSHPCQNAE AEEGGPETS. ....VCSGSAF LKAWVYRPGE
GADD34   GEADPEPHRA GKYQLCQNAE AEEEEEAKVS SLSVSSGNAF LKAWVYRPGE
MYD116   GEAKVEAHRA GQGHPCRNAE AEEGGPETT. ...FVCTGNAF LKAWVYRPGE 301                                                       350
PEG-3    DTEEEEDSDL DSAEEDT.AH TCTTPHTSAF LKAWVYRPGE DTEEED....
GADD34   DTEDDDDSDW GSAEEEGKAL SSPTSPEHDF LKAWVYRPGE DTEDDDDSDW
MYD116   DTEEEDNSDS DSAEEDT.AQ TGATPHTSAF LKAWVYRPGE DTEEEDSD..
```

FIG.3A

```
              351                                                      400
PEG-3    .......... .......... .......... .......DGDW DSAEEDA.SQ
GADD34   GSAEEEGKAL SSPTSPEHDF LKAWVYRPGE DTEDDQDSDW GSAEKDGLAQ
MYD116   SDSAEEDTAG TGATPHTSAF LKAWVYRPGE DTEEE.NSDL DSAEEDT.AQ 401                                                      450
PEG-3    SCTTPHTSAF LKAWVYRPGE .......... .......... ..........
GADD34   TFATPHTSAF LKTWVCCPGE DT........ .......... ..........
MYD116   TGATPHTSAF LKAWVYRPGE DTEEENSDLD SAEEDTAQTG ATPHTSPFLK 451                                                      500
PEG-3    .......... ..DTEEEDDS ENVAPVDSET VDSCQS.... TQHCLPVEKT
GADD34   .......... .....EDDDC EVVMPEDSEA ADPDKSPSHE AQGCLPGEQT
MYD116   AWVYRPGEDT EDDTEEEEDS ENVAPGDSET ADSSQSPCLQ PQRCLPGEKT 501                                                      550
PEG-3    KGCGEAEPPP FQWPSIYL.. ......DRSQH HLGLPLSCP. ..FDCRSGSD
GADD34   EGLVEAEHSL FQ.VAFYLPG EKPAPPWTAP KLPLRLQRRL TLLRTPTQDQ
MYD116   KGRGE.EPPL FQ.VAFYLPG EKPESPWAAP KLPLRLQRRL RLFKAPTRDQ 551                                                      600
PEG-3    LSKPPPGIRA LRFL...... .......... .......... ..........
GADD34   DPETPLRARK VHFSENVTVH FLAVWAGPAQ AARRGPWEQL ARDRSRFARR
MYD116   DPEIPLKARK VHFAEKVTVH FLAVWAGPAQ AARRGPWEQF ARDRSRFARR 601                                                      650
PEG-3    .......... .......... .......... .......... ..........
GADD34   IAQAEEKLGP YLTPAFRARA WARLGNPSLP LALEPICDHT FFPSQ.....
MYD116   IAQAEEKLGP YLTPDSRARA WARLRNPSLP QSEPRSSSEA TPLTQDVTTP 651        699
PEG-3    .......... ..........
GADD34   .......... ..........
MYD116   SPLPSETPSP SLYLGGRRG
```

FIG.3B

| | | | | | |
|---|---|---|---|---|---|
| CTGCAGTACT | TGTACATTGC | TAAATAAAGA | GAGGGACTCC | AGGAGGAGCA | GCCTGGGTCT | 60
| AAGAGGTAGG | CAGAAGGAGG | TTTTAGGGGC | CTGAGCACAA | GCTTGAGGAG | AGAAAGGTTA | 120
| TTAAAAAGCC | AGACGCTTAC | AGGTCTCAGA | AGGGCTAGCC | AGAAACTGTG | GCTGGGGTTA | 180
| AGGAAAGGGT | TTAAGAGTGT | GGGCTTTTGG | TTCTGAGGAT | GTAGAACGTG | AATGTTGAGA | 240
| GAAGAACCAA | GTGGCGGAGT | TGGGTGTGAG | CAATGCTATT | AGGAATTTGA | GGCAGGGATT | 300
| CACGCGCTGC | TGTGACTATT | TTTTAACAAT | GACTCAGTGC | TGTGACCTGA | TACTGTTTCC | 360
| AGAGCGACTT | CTAAACAAAT | TCCCCCTTTC | TAGGCCAGAC | AC<u>ATG</u>GCCCC | AAGCCCAAGA | 420
| CCCCAGCATG | TCCTGCACTG | GAAGGAAGCC | CACTCTTTCT | ACCTCCTGTC | TCCACTGATG | 480
| GGCTTCCTCA | GCCGGGCCTG | GAGCCGCCTG | AGGGGGCCCG | AGGTCTCAGA | GGCCTGGTTG | 540
| GCAGAAACAG | TAGCAGGAGC | AAACCAGATA | GAGGCTGATG | CTCTGTTGAC | GCCTCCCCCG | 600
| GTCTCTGAAA | ATCACCTACC | TCTCCGAGAG | ACTGAAGGAA | ATGGAACTCC | TGAATGGAGT | 660
| AAAGCAGCCC | AGAGGCTCTG | CCTTGATGTG | GAAGCCCAAA | GTTCCCCTCC | TAAAACTTGG | 720
| GGACTTTCAG | ATATTGATGA | ACATAATGGG | AAGCCAGGAC | AAGATGGCCT | TAGAGAGCAA | 780
| GAAGTGGAGC | ACACAGCTGG | CCTGCCTACA | CTACAGCCCC | TTCACCTGCA | AGGGGCAGAT | 840
| AAGAAAGTTG | GGGAGGTGGT | GGCTAGAGAA | GAGGGTGTGT | CCGAGCTGGC | TTACCCCACA | 900
| TCACACTGGG | AGGGTGGTCC | AGCTGAGGAT | GAAGAGGATA | CAGAAACCGT | GAAGAAGGCT | 960
| CACCAGGCCT | CTGCTGCTTC | CATAGCTCCA | GGATATAAAC | CCAGCACTTC | TGTGTATTGC | 1020
| CCAGGGGAGG | CAGAACATCG | AGCCACGGAG | GAAAAAGGAA | CAGACAATAA | GGCTGAACCC | 1080
| TCAGGCTCCC | ACTCCAGAGT | CTGGGAGTAC | CACACTAGAG | AGAGGCCTAA | GCAGGAGGGA | 1140
| GAAACTAAGC | CAGAGCAACA | CAGGGCAGGG | CAGAGTCACC | CTTGTCAGAA | TGCAGAGGCT | 1200
| GAGGAAGGAG | GACCTGAGAC | TTCTGTCTGT | TCTGGCAGTG | CCTTCCTGAA | GGCCTGGGTG | 1260
| TATCGCCCAG | GAGAGGACAC | AGAGGAGGAA | GAAGACAGTG | ATTTGGATTC | AGCTGAGGAA | 1320
| GACACAGCTC | ATACCTGTAC | CACCCCCCAT | ACAAGTGCCT | TCCTGAAGGC | CTGGGTCTAT | 1380
| CGCCCAGGAG | AGGACACAGA | AGAGGAAGAT | GACGGTGATT | GGGATTCAGC | TGAGGAAGAC | 1440
| GCGTCTCAGA | GCTGTACCAC | CCCCCATACA | AGTGCCTTCC | TGAAGGCCTG | GGTCTATCGC | 1500

FIG.11A

```
CCAGGAGAGG ACACAGAAGA GGAAGACGAC AGTGAGAATG TGGCCCCAGT TGACTCAGAA    1560

ACAGTTGACT CTTGCCAGAG TACCCAGCAT TGTCTACCAG TAGAGAAGAC CAAGGGATGT    1620

GGAGAAGCAG AGCCCCCTCC CTTCCAGTGG CCTTCTATTT ACCTGGACAG AAGCCAGCAC    1680

CACCTTGGGC TGCCCCTAAG CTGCCCCTTC GACTGCAGAA GCGGCTCAGA TCTTTCAAAG    1740

CCCCCGCCCG GAATCAGGGC CCTGAGATTC CTCTGAAGGG TAGAAAGGTG CACTTCTCTG    1800

AGAAAGTTAC AGTCCATTTC CTTGCTGTCT GGGCAGGACC AGCCCAGGCT GCTCGTCGAG    1860

GCCCCTGGGA GCAGTTTGCA CGAGATCGAA GCCGCTTTGC TCGACGCATT GCCGTCCTCG    1920

TCTCTTCCAC TGCCTGAGCC TTGCTCTTCC ACTGAGGCCA CACCCCTCAG CCAAGATGTG    1980

ACCACTCCCT CTCCCCTTCC CAGTGAAATC CCTCCTCCCA GCCTGGACTT GGGAGGAAGG    2040

CGGGCTAAGC CTGAGTAGTT TTTTGTGTAT TCTATGAGTG TTAGTCTCTT AATACGAATA    2100

TGTAACGCCT TTTGCATTTG TAAAAAAAAA AAAAAAA                              2137
```

FIG. 11B

```
Met Ala Pro Ser Pro Arg Pro Gln His Val Leu His Trp Lys Glu Ala
1               5                   10                  15
His Ser Phe Tyr Leu Leu Ser Pro Leu Met Gly Phe Leu Ser Arg Ala
            20                  25                  30
Trp Ser Arg Leu Arg Gly Pro Glu Val Ser Glu Ala Trp Leu Ala Glu
        35                  40                  45
Thr Val Ala Gly Ala Asn Gln Ile Glu Ala Asp Ala Leu Leu Thr Pro
    50                  55                  60
Pro Pro Val Ser Glu Asn His Leu Pro Leu Arg Glu Thr Glu Gly Asn
65                  70                  75                  80
Gly Thr Pro Glu Trp Ser Lys Ala Ala Gln Arg Leu Cys Leu Asp Val
                85                  90                  95
Glu Ala Gln Ser Ser Pro Pro Lys Thr Trp Gly Leu Ser Asp Ile Asp
                100                 105                 110
Glu His Asn Gly Lys Pro Gly Gln Asp Gly Leu Arg Glu Gln Glu Val
            115                 120                 125
Glu His Thr Ala Gly Leu Pro Thr Leu Gln Pro Leu His Leu Gln Gly
    130                 135                 140
Ala Asp Lys Lys Val Gly Glu Val Val Ala Arg Glu Glu Gly Val Ser
145                 150                 155                 160
Glu Leu Ala Tyr Pro Thr Ser His Trp Glu Gly Gly Pro Ala Glu Asp
                165                 170                 175
Glu Glu Asp Thr Glu Thr Val Lys Lys Ala His Gln Ala Ser Ala Ala
            180                 185                 190
Ser Ile Ala Pro Gly Tyr Lys Pro Ser Thr Ser Val Tyr Cys Pro Gly
        195                 200                 205
Glu Ala Glu His Arg Ala Thr Glu Glu Lys Gly Thr Asp Asn Lys Ala
    210                 215                 220
Glu Pro Ser Gly Ser His Ser Arg Val Trp Glu Tyr His Thr Arg Glu
225                 230                 235                 240
Arg Pro Lys Gln Glu Gly Glu Thr Lys Pro Glu Gln His Arg Ala Gly
                245                 250                 255
Gln Ser His Pro Cys Gln Asn Ala Glu Ala Glu Gly Gly Pro Glu
            260                 265                 270
Thr Ser Val Cys Ser Gly Ser Ala Phe Leu Lys Ala Trp Val Tyr Arg
            275                 280                 285
Pro Gly Glu Asp Thr Glu Glu Glu Asp Ser Asp Leu Asp Ser Ala
            290                 295                 300
Glu Glu Asp Thr Ala His Thr Cys Thr Thr Pro His Thr Ser Ala Phe
305                 310                 315                 320
Leu Lys Ala Trp Val Tyr Arg Pro Gly Asp Thr Glu Glu Glu Asp
                325                 330                 335
Asp Gly Asp Trp Asp Ser Ala Glu Glu Asp Ala Ser Gln Ser Cys Thr
            340                 345                 350
Thr Pro His Thr Ser Ala Phe Leu Lys Ala Trp Val Tyr Arg Pro Gly
    355                 360                 365
Glu Asp Thr Glu Glu Glu Asp Asp Ser Glu Asn Val Ala Pro Val Asp
    370                 375                 380
```

FIG.12A

Ser Glu Thr Val Asp Ser Cys Gln Ser Thr Gln His Cys Leu Pro Val
385                 390                 395                 400
Glu Lys Thr Lys Gly Cys Gly Glu Ala Glu Pro Pro Pro Phe Gln Trp
                405                 410                 415
Pro Ser Ile Tyr Leu Asp Arg Ser Gln His His Leu Gly Leu Pro Leu
                420                 425                 430
Ser Cys Pro Phe Asp Cys Arg Ser Gly Ser Asp Leu Ser Lys Pro Pro
                435                 440                 445
Pro Gly Ile Arg Ala Leu Arg Phe Leu
                450                 455

FIG.12B

```
tgagattgac tcagttcgca gcttgtggaa gattacatgc gagaaaaagc gcgactccgc      60
atcccttgc  cgggacagcc cttgcgacag cccgtgagac atcacgtccc cgagccccac    120
ctttgccggg acagcctttg cgacagcccg tgagacatca cgtccccgag ccccacgcct    180
gagggcgaca tgaacgcgct ggccttgaga gcaatccgga cccacgaccg cttttggcaa    240
accgaaccgg acctccagcc cccggggtga cgcgcagccc gccggccaga cac atg       296
                                                             Met
                                                               1
```

```
gcc cca agc cca aga ccc gag cat gtc ctg cac tgg aag gaa gcc cac      344
Ala Pro Ser Pro Arg Pro Glu His Val Leu His Trp Lys Glu Ala His
            5               10              15
```

```
tct ttc tac ctc ctg tct cca ctg atg ggc ttc ctc agc cgg gcc tgg      392
Ser Phe Tyr Leu Leu Ser Pro Leu Met Gly Phe Leu Ser Arg Ala Trp
            20              25              30
```

```
agc cgc ctg agg ggg ccc gag gtc tca gag gcc tgg ttg gca gaa aca      440
Ser Arg Leu Arg Gly Pro Glu Val Ser Glu Ala Trp Leu Ala Glu Thr
        35              40              45
```

```
gta gca gga gca aac cag ata cag gct gat gct ctg ttg acg cct ccc      488
Val Ala Gly Ala Asn Gln Ile Gln Ala Asp Ala Leu Leu Thr Pro Pro
50              55              60              65
```

```
ccg gtc tct gaa aat cac cta cct ctc cga gag act gaa gga aat gga      536
Pro Val Ser Glu Asn His Leu Pro Leu Arg Glu Thr Glu Gly Asn Gly
                70              75              80
```

```
act cct gaa tgg agt aaa gca gcc cag agg ctc tgc ctt gat gtg gaa      584
Thr Pro Glu Trp Ser Lys Ala Ala Gln Arg Leu Cys Leu Asp Val Glu
            85              90              95
```

```
gcc caa agt tcc cct cct aaa act tgg gga ctt tca gat att gat gaa      632
Ala Gln Ser Ser Pro Pro Lys Thr Trp Gly Leu Ser Asp Ile Asp Glu
        100             105             110
```

```
cat aat ggg aag cca gga caa gat ggc ctt aga gag caa gaa gtg gag      680
His Asn Gly Lys Pro Gly Gln Asp Gly Leu Arg Glu Gln Glu Val Glu
    115             120             125
```

```
cac aca gct ggc ctg cct aca cta cag ccc ctt cac ctg caa ggg gca      728
His Thr Ala Gly Leu Pro Thr Leu Gln Pro Leu His Leu Gln Gly Ala
130             135             140             145
```

FIG.13A

```
gat aag aaa gtt ggg gag gtg gtg gct aga gaa gag ggt gtg tcc gag      776
Asp Lys Lys Val Gly Glu Val Val Ala Arg Glu Glu Gly Val Ser Glu
            150             Val         155                 160 ctg gct tac ccc aca tca cac tgg gag ggt ggt cca gct gag gat gaa      824
Leu Ala Tyr Pro Thr Ser His Trp Glu Gly Gly Pro Ala Glu Asp Glu
            165                     170                 175 gag gat aca gaa acc gtg aag aag gct cac cag gcc tct gct gct tcc      872
Glu Asp Thr Glu Thr Val Lys Lys Ala His Gln Ala Ser Ala Ala Ser
            180                 185                 190 ata gct cca gga tat aaa ccc agc act tct gtg tat tgc cca ggg gag      920
Ile Ala Pro Gly Tyr Lys Pro Ser Thr Ser Val Tyr Cys Pro Gly Glu
            195                 200                 205 gca gaa cat cga gcc acg gag gaa aaa gga aca gac aat aag gct gaa      968
Ala Glu His Arg Ala Thr Glu Glu Lys Gly Thr Asp Asn Lys Ala Glu
210             215                 220                 225 ccc tca ggc tcc cac tcc aga ttc tgg gag tac cac act aga gag agg     1016
Pro Ser Gly Ser His Ser Arg Phe Trp Glu Tyr His Thr Arg Glu Arg
            230                 235                 240 cct aag cag gag gga gaa act aag cca gag caa cac agg gca ggg cag     1064
Pro Lys Gln Glu Gly Glu Thr Lys Pro Glu Gln His Arg Ala Gly Gln
            245                 250                 255 agt cac cct tgt cag aat gca gag tct gag gaa gga gga cct gag act     1112
Ser His Pro Cys Gln Asn Ala Glu Ser Glu Glu Gly Gly Pro Glu Thr
            260                 265                 270 tct gtc tgt tct ggc agt gcc ttc ctg aag gcc tgg gtg tat cgc cca     1160
Ser Val Cys Ser Gly Ser Ala Phe Leu Lys Ala Trp Val Tyr Arg Pro
            275                 280                 285 gga gag gac aca gag gag gaa gaa gac cct gat ttg gat tca gct gag     1208
Gly Glu Asp Thr Glu Glu Glu Glu Asp Pro Asp Leu Asp Ser Ala Glu
290             295                 300                 305 gaa gac aca gct cat acc tgt acc acc ccc cat aca agt gcc ttc ctg     1256
Glu Asp Thr Ala His Thr Cys Thr Thr Pro His Thr Ser Ala Phe Leu
            310                 315                 320
```

FIG.13B

```
aag gcc tgg gtc tat cgc cca gga gag gac aca gaa gag gaa gat gac    1304
Lys Ala Trp Val Tyr Arg Pro Gly Glu Asp Thr Glu Glu Glu Asp Asp
            325                 330                 335 ggt gat tgg gat tca gct gag gaa gac gca gct cag agc tgt acc acc    1352
Gly Asp Trp Asp Ser Ala Glu Glu Asp Ala Ala Gln Ser Cys Thr Thr
            340                 345                 350 ccc cat aca agt gcc ttc ctg aag gcc tgg gtc tat cgc cca gga gag    1400
Pro His Thr Ser Ala Phe Leu Lys Ala Trp Val Tyr Arg Pro Gly Glu
            355                 360                 365 gac aca gaa gag gaa gac gac agt gag aat gtg gcc cca gtt gac tca    1448
Asp Thr Glu Glu Glu Asp Asp Ser Glu Asn Val Ala Pro Val Asp Ser
370                 375                 380                 385 gaa aca gtt gac tct tgc cag agt acc cag cat tgt cta cca gta gag    1496
Glu Thr Val Asp Ser Cys Gln Ser Thr Gln His Cys Leu Pro Val Glu
            390                 395                 400 aag acc aag gga tgt gga gaa gca gag ccc cct ccc ttc cag gtg gcc    1544
Lys Thr Lys Gly Cys Gly Glu Ala Glu Pro Pro Pro Phe Gln Val Ala
            405                 410                 415 ttc tat tta cct gga cag aag cca gca cca cct tgg gca gcc cct aag    1592
Phe Tyr Leu Pro Gly Gln Lys Pro Ala Pro Pro Trp Ala Ala Pro Lys
            420                 425                 430 ctg ccc ctt cga ctg cag aag cgg ctc aga tct ttc aaa gcc ccc gcc    1640
Leu Pro Leu Arg Leu Gln Lys Arg Leu Arg Ser Phe Lys Ala Pro Ala
            435                 440                 445 cgg aat cag ggc cct gag att cct ctg aag ggt aga aag gtg cac ttc    1688
Arg Asn Gln Gly Pro Glu Ile Pro Leu Lys Gly Arg Lys Val His Phe
450                 455                 460                 465 tct gag aaa gtt aca gtc cat ttc ctt gct gtc tgg gca gga cca gcc    1736
Ser Glu Lys Val Thr Val His Phe Leu Ala Val Trp Ala Gly Pro Ala
            470                 475                 480 cag gct gct cgt cga ggc ccc tgg gag cag ttt gca cga gat cga agc    1784
Gln Ala Ala Arg Arg Gly Pro Trp Glu Gln Phe Ala Arg Asp Arg Ser
            485                 490                 495
```

FIG. 13C

| | |
|---|---|
| cgc ttt gct cga cgc att gcc cag gca gag gag cag ctg ggt cct tac<br>Arg Phe Ala Arg Arg Ile Ala Gln Ala Glu Glu Gln Leu Gly Pro Tyr<br>        500                   505                510 | 1832 |
| ctt acc cct gct ttc agg gcc aga gca tgg aca cgc ctt aga aac cta<br>Leu Thr Pro Ala Phe Arg Ala Arg Ala Trp Thr Arg Leu Arg Asn Leu<br>        515                   520                525 | 1880 |
| ccc ctt cct ctg tcg tcc tcg tct ctt cca ctg cct gag cct tgc tct<br>Pro Leu Pro Leu Ser Ser Ser Ser Leu Pro Leu Pro Glu Pro Cys Ser<br>530                 535                540                545 | 1928 |
| tcc act gag gcc aca ccc ctc agc caa gat gtg acc act ccc tct ccc<br>Ser Thr Glu Ala Thr Pro Leu Ser Gln Asp Val Thr Thr Pro Ser Pro<br>                550                555              560 | 1976 |
| ctt ccc agt gaa atc cct cct ccc agc ctg gac ttg gga gga agg cgg<br>Leu Pro Ser Glu Ile Pro Pro Pro Ser Leu Asp Leu Gly Gly Arg Arg<br>                565                570              575 | 2024 |
| ggc taagcctgag tagtttttg ttatttattt attttaatac gaaataaagc<br>Gly | 2077 |
| cttttgattt gtagtgaaaa aaaaaaaaaa aaaa | 2111 |

FIG. 13D

```
acatgggcac gcgtggtcga cggcccgggc tggctgggca cacgggttc agcccaggtt    60
tcatagtaag ttccagacac tcctggaaaa acaatacagg tccctgacaa agaaaaaac  120
aaaacaaagg aaacagaaac atgcgttttt aaaaagaag gaggagactc catgaaggca  180
ggccttgggt ggggtcactg cttctctgta cacaggagga gaattgccaa gatcttccgg  240
acagtgtgga ctatactgta agaccctctc aatacagaca gactggacag gcatagtgac  300
acatgccttt aatgcctgca gtactcagga ggaggtggca ggtggaacgg ctgttctttg  360
aggttcaaga ccagcgtgga ctacagagtg agttccagga caggcagggc tacacagaaa  420
aatcctgtct gaaaacaaaa caaaacccag acagacacac caaaaacagc caagggacca  480
gagagatggg tcagggccta atcacttgct actctttgca gaggacccaa atttagttcc  540
tataaccctc catgagaagc ttcacaattg tctctaactc aattccaccc gtgttccgac  600
ctccatatgc accagacatg atatactcac acatacgcac aaacacacac acacacacac  660
acacacacac acacacacac acacacacac ggaaaacata taaaataaag atttaaaaaa  720
tctttttctt ttggccgggg tgtgtgggag agcatctgag ccatctcacc agcccagggt  780
gcagctcttt ttctttttt cggagctggg gaccgaaccc agagccttgt gcttgctagg  840
caagtgctct accactgagc taaatcccca accccggagc acgtctttaa tcccagaatc  900
aggaggtaga ggtaatgaga tcccagtgag cccaaggtca gccgagtcta caaagtgagt  960
tccaggacag ccagaactaa tcttggaaaa acaaacaagg gctggtgagg tggttcagta 1020
gttaagaaca ctggctgctc ttccagaggt cctgagttca ttctcagtaa ccacatggtg 1080
gggatctgat gcctgttctg gcatgcagat atacatgcag atagtgcact cctacattta 1140
aaaaaaaaag acataaataa tattttaaaa cattgggcgt tttgtcttct aataaaactt 1200
cactgctatc ttctaataaa aattcactgc tagccgcggg gtgtggtggc cccatacctt 1260
taatcccaac aacttgagag gcagaggcag gcggaccttt gagtttgaag ctagcctggt 1320
ctacagagtg agttcaagat agccacggat agtcagaaag tcctgtttcg aacctctccc 1380
caaccaaatc actcctgtaa tcccagcact ctggaggcag tagcaggtta gtccctgctt 1440
ctcagagaga ggagagagag agagagagag agagagagga gacacacaca cacagagaca 1500
```

FIG.14A

```
gagaggagag agaaagagaa agagaatggg acagcatgtg actgcctgat gaagttggcg 1560
tgcttgctca aaagttctgc gagattgacg gctctctgga tttgagccaa ggacacgcct 1620
gggaagccac ggtgacctca caaggcccgg aatctccgcg agaatttcag tgttgttttc 1680
ctctctccac ctttctcagg gacttccgaa actccgcctc tccggtgacg tcagatagcg 1740
ctcgtcagac tataaactcc cgggtgatcg tgttggcgca gattgactca gttcgcagct 1800
tgtggaagat tacatgcgag accccgcgcg actccgcatc cctttgccgg acagcctttt 1860
gcgacagccc gtgagacatc acgtccccga ccccagcct gagggcgaca tgaacgcgct 1920
ggccttgaga gcaatccgga cccacgatcg cttttggcaa accgaaccgg accgaaccgg 1980
acctccagcc cccggggtga cgcgcagtcg ccggtgagtg ggggatgggg cggcctttgg 2040
gggagtgctg gggaggactt tctttggcga tggaggctag gagagtgttg tgggatctag 2100
gggagactgg ggaggaaccc agatttgagg aaacggcact gaaagccgga tgctttattt 2160
ggtccgagag aggagagccc aggtctagtc tctacattga agggcagggg tcctgaacta 2220
gaactgcagt acttgtacat tgctaaataa agagagggac tccaggagga gcagcctggg 2280
tctaagaggt aggcaggaga aggttttagg ggcctgagca caagcttgag gagagaaagg 2340
ttattaaaaa gccagacgtt acaggtctca gaagggctag ccagaaactg tggcttgggg 2400
ttaaggaaag ggtttaagag tgtgggcttt tggttctgag gatgtaggaa cgtgaatgtt 2460
gagagaagaa ccaagtggcg gagttgggtg tgagcaatgc tattaggaat ttgaggcagg 2520
gattcacgct gctgtgacta tttttttaaca atgactcagt gctgtgacct gatactgttt 2580
ccagagcgac ttctaaacaa attcccccct ttct                               2614
```

FIG. 14B

SEQUENCE LISTING

<160> NUMBER OF SEQ ID NOS: 13

<210> SEQ ID NO 1
<211> LENGTH: 457
<212> TYPE: PRT
<213> ORGANISM: rat

<400> SEQUENCE: 1

```
Met Ala Pro Ser Pro Arg Pro Gln His Val Leu His Trp Lys Glu Ala
  1               5                  10                  15

His Ser Phe Tyr Leu Leu Ser Pro Leu Met Gly Phe Leu Ser Arg Ala
             20                  25                  30

Trp Ser Arg Leu Arg Gly Pro Glu Val Ser Glu Ala Trp Leu Ala Glu
         35                  40                  45

Thr Val Ala Gly Ala Asn Gln Ile Glu Ala Asp Ala Leu Leu Thr Pro
     50                  55                  60

Pro Pro Val Ser Glu Asn His Leu Pro Leu Arg Glu Thr Gly Asn
 65                  70                  75                  80

Gly Thr Pro Glu Trp Ser Lys Ala Ala Gln Arg Leu Cys Leu Asp Val
                 85                  90                  95

Glu Ala Gln Ser Ser Pro Pro Lys Thr Trp Gly Leu Ser Asp Ile Asp
            100                 105                 110

Glu His Asn Gly Lys Pro Gly Gln Asp Gly Leu Arg Glu Gln Glu Val
        115                 120                 125

Glu His Thr Ala Gly Leu Pro Thr Leu Gln Pro Leu His Leu Gln Gly
    130                 135                 140

Ala Asp Lys Lys Val Gly Glu Val Val Ala Arg Glu Glu Gly Val Ser
145                 150                 155                 160

Glu Leu Ala Tyr Pro Thr Ser His Trp Glu Gly Gly Pro Ala Glu Asp
                165                 170                 175

Glu Glu Asp Thr Glu Thr Val Lys Lys Ala His Gln Ala Ser Ala Ala
            180                 185                 190

Ser Ile Ala Pro Gly Tyr Lys Pro Ser Thr Ser Val Tyr Cys Pro Gly
        195                 200                 205

Glu Ala Glu His Arg Ala Thr Glu Glu Lys Gly Thr Asp Asn Lys Ala
    210                 215                 220

Glu Pro Ser Gly Ser His Ser Arg Val Trp Glu Tyr His Thr Arg Glu
225                 230                 235                 240

Arg Pro Lys Gln Glu Gly Glu Thr Lys Pro Glu Gln His Arg Ala Gly
                245                 250                 255

Gln Ser His Pro Cys Gln Asn Ala Glu Ala Glu Gly Gly Pro Glu
            260                 265                 270

Thr Ser Val Cys Ser Gly Ser Ala Phe Leu Lys Ala Trp Val Tyr Arg
        275                 280                 285

Pro Gly Glu Asp Thr Glu Glu Glu Asp Ser Asp Leu Asp Ser Ala
    290                 295                 300

Glu Glu Asp Thr Ala His Thr Cys Thr Thr Pro His Thr Ser Ala Phe
305                 310                 315                 320

Leu Lys Ala Trp Val Tyr Arg Pro Gly Glu Asp Thr Glu Glu Glu Asp
                325                 330                 335

Asp Gly Asp Trp Asp Ser Ala Glu Glu Asp Ala Ser Gln Ser Cys Thr
            340                 345                 350

Thr Pro His Thr Ser Ala Phe Leu Lys Ala Trp Val Tyr Arg Pro Gly
```

```
                    355                 360                 365
Glu Asp Thr Glu Glu Asp Asp Ser Glu Asn Val Ala Pro Val Asp
        370                 375                 380

Ser Glu Thr Val Asp Ser Cys Gln Ser Thr Gln His Cys Leu Pro Val
385                 390                 395                 400

Glu Lys Thr Lys Gly Cys Gly Glu Ala Glu Pro Pro Phe Gln Trp
                405                 410                 415

Pro Ser Ile Tyr Leu Asp Arg Ser Gln His Leu Gly Leu Pro Leu
                420                 425                 430

Ser Cys Pro Phe Asp Cys Arg Ser Gly Ser Asp Leu Ser Lys Pro Pro
                435                 440                 445

Pro Gly Ile Arg Ala Leu Arg Phe Leu
                450                 455

<210> SEQ ID NO 2
<211> LENGTH: 590
<212> TYPE: PRT
<213> ORGANISM: rat

<400> SEQUENCE: 2

Met Ala Pro Ser Pro Arg Pro Gln His Ile Leu Leu Trp Arg Asp Ala
 1               5                  10                  15

His Ser Phe His Leu Leu Ser Pro Leu Met Gly Phe Leu Ser Arg Ala
                20                  25                  30

Trp Ser Arg Leu Arg Val Pro Glu Ala Pro Glu Pro Trp Pro Ala Glu
            35                  40                  45

Thr Val Thr Gly Ala Asp Gln Ile Glu Ala Asp Ala His Pro Ala Pro
    50                  55                  60

Pro Leu Val Pro Glu Asn His Pro Pro Gln Gly Glu Ala Glu Glu Ser
65                  70                  75                  80

Gly Thr Pro Glu Glu Gly Lys Ala Ala Gln Gly Pro Cys Leu Asp Val
                85                  90                  95

Gln Ala Asn Ser Ser Pro Pro Glu Thr Leu Gly Leu Ser Asp Asp Asp
                100                 105                 110

Lys Gln Gly Gln Asp Gly Pro Arg Glu Gln Gly Arg Ala His Thr Ala
                115                 120                 125

Gly Leu Pro Ile Leu Leu Ser Pro Gly Leu Gln Ser Ala Asp Lys Ser
                130                 135                 140

Leu Gly Glu Val Val Ala Gly Glu Glu Gly Val Thr Glu Leu Ala Tyr
145                 150                 155                 160

Pro Thr Ser His Trp Glu Gly Cys Pro Ser Glu Glu Glu Asp Gly
                165                 170                 175

Glu Thr Val Lys Lys Ala Phe Arg Ala Ser Ala Asp Ser Pro Gly His
                180                 185                 190

Lys Ser Ser Thr Ser Val Tyr Cys Pro Gly Glu Ala Glu His Gln Ala
                195                 200                 205

Thr Glu Glu Lys Gln Thr Glu Asn Lys Ala Asp Pro Pro Ser Ser Pro
                210                 215                 220

Ser Gly Ser His Ser Arg Ala Trp Glu Tyr Cys Ser Lys Gln Glu Gly
225                 230                 235                 240

Glu Ala Asp Pro Glu Pro His Arg Ala Gly Lys Tyr Gln Leu Cys Gln
                245                 250                 255

Asn Ala Glu Ala Glu Glu Glu Glu Ala Lys Val Ser Ser Leu Ser
                260                 265                 270
```

```
Val Ser Ser Gly Asn Ala Phe Leu Lys Ala Trp Val Tyr Arg Pro Gly
        275                 280                 285

Glu Asp Thr Glu Asp Asp Asp Ser Asp Trp Gly Ser Ala Glu Glu
    290                 295                 300

Glu Gly Lys Ala Leu Ser Ser Pro Thr Ser Pro Glu His Asp Phe Leu
305                 310                 315                 320

Lys Ala Trp Val Tyr Arg Pro Gly Glu Asp Thr Glu Asp Asp Asp
                325                 330                 335

Ser Asp Trp Gly Ser Ala Glu Glu Gly Lys Ala Leu Ser Ser Pro
        340                 345                 350

Thr Ser Pro Glu His Asp Phe Leu Lys Ala Trp Val Tyr Arg Pro Gly
        355                 360                 365

Glu Asp Thr Glu Asp Asp Gln Asp Ser Asp Trp Gly Ser Ala Glu Lys
    370                 375                 380

Asp Gly Leu Ala Gln Thr Phe Ala Thr Pro His Thr Ser Ala Phe Leu
385                 390                 395                 400

Lys Thr Trp Val Cys Cys Pro Gly Glu Asp Thr Glu Asp Asp Asp Cys
                405                 410                 415

Glu Val Val Pro Glu Asp Ser Glu Ala Ala Asp Pro Asp Lys Ser
        420                 425                 430

Pro Ser His Glu Ala Gln Gly Cys Leu Pro Gly Glu Gln Thr Glu Gly
        435                 440                 445

Leu Val Glu Ala Glu His Ser Leu Phe Gln Val Ala Phe Tyr Leu Pro
    450                 455                 460

Gly Glu Lys Pro Ala Pro Pro Trp Thr Ala Pro Lys Leu Pro Leu Arg
465                 470                 475                 480

Leu Gln Arg Arg Leu Thr Leu Leu Arg Thr Pro Thr Gln Asp Gln Asp
                485                 490                 495

Pro Glu Thr Pro Leu Arg Ala Arg Lys Val His Phe Ser Glu Asn Val
        500                 505                 510

Thr Val His Phe Leu Ala Val Trp Ala Gly Pro Ala Gln Ala Ala Arg
        515                 520                 525

Arg Gly Pro Trp Glu Gln Leu Ala Arg Asp Arg Ser Arg Phe Ala Arg
    530                 535                 540

Arg Ile Ala Gln Ala Glu Glu Lys Leu Gly Pro Tyr Leu Thr Pro Ala
545                 550                 555                 560

Phe Arg Ala Arg Ala Trp Ala Arg Leu Gly Asn Pro Ser Leu Pro Leu
                565                 570                 575

Ala Leu Glu Pro Ile Cys Asp His Thr Phe Phe Pro Ser Gln
        580                 585                 590

<210> SEQ ID NO 3
<211> LENGTH: 657
<212> TYPE: PRT
<213> ORGANISM: rat

<400> SEQUENCE: 3

Met Ala Pro Ser Pro Arg Phe Gln His Val Leu His Trp Arg Asp Ala
  1               5                  10                  15

His Asn Phe Tyr Leu Leu Ser Pro Leu Met Gly Leu Leu Ser Arg Ala
             20                  25                  30

Trp Ser Arg Leu Arg Gly Pro Glu Val Pro Glu Ala Trp Leu Ala Lys
         35                  40                  45

Thr Val Thr Gly Ala Asp Gln Ile Glu Ala Ala Ala Leu Leu Thr Pro
     50                  55                  60
```

-continued

```
Thr Pro Val Ser Gly Asn Leu Leu Pro His Gly Glu Thr Glu Glu Ser
 65                  70                  75                  80

Gly Ser Pro Glu Gln Ser Gln Ala Ala Gln Arg Leu Cys Leu Val Glu
                 85                  90                  95

Ala Glu Ser Ser Pro Pro Glu Thr Trp Gly Leu Ser Asn Val Asp Glu
            100                 105                 110

Tyr Asn Ala Lys Pro Gly Gln Asp Asp Leu Arg Glu Lys Glu Met Glu
            115                 120                 125

Arg Thr Ala Gly Lys Ala Thr Leu Gln Pro Ala Gly Leu Gln Gly Ala
130                 135                 140

Asp Lys Arg Leu Gly Glu Val Val Ala Arg Glu Gly Val Ala Glu
145                 150                 155                 160

Pro Ala Tyr Pro Thr Ser Gln Leu Glu Gly Gly Pro Ala Glu Asn Glu
                165                 170                 175

Glu Asp Gly Glu Thr Val Lys Thr Tyr Gln Ala Ser Ala Ala Ser Ile
            180                 185                 190

Ala Pro Gly Tyr Lys Pro Ser Thr Pro Val Pro Phe Leu Gly Glu Ala
            195                 200                 205

Glu His Gln Ala Thr Glu Glu Lys Gly Thr Glu Asn Lys Ala Asp Pro
210                 215                 220

Ser Asn Ser Pro Ser Ser Gly Ser His Ser Arg Ala Trp Glu Tyr Tyr
225                 230                 235                 240

Ser Arg Glu Lys Pro Lys Gln Glu Gly Glu Ala Lys Val Glu Ala His
                245                 250                 255

Arg Ala Gly Gln Gly His Pro Cys Arg Asn Ala Glu Ala Glu Glu Gly
            260                 265                 270

Gly Pro Glu Thr Thr Phe Val Cys Thr Gly Asn Ala Phe Leu Lys Ala
            275                 280                 285

Trp Val Tyr Arg Pro Gly Glu Asp Thr Glu Glu Asp Asn Ser Asp
290                 295                 300

Ser Asp Ser Ala Glu Glu Asp Thr Ala Gln Thr Gly Ala Thr Pro His
305                 310                 315                 320

Thr Ser Ala Phe Leu Lys Ala Trp Val Tyr Arg Pro Gly Glu Asp Thr
                325                 330                 335

Glu Glu Glu Asp Ser Asp Ser Asp Ser Ala Glu Glu Asp Thr Ala Gln
            340                 345                 350

Thr Gly Ala Thr Pro His Thr Ser Ala Phe Leu Lys Ala Trp Val Tyr
            355                 360                 365

Arg Pro Gly Glu Asp Thr Glu Glu Asn Ser Asp Leu Asp Ser Ala
370                 375                 380

Glu Glu Asp Thr Ala Gln Thr Gly Ala Thr Pro His Thr Ser Ala Phe
385                 390                 395                 400

Leu Lys Ala Trp Val Tyr Arg Pro Gly Glu Asp Thr Glu Glu Asn
                405                 410                 415

Ser Asp Leu Asp Ser Ala Glu Glu Asp Thr Ala Gln Thr Gly Ala Thr
            420                 425                 430

Pro His Thr Ser Pro Phe Leu Lys Ala Trp Val Tyr Arg Pro Gly Glu
            435                 440                 445

Asp Thr Glu Asp Asp Thr Glu Glu Glu Asp Ser Glu Asn Val Ala
450                 455                 460

Pro Gly Asp Ser Glu Thr Ala Asp Ser Gln Ser Pro Cys Leu Gln
465                 470                 475                 480
```

```
Pro Gln Arg Cys Leu Pro Gly Glu Lys Thr Lys Gly Arg Gly Glu Glu
                485                 490                 495
Pro Pro Leu Phe Gln Val Ala Phe Tyr Leu Pro Gly Glu Lys Pro Glu
            500                 505                 510
Ser Pro Trp Ala Ala Pro Lys Leu Pro Leu Arg Leu Gln Arg Arg Leu
        515                 520                 525
Arg Leu Phe Lys Ala Pro Thr Arg Asp Gln Asp Pro Glu Ile Pro Leu
    530                 535                 540
Lys Ala Arg Lys Val His Phe Ala Glu Lys Val Thr Val His Phe Leu
545                 550                 555                 560
Ala Val Trp Ala Gly Pro Ala Gln Ala Arg Arg Gly Pro Trp Glu
                565                 570                 575
Gln Phe Ala Arg Asp Arg Ser Arg Phe Ala Arg Arg Ile Ala Gln Ala
                580                 585                 590
Glu Glu Lys Leu Gly Pro Tyr Leu Thr Pro Asp Ser Arg Ala Arg Ala
            595                 600                 605
Trp Ala Arg Leu Arg Asn Pro Ser Leu Pro Gln Ser Glu Pro Arg Ser
        610                 615                 620
Ser Ser Glu Ala Thr Pro Leu Thr Gln Asp Val Thr Thr Pro Ser Pro
625                 630                 635                 640
Leu Pro Ser Glu Thr Pro Ser Pro Ser Leu Tyr Leu Gly Gly Arg Arg
                645                 650                 655
Gly

<210> SEQ ID NO 4
<211> LENGTH: 2137
<212> TYPE: DNA
<213> ORGANISM: rat

<400> SEQUENCE: 4
ctgcagtact tgtacattgc taaataaaga gagggactcc aggaggagca gcctgggtct      60
aagaggtagg cagaaggagg ttttagggc ctgagcacaa gcttgaggag agaaaggtta     120
ttaaaaagcc agacgcttac aggtctcaga agggctagcc agaaactgtg gctggggtta     180
aggaaagggt ttaagagtgt gggcttttgg ttctgaggat gtagaacgtg aatgttgaga     240
gaagaaccaa gtggcggagt tgggtgtgag caatgctatt aggaatttga ggcagggatt     300
cacgcgctgc tgtgactatt ttttaacaat gactcagtgc tgtgacctga tactgttttcc    360 agagcgactt ctaaacaaat tcccccttc taggccagac acatggcccc aagcccaaga     420
ccccagcatg tcctgcactg gaaggaagcc cactctttct acctcctgtc tccactgatg     480
ggcttcctca gccgggcctg gagccgcctg agggggcccg aggtctcaga ggcctggttg     540
gcagaaacag tagcaggagc aaaccagata gaggctgatg ctctgttgac gcctcccccg     600
gtctctgaaa tcacctacc tctccgagag actgaaggaa atggaactcc tgaatggagt      660
aaagcagccc agaggctctg ccttgatgtg gaagcccaaa gttcccctcc taaaacttgg     720
ggactttcag agtattgatg aacataatgg gaagccagga caagatggcc ttagagagca     780
agaagtggag cacacagctg gcctgcctac actacagccc cttcacctgc aaggggcaga     840
taagaaagtt gggaggtgg tggctagaga agaggtgtg tccgagctgg cttaccccac       900
atcacactgg gagggtggtc cagctgagga tgaagaggat acagaaaccg tgaagaaggc     960
tcaccaggcc tctgctgctt ccatagctcc aggatataaa cccagcactt ctgtgtattg    1020
cccaggggag gcagaacatc gagccacgga ggaaaaagga acagacaata aggctgaacc    1080
```

-continued

```
ctcaggctcc cactccagag tctgggagta ccacactaga gagaggccta agcaggaggg    1140
agaaactaag ccagagcaac acagggcagg gcagagtcac ccttgtcaga atgcagaggc    1200
tgaggaagga ggacctgaga cttctgtctg ttctggcagt gccttcctga aggcctgggt    1260
gtatcgccca ggagaggaca cagaggagga agaagacagt gatttggatt cagctgagga    1320
agacacagct catacctgta ccaccccca tacaagtgcc ttcctgaagg cctgggtcta    1380
tcgcccagga gaggacacag aagaggaaga tgacggtgat tgggattcag ctgaggaaga    1440
cgcgtctcag agctgtacca cccccatac aagtgccttc ctgaggcctg gtctatcgc     1500 ccaggagagg acacagaaga ggaagacgac agtgagaatg tggccccagt tgactcagaa    1560
acagttgact cttgccagag tacccagcat tgtctaccag tagagaagac caagggatgt    1620
ggagaagcag agccccctcc cttccagtgg ccttctattt acctggacag aagccagcac    1680
caccttgggc tgccccttaag ctgccccttc gactgcagaa gcggctcaga tctttcaaag    1740 ccccgcccg gaatcagggc cctgagattc ctctgaaggg tagaaaggtg cacttctctg     1800
agaaagttac agtccatttc cttgctgtct gggcaggacc agcccaggct gctcgtcgag    1860
gcccctggga gcagtttgca cgagatcgaa gccgctttgc tcgacgcatt gccgtcctcg    1920
tctcttccac tgcctgagcc ttgctcttcc actgaggcca caccctcag ccaagatgtg     1980 accactccct ctccccttcc cagtgaaatc cctcctccca gcctgactt gggaggaagg     2040 cgggctaagc ctgagtagtt ttttgtgtat tctatgagtg ttagtctctt aatacgaata    2100
tgtaacgcct tttgcatttg taaaaaaaaa aaaaaaa                             2137
```

<210> SEQ ID NO 5
<211> LENGTH: 457
<212> TYPE: PRT
<213> ORGANISM: rat

<400> SEQUENCE: 5

```
Met Ala Pro Ser Pro Arg Pro Gln His Val Leu His Trp Lys Glu Ala
 1               5                  10                  15

His Ser Phe Tyr Leu Leu Ser Pro Leu Met Gly Phe Leu Ser Arg Ala
            20                  25                  30

Trp Ser Arg Leu Arg Gly Pro Glu Val Ser Glu Ala Trp Leu Ala Glu
        35                  40                  45

Thr Val Ala Gly Ala Asn Gln Ile Glu Ala Asp Ala Leu Leu Thr Pro
    50                  55                  60

Pro Pro Val Ser Glu Asn His Leu Pro Leu Arg Glu Thr Glu Gly Asn
65                  70                  75                  80

Gly Thr Pro Glu Trp Ser Lys Ala Ala Gln Arg Leu Cys Leu Asp Val
                85                  90                  95

Glu Ala Gln Ser Ser Pro Pro Lys Thr Trp Gly Leu Ser Asp Ile Asp
            100                 105                 110

Glu His Asn Gly Lys Pro Gly Gln Asp Gly Leu Arg Glu Gln Glu Val
        115                 120                 125

Glu His Thr Ala Gly Leu Pro Thr Leu Gln Pro His Leu Gln Gly
    130                 135                 140

Ala Asp Lys Lys Val Gly Glu Val Val Arg Glu Glu Gly Val Ser
145                 150                 155                 160

Glu Leu Ala Tyr Pro Thr Ser His Trp Glu Gly Gly Pro Ala Glu Asp
                165                 170                 175

Glu Glu Asp Thr Glu Thr Val Lys Lys Ala His Gln Ala Ser Ala Ala
            180                 185                 190
```

```
Ser Ile Ala Pro Gly Tyr Lys Pro Ser Thr Ser Val Tyr Cys Pro Gly
        195                 200                 205

Glu Ala Glu His Arg Ala Thr Glu Lys Gly Thr Asp Asn Lys Ala
    210                 215                 220

Glu Pro Ser Gly Ser His Ser Arg Val Trp Glu Tyr His Thr Arg Glu
225                 230                 235                 240

Arg Pro Lys Gln Glu Gly Thr Lys Pro Glu Gln His Arg Ala Gly
            245                 250                 255

Gln Ser His Pro Cys Gln Asn Ala Glu Ala Glu Gly Gly Pro Glu
        260                 265                 270

Thr Ser Val Cys Ser Gly Ser Ala Phe Leu Lys Ala Trp Val Tyr Arg
            275                 280                 285

Pro Gly Glu Asp Thr Glu Glu Glu Asp Ser Asp Leu Asp Ser Ala
290                 295                 300

Glu Glu Asp Thr Ala His Thr Cys Thr Thr Pro His Thr Ser Ala Phe
305                 310                 315                 320

Leu Lys Ala Trp Val Tyr Arg Pro Gly Glu Asp Thr Glu Glu Asp
                325                 330                 335

Asp Gly Asp Trp Asp Ser Ala Glu Glu Asp Ala Ser Gln Ser Cys Thr
                340                 345                 350

Thr Pro His Thr Ser Ala Phe Leu Lys Ala Trp Val Tyr Arg Pro Gly
        355                 360                 365

Glu Asp Thr Glu Glu Asp Ser Glu Asn Val Ala Pro Val Asp
            370                 375                 380

Ser Glu Thr Val Asp Ser Cys Gln Ser Thr Gln His Cys Leu Pro Val
385                 390                 395                 400

Glu Lys Thr Lys Gly Cys Gly Glu Ala Glu Pro Pro Phe Gln Trp
                405                 410                 415

Pro Ser Ile Tyr Leu Asp Arg Ser Gln His Leu Gly Leu Pro Leu
            420                 425                 430

Ser Cys Pro Phe Asp Cys Arg Ser Gly Ser Asp Leu Ser Lys Pro Pro
            435                 440                 445

Pro Gly Ile Arg Ala Leu Arg Phe Leu
    450                 455

<210> SEQ ID NO 6
<211> LENGTH: 2111
<212> TYPE: DNA
<213> ORGANISM: human
<220> FEATURE:
<221> NAME/KEY: CDS
<222> LOCATION: (294)...(2027)

<400> SEQUENCE: 6
tgagattgac tcagttcgca gcttgtggaa gattacatgc gagaaaaagc gcgactccgc      60 atcccttgc  cgggacagcc cttgcgacag cccgtgagac atcacgtccc cgagccccac    120
ctttgccggg acagcctttg cgacagcccg tgagacatca cgtccccgag ccccacgcct    180
gagggcgaca tgaacgcgct ggccttgaga gcaatccgga cccacgaccg ctttggcaa     240 accgaaccgg acctccagcc cccggggtga cgcgcagccc gccggccaga cac atg      296
                                                              Met
                                                                1 gcc cca agc cca aga ccc gag cat gtc ctg cac tgg aag gaa gcc cac      344
Ala Pro Ser Pro Arg Pro Glu His Val Leu His Trp Lys Glu Ala His
        5                   10                  15
```

```
tct ttc tac ctc ctg tct cca ctg atg ggc ttc ctc agc cgg gcc tgg      392
Ser Phe Tyr Leu Leu Ser Pro Leu Met Gly Phe Leu Ser Arg Ala Trp
         20                  25                  30 agc cgc ctg agg ggg ccc gag gtc tca gag gcc tgg ttg gca gaa aca      440
Ser Arg Leu Arg Gly Pro Glu Val Ser Glu Ala Trp Leu Ala Glu Thr
 35                  40                  45 gta gca gga gca aac cag ata cag gct gat gct ctg ttg acg cct ccc      488
Val Ala Gly Ala Asn Gln Ile Gln Ala Asp Ala Leu Leu Thr Pro Pro
 50                  55                  60                  65 ccg gtc tct gaa aat cac cta cct ctc cga gag act gaa gga aat gga      536
Pro Val Ser Glu Asn His Leu Pro Leu Arg Glu Thr Glu Gly Asn Gly
                 70                  75                  80 act cct gaa tgg agt aaa gca gcc cag agg ctc tgc ctt gat gtg gaa      584
Thr Pro Glu Trp Ser Lys Ala Ala Gln Arg Leu Cys Leu Asp Val Glu
             85                  90                  95 gcc caa agt tcc cct cct aaa act tgg gga ctt tca gat att gat gaa      632
Ala Gln Ser Ser Pro Pro Lys Thr Trp Gly Leu Ser Asp Ile Asp Glu
        100                 105                 110 cat aat ggg aag cca gga caa gat ggc ctt aga gag caa gaa gtg gag      680
His Asn Gly Lys Pro Gly Gln Asp Gly Leu Arg Glu Gln Glu Val Glu
    115                 120                 125 cac aca gct ggc ctg cct aca cta cag ccc ctt cac ctg caa ggg gca      728
His Thr Ala Gly Leu Pro Thr Leu Gln Pro Leu His Leu Gln Gly Ala
130                 135                 140                 145 gat aag aaa gtt ggg gag gtg gtg gct aga gaa gag ggt gtg tcc gag      776
Asp Lys Lys Val Gly Glu Val Val Ala Arg Glu Glu Gly Val Ser Glu
                150                 155                 160 ctg gct tac ccc aca tca cac tgg gag ggt ggt cca gct gag gat gaa      824
Leu Ala Tyr Pro Thr Ser His Trp Glu Gly Gly Pro Ala Glu Asp Glu
            165                 170                 175 gag gat aca gaa acc gtg aag aag gct cac cag gcc tct gct gct tcc      872
Glu Asp Thr Glu Thr Val Lys Lys Ala His Gln Ala Ser Ala Ala Ser
        180                 185                 190 ata gct cca gga tat aaa ccc agc act tct gtg tat tgc cca ggg gag      920
Ile Ala Pro Gly Tyr Lys Pro Ser Thr Ser Val Tyr Cys Pro Gly Glu
    195                 200                 205 gca gaa cat cga gcc acg gag gaa aaa gga aca gac aat aag gct gaa      968
Ala Glu His Arg Ala Thr Glu Glu Lys Gly Thr Asp Asn Lys Ala Glu
210                 215                 220                 225 ccc tca ggc tcc cac tcc aga ttc tgg gag tac cac act aga gag agg     1016
Pro Ser Gly Ser His Ser Arg Phe Trp Glu Tyr His Thr Arg Glu Arg
                230                 235                 240 cct aag cag gag gga gaa act aag cca gag caa cac agg gca ggg cag     1064
Pro Lys Gln Glu Gly Glu Thr Lys Pro Glu Gln His Arg Ala Gly Gln
            245                 250                 255 agt cac cct tgt cag aat gca gag tct gag gaa gga gga cct gag act     1112
Ser His Pro Cys Gln Asn Ala Glu Ser Glu Glu Gly Gly Pro Glu Thr
        260                 265                 270 tct gtc tgt tct ggc agt gcc ttc ctg aag gcc tgg gtg tat cgc cca     1160
Ser Val Cys Ser Gly Ser Ala Phe Leu Lys Ala Trp Val Tyr Arg Pro
    275                 280                 285 gga gag gac aca gag gag gaa gaa gac cct gat ttg gat tca gct gag     1208
Gly Glu Asp Thr Glu Glu Glu Glu Asp Pro Asp Leu Asp Ser Ala Glu
290                 295                 300                 305 gaa gac aca gct cat acc tgt acc acc ccc cat aca agt gcc ttc ctg     1256
Glu Asp Thr Ala His Thr Cys Thr Thr Pro His Thr Ser Ala Phe Leu
                310                 315                 320 aag gcc tgg gtc tat cgc cca gga gag gac aca gaa gag gaa gat gac     1304
Lys Ala Trp Val Tyr Arg Pro Gly Glu Asp Thr Glu Glu Glu Asp Asp
            325                 330                 335
```

-continued

```
ggt gat tgg gat tca gct gag gaa gac gca gct cag agc tgt acc acc    1352
Gly Asp Trp Asp Ser Ala Glu Glu Asp Ala Ala Gln Ser Cys Thr Thr
        340                 345                 350 ccc cat aca agt gcc ttc ctg aag gcc tgg gtc tat cgc cca gga gag    1400
Pro His Thr Ser Ala Phe Leu Lys Ala Trp Val Tyr Arg Pro Gly Glu
355                 360                 365 gac aca gaa gag gaa gac gac agt gag aat gtg gcc cca gtt gac tca    1448
Asp Thr Glu Glu Glu Asp Asp Ser Glu Asn Val Ala Pro Val Asp Ser
370                 375                 380                 385 gaa aca gtt gac tct tgc cag agt acc cag cat tgt cta cca gta gag    1496
Glu Thr Val Asp Ser Cys Gln Ser Thr Gln His Cys Leu Pro Val Glu
                390                 395                 400 aag acc aag gga tgt gga gaa gca gag ccc cct ccc ttc cag gtg gcc    1544
Lys Thr Lys Gly Cys Gly Glu Ala Glu Pro Pro Pro Phe Gln Val Ala
            405                 410                 415 ttc tat tta cct gga cag aag cca gca cca cct tgg gca gcc cct aag    1592
Phe Tyr Leu Pro Gly Gln Lys Pro Ala Pro Pro Trp Ala Ala Pro Lys
        420                 425                 430 ctg ccc ctt cga ctg cag aag cgg ctc aga tct ttc aaa gcc ccc gcc    1640
Leu Pro Leu Arg Leu Gln Lys Arg Leu Arg Ser Phe Lys Ala Pro Ala
435                 440                 445 cgg aat cag ggc cct gag att cct ctg aag ggt aga aag gtg cac ttc    1688
Arg Asn Gln Gly Pro Glu Ile Pro Leu Lys Gly Arg Lys Val His Phe
450                 455                 460                 465 tct gag aaa gtt aca gtc cat ttc ctt gct gtc tgg gca gga cca gcc    1736
Ser Glu Lys Val Thr Val His Phe Leu Ala Val Trp Ala Gly Pro Ala
                470                 475                 480 cag gct gct cgt cga ggc ccc tgg gag cag ttt gca cga gat cga agc    1784
Gln Ala Ala Arg Arg Gly Pro Trp Glu Gln Phe Ala Arg Asp Arg Ser
            485                 490                 495 cgc ttt gct cga cgc att gcc cag gca gag gag cag ctg ggt cct tac    1832
Arg Phe Ala Arg Arg Ile Ala Gln Ala Glu Glu Gln Leu Gly Pro Tyr
        500                 505                 510 ctt acc cct gct ttc agg gcc aga gca tgg aca cgc tta aga aac cta    1880
Leu Thr Pro Ala Phe Arg Ala Arg Ala Trp Thr Arg Leu Arg Asn Leu
    515                 520                 525 ccc ctt cct ctg tcg tcc tcg tct ctt cca ctg cct gag cct tgc tct    1928
Pro Leu Pro Leu Ser Ser Ser Ser Leu Pro Leu Pro Glu Pro Cys Ser
530                 535                 540                 545 tcc act gag gcc aca ccc ctc agc caa gat gtg acc act ccc tct ccc    1976
Ser Thr Glu Ala Thr Pro Leu Ser Gln Asp Val Thr Thr Pro Ser Pro
                550                 555                 560 ctt ccc agt gaa atc cct cct ccc agc ctg gac ttg gga gga agg cgg    2024
Leu Pro Ser Glu Ile Pro Pro Pro Ser Leu Asp Leu Gly Gly Arg Arg
            565                 570                 575 ggc taagcctgag tagttttttg ttatttattt attttaatac gaaataaagc         2077
Gly cttttgattt gtagtgaaaa aaaaaaaaaa aaaa                              2111
```

<210> SEQ ID NO 7
<211> LENGTH: 578
<212> TYPE: PRT
<213> ORGANISM: human

<400> SEQUENCE: 7

```
Met Ala Pro Ser Pro Arg Pro Glu His Val Leu His Trp Lys Glu Ala
1               5                   10                  15

His Ser Phe Tyr Leu Leu Ser Pro Leu Met Gly Phe Leu Ser Arg Ala
            20                  25                  30
```

```
Trp Ser Arg Leu Arg Gly Pro Glu Val Ser Glu Ala Trp Leu Ala Glu
        35                  40                  45

Thr Val Ala Gly Ala Asn Gln Ile Gln Ala Asp Ala Leu Leu Thr Pro
    50                  55                  60

Pro Pro Val Ser Glu Asn His Leu Pro Leu Arg Glu Thr Glu Gly Asn
65                  70                  75                  80

Gly Thr Pro Glu Trp Ser Lys Ala Ala Gln Arg Leu Cys Leu Asp Val
                85                  90                  95

Glu Ala Gln Ser Ser Pro Pro Lys Thr Trp Gly Leu Ser Asp Ile Asp
                100                 105                 110

Glu His Asn Gly Lys Pro Gly Gln Asp Gly Leu Arg Glu Gln Glu Val
            115                 120                 125

Glu His Thr Ala Gly Leu Pro Thr Leu Gln Pro Leu His Leu Gln Gly
            130                 135                 140

Ala Asp Lys Lys Val Gly Glu Val Val Ala Arg Glu Glu Gly Val Ser
145                 150                 155                 160

Glu Leu Ala Tyr Pro Thr Ser His Trp Glu Gly Gly Pro Ala Glu Asp
                165                 170                 175

Glu Glu Asp Thr Glu Thr Val Lys Lys Ala His Gln Ala Ser Ala Ala
            180                 185                 190

Ser Ile Ala Pro Gly Tyr Lys Pro Ser Thr Ser Val Tyr Cys Pro Gly
        195                 200                 205

Glu Ala Glu His Arg Ala Thr Glu Glu Lys Gly Thr Asp Asn Lys Ala
        210                 215                 220

Glu Pro Ser Gly Ser His Ser Arg Phe Trp Glu Tyr His Thr Arg Glu
225                 230                 235                 240

Arg Pro Lys Gln Glu Gly Glu Thr Lys Pro Glu Gln His Arg Ala Gly
                245                 250                 255

Gln Ser His Pro Cys Gln Asn Ala Glu Ser Glu Glu Gly Gly Pro Glu
            260                 265                 270

Thr Ser Val Cys Ser Gly Ser Ala Phe Leu Lys Ala Trp Val Tyr Arg
            275                 280                 285

Pro Gly Glu Asp Thr Glu Glu Glu Asp Pro Asp Leu Asp Ser Ala
290                 295                 300

Glu Glu Asp Thr Ala His Thr Cys Thr Thr Pro His Thr Ser Ala Phe
305                 310                 315                 320

Leu Lys Ala Trp Val Tyr Arg Pro Gly Glu Asp Thr Glu Glu Glu Asp
                325                 330                 335

Asp Gly Asp Trp Asp Ser Ala Glu Glu Asp Ala Ala Gln Ser Cys Thr
            340                 345                 350

Thr Pro His Thr Ser Ala Phe Leu Lys Ala Trp Val Tyr Arg Pro Gly
            355                 360                 365

Glu Asp Thr Glu Glu Asp Ser Glu Asn Val Ala Pro Val Asp
        370                 375                 380

Ser Glu Thr Val Asp Ser Cys Gln Ser Thr Gln His Cys Leu Pro Val
385                 390                 395                 400

Glu Lys Thr Lys Gly Cys Gly Glu Ala Glu Pro Pro Phe Gln Val
                405                 410                 415

Ala Phe Tyr Leu Pro Gly Gln Lys Pro Ala Pro Pro Trp Ala Ala Pro
            420                 425                 430

Lys Leu Pro Leu Arg Leu Gln Lys Arg Leu Arg Ser Phe Lys Ala Pro
            435                 440                 445
```

```
Ala Arg Asn Gln Gly Pro Glu Ile Pro Leu Lys Gly Arg Lys Val His
        450                 455                 460

Phe Ser Glu Lys Val Thr Val His Phe Leu Ala Val Trp Ala Gly Pro
465                 470                 475                 480

Ala Gln Ala Ala Arg Arg Gly Pro Trp Glu Gln Phe Ala Arg Asp Arg
                    485                 490                 495

Ser Arg Phe Ala Arg Ile Ala Gln Ala Glu Gln Leu Gly Pro
                500                 505                 510

Tyr Leu Thr Pro Ala Phe Arg Ala Arg Ala Trp Thr Arg Leu Arg Asn
            515                 520                 525

Leu Pro Leu Pro Leu Ser Ser Ser Leu Pro Leu Pro Glu Pro Cys
        530                 535                 540

Ser Ser Thr Glu Ala Thr Pro Leu Ser Gln Asp Val Thr Thr Pro Ser
545                 550                 555                 560

Pro Leu Pro Ser Glu Ile Pro Pro Ser Leu Asp Leu Gly Gly Arg
                565                 570                 575

Arg Gly
```

<210> SEQ ID NO 8
<211> LENGTH: 2614
<212> TYPE: DNA
<213> ORGANISM: rat

<400> SEQUENCE: 8

```
acatgggcac gcgtggtcga cggcccgggc tggctgggca acacgggttc agcccaggtt      60
tcatagtaag ttccagacac tcctggaaaa acaataaagg tccctgacaa agaaaaaaac     120
aaaacaaagg aaacagaaac atgcgttttt aaaaagaag gaggactc catgaaggca       180
ggccttgggt ggggtcactg cttctctgta cacaggagga gaattgccaa gatcttccgg     240
acagtgtgga ctatactgta agaccctctc aatacagaca gactggacag gcatagtgac     300
acatgccttt aatgcctgca gtactcagga ggaggtggca ggtggaacgg ctgttctttg     360
aggttcaaga ccagcgtgga ctacagagtg agttccagga caggcagggc tacacagaaa     420
aatcctgtct gaaaacaaaa caaacccag acagacacac caaaaacagc caagggacca       480
gagagatggg tcagggccta atcacttgct actctttgca gaggacccaa atttagttcc     540
tataaccctc catgagaagc ttcacaattg tctctaactc aattccaccc gtgttccgac     600
ctccatatgc accagacatg atatactcac acatacgcac aaacacacac acacacacac     660
acacacacac acacacacac acacacacac ggaaaacata taaataaag atttaaaaaa       720
tcttttcttt ttggccgggg tgtgtgggag agcatctgag ccatctcacc agcccagggt     780
gcagctcttt ttcttttttt cggagctggg gaccgaaccc agagccttgt gcttgctagg     840
caagtgctct accactgagc taaatcccca accccggagc acgtctttaa tcccagaatc     900
aggaggtaga ggtaatgaga tcccagtgag cccaaggtca gccgagtcta caaagtgagt     960
tccaggacag ccagaactaa tcttggaaaa acaaacaagg gctggtgagg tggttcagta    1020
gttaagaaca ctggctgctc ttccagaggt cctgagttca ttctcagtaa ccacatggtg    1080
gggatctgat gcctgttctg gcatgcagat atacatgcag atagtgcact cctacattta    1140
aaaaaaaaag acataaataa tattttaaaa cattgggcgt tttgtcttct aataaaactt    1200
cactgctatc ttctaataaa aattcactgc tagccgcggg gtgtggtggc cccatacctt    1260
taatcccaac aacttgagag gcagaggcag gcggacctt gagtttgaag ctagcctggt       1320
ctacagagtg agttcaagat agccacggat agtcagaaag tcctgttt cg aacctctccc    1380
```

```
caaccaaatc actcctgtaa tcccagcact ctggaggcag tagcaggtta gtccctgctt    1440
ctcagagaga ggagagagag agagagagag agagagagga gacacacaca cacagagaca    1500
gagaggagag agaaagagaa agagaatggg acagcatgtg actgcctgat gaagttggcg    1560
tgcttgctca aaagttctgc gagattgacg gctctctgga tttgagccaa ggacacgcct    1620
gggaagccac ggtgacctca caaggcccgg aatctccgcg agaatttcag tgttgttttc    1680
ctctctccac ctttctcagg gacttccgaa actccgcctc tccggtgacg tcagatagcg    1740
ctcgtcagac tataaactcc cgggtgatcg tgttggcgca gattgactca gttcgcagct    1800
tgtggaagat tacatgcgag accccgcgcg actccgcatc cctttgccgg gacagccttt    1860
gcgacagccc gtgagacatc acgtccccga gccccagcct gagggcgaca tgaacgcgct    1920
ggccttgaga gcaatccgga cccacgatcg cttttggcaa accgaaccgg accgaaccgg    1980
acctccagcc cccggggtga cgcgcagtcg ccggtgagtg ggggatgggg cggcctttgg    2040
gggagtgctg gggaggactt tctttggcga tggaggctag gagagtgttg tgggatctag    2100
gggagactgg ggaggaaccc agatttgagg aaacggcact gaaagccgga tgctttattt    2160
ggtccgagag aggagagccc aggtctagtc tctacattga agggcagggg tcctgaacta    2220
gaactgcagt acttgtacat tgctaaataa agagagggac tccaggagga gcagcctggg    2280
tctaagaggt aggcaggaga aggttttagg ggcctgagca caagcttgag gagagaaagg    2340
ttattaaaaa gccagacgtt acaggtctca gaagggctag ccagaaactg tggcttgggg    2400
ttaaggaaag ggtttaagag tgtgggcttt tggttctgag gatgtaggaa cgtgaatgtt    2460
gagagaagaa ccaagtggcg gagttgggtg tgagcaatgc tattaggaat ttgaggcagg    2520
gattcacgct gctgtgacta ttttttaaca atgactcagt gctgtgacct gatactgttt    2580
ccagagcgac ttctaaacaa attcccccct ttct                                2614
```

<210> SEQ ID NO 9
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 9

```
ctaaggcgtg tccatgctct ggcc                                             24
```

<210> SEQ ID NO 10
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 10

```
ctcctctgcc tgggcaatg                                                   19
```

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11

```
cgagcaaagc ggcttcgatc                                                  20
```

```
<210> SEQ ID NO 12
<211> LENGTH: 10
<212> TYPE: DNA
<213> ORGANISM: Artificial Sequence
<220> FEATURE:
<223> OTHER INFORMATION: synthetic oligonucleotide

<400> SEQUENCE: 12
tccccaaccc                                                                10

<210> SEQ ID NO 13
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 13
tggatttgag cca                                                            13
```

RAT PEG-3 PROMOTER

This application is a continuation-in-part of International Application No. PCT/US98/05783, filed Mar. 20, 1998, which is a continuation-in-part of U.S. application Ser. No. 08/821,818, filed Mar. 21, 1997 now U.S. Pat. No. 6,146, 877. The content of both International Application No. PCT/US98/05783 and U.S. application Ser. No. 08/821,818 is hereby incorporated into this application by reference.

The invention disclosed disclosed herein was made with United States Government support under National Institute of Health Grant CA 35675. Accordingly, the United States Government has certain rights in this invention.

Throughout this application, various references are referred to within parentheses. Disclosures of these publications in their entireties are hereby incorporated by reference into this application to more fully describe the state of the art to which this invention pertains. Full bibliographic citations for these references may be found at the end of this application, preceding the claims.

BACKGROUND OF THE INVENTION

The carcinogenic process involves a series of sequential changes in the phenotype of a cell resulting in the acquisition of new properties or a further elaboration of transformation-associated traits by the evolving tumor cell (1–4). Although extensively studied, the precise genetic mechanisms underlying tumor cell progression during the development of most human cancers remain enigmas. Possible factors contributing to transformation progression, include: activation of cellular genes that promote the cancer cell phenotype, i.e., oncogenes; activation or modification of genes that regulate genomic stability, i.e., DNA repair genes; loss or inactivation of cellular genes that function as inhibitors of the cancer cell phenotype, i.e. tumor suppressor genes; and/or combinations of these genetic changes in the same tumor cell (1–6). A useful model system for defining the genetic and biochemical changes mediating tumor progression is the type 5 adenovirus (Ad5)/early passage rat embryo (RE) cell culture system (1,7–14). Transformation of secondary RE cells by Ad5 is often a sequential process resulting in the acquisition of and further elaboration of specific phenotypes by the transformed cell (7–10). Progression in the Ad5-transformation model is characterized by the development of enhanced anchorage-independence and tumorigenic potential (as indicated by a reduced latency time for tumor formation in nude mice) by progressed cells (1,10). The progression phenotype in Ad5-transformed RE cells can be induced by selection for growth in agar or tumor formation in nude mice (7–10), referred to as spontaneous-progression, by transfection with oncogenes (13), such as Ha-ras, v-src, v-raf or the E6/E7 region of human papillomavirus type (HPV)-18, referred to as oncogene-mediated progression, or by transfection with specific signal transducing genes (14), such as protein kinase C, referred to as growth factor-related, gene-induced progression.

Progression, induced spontaneously or after gene transfer, is a stable cellular trait that remains undiminished in Ad5-transformed RE cells even after extensive passage (>100) in monolayer culture (13). However, a single-treatment with the demethylating agent 5-azacytidine (AZA) results in a stable reversion in transformation progression in >95% of cellular clones (10,13,14). The progression phenotype is also suppressed in somatic cell hybrids formed between normal or unprogressed transformed cells and progressed cells (11–13). These findings suggest that progression may result from the activation of specific progression-promoting genes or the selective inhibition of progression-suppressing genes, or possibly a combination of both processes.

The final stage in tumor progression is acquisition by transformed cells of the ability to invade local tissue, survive in the circulation and recolonize in a new area of the body, i.e., metastasis (15–17). Transfection of a Ha-ras oncogene into cloned rat embryo fibroblast (CREF) cells (18) results in morphological transformation, anchorage-independence and acquisition of tumorigenic and metastatic potential (19–21). Ha-ras-transformed CREF cells exhibit major changes in the transcription and steady-state levels of genes involved in suppression and induction of oncogenesis (21, 22). Simultaneous overexpression of the Ha-ras suppressor gene Krev-1 in Ha-ras-transformed CREF cells results in morphological reversion, suppression of agar growth capacity and a delay in in vivo oncogenesis (21). Reversion of transformation in Ha-ras+Krev-1 transformed CREF cells correlates with a return in the transcriptional and steady-state mRNA profile to that of untransformed CREF cells (21,22). Following long latency times, Ha-ras+Krev-1 transformed CREF cells form both tumors and metastases in athymic nude mice (21). The patterns of gene expression changes observed during progression, progression suppression and escape from progression suppression supports the concept of "transcriptional switching" as a major component of Ha-ras-induced transformation (21,22).

To identify potential progression inducing genes with elevated expression in progressed versus unprogressed Ad5-transformed cells we used subtraction hybridization (13,23). This approach resulted in the cloning of PEG-3 that is expressed at elevated levels in progressed cells (spontaneous, oncogene-induced and growth factor-related, gene-induced) than in unprogressed cells (parental Ad5-transformed, AZA-suppressed, and suppressed hybrids). Transfection of PEG-3 into unprogressed parental Ad5-transformed cells induces the progression phenotype, without significantly altering colony formation in monolayer culture or affecting cell growth. PEG-3 expression is also elevated following DNA damage and oncogenic transformation of CREF cells by various oncogenes. Sequence analysis indicates that PEG-3 has 73 and 68% nucleotide (nt) and 59 and 72% amino acid (aa) similarities, respectively, with the gadd34 and MyD116 gene. However, unlike gadd34 and MyD116 that encode proteins of ~65 and ~72 kDa, respectively, PEG-3 encodes a protein of ~50 kDa with only ~28 and ~40% aa similarities to gadd34 and Myd116, respectively, in its carboxyl terminus. These results indicate that PEG-3 represents a new member of the gadd34/MyD116 gene family with both similar and distinct properties. Unlike gadd34 and MyD116, which dramatically suppress colony formation (24), PEG-3 only modestly alters colony formation following transfection, i.e., ≦20% reduction in colony formation in comparison with vector transfected cells. Moreover, a direct correlation only exists between expression of PEG-3, and not gadd34 or Myd116, and the progression phenotype in transformed rodent cells. These findings provide evidence for a potential link between constitutive induction of a stress response, characteristic of DNA damage, and induction of cancer progression.

SUMMARY OF THE INVENTION

This invention further provides an inducible PEG-3 regulatory region functionally linked to a gene encoding a product that causes or may be induced to cause the death or inhibition of cancer cell growth.

In addition, this invention further provides the above-described vectors, wherein the inducible PEG-3 regulatory region is a promoter.

This invention further provides the above-described vectors, wherein the gene encodes an inducer of apoptosis.

In addition, this invention provides the above-described vectors, wherein the gene is a tumor suppressor gene.

In addition, this invention provides the above-described vectors, wherein the gene encodes a viral replication protein.

This invention also further provides the above-described vectors, wherein the gene encodes a product toxic to cells or an intermediate to a product toxic to cells.

In addition, this invention provides the above-described vectors, wherein the gene encodes a product causing enhanced immune recognition of the cell.

This invention further provides the above-described vectors, wherein the gene encodes a product causing the cell to express a specific antigen.

In addition, this invention provides a method of treating cancer in a subject, comprising: a) administering one of the above-described vectors to the subject; and b) administering an antibody or a fragment of an antibody to the the above-described antigen to the subject.

BRIEF DESCRIPTION OF THE FIGURES

FIG. 3: Predicted amino acid sequences of the rat PEG-3, gadd34 and MyD116 proteins. Sequences shared by the three genes are shaded. PEG-3 encodes a putative protein of 457 aa (MW of ~50 kDa), (SEQ ID NO: 1) the gadd34 gene encodes a putative protein of 589 aa (MW ~65 kDa) (SEQ ID NO: 2) and the MyD116 gene encodes a putative protein of 657 aa (MW of ~72 kDa). Panel A shows amino acids 1–350. Panel B shows amino acids 351–699.

FIG. 11: Nucleotide sequence of rat Progression Elevated Gene-3 (PEG-3). The initiation and termination codons are underlined. Panel A shows nucleotides 1–1500. Panel B shows nucleotides 1501–2137.

FIG. 12: Amino acid sequence of Progression Elevated Gene-3 (PEG-3). PEG-3 protein contains 457 amino acids and with M.W. of approximately 50 kDa. Panel A shows amino acids 1–384. Panel B shows amino acids 385–457.

FIG. 13: Nucleotide (SEQ ID NO:6) and amino acid sequence (SEQ ID NO:7) of a human PEG-3 cDNA. Panel A shows nucleotides 1–728 and amino acids 1–145. Panel B shows nucleotides 729–1256 and amino acids 146–321. Panel C shows nucleotides 1257–1784 and amino acids 322–497. Panel D shows nucleotides 1785–2111 and amino acids 500–578.

FIG. 14: Sequence of the rat PEG-3 promoter. This region of DNA consists of 2,614 nucleotides. This DNA sequence contains the putative initiation site of transcription of the rat PEG-3 gene. For luciferase assays a ~2,200 nucleotide region of the PEG-3 promoter was cloned into a luciferase reporter vector. Panel A shows nucleotides 1–1500. Panel B shows nucleotides 1501–2614.

MCF-7, T47D: human breast carcinoma

LNCaP, PC-3: human prostate carcinoma

T98G, GBM-18: human glioblastoma

HO-1, LO-1, SH-1,C8161, FO-1: human melanoma

NhPEC: normal human prostate epithelial cells (Clonetics)

HBL-100: immortalized normal human breast cells

HeLa: human ovarian carcinoma

REF(RAD): irradiated CREF-Trans 6 cells

E11, E11NMT: Sprague Dawley rat embryo cells transformed with mutant adenovirus H5ts125

4NMT: CREF-Trans 6 cells transformed with LNCaP high molecular weight DNA

HONE-1: human nasopharyngeal carcinoma

Figure 20:
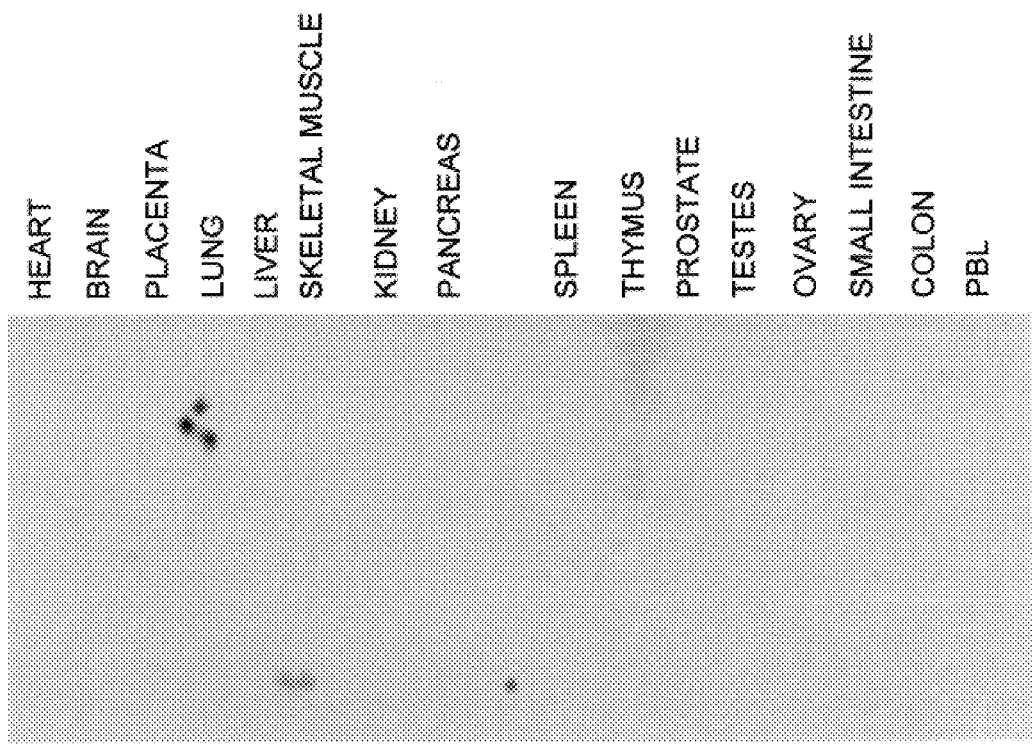

FIG. 20: Northern blot analysis of human PEG-3. A 500 bp probe from the 3' end of the human PEG-3 gene was used to probe a normal human tissue blot (Clonetics)

Figure 21:
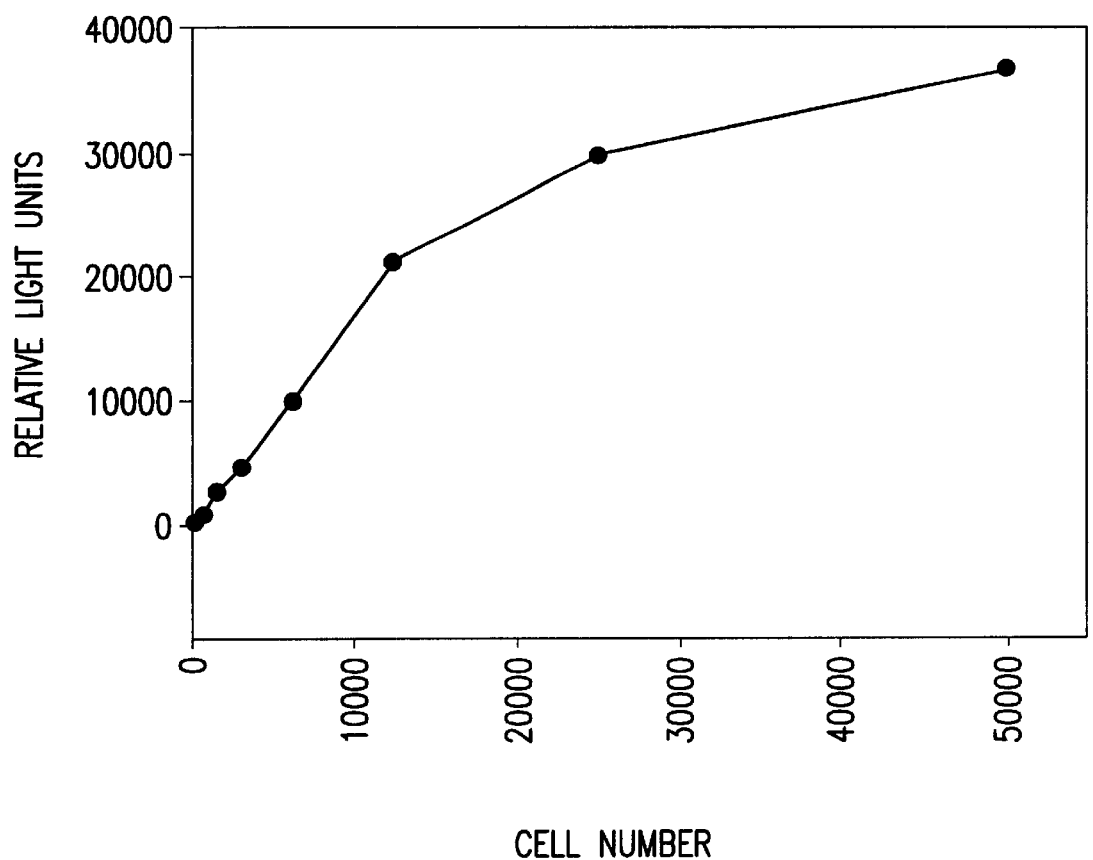

FIG. 21: Titration of CREF-Trans 6 4NMT cells containing the rat PEG-3 promoter/luciferase reporter gene. Cells were grown in 96 well plates, lysed as described and the luciferase activity was read in a luminometer.

Figure 22:
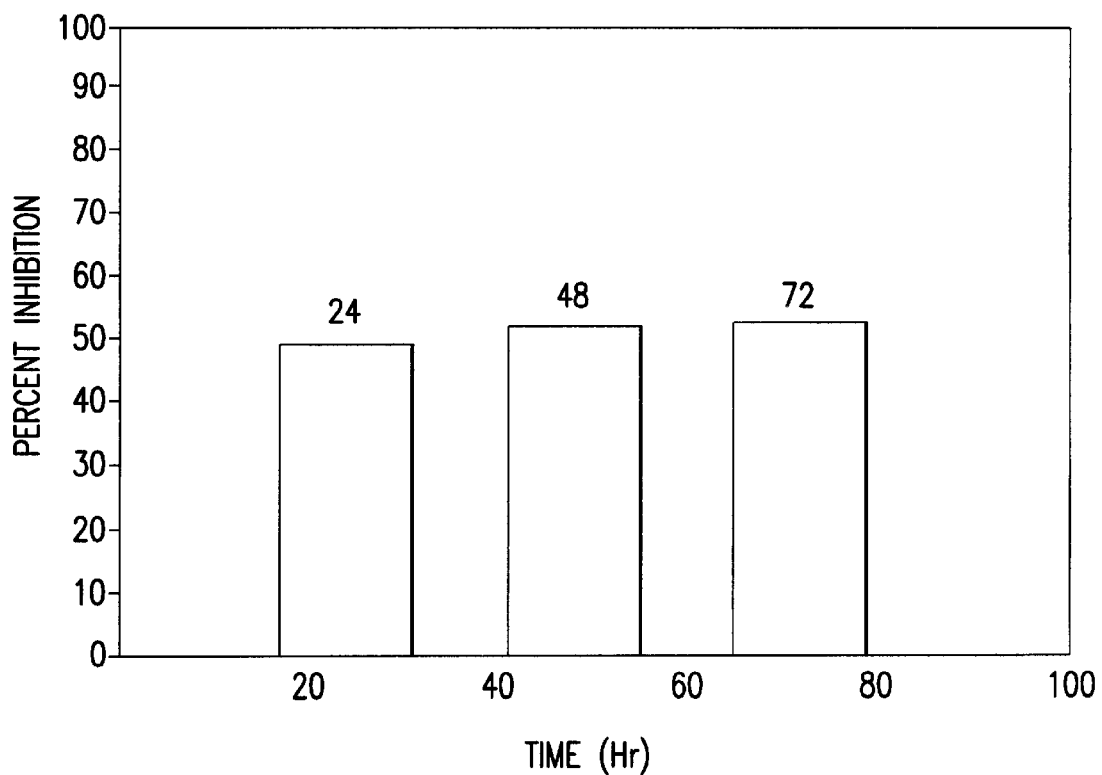

FIG. 22: Effects of an antisense oligonucleotide to the PTI-1 oncogene on expression of the rat PEG-3 promoter/luciferase reporter gene in CREF-Trans 6 4NMT cells. 4NMT cells were treated with an antisense oligonucleotide to the bridge region of the PTI-1 gene for 24, 48, and 72 hours. Cells were lysed and luciferase activity was determined using a luminometer.

Figure 23:
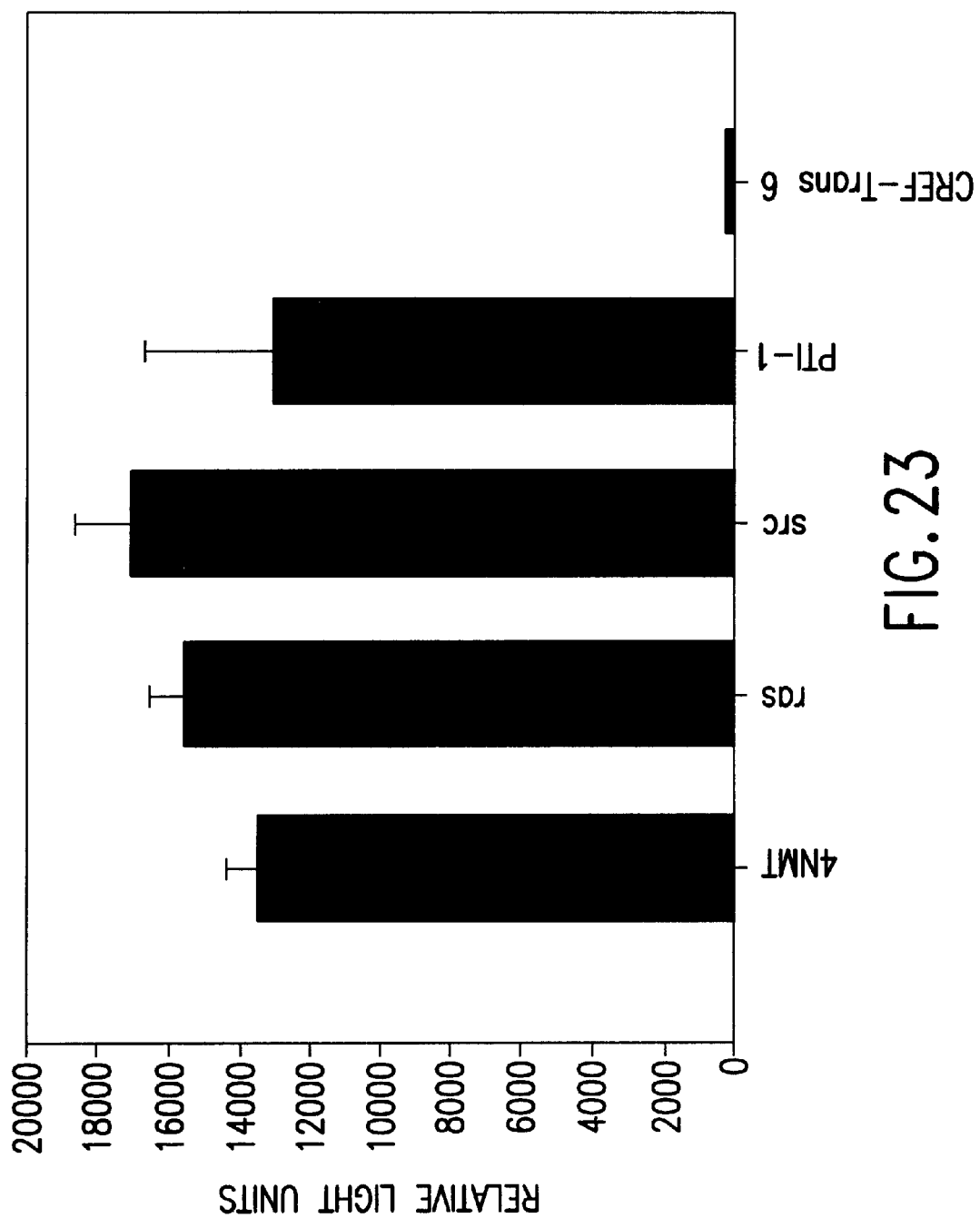

FIG. 23: Luciferase activation in the presence of various oncogenes expressed in CREF-Trans 6 cells transfected with the rat PEG-3 promoter/luciferase reporter. CREF-Trans 6 cells were stably transfected with the following oncogenes: ras, src, and PTI-1. 4NMT cells were transfected with high molecular weight DNA from the human prostate carcinoma cell line LNCaP and expresses PTI-1. Cells grown in 96 well microtiter plates, lysed, and assayed for luciferase activity.

Figure 24:
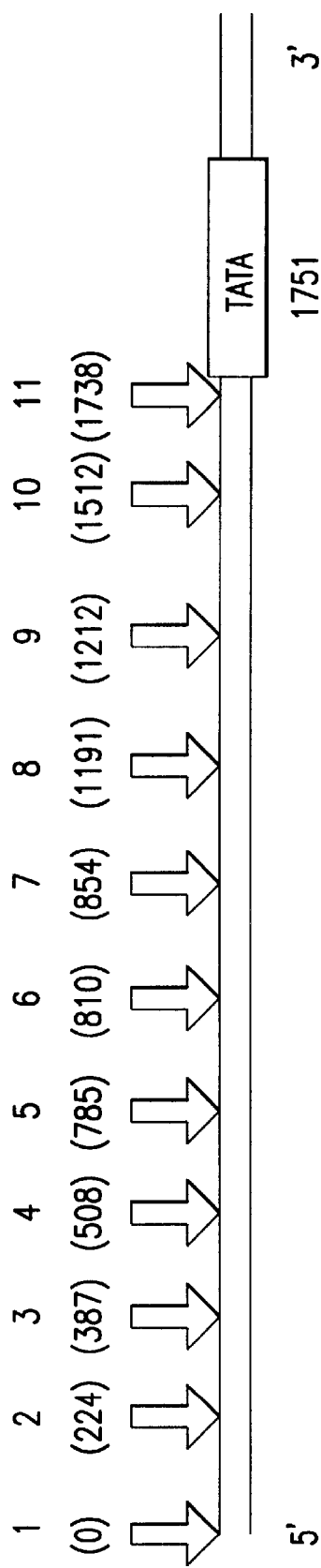

FIG. 24: Schematic diagram of specific deletion mutants in the rat PEG-3 promoter. The deletion mutants are labeled as 2 to 11, with 1 being the unmodified promoter. Numbers in brackets indicate the beginning nucleotide remaining after deletion from the 50 region of the rat PEG-3 promoter. The TATA box is located at nucleotide 1751 from the 5' region of the promoter.

Figure 25:
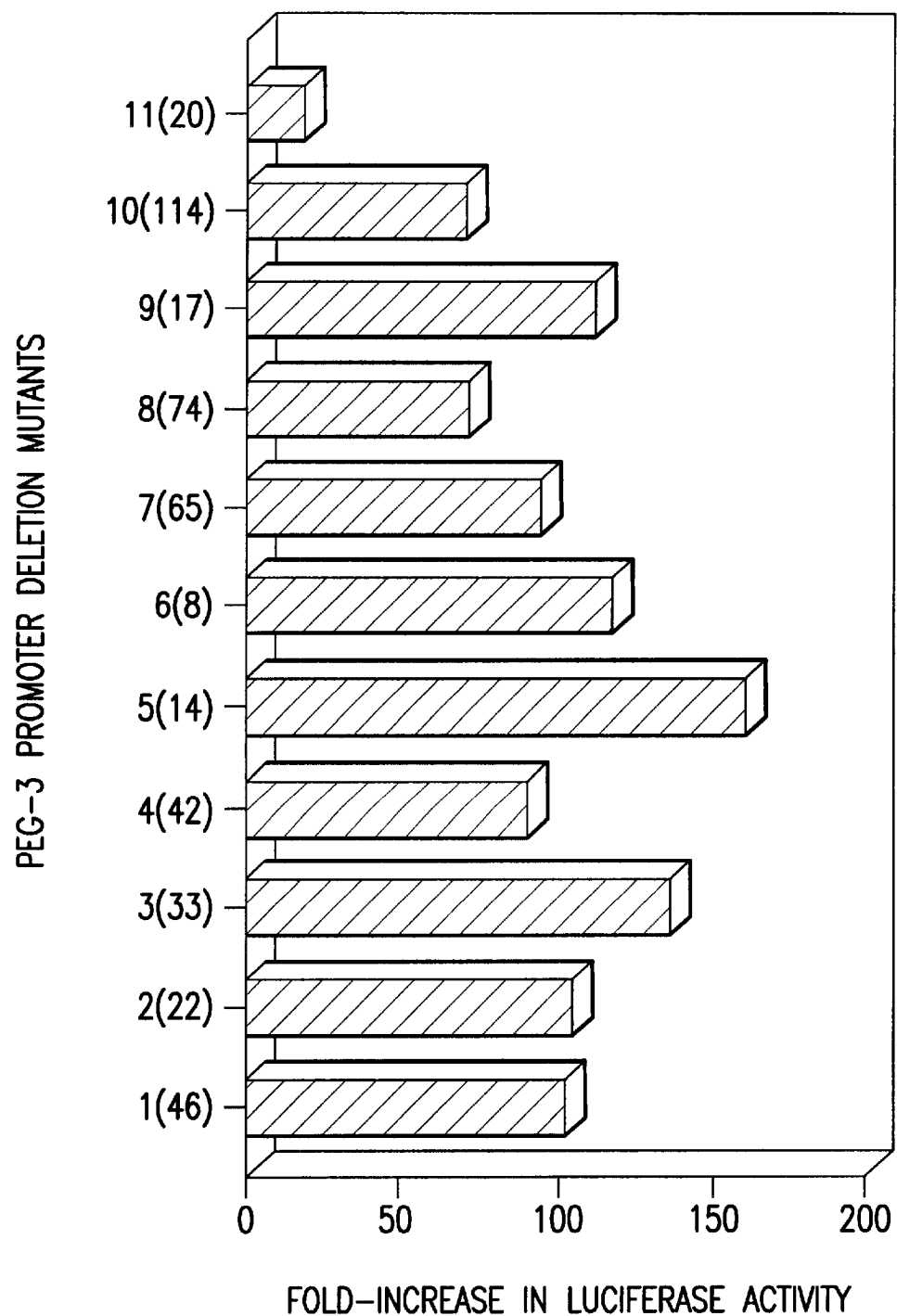

FIG. 25: Relative PEG-3 promoter luciferase activity in E11 cells after transfection with an intact rat PEG-3 promoter (1) and various deletion mutants of the rat PEG-3 promoter (2 through 11). Further information in FIG. 24.

Figure 26:
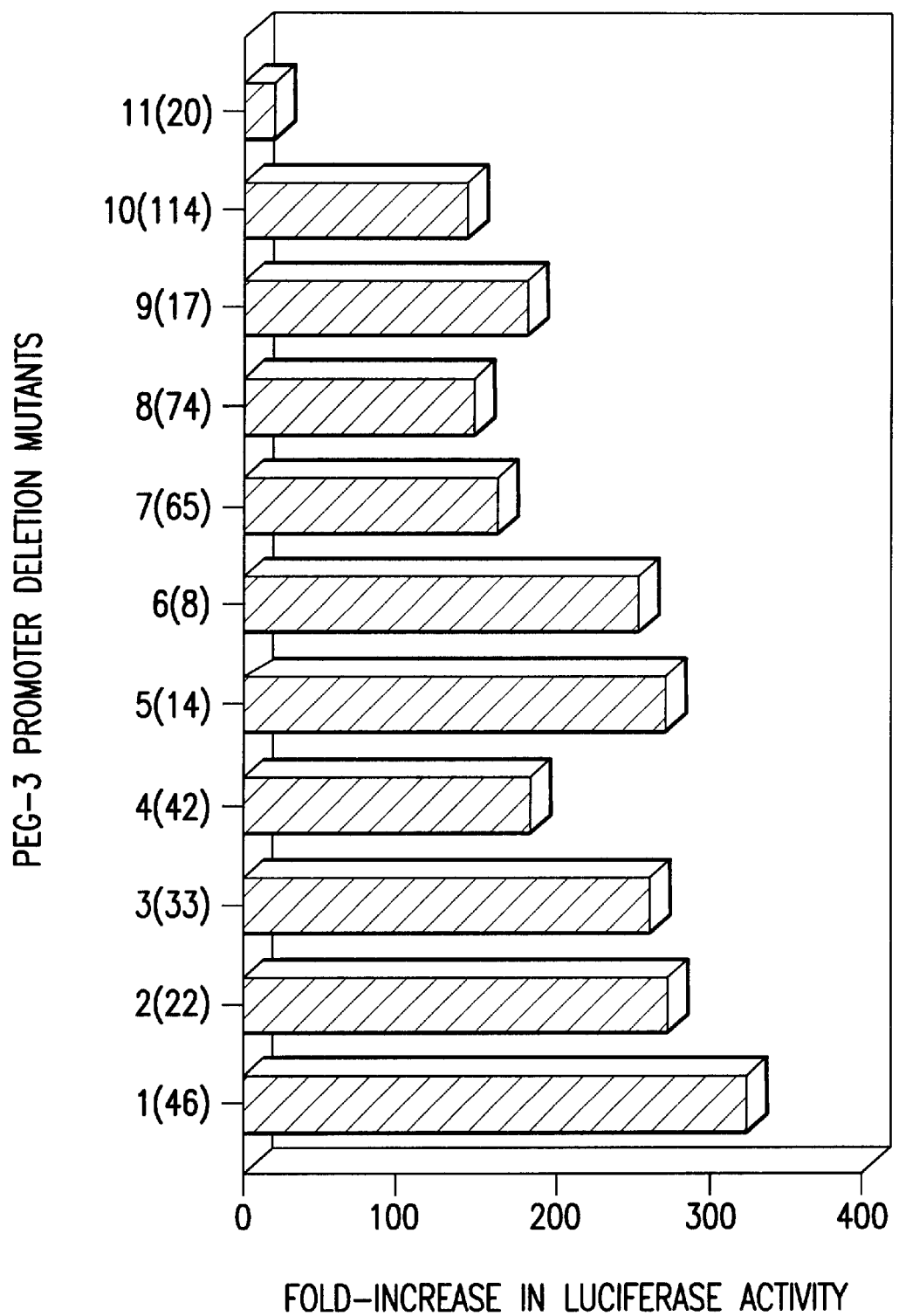

FIG. 26: Relative PEG-3 promoter luciferase activity in E11-NMT cells after transfection with an intact rat PEG-3 promoter (1) or various deletion mutants of the rat PEG-3 promoter (2 through 11). Further information in FIG. 24.

Figure 27:
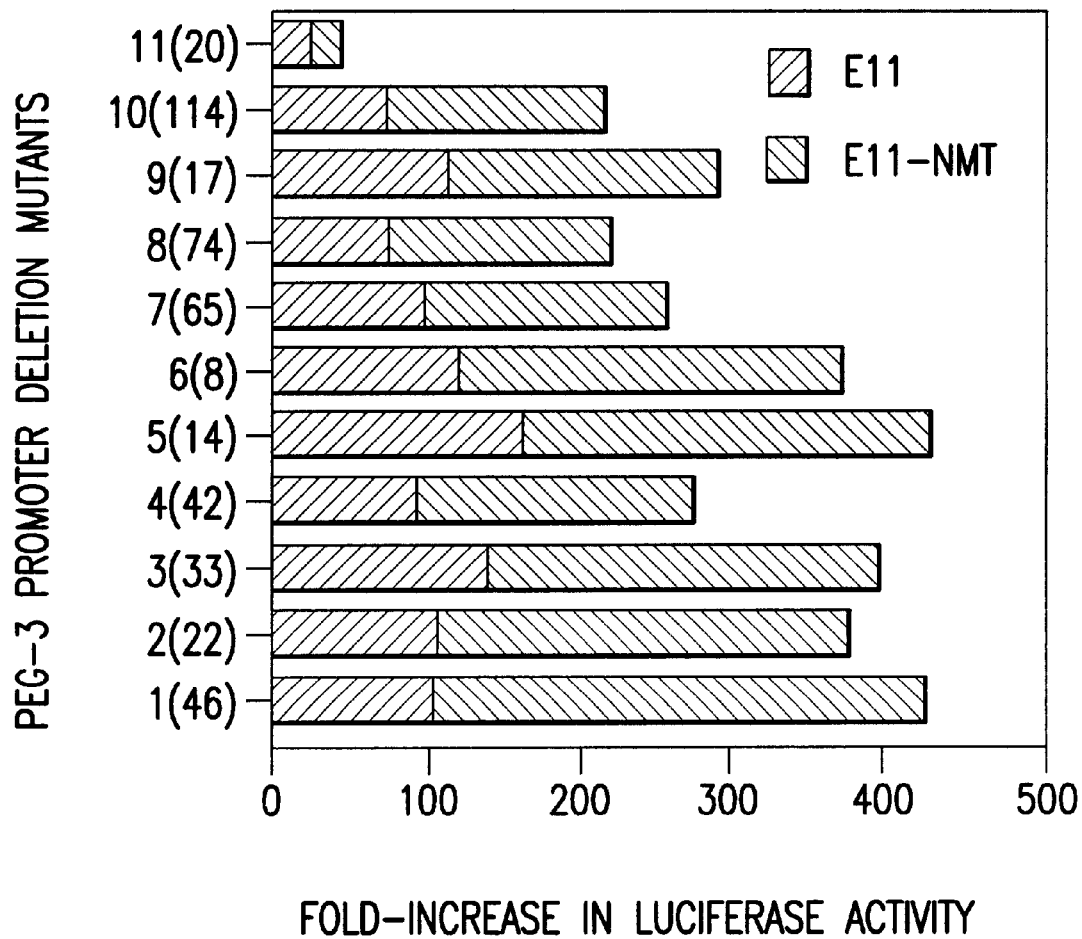

FIG. 27: Comparison of the relative PEG-3 promoter luciferase activity in E11 and E11-NMT cells after transfection with an intact rat PEG-3 promoter (1) or various deletion mutants of the rat PEG-3 promoter (2 through 11). Further information in FIG. 24.

Figure 28:
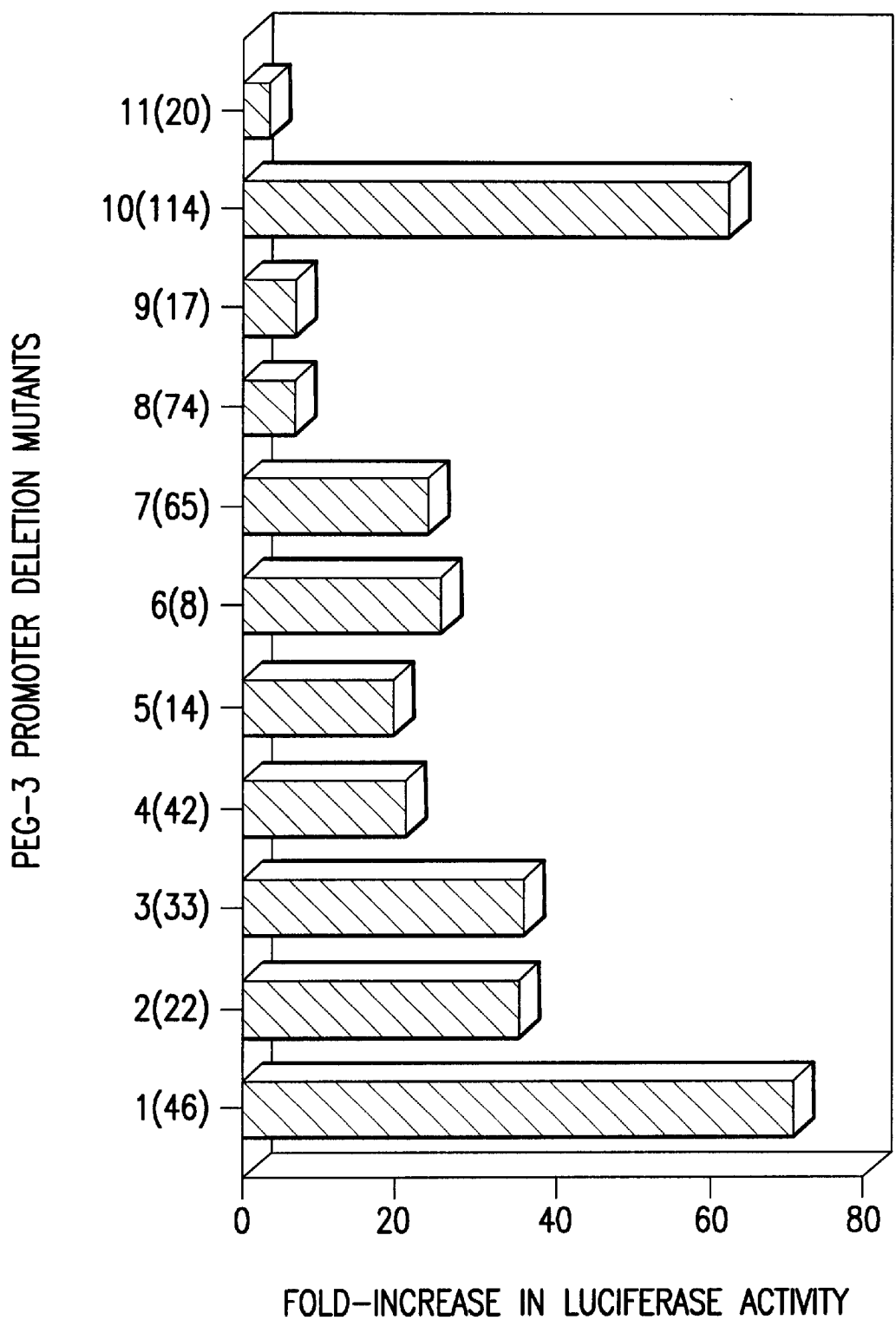

FIG. 28: Relative PEG-3 promoter luciferase activity in E11 cells transformed by the PKC β gene (E11-PKC) after transfection with an intact rat PEG-3 promoter (1) or various deletion mutants of the rat PEG-3 promoter (2 through 11). Further information in FIG. 24.

Figure 29:
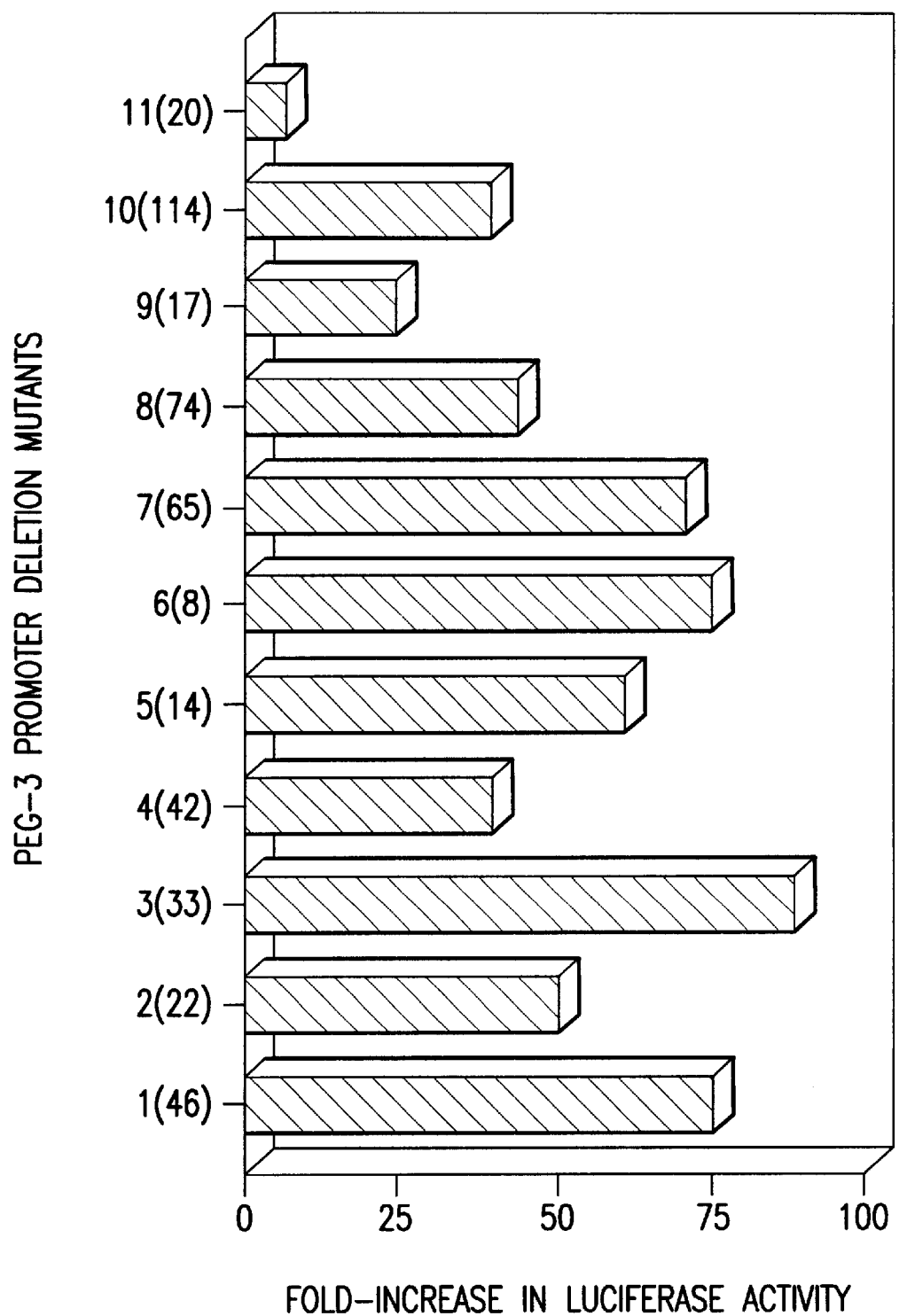

FIG. 29: Relative PEG-3 promoter luciferase activity in CREF cells transformed by human papilloma virus type 18 (CREF-HPV) after transfection with an intact rat PEG-3 promoter (1) or various deletion mutants of the rat PEG-3 promoter (2 through 11). Further information in FIG. 24.

Figure 30:
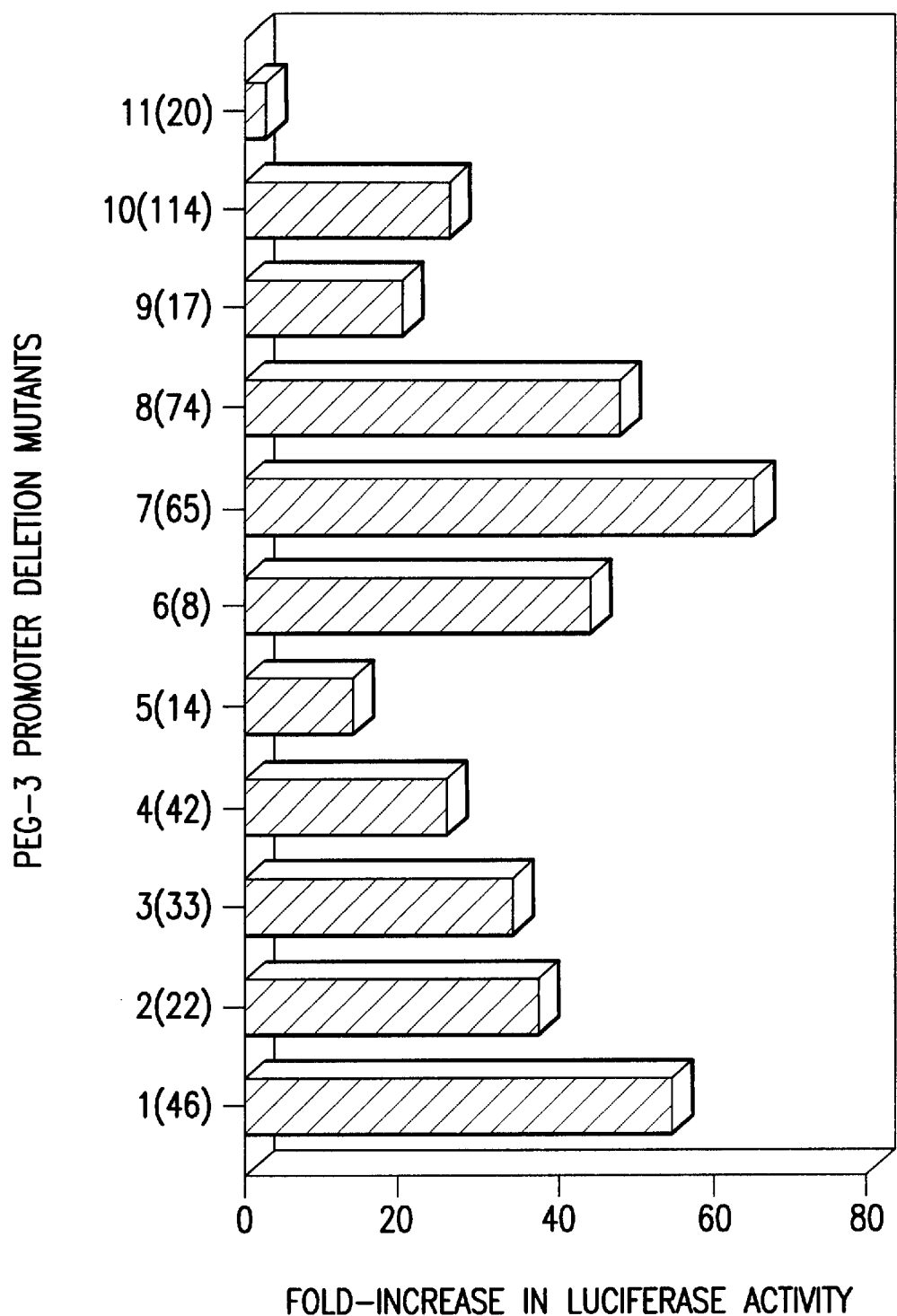

FIG. 30: Relative PEG-3 promoter luciferase activity in CREF cells transformed by the Ha-ras oncogene (CREF-ras) after transfection with an intact rat PEG-3 promoter (1) or various deletion mutants of the rat PEG-3 promoter (2 through 11). Further information in FIG. 24.

Figure 31:
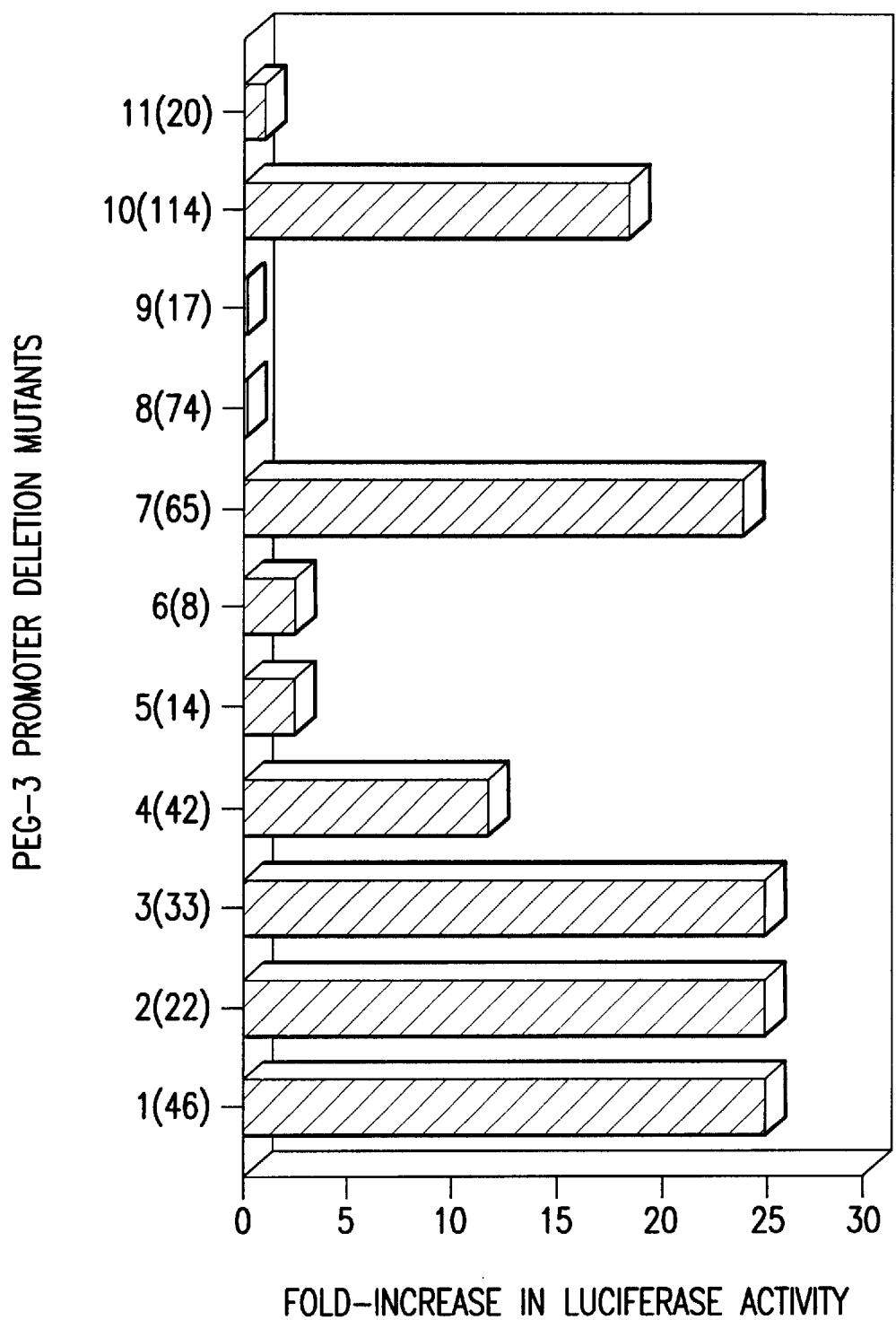

FIG. 31: Relative PEG-3 promoter luciferase activity in CREF-Trans 6 cells transformed by human prostatic carcinoma (LNCaP) DNA (CREF-Trans 6:4 NMT) after transfection with an intact rat PEG-3 promoter (1) or various deletion mutants of the rat PEG-3 promoter (2 through 11). Further information in FIG. 24.

Figure 32:
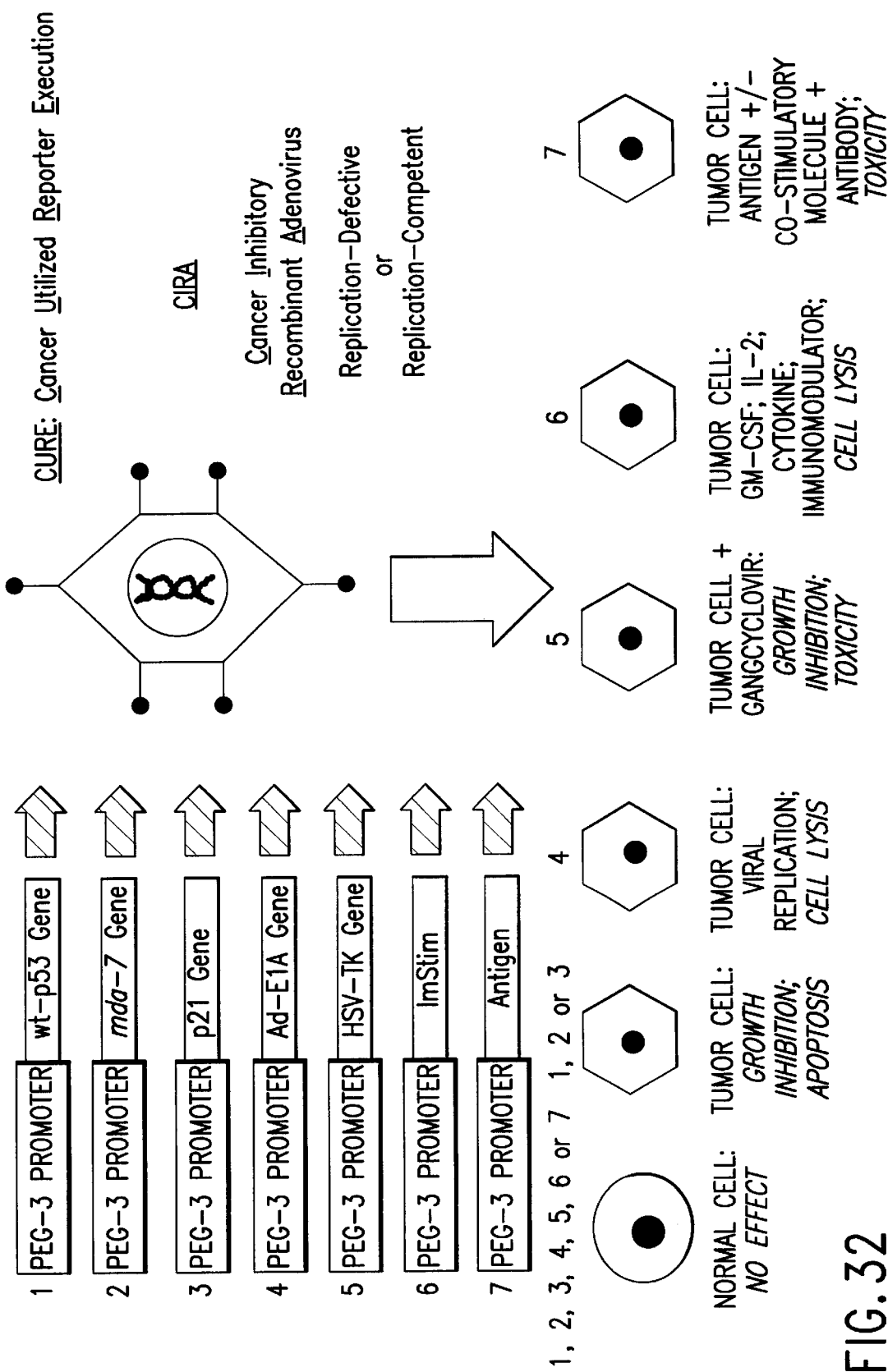

FIG. 32: Schematic outline of CURE (Cancer Utilized Reporter Execution) strategy and construction of CIRAs (Cancer Inhibitory Recombinant Adenoviruses). The PEG-3 promoter is linked to various genes, including (1) wt-p53, (2) mda-7, (3) p21, (4) Ad-E1A, (5) HSV-TK, (6) ImStim (immunostimulatory gene, or (7) Antigen (molecule encoding an immunogenic molecule increasing tumor reactivity with immune cells). The various constructs display slective gene expression as a function of PEG-3 promoter activation, which is restricted to cancer cells. The genes are incorporated into a replication defective (1, 2, 3, 5, 6, and 7) or replication competent (1, 2, 3, 4, 5, 6, and 7) adenovirus (Ad). These adenoviruses can then be used to infect human cancer cells resulting in PEG-3 promoter activation of gene expression resulting in transcription of the linked gene and production of the encoded gene product. When normal cells are infected with any of the adenovirus constructs (CIRAs), the promoter is inactive or marginally active resulting in either no or small quantities of the encoded gene product. In these contexts, no physiological change should occur in normal cells. In contrast, when expressed in tumor cells the PEG-3 promoter is active resulting in transcription of the linked gene and production of the encoded gene product. In the case of Ad 1, 2, and 3, infection of cancer cells results in wt-p53, mda-7 or p21 protein. These proteins will result in inhibition of cancer growth and in specific contexts will induce programmed cell death (apoptosis). In the case of Ad 4, which is a replication competent Ad, induction of Ad E1A will result in viral replication and lysis of the cancer cell. In the case of Ad 5, induction of the HSV-TK gene renders the cell sensitive to growth inhibition and toxicity following administration of gangcyclovir or acyclovir. In the case of Ad 6, induction of an ImStim (Immunostimulatory gene), such as GM-CSF, IL-2, a cytokine (immune interferon, interleukin 6, etc.) or an immunomodulating protein, renders the cancer cell susceptible to immunological attack and cell lysis. In the case of Ad 7, induction of antigenic expression (with and without expression of co-stimulatory molecules), renders the cancer cell susceptible to antibody mediated toxicity. This can result from an interaction with an antibody with direct antitumor activity, an antibody linked to an immunotoxin, an antibody linked to a high energy radionuclide, etc. Ad 7 CIRAs expressing proteins with T-cell epitopes or T-cell epitopes themselves can be used to sensitize cancer cells to killing by CD8 cytotoxic killer T-cells. In principle, CIRAs can be produced that will result in the targeted destruction of only cancer cells (the basis of the CURE technology). In addition to using CIRAs, CURE can also be used with alternative transfer systems, including a retrovirus, an adeno-associated virus, a herpes virus, a vaccinia virus, a liposome preparation, physical delivery technology, naked DNA technology, etc.

DETAILED DESCRIPTION OF THE INVENTION

This invention provides an isolated nucleic acid molecule encoding a Progression Elevated Gene-3 protein. The nucleic acid may be DNA, cDNA, genomic DNA or RNA.

This invention also encompasses DNAs and cDNAs which encode amino acid sequences which differ from those of Progression Elevated Gene-3 protein, but which should not produce phenotypic changes. Alternatively, this invention also encompasses DNAs and cDNAs which hybridize to the DNA and cDNA of the subject invention. Hybridization methods are well-known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and additional analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

Moreover, the isolated nucleic acid molecules encoding a Progression Elevated Gene-3 are useful for the development of probes to study the progression of cancer. This invention also provides isolated nucleic acid molecule encoding a human Progression Elevated Gene-3 protein.

This invention provides a nucleic acid molecule of at least 12 nucleotides capable of specifically recognizing a nucleic acid molecule encoding a Progression Elevated Gene-3 protein. In a preferred embodiment, this nucleic acid molecule has a unique sequence of the Progression Elevated Gene-3. The unique sequence of the Progression Elevated Gene-3 may easily be determined by comparing its sequence with known sequences which are available in different databases. The nucleic acid molecule may be DNA or RNA.

This nucleic acid molecule of at least 15 nucleotides capable of specifically hybridizing with a sequence of a nucleic acid molecule encoding a Progression Elevated Gene-3 protein can be used as a probe. Nucleic acid probe technology is well-known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes Progression Elevated Gene-3 protein into suitable vectors, such as plasmids or bacteriophages, followed by transforming into suitable bacterial host cells. replication in the transformed bacterial host cells and harvesting of the DNA probes, using methods well-known in the art. Alternatively, probes may be generated chemically from DNA synthesizers.

RNA probes may be generated by inserting the Progression Elevated Gene-3 molecule downstream of a bacteriophage promoter such as T3, T7 or SP6. Large amounts of RNA probe may be produced by incubating the labeled nucleotides with the linearized Progression Elevated Gene-3 fragment where it contains an upstream promoter in the presence of the appropriate RNA polymerase.

This invention provides a method of detecting expression of the Progression Elevated Gene-3 in a sample which contains cells comprising steps of: (a) obtaining RNA from the cells; (b) contacting the RNA so obtained with a labelled probe of the Progression Elevated Gene-3 under hybridizing conditions permitting specific hybridization of the probe and the RNA; and (c) determining the presence of RNA hybridized to the molecule, thereby detecting the expression of the Progression Elevated Gene-3 in the sample. mRNA from the cell may be isolated by many procedures well-known to a person of ordinary skill in the art. The hybridizing conditions of the labelled nucleic acid molecules may be determined by routine experimentation well-known in the art. The presence of mRNA hybridized to the probe may be determined by gel electrophoresis or other methods known in the art. By measuring the amount of the hybrid made, the expression of the Progression Elevated Gene-3 protein by the cell can be determined. The labelling may be radioactive. For an example, one or more radioactive nucleotides can be incorporated in the nucleic acid when it is made.

The RNA obtained in step (a) may be amplified by polymerase chain reaction (PCR) with appropriate primers. The appropriate primers may be selected from the known Progression Elevated Gene-3 sequences. Instead of detection by specific PEG-3 probe as described in the preceding paragraph, the specific amplified DNA by PCR is an indication that there is expression of Progression Elevated Gene-3.

This invention provides an isolated nucleic acid molecule encoding a Progression Elevated Gene-3 protein operatively linked to a regulatory element. In an embodiment, the vector is a plasmid.

This invention provides a host vector system for the production of a polypeptide having the biological activity of a Progression Elevated Gene-3 protein which comprises the vector having the sequence of Progression Elevated Gene-3 and a suitable host. The suitable host includes but is not limited to a bacterial cell, yeast cell, insect cell, or animal cell.

The isolated Progression Elevated Gene-3 sequence can be linked to different vector systems. Various vectors including plasmid vectors, cosmid vectors, bacteriophage vectors and other viruses are well-known to ordinary skilled practitioners. This invention further provides a vector which comprises the isolated nucleic acid molecule encoding for the Progression Elevated Gene-3 protein.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

In an embodiment, the rat PEG-3 sequence is cloned in the EcoRI site of pZeoSV vector. This plasmid, pPEG-3, was deposited on March 6, 1997 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pPEG-3, was accorded ATCC Accession Number 97911.

This invention further provides a host vector system for the production of a polypeptide having the biological activity of the Progression Elevated Gene-3 protein. These vectors may be transformed into a suitable host cell to form a host cell vector system for the production of a polypeptide having the biological activity of the Progression Elevated Gene-3 protein.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general. Expression vectors are useful to produce cells that express the Progression Elevated Gene-3 protein.

This invention further provides an isolated DNA, cDNA or genomic DNA molecule described hereinabove wherein the host cell is selected from the group consisting of bacterial cells (such as E. coli), yeast cells, fungal cells, insect cells and animal cells. Suitable animal cells include, but are not limited to Vero cells, HeLa cells, Cos cells, CV1 cells and various primary mammalian cells.

This invention further provides a method of producing a polypeptide having the biological activity of the Progression Elevated Gene-3 protein which comprising growing host cells of a vector system containing Progression Elevated Gene-3 sequence under suitable conditions permitting production of the polypeptide and recovering the polypeptide so produced.

This invention provides a mammalian cell comprising a DNA molecule encoding a Progression Elevated Gene-3 protein, such as a mammalian cell comprising a plasmid adapted for expression in a mammalian cell, which comprises a DNA molecule encoding a Progression Elevated Gene-3 protein and the regulatory elements necessary for expression of the DNA in the mammalian cell so located relative to the DNA encoding the Progression Elevated Gene-3 protein as to permit expression thereof.

Various mammalian cells may be used as hosts, including, but not limited to, the mouse fibroblast cell NIH3T3, CHO cells, HeLa cells, Ltk-cells, Cos cells, etc. Expression plasmids such as that described supra may be used to transfect mammalian cells by methods well-known in the art such as calcium phosphate precipitation, electroporation or DNA encoding the Progression Elevated Gene-3 protein may be otherwise introduced into mammalian cells, e.g., by microinjection, to obtain mammalian cells which comprise DNA, e.g., cDNA or a plasmid, encoding a Progression Elevated Gene-3 protein.

This invention also provides a purified Progression Elevated Gene-3 protein and a fragment thereof. As used herein, the term "purified Progression Elevated Gene-3 protein" shall mean isolated naturally-occurring Progression Elevated Gene-3 protein or protein manufactured such that the primary, secondary and tertiary conformation, and post-translational modifications are identical to naturally-occurring material as well as non-naturally occurring polypeptides having a primary structural conformation (i.e. continuous sequence of amino acid residues). Such polypeptides include derivatives and analogs. The fragment should bear biological activity similar to the full-length Progression Elevated Gene-3 protein.

This invention also provides a polypeptide encoded by the isolated vertebrate nucleic acid molecule having a sequence of a Progression Elevated Gene-3.

This invention provides an antibody capable of specifically binding to a Progression Elevated Gene-3 protein. The antibody may be polyclonal or monoclonal. This invention provides a method to select specific regions on the Progression Elevated Gene-3 to generate antibodies. The protein sequence may be determined from the DNA sequence. The hydrophobic or hydrophilic regions in the protein will be identified. Usually, the hydrophilic regions will be more immunogenic than the hydrophobic regions. Therefore the hydrophilic amino acid sequences may be selected and used to generate antibodies specific to the Progression Elevated Gene-3 protein.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. Specific antibody which only recognizes the Progression Elevated Gene-3 protein will then be selected. The selected antibody is useful to detect the expression of the Progression Elevated Gene-3 in living animals, in humans, or in biological tissues or fluids isolated from animals or humans.

This invention provides a method of transforming cells which comprises transfecting a host cell with a suitable vector having the sequence of a Progression Elevated Gene-3. This invention also provides the transformed cells produced by this method.

This invention provides a method for determining whether cells are in progression comprising steps of: a) measuring the expression of the Progression Elevated Gene-3; and b) comparing the expression measured in step a) with the expression of Progression Elevated Gene-3 in cells which are known not to be in progression, wherein an increase of the expression indicates that the cells are in progression. In an embodiment, the expression of Progression Elevated Gene-3 is measured by the amount of Progression Elevated Gene-3 mRNA expressed in the cells. In another embodiment, the expression of Progression Elevated Gene-3 is measured by the amount of the Progression Elevated Gene-3 protein expressed in the cells.

This invention provides a method for determining whether a cancer cell is in a progression stage comprising measuring the expression of Progression Elevated Gene-3 in the cancer cell, wherein an increase in the amount indicates that the cancer cell is in progression.

This invention provides a method for diagnosing the aggressiveness of cancer cells comprising measuring the expression of Progression Elevated Gene-3 in the cancer cell, wherein an increase in the amount of the expression indicates that the cancer cell is more aggressive.

This invention provides a pharmaceutical composition for reversing the progression state of cells comprising an amount of the nucleic acid molecule capable of specifically hybridizing the Progression Elevated Gene-3 protein effective to inhibit the expression of Progression Elevated Gene-3 and a pharmaceutically acceptable carrier.

Pharmaceutically acceptable carriers are well-known to those skilled in the art. Such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a pharmaceutical composition for reversing the progression state of cells comprising an amount of the antibody or a functional fragment thereof which is capable of specifically recognizing the Progression Elevated Gene-3 protein effective to neutralize the action of the Progression Elevated Gene-3 protein and a pharmaceutically acceptable carrier.

This invention provides a method for producing cells which are resistant to progression comprising inhibiting or eliminating the expression of Progression Elevated Gene-3 in the cells. This invention also provides cells resulting from the method.

This invention provides a method for protecting cells from therapeutic damage comprising inhibiting or eliminating the expression of Progression Elevated Gene-3 in the cells. In an embodiment, the damage is resulted from chemotherapy. In another embodiment, the damage is resulted from physical agent. Such physical agent includes but is not limited to gamma-irradiation.

One method to inhibit the expression of Progression Elevated Gene-3 is by expression of effective amount anti-sense RNA in the cell thereby inhibiting the expression of Progression Elevated Gene-3. The expression of Progression Elevated Gene-3 may be eliminated by deletion of the gene or introduction of mutation(s) to the gene.

This invention provides a transgenic nonhuman living organism expressing Progression Elevated Gene-3 protein.

In an embodiment, the living organism is animal.

One means available for producing a transgenic animal, with a mouse as an example, is as follows: Female mice are mated, and the resulting fertilized eggs are dissected out of their oviducts. The eggs are stored in an appropriate medium. DNA or cDNA encoding a Progression Elevated Gene-3 is purified from a vector by methods well-known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention provides a cell having an exogenous indicator gene under the control of the regulatory element of a Progression Elevated Gene-3. In an embodiment, the cell is at progression. This cell may be produced by introducing an indicator gene to an E11-NMT, CREF-ras or CREF-src cell.

In a separate embodiment, the cell having an exogenous indicator gene under the control of the regulatory element of a Progression Elevated Gene-3 is not at progression. This cell may be produced by introducing an indicator gene to the E11 or the CREF cell.

The indicator gene codes for beta-galactosidase, luciferase, chloramphenicol transferase or secreted alkaline phosphatase. Other indicator gene such as the Green Fluorescent Protein gene may be similar used in this invention. The indicator provides an easily detectable signal when the PEG-3 is expressed.

This invention provides a method for determining whether an agent is capable of inhibiting DNA damage and repair pathways, cancer progression or oncogene mediated transformation comprising contacting an amount of the agent with the cell having an exogenous indicator gene under the control of the regulatory element of a Progression Elevated Gene-3, wherein a decrease of expression of the indicator gene indicates that the agent is capable of inhibiting DNA damage and repair pathways, cancer progression or oncogene mediated transformation. This invention provides a method for determining whether an agent is capable of inducing DNA damage and repair pathways, cancer progression or oncogene mediated transformation comprising contacting an amount of the agent with the cell having an exogenous indicator gene under the control of the regulatory element of a Progression Elevated Gene-3 is not at progression, wherein an increase of expression of the indicator gene after the contact indicates that the agent is capable of inducing DNA damage and repair pathways, cancer progression or oncogene mediated transformation.

Large scale of agents may be screened by the above two methods through automation. Indicator gene which produces color reaction may be selected.

This invention provides a cell having an exogenous suicidal gene or genes under the control of the regulatory element of a Progression Elevated Gene-3. Such "suicidal gene" will disrupt the normal progress of the cell. Preferably, the switching on of the suicidal gene will lead to cell death or halt in cell growth. Example of such genes are genes which lead to apotosis.

This invention provides a nucleic acid molecule comprising a sequence of the promoter of a Progression Elevated Gene-3 protein.

This invention also provides a nucleic acid molecule comprising Cis-Acting Regulatory Elements of the promoter of a Progression Elevated Gene-3 protein.

This invention also provides a Trans-Acting Regulatory Element that activates the expression of Progression Elevated Gene-3.

This invention further provides Trans-Acting Regulatory Element that suppresses the expression of Progression Elevated Gene-3.

This invention also provide an isolated nucleic acid molecule comprising sequence encoding the Trans-Acting Regulatory Element.

This invention provides an isolated nucleic acid molecule encoding a Progression Elevated Gene-3 protein.

This invention also provides the above-described nucleic acid, wherein the nucleic acid encodes a human Progression Elevated Gene-3 protein.

In addition, this invention provides the above-described nucleic acid, wherein the nucleic acid encodes a rodent Progression Elevated Gene-3 protein.

This invention further provides an isolated nucleic acid comprising substantially the same sequence as the sequence set forth in FIG. 11 or 13 or the complement of the sequence set forth in FIG. 11 or 13.

This invention also provides an isolated nucleic acid sequence comprising a nucleic acid sequence that specifically hybridizes to the sequence set forth in FIG. 11 or 13 or the complement of the sequence set forth in FIG. 11 or 13.

This invention provides an isolated nucleic acid comprising substantially the same sequence as the nucleic acid sequence encoding the 80 C-terminal-most amino acids, wherein the nucleic acid sequence is set forth in FIG. 11 or 13 or the complement of the sequence set forth in FIG. 11 or 13.

This invention also provides an isolated nucleic acid comprising substantially the same sequence as the nucleic acid sequence encoding the 80 C-terminal-most amino acids, wherein the nucleic acid sequence is set forth in FIG. 11 or 13 or the complement of the sequence set forth in FIG. 11 or 13.

This invention also provides an isolated nucleic acid sequence comprising a nucleic acid sequence that specifically hybridizes to the nucleic acid sequence encoding the 80 C-terminal-most amino acids, wherein the nucleic acid sequence is set forth in FIG. 11 or 13 or the complement of the sequence set forth in FIG. 11 or 13.

This invention further provides the above-described nucleic acid, wherein the nucleic acid is DNA, cDNA, genomic DNA, or RNA.

This invention provides a nucleic acid molecule comprising a promoter of Progression Elevated Gene-3.

This invention also provides a nucleic acid molecule comprising cis-acting regulatory element of Progression Elevated Gene-3 protein.

In addition, this invention provides a trans-acting regulatory element that activates the expression of Progression Elevated Gene-3.

This invention also provides a trans-acting regulatory element that suppresses the expression of Progression Elevated Gene-3.

This invention further provides an isolated nucleic acid molecule comprising sequence encoding the trans-acting regulatory element of claim 12 or 13.

This invention provides a purified Progression Elevated Gene-3 protein.

This invention provides the polypeptide encoded by the above-described nucleic acids.

This invention also provides an isolated polypeptide comprising substantially the same sequence as the sequence set forth in FIG. 12 or 13.

This invention provides the above-described polypeptide, wherein the polypeptide has tumor progression activity or the presence of the polypeptide positively correlates with the progression phenotype.

In addition, this invention also provides an isolated polypeptide comprising substantially the same sequence as the sequence of the 80 C-terminal-most amino acids set forth in FIG. 12 or 13 or the complement of the sequence set forth in FIG. 12 or 13.

This invention provides a nucleic acid molecule comprising 12 or more nucleotides that specifically hybridize with the above-described nucleic acids.

This invention also provides an antisense polynucleotide comprising a sequence complementary to the above-described nucleic acids.

This invention further provides an upstream nucleic acid sequence comprising nucleotides 1–500 as set forth in FIG. 14.

In addition, this invention provides an upstream nucleic acid sequence comprising nucleotides 1–1000 as set forth in FIG. 14.

This invention provides an upstream nucleic acid sequence comprising the nucleic acid sequence set forth in FIG. 14.

This invention also provides an antisense nucleic acid comprising 15 or more nucleotides capable of specifically hybridizing to the above-described upstream nucleic acid sequences.

This invention further provides an antisense nucleic acid comprising 15 or more nucleotides that specifically hybridizes to the nucleotides 1–500 as set forth in FIG. 14.

This invention provides an isolated polypeptide comprising at least a portion of a progression-associated protein, or a variant thereof, wherein: a) the progression-associated protein comprises a sequence encoded by a nucleotide sequence set forth in FIG. 11 or 13; and b) the portion retains at least one immunological or biological activity characteristic of the progression-associated protein.

This invention provides the above-described polypeptides, wherein the portion is immunologically active.

This invention also provides an isolated nucleic encoding the above-described polypeptides.

This invention provides a vector which comprises the above-described isolated nucleic acids.

This invention also provides the above-described isolated nucleic acids operatively linked to a regulatory element.

This invention further provides the above-described vector, wherein the vector is a plasmid.

This invention also provides the above-described plasmid, designated PGEN-3 (ATCC Accession No. 97911).

This invention provides a host vector system for the production of a polypeptide having the biological activity of a Progression Elevated Gene-3 protein which comprises the above-described vectors and a suitable host.

This invention further provides the above-described vectors, wherein the suitable host is a bacterial cell, yeast cell, insect cell, or animal cell.

In addition, this invention also provides an expression vector comprising the above-described nucleic acids.

This invention provides a host cell transformed or transfected with the above-described expression vectors.

This invention further provides an antibody or antigen-binding fragment thereof that specifically binds to the above-described polypeptides.

This invention provides a kit for inhibiting tumor progression, comprising an antisense nucleic acid capable of specifically hybridizing to the above-described nucleic acids.

This invention provides the above-described kit, wherein the antisense nucleic acid is linked to a promoter.

This invention further provides the above-described kits, wherein the antisense nucleic acid linked to a promoter is part of an expression vector.

In addition, this invention provides the above-described kits, wherein the expression vector is adapted for expression in a mammalian cell.

This invention further provides a method of detecting expression of the Progression Elevated Gene-3 in a sample which contains cells comprising steps of: a) obtaining RNA from the cells; b) contacting the nucleic acid so obtained with a labeled form of the above-described nucleic acids under hybridizing conditions; and c) detecting the presence of RNA hybridized to the molecule, thereby detecting the expression of the Progression Elevated Gene-3 in the sample.

This invention also provides the above-described method, further comprising amplification of the RNA obtained in step a prior to the contacting of step b.

In addition, this invention provides the above-described methods, wherein the expression of Progression Elevated Gene-3 is measured by the amount of Progression Elevated Gene-3 mRNA expressed in the cells.

This invention provides the above-described methods, wherein the expression of Progression Elevated Gene-3 is measured by the amount of the Progression Elevated Gene-3 protein expressed in the cells.

This invention provides a method for determining whether a cancer cell is in a progression stage comprising measuring the expression of Progression Elevated Gene-3 in the cancer cell, wherein an increase in the amount indicates that the cancer cell is in progression.

This invention provides a method for diagnosing the aggressiveness of cancer cells comprising measuring the expression of Progression Elevated Gene-3 in the cancer cell, wherein an increase in the amount of the expression indicates that the cancer cell is more aggressive.

This invention further provides a method of monitoring tumor progression in a subject, comprising: a) obtaining at least one nucleic acid sample from the subject; and b) determining the quantity of the above-described nucleic acids in the nucleic acid sample.

This invention provides a method of monitoring DNA damage in a subject, comprising: a) obtaining at least one nucleic acid sample from the subject; and b) determining the quantity of the above-described nucleic acids in the nucleic acid sample.

In addition, this invention provides the above-described methods, wherein the quantity of nucleic acid positively correlates with transformation progression.

This invention also provides the above-described methods, wherein two or more nucleic acid samples are taken from the subject at different times.

This invention also provides the above-described methods, further comprising using the nucleic acid samples in determining differences in the expression of the above-described nucleic acids over time.

This invention further provides a kit for diagnosing tumor progression, comprising a nucleic acid consisting of a sequence of 15 or more nucleotides that specifically hybridizes to the above-described nucleic acids.

In addition, this invention also provides a kit for diagnosing tumor progression, comprising an antibody to the above-described polypeptides.

This invention provides a method for determining whether cells are in progression, comprising the steps of: a) measuring expression of PEG-3 in a sample of cells; and b) comparing the expression measured in step a with the expression of PEG-3 in cells that are not in progression, thereby determining whether the cells are in progression.

This invention further provides a method for determining whether a cancer in a patient is in progression, comprising detecting in a biological sample obtained from the patient the above-described polypeptides, thereby determining whether a cancer in the patient is in progression.

A method for determining whether a cancer in a patient is in progression, comprising detecting, in a biological sample obtained from the patient, a nucleic acid encoding the above-described polypeptides or a portion thereof, thereby determining whether a cancer in the patient is in progression.

This invention provides the above-described methods, wherein the detecting comprises: preparing cDNA from RNA molecules in the biological sample; and specifically amplifying cDNA molecules encoding at least a portion of the above-described polypeptides.

This invention also provides a method for monitoring the progression of a cancer in a patient, comprising: a) detecting, in a biological sample obtained from a patient, the above-described polypeptides at a first point in time; b) repeating step (a) at a subsequent point in time; and c)

comparing the amounts of polypeptide detected in steps a and b, thereby monitoring the progression of a cancer in the patient.

This invention further provides the above-described methods, wherein the step of detecting comprises contacting a portion of the biological sample with a monoclonal antibody that specifically recognizes the above-described polypeptides.

This invention provides the above-described methods, wherein the biological sample is a portion of a tumor.

This invention provides a method for monitoring the progression of a cancer in a patient, comprising: a) detecting, in a biological sample obtained from a patient, an amount of an RNA molecule encoding the above-described polypeptides at a first point in time; b) repeating step a at a subsequent point in time; and c) comparing the amounts of RNA molecules detected in steps a and b, thereby monitoring the progression of a cancer in the patient.

This invention also provides a diagnostic kit, comprising: a) the above-described antibody or fragment thereof; and b) a second antibody or fragment thereof that binds to (i) the monoclonal antibody recited in step a; or (ii) the above-described polypeptide; wherein the second monoclonal antibody is conjugated to a reporter group.

This invention provides a cell comprising an exogenous indicator gene under the control of the regulatory element of a Progression Elevated Gene-3.

This invention further provides above-described cell, wherein the cell is an E11 or CRF.

This invention further provides above-described cell, wherein the cell is not at progression.

In addition, this invention provides above-described cell, wherein the cell is an E11-NMT, CREF-ras, CREF-HPV, or CREF-src cell.

This invention also provides above-described cell, wherein the cell is at progression.

This invention provides above-described cell, wherein the indicator gene encodes beta-galactosidase, luciferase, chloramphenicol transferase or a secreted alkaline phosphatase.

This invention further provides a method for determining whether an agent is capable of inhibiting DNA damage and repair pathways, cancer progression or oncogene mediated transformation, comprising contacting the agent with the above-described cells, wherein a decrease of expression of the indicator gene indicates that the agent is capable of inhibiting DNA damage and repair pathways, cancer progression or oncogene mediated transformation.

This invention also provides a method for determining whether an agent is capable of inducing DNA damage and repair pathways, cancer progression or oncogene mediated transformation, comprising contacting the agent with the above-described cells, wherein an increase of expression of the indicator gene after the contact indicates that the agent is capable of inducing DNA damage and repair pathways, cancer progression or oncogene mediated transformation.

This invention provides a method for identifying an agent that modulates the expression of PEG-3, comprising: a) contacting a candidate agent with a cell transformed or transfected with a reporter gene under the control of a PEG-3 promoter or a regulatory element thereof under conditions and for a time sufficient to allow the candidate agent to directly or indirectly alter expression of the promoter or regulatory element thereof; and b) determining the effect of the candidate agent on the level of reporter protein produced by the cell, thereby identifying an agent that modulates expression of PEG-3.

This invention also provides the above-described method, wherein the agent activates the PEG-3 promoter indirectly by interacting with an oncogene.

This invention further provides a method for identifying an agent that modulates the ability of PEG-3 to induce progression, comprising: a) contacting a candidate agent with the above-described polypeptides, under conditions and for a time sufficient to allow the candidate agent and polypeptide to interact; and b) determining the effect of the candidate agent on the ability of the polypeptide to induce progression, thereby identifying an agent that modulates the ability of PEG-3 to induce progression.

This invention also provides a cell comprising the above-described nucleic acids encoding PEG-3 linked to a tissue specific promoter.

This invention provides a cell comprising a reporter gene linked to a PEG-3 promoter.

In addition, this invention provides the above-described cells, wherein the reporter gene encodes luciferase or beta galactosidase.

This invention further provides the above-described cell, wherein the cell comprises 4NMT or tumorigenic CREF-Trans 6 cells.

This invention provides the above-described cell, wherein the cell comprises CREF-ras, CREF-src, or CREF-HPV cells.

This invention further provides the above-described cell, wherein the reporter gene encodes a cell surface protein.

This invention provides the above-described cell, wherein the cell surface protein is in a position accessible for binding to an antibody.

This invention provides a transgenic animal, comprising the above-described cells.

This invention further provides the use of the above-described cells to identify compounds that induce DNA damage.

This invention also provides the use of the above-described cells to identify compounds that induce cancer progression.

This invention provides the use of the above-described cells to identify compounds that induce oncogenic transformation.

In addition, this invention provides the use of the above-described cells to identify compounds that induce or inhibit angiogenesis.

This invention further provides a method of identifying compounds that induce oncogenic transformation, comprising: exposing the above-described cells to the compound and identifying compounds that activate the PEG-3 promoter.

This invention further provides a method of identifying compounds that induce DNA damage, comprising: exposing the above-described cells to the compound and identifying compounds that activate the PEG-3 promoter.

This invention provides a method of identifying compounds that regulate angiogenesis, comprising: exposing the above-described cells to the compound and identifying compounds that affect the activity of the PEG-3 promoter.

This invention provides above-described method, wherein the activity of the PEG-3 promoter is monitor by assessing the level of expression of the reporter gene.

This invention further provides above-described method, wherein cells are plated in microtiter plates for rapid screening.

This invention provides above-described method, wherein the cell is obtained from a transgenic animal and exposed to the compound in vitro.

This invention also provides above-described method, wherein the cell is obtained by transfection or transformation and exposed to the compound in vitro.

This invention further provides a method of identifying compounds that induce oncogenic transformation, comprising: exposing the above-described transgenic animal to the compound and identifying compounds that activate the PEG-3 promoter.

In addition, this invention provides a method of identifying compounds that induce DNA damage, comprising: exposing the above-described transgenic animal to the compound and identifying compounds that activate the PEG-3 promoter.

This invention further provides a method of identifying compounds that regulate angiogenesis, comprising: exposing the above-described transgenic animal to the compound and identifying compounds that affect the activity of the PEG-3 promoter.

This invention provides the above-described methods, wherein the activity of the PEG-3 promoter is monitor by assessing the level of expression of the reporter gene.

This invention also provides a method of producing a Progression Elevated Gene-3 protein which comprises growing the above-described vector under conditions permitting production of the protein and recovering the protein so produced.

This invention further provides a pharmaceutical composition for reversing the progression state of cells comprising an amount of the above-described nucleic acids effective to inhibit the expression of Progression Elevated Gene-3 and a pharmaceutically acceptable carrier.

This invention provides a pharmaceutical composition for reversing the progression state of cells comprising an amount of the above-described antibody or a functional fragment thereof effective to neutralize the action of the Progression Elevated Gene-3 protein and a pharmaceutically acceptable carrier.

This invention further provides a method for producing cells which are resistant to progression comprising inhibiting or eliminating the expression of Progression Elevated Gene-3 in the cells.

In addition, this invention provides the cells resulting from the above-described methods.

This invention provides a transgenic nonhuman living organism expressing the above-described polypeptides.

In addition, this invention provides above-described transgenic, wherein the organism is an animal.

This invention further provides a pharmaceutical composition, comprising: a) the above-described polypeptides; and b) a physiologically acceptable carrier.

This invention provides a vaccine, comprising: a) the above-described polypeptides; and b) an immune response enhancer.

This invention further provides a pharmaceutical composition, comprising: a) the above-described nucleic acids; and b) a physiologically acceptable carrier.

This invention provides a pharmaceutical composition, comprising: a) the above-described antibody; and b) a physiologically acceptable carrier.

This invention further provides a method for inhibiting the progression of a cancer in a subject, comprising administering to the subject an agent that inhibits expression of PGEN-3.

This invention provides the above-described methods, wherein PGEN-3 is one of the above-described polypeptides.

This invention provides the above-described methods, wherein agent is one of the above-described nucleic acids.

In addition, this invention provides a method for preparing the above-described polypeptides, comprising the steps of: a) culturing one of the above-described host cells under conditions suitable for the expression of the polypeptide; and b) recovering the polypeptide from the host cell culture.

This invention further provides a method for producing cells that are resistant to progression, comprising inhibiting or eliminating the expression of a PEG-3 gene in the cells.

This invention further provides a method for protecting cells from chemotherapeutic damage, comprising inhibiting or eliminating the expression of PEG-3 in the cells.

This invention provides a cell transformed or transfected with a reporter gene under the control of a human PEG-3 promoter or regulatory element thereof.

This invention provides the above-described polypeptides, wherein the progression phenotype comprises anchorage-independent growth, tumorigenesis, angiogenesis, or metastasis.

This invention further provides the above-described methods, wherein the cancer is melanoma.

This invention provides the above-described methods, wherein the cancer is brain cancer.

This invention further provides the above-described methods, wherein the cancer is cervical cancer.

This invention provides the above-described methods, wherein the cancer is prostate cancer.

In addition, this invention provides the above-described methods, wherein the cancer is breast cancer.

This invention further provides the above-described methods, wherein the cancer is nasal pharyngeal cancer.

In addition, this invention provides the above-described methods, wherein the cancer is neoblastoma multiforme cancer.

Methods to introduce a nucleic acid molecule into cells have been well known in the art. Naked nucleic acid molecule may be introduced into the cell by direct transformation. Alternatively, the nucleic acid molecule may be embedded in liposomes. Accordingly, this invention provides the above methods wherein the nucleic acid is introduced into the cells by naked DNA technology, adenovirus vector, adeno-associated virus vector, Epstein-Barr virus vector, Herpes virus vector, attenuated HIV vector, retroviral vectors, vaccinia virus vector, liposomes, antibody-coated liposomes, mechanical or electrical means. The above recited methods are merely served as examples for feasible means of introduction of the nucleic acid into cells. Other methods known may be also be used in this invention.

This invention further provides the above-described methods, wherein the cancer is melanoma.

This invention provides the above-described methods, wherein the cancer is epithelial cancer.

This invention provides the above-described methods, wherein the epithelial cancer is brain, breast, cervical, prostate, lung or colorectal cancer.

In addition, this invention further provides the above-described methods, wherein the cancer is derived from a central nervous system tumor.

This invention provides the above-described methods, wherein the central nervous system tumor comprises a neuroblastoma or glioblastoma cancer.

This invention further provides the above-described methods, wherein the cell comprises an endothelial cells.

In addition, this invention provides the above-described methods, wherein endothelial cell growth or proliferation is induced.

This invention further provides the above-described methods, wherein endothelial cell growth or proliferation is inhibited.

This invention provides an inducible PEG-3 regulatory region functionally linked to a gene encoding a product that causes or may be induced to cause the death or inhibition of cancer cells.

This invention further provides an inducible PEG-3 regulatory region functionally linked to a gene encoding a product that causes or may be induced to cause the death or inhibition of cancer cell growth.

This invention also provides a vector suitable for introduction into a cell, comprising: a) an inducible PEG-3 regulatory region; and b) a gene encoding a product that causes or may be induced to cause the death or inhibition of cancer cell growth.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MOMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk-cells and COS cells. Mammalian cells may be transfected by methods well known in the art such as calcium phosphate precipitation, electroporation and microinjection.

In an embodiment, inducible promoters may be fused with the coding region of the DNA to provide an experimental means to regulate expression. Alternatively or in addition, tissue specific regulatory elements may be fused with the coding region to permit tissue-specific expression.

In addition, this invention further provides the above-described vectors, wherein the inducible PEG-3 regulatory region is a promoter.

This invention also provides the above-described vectors, wherein the inducible PEG-3 regulatory region is an enhancer.

This invention further provides the above-described vectors, wherein the gene encodes an inducer of apoptosis.

In addition, this invention provides the above-described vectors, wherein the gene is a tumor suppressor gene.

In an embodiment, tumor suppressors include agents that inhibit tumor growth. In another embodiment, tumor suppressors include agents that inhibit, reverse, or reduce the cancer progression phenotype.

This invention also provides the above-described vectors, wherein the tumor suppressor gene is pS3.

In addition, this invention provides the above-described vectors, wherein the tumor suppressor gene is mda-7.

This invention also provides the above-described vectors, wherein the tumor suppressor gene is p21.

In addition, this invention provides the above-described vectors, wherein the gene encodes a viral replication protein.

This invention further provides the above-described vectors, wherein the gene is E1A.

This invention also provides the above-described vectors, wherein the gene is E1B.

This invention also further provides the above-described vectors, wherein the gene encodes a product toxic to cells or an intermediate to a product toxic to cells.

In an embodiment, products toxic to cells include chemicals that reduce a cells chances and/or duration of survival. In an embodiment, the products toxic to cells are radioactive. In another embodiment, the products toxic to cells induce DNA damage. In another embodiment, the products toxic to cells inhibit a critical enzyme or regulatory protein. In another embodiment, the products toxic to cells contain or induce free radicals. One skilled in the art would recognize a vast array of other products that are toxic to cells.

Further, this invention provides the above-described vectors, wherein the gene encodes thymidine kinase.

In addition, this invention provides the above-described vectors, wherein the gene encodes a product causing enhanced immune recognition of the cell.

Further, this invention provides the above-described vectors, wherein the gene is GM-CSF.

This invention also provides the above-described vectors, wherein the gene is IL-2.

This invention also provides the above-described vector, wherein the gene encodes a cytokine.

Further, this invention provides the above-described vector, wherein the cytokine is IF-gamma.

In addition, this invention provides the above-described vector, wherein the cytokine is IL-6.

This invention also provides the above-described vector, wherein the gene encodes an immunomodulator.

Further, this invention provides the above-described vector, wherein the gene encodes a T-cell epitope.

This invention also provides the above-described vector, wherein the gene encodes a T-cell reactive protein.

This invention further provides the above-described vectors, wherein the gene encodes a product causing the cell to express a specific antigen.

In an embodiment, the gene causes the cells to express an antigen on their surface; thus, allowing the cells to be targeted by antibodies specific to the antigen.

This invention also provides a method of treating cancer in a subject, comprising: a) administering the one or more of the above-described vectors to the subject; and b) administering gancyclovir or acyclovir to the subject.

In addition, this invention provides a method of treating cancer in a subject, comprising: a) administering one of the above-described vectors to the subject; and b) administering an antibody or a fragment of an antibody to the the above-described antigen to the subject.

Further, this invention provides the above-described methods, wherein the antibody is toxic or linked to a toxic substance.

This invention also provides the above-described methods, wherein the antibody is labeled and used for tumor imaging.

Methods of labeling include, but are not limited to, radioactive labeling; enzymatic labeling, wherein the enzyme directly or indirectly produces a detectable product; and fluorescent labeling.

Further, this invention provides the above-described methods, wherein the antibody is radioactive.

In addition, this invention provides a pharmaceutical composition comprising one or more of the the above-described vectors and a carrier.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention will be better understood by reference to the Experimental Details which follow, but those skilled in the art will readily appreciate that the specific experiments detailed are only illustrative of the invention as described more fully in the claims which follow thereafter.

Experimental Details

Cancer is a progressive multigenic disorder characterized by defined changes in the transformed phenotype that culminates in metastatic disease. Determining the molecular basis of progression should lead to new opportunities for improved diagnostic and therapeutic modalities. Through the use of subtraction hybridization, a gene associated with transformation progression in virus and oncogene transformed rat embryo cells, progression elevated gene-3 (PEG-3), has been cloned. PEG-3 shares significant nucleotide and amino acid sequence homology with the hamster growth arrest and DNA damage inducible gene gadd34 and a homologous murine gene, MyD116, that is induced during induction of terminal differentiation by interleukin-6 in murine myeloid leukemia cells. PEG-3 expression is elevated in rodent cells displaying a progressed transformed phenotype and in rodent cells transformed by various oncogenes, including Ha-ras, v-src, mutant type 5 adenovirus (Ad5) and human papilloma virus-18. The PEG-3 gene is transcriptionally activated in rodent cells, as is gadd34 and MyD116, after treatment with DNA damaging agents, including methyl methanesulfonate and gamma irradiation. In contrast, only PEG-3 is transcriptionally active in rodent cells displaying a progressed phenotype. Although transfection of PEG-3 into normal and Ad5-transformed cells only marginally suppresses colony formation, stable overexpression of PEG-3 in Ad5-transformed rat embryo cells elicits the progression phenotype. These results indicate that PEG-3 is a new member of the gadd and MyD gene family with similar yet distinct properties and this gene may directly contribute to the transformation progression phenotype. Moreover, these studies support the hypothesis that constitutive expression of a DNA damage response may mediate cancer progression.

First Series of Experiments

Materials and Methods

Cell Lines, Culture Conditions and Anchorage-Independent Growth Assays.

The isolation, properties and growth conditions of the E11, E11-NMT, E11-NMT X CREF somatic cell hybrids, E11X E11-NMT somatic cell hybrids and the E11-NMT AZA clones have been described (1,7–13). E11-ras R12 and E11-HPV E6/E7 clones were isolated by transfection with the Ha-ras or the HPV-18 E6/E7 genes, respectively. The isolation, properties and growth conditions of CREF, CREF-H5hr1 A2, CREF-ras, the CREF-ras/Krev1 B1, B1 T and B1 M and the CREF-ras/Krev1 B2, B2T, and B2M clones have been described (21). CREF-src and CREF-HPV 18 clones were isolated by transfection with the v-src and HPV-18 E6/E7 genes, respectively. All cells were grown in Dulbecco's modified Eagle's minimum essential medium supplemented with 5% fetal bovine serum at 37° C. in a 5% $CO_2$ plus 95% air humidified incubator. Anchorage independence assays were performed by seeding various cell densities in 0.4% Noble agar on a 0.8% agar base layer both of which contain growth medium (7).

Cloning and Sequencing of the PEG-3 cDNA.

The PEG-3 gene was cloned from E11-NMT cells using subtraction hybridization as described (23). A full-length PEG-3 cDNA was obtained using the rapid amplification of cDNA end (RACE) procedure and direct ligation (25,26). Sequencing was performed by the dideoxy-chain termination (Sanger) method (27). The coding region of PEG-3 was cloned into a pZeoSV vector (Invitrogen) as described (25,26).

RNA Analysis and In Vitro Transcription Assays.

Total cellular RNA was isolated by the guanidinium/phenol extraction method and Northern blotting was performed as described (28). Fifteen μg of RNA were denatured with glyoxal/DMSO and electrophoresed in 1% agarose gels, transferred to nylon membranes and hybridized sequentially with $^{32}$P-labeled PEG-3, Ads E1A and GAPDH probes (28,29). Following hybridization, the filters were washed and exposed for autoradiography. The transcription rates of PEG-3, gadd34, MyD116, GAPDH and pBR322 was determined by nuclear run-on assays (12,21).

In Vitro Translation of PEG-3.

Plasmid, pZeoSV, containing PEG-3 cDNA was linearized by digestion with Xho I and used as a template to synthesize mRNA. In vitro translation of PEG-3 mRNA was performed with a rabbit relticulocyte lysate translation kit as described by Promega.

DNA Transfection Assays.

To study the effect of PEG-3 on monolayer colony formation the vector (pZeoSV) containing no insert or a pZeoSV-PEG-3 construct containing the PEG-3 coding region were transfected into the various cell types by the lipofectin method (GIBCO/BRL) and Zeocin resistant clones were isolated or efficiency of Zeocin colony formation was determined (29,30).

Results and Discussion

Expression of the PEG-3 Gene Correlates Directly with the Progression Phenotype in Viral and Oncogene Transformed Rodent Cells.

A critical component of cancer development is progression, a process by which a tumor cell develops either qualitatively new properties or displays an increase in the expression of traits that enhance the aggressiveness of a tumor (1–4). Insight into this process offers the potential of providing important new targets for intervening in the neoplastic process (1–4). In the Ad5 transformed RE cell culture model system, enhanced anchorage-independent growth and in vivo tumorigenic aggressiveness, i.e., markers of the progression phenotype, are stable traits that can be induced spontaneously or by gene transfer (oncogenes and growth factor-related genes) (Table 1).

TABLE 1

Expression of PEG-3 in Ad5-transformed RE cells directly correlates with expression of the progression phenotype

| Cell Type[a] | Agar Cloning Efficiency (%)[b] | Tumorigenicity in Nude Mice[c] | Progression Phenotype[d] |
|---|---|---|---|
| RE | <0.001 | 0/10 | Prog⁻ |
| CREF | <0.001 | 0/18 | Prog⁻ |
| E11 | 2.9 ± 0.3 | 8/8 (36) | Prog⁻ |
| E11-NMT | 34.3 ± 4.1 | 6/6 (20) | Prog⁺ |
| CREF X E11-NMT F1 | 2.0 ± 0.3 | 0/6 | Prog⁻ |
| CREF X E11-NMT F2 | 1.5 ± 0.1 | 0/6 | Prog⁻ |
| CREF X E11-NMT R1 | 72.5 ± 9.4 | 3/3 (17) | Prog⁺ |
| CREF X E11-NMT R2 | 57.4 ± 6.9 | 3/3 (17) | Prog⁺ |
| E11 X E11-NMT IIId | 5.6 ± 0.7 | 3/3 (56) | Prog⁻ |
| E11 X E11-NMT IIIdTD | 41.0 ± 4.9 | 3/3 (19) | Prog⁺ |
| E11 X E11-NMT A6 | 0.3 ± 0.0 | 3/3 (44) | Prog⁻ |
| E11 X E11-NMT A6TD | 29.3 ± 3.5 | N.T. | Prog⁺ |
| E11 X E11-NMT 3b | 1.5 ± 0.2 | 3/3 (31) | Prog⁻ |
| E11 X E11-NMT IIA | 29.5 ± 2.8 | 3/3 (23) | Prog⁺ |
| E11-NMT AZA C1 | 2.8 ± 0.5 | N.T. | Prog⁻ |
| E11-NMT AZA B1 | 1.6 ± 0.3 | 3/3 (41) | Prog⁻ |
| E11-NMT AZA C2 | 2.0 ± 0.1 | 3/3 (50) | Prog⁻ |
| E11-ras R12 | 36.8 ± 4.6 | 3/3 (18) | Prog⁺ |
| E11-HPV E6/E7 | 31.7 ± 3.1 | 3/3 (22) | Prog⁺ |

[a]Cell line descriptions can be found in Materials and Methods.
[b]Anchorage-independent growth was determined by seeding variable numbers of cells in 0.4% agar on a 0.8% agar base layer. Results are the average number of colonies from 4 replicate plates ± S.D.
[c]Tumorigenicity was determined by injecting nude mice with $2 \times 10^6$ or $1 \times 10^7$ (RE, CREF and CREF X E11-NMT hybrids). Results are the number of animals with tumors per number of animals injected and the number in parentheses indicate average latency time in days, i.e., first appearance of a palpable tumor. N.T. = not tested.
[d]Prog⁻ = progression; phenotype is not expressed; Prog⁺ = progression phenotype is expressed.

Upon treatment of progressed cells with AZA, the progression phenotype can be stably reversed (1,10). A reversion of progression also occurs following somatic cell hybridization of progressed cells with unprogressed Ad5-transformed cells or with normal CREF cells. A further selection of these unprogressed Ad5-transformed cells by injection into nude mice results in acquisition of the progressed phenotype following tumor formation and establishment in cell culture. These studies document that progression in this model system is a reversible process that can be stably produced by appropriate cellular manipulation. In this context, the Ad5-transformed RE model represents an important experimental tool for identifying genes that are associated with and that mediate cancer progression.

Figure 1:
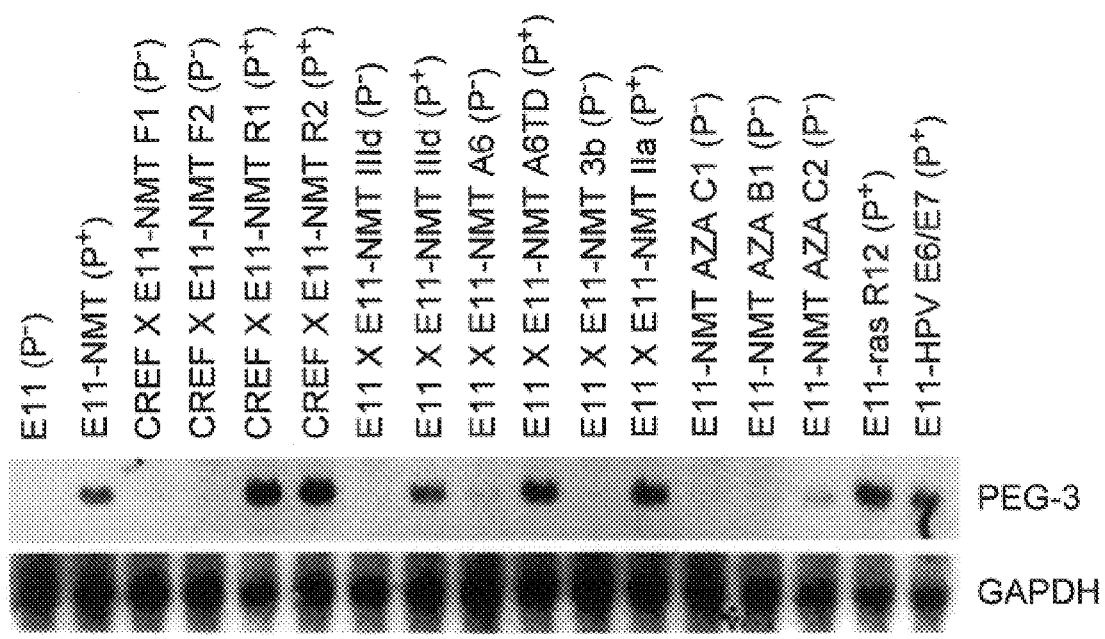
FIG. 1: Northern blot illustrating PEG-3 expression in Ad5-transformed RE cells displaying different stages of transformation progression. Fifteen μg of cellular RNA isolated from the indicated cell types, were electrophoresed, transferred to nylon membranes and hybridized with an ~700 bp 3' region of the PEG-3 gene (top) and then stripped and probed with GAPDH (bottom).

To directly isolate genes elevated during progression we employed an efficient subtraction hybridization approach previously used to clone the p21 gene (melanoma differentiation associated gene-6; mda-6) (23,25) and a novel cancer growth suppressing gene mda-7 (26,29). For this approach, cDNA libraries from a progressed mutant Ad5 (H5ts125)-transformed RE clone, E11-NMT (10), and its parental unprogressed cells, E11(10,31), were directionally cloned into the λ Uni-ZAP phage vector and subtraction hybridization was performed between double-stranded tester (E11-NMT) and single-stranded driver DNA (E11) by mass excision of the libraries (23). With this strategy in combination with the RACE procedure and DNA ligation techniques a full-length PEG-3 cDNA displaying elevated expression in E11-NMT versus E11 cells was cloned. Northern blotting analysis indicates that PEG-3 expression is ≧10-fold higher in all progressed Ad5-transformed RE cells, including E11-NMT, specific E11-NMT X CREF somatic cell hybrid clones, R1 and R2, expressing an aggressive transformed phenotype and specific E11X E11-NMT somatic cell hybrid clones, such as 11a that display the progression phenotype (FIG. 1 and Table 1). PEG-3 mRNA levels also increase following induction of progression by stable expression of the Ha-ras and HPV-18 E6/E7 oncogenes in E11 cells (FIG. 1). A further correlation between expression of PEG-3 and the progression phenotype is provided by E11X E11-NMT clones, such as IIId and A6, that initially display a suppression of the progression phenotype and low PEG-3 expression, but regain the progression phenotype and PEG-3 expression following tumor formation in nude mice, i.e., IIIdTD and A6TD (Table 1 and FIG. 1). In contrast, unprogressed Ad5-transformed cells, including E11, E11-NMT X CREF clones F1 and F2, E11X E11-NMT clones IIId, A6 and 3b and AZA-treated E11-NMT clones B1, C1 and C2, have low levels of PEG-3 RNA. These results provide evidence for a direct relationship between the progression phenotype and PEG-3 expression in this Ad5-transformed RE cell culture system. They also demonstrate that the final cellular phenotype, i.e., enhanced anchorage-independence and aggressive tumorigenic properties, is a more important determinant of PEG-3 expression than is the agent (oncogene) or circumstance (selection for tumor formation in nude mice) inducing progression.

Figure 2:
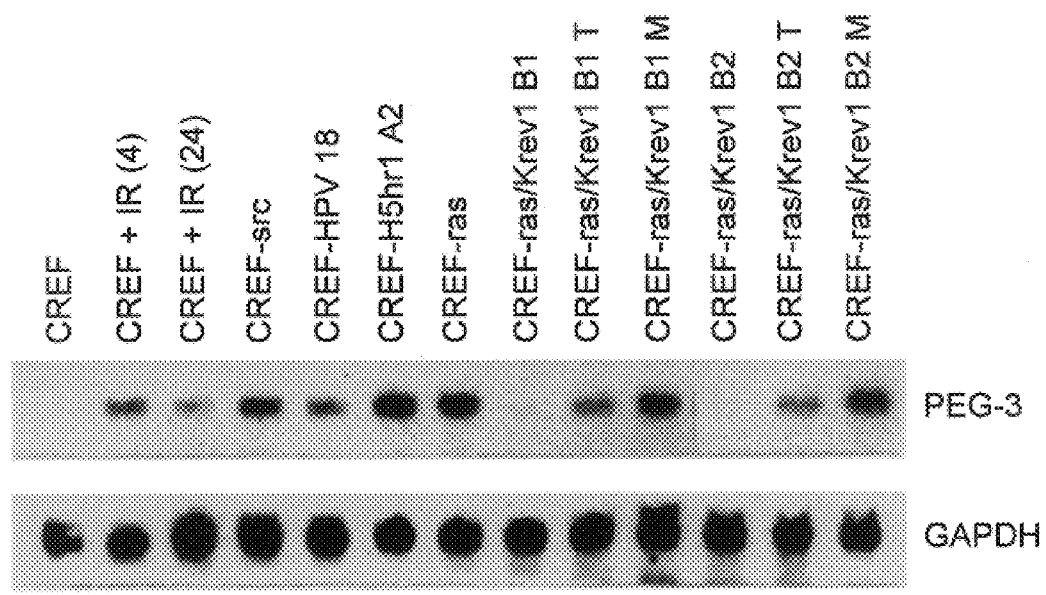
FIG. 2: Northern blot illustrating PEG-3 expression in gamma irradiated and oncogene transformed CREF cells. The experimental procedure was as described in the legend to FIG. 1. CREF cells were gamma irradiated with 10 Gy and RNA was isolated 4 and 24 hr later. Fifteen μg of cellular RNA isolated from the indicated cell types, were electrophoresed, transferred to nylon membranes and hybridized with an ~700 bp 3' region of the PEG-3 gene (top) and then stripped and probed with GAPDH (bottom).

A second rodent model used to study the process of cancer progression employs CREF clones modified by transfection to express dominant acting oncogenes (such as Ha-ras, v-src, HPV-18 and the mutant adenovirus H5hr1) and tumor suppressor genes (such as Krev-1, RB and wild-type p53) (19–22 and unpublished data). In this model system, Ha-ras-transformed CREF cells are morphologically transformed, anchorage-independent and induce both tumors and lung metastases in syngeneic rats and athymic nude mice (19–22). The Krev-1 (Ha-ras) suppressor gene reverses the in vitro and in vivo properties in Ha-ras transformed cells (21). Although suppression is stable in vitro, Ha-ras/Krev-1 CREF cells induce both tumors and metastases after extended times in nude mice (21). Expression of PEG-3 is not apparent in CREF cells, whereas tumorigenic CREF cells transformed by v-src, HPV-18, H5hr1 and Ha-ras contain high levels of PEG-3 RNA (FIG. 2). Suppression of Ha-ras induced transformation by Krev-1 inhibits PEG-3 expression. However, when Ha-ras/Krev-1 cells escape tumor suppression and form tumors and metastases in nude mice, PEG-3 expression reappears, with higher expression in metastatic-derived than tumor-derived clones (FIG. 2). These findings provide further documentation of a direct relationship between induction of a progressed and oncogenic phenotype in rodent cells and PEG-3 expression. As indicated above, it is the phenotype rather than the inducing agent that appears to be the primary determinant of PEG-3 expression in rodent cells.

The PEG-3 Gene Displays Sequence Homology with the Hamster gadd34 and Mouse MyD116 Genes and is Inducible by DNA Damage.

The cDNA sizes of PEG-3, gadd34 and MyD116 are 2210, 2088 and 2275 nt, respectively. The nt sequence of PEG-3 is ~73% and the aa sequence is ~59% homologous to the gadd34 (32) gene (FIG. 3 and data not shown). PEG-3 also shares significant sequence homology, ~68% nt and ~72% aa, with the murine homologue of gadd34, MyD116 (33,34) (FIG. 3 and data not shown). Differences are apparent in the structure of the 3' untranslated regions of PEG-3 versus gadd34/MyD116. ATTT motifs have been associated with mRNA destabilization. In this context, the presence of 3 ATTT sequences in Gadd34 and 6 tandem ATTT motifs in MyD116 would predict short half-lives for these messages. In contrast, PEG-3 contains only 1 ATTT motif suggesting that this mRNA may be more stable. The sequence homologies between PEG-3 and gadd34/MyD116 are highest in the amino terminal region of their encoded proteins, i.e., ~69 and ~76% homology with gadd34 and Myd116, respectively, in the first 279 aa. In contrast, the sequence of the carboxyl terminus of PEG-3 significantly diverges from gadd34/Myd116, i.e., only ~28 and ~40% homology in the carboxyl terminal 88 aa. In gadd34 and MyD116 a series of similar 39 aa are repeated in the protein, including 3.5 repeats in gadd34 and 4.5 repeats in MyD116. In contrast, PEG-3 contains only 1 of these 39 aa regions, with ~64% and ~85% homology to gadd34 and MyD116, respectively.

Figure 4:
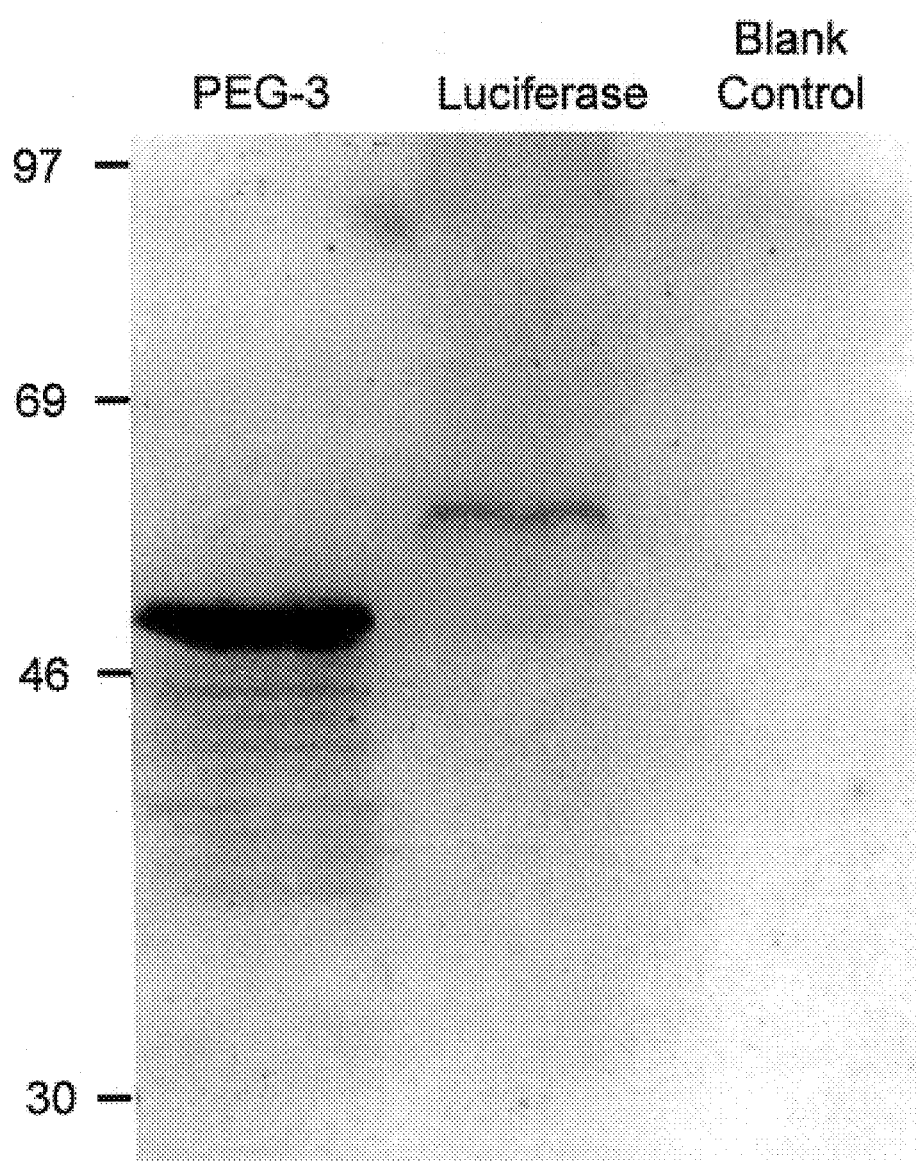
FIG. 4: Results of in vitro translation of the rat PEG-3 gene. Lane Luciferase is the in vitro translation of the luciferase gene (~61 kDa), positive control. The blank lane contains the same reaction mixture without mRNA, negative control. Lane PEG-3 contains the translated products of this cDNA. Rainbow protein standards (Amersham) were used to determine the sizes of the in vitro translated products.

On the basis of sequence analysis, the PEG-3 gene should encode a protein of 457 aa with a predicted MW of ~50 kDa. To confirm this prediction, in vitro translation analyses of proteins encoded by the PEG-3 cDNA were determined (FIG. 4). A predominant protein after in vitro translation of PEG-3 has a molecular mass of ~50 kDa (FIG. 4). In contrast, gadd34 encodes a predicted protein of 589 aa with an $M_w$ of ~65 kDa and MyD116 encodes a predicted protein of 657 aa with an $M_w$ of ~72 kDa. The profound similarity in the structure of PEG-3 versus gadd34/MyD116 cDNA and their encoded proteins suggest that PEG-3 is a new member of this gene family. Moreover, the alterations in the carboxyl terminus of PEG-3 may provide a functional basis for the different properties of this gene versus gadd34/MyD116.

Figure 5:
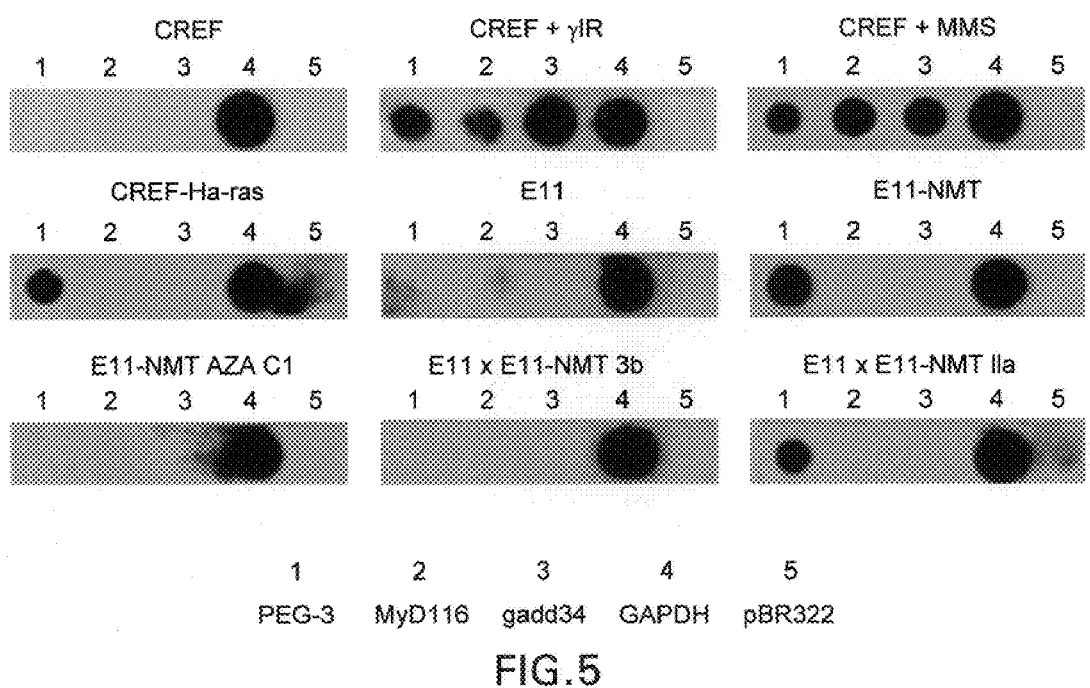
FIG. 5: An autoradiogram illustrating the transcription of the rat PEG-3, gadd34 and MyD116 genes as a function of DNA damage and transformation progression. Nuclear run-on assays were performed to determine comparative rates of transcription. Nuclei were isolated from CREF cells treated with MMS (100 μg/ml for 2 hr followed by growth for 4 hr in complete medium) or gamma irradiation (10 Gy followed by 2 hr growth in complete medium). DNA probes include, PEG-3 (1), MyD116 (2), gadd34 (3), GAPDH (4) and pBR322 (5).

The specific role of the gadd34/MyD116 gene in cellular physiology is not known. Like hamster gadd34 and its murine homologue MyD116, PEG-3 steady-state mRNA and RNA transcriptional levels are increased following DNA damage by methyl methanesulfonate (MMS) and gamma irradiation ($\gamma$IR) (FIGS. 2 and 5 and data not shown). In contrast, nuclear run-on assays indicate that only the PEG-3 gene is transcriptionally active (transcribed) as a function of transformation progression (FIG. 5). This is apparent in CREF cells transformed by Ha-ras and in E11-NMT and various E11-NMT subclones either expressing or not expressing the progression phenotype (FIG. 5). The gadd34/MyD116 gene, as well as the gadd45, MyD118 and gadd153 genes, encode acidic proteins with very similar and unusual charge characteristics (24). PEG-3 also encodes a putative protein with acidic properties similar to the gadd and MyD genes (FIG. 3). The carboxyl-terminal domain of the murine MyD116 protein is homologous to the corresponding domain of the herpes simplex virus 1 $\gamma_1$34.5 protein, that prevents the premature shutoff of total protein synthesis in infected human cells (35,36). Replacement of the carboxyl-terminal domain of $\gamma_1$34.5 with the homologous region from MyD116 results in a restoration of function to the herpes viral genome, i.e., prevention of early host shutoff of protein synthesis (36). Although further studies are required, preliminary results indicate that expression of a carboxyl terminus region of MyD116 results in nuclear localization (36). Similarly, gadd45, gadd153 and MyD118 gene products are nuclear proteins (24,37). Moreover, both gadd45 and MyD118 interact with the DNA replication and repair protein proliferating cell nuclear antigen (PCNA) and the cyclin-dependent kinase inhibitor p21 (37). MyD118 and gadd45 also modestly stimulate DNA repair in vitro (37). The carboxyl terminus of PEG-3 is significantly different than that of MyD116 (FIG. 3). Moreover, the carboxyl-terminal domain region of homology between MyD116 and the T34.5 protein is not present in PEG-3. In this context, the localization, protein interactions and properties of PEG-3 may be distinct from gadd and MyD genes. Once antibodies with the appropriate specificity are produced it will be possible to define PEG-3 location within cells and identify potentially important protein interactions mediating biological activity. This information will prove useful in elucidating the function of the PEG-3 gene in DNA damage response and cancer progression.

PEG-3 Lacks Potent Growth Suppressing Properties Characteristic of the gadd and Myd Genes.

An attribute shared by the gadd and MyD genes is their ability to markedly suppress growth when expressed in human and murine cells (24,37). When transiently expressed in various human tumor cell lines, gadd34/MyD116 is growth inhibitory and this gene can synergize with gadd45 or gadd153 in suppressing cell growth (24). These results and those discussed above suggest that gadd34/MyD116, gadd45, gadd153 and MyD118, represent a novel class of mammalian genes encoding acidic proteins that are regulated during DNA damage and stress and involved in controlling cell growth (24,37). In this context, PEG-3 would appear to represent a paradox, since its expression is elevated in cells displaying an in vivo proliferative advantage and a progressed transformed and tumorigenic phenotype.

Figure 6:
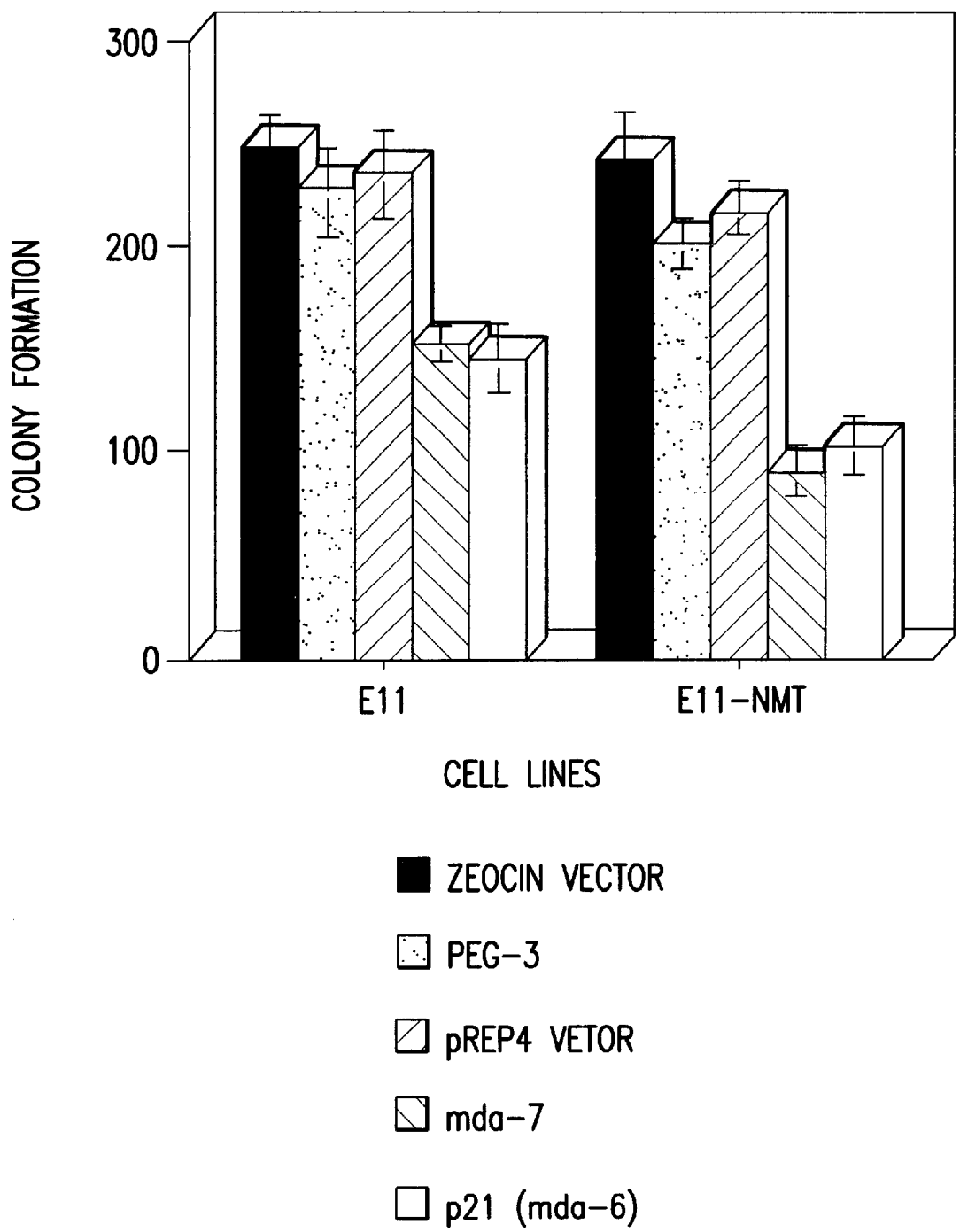
FIG. 6: Histogram illustrating the effect of transfection with PEG-3, mda-7 and p21 (mda-6) on colony formation of E11 and E11-NMT cells in monolayer culture. Target cells were transfected with 10 μg of a Zeocin vector (pZeoSV), the PEG-3 gene cloned in pZeoSV (PEG-3), the pREP4 vector, the mda-7 gene cloned in pREP4 (mda-7) and the mda-6 (p21) gene cloned in pREP4 (p21 (mda-6)), as indicated. Data represents the average number of Zeocin or hygromycin (pREP4 transfection) resistant colonies±S.D. for 4 plates seeded at 1×10$^5$ cells/6-cm plate.

To determine the effect of PEG-3 on growth, E11 and E11-NMT cells were transfected with the protein coding region of the PEG-3 gene cloned into a Zeocin expression vector, pZeoSV (FIG. 6). This construct permits an evaluation of growth in Zeocin in the presence and absence of PEG-3 expression. E11 and E11-NMT cells were also transfected with the p21 (mda-6) and mda-7 genes, previously shown to display growth inhibitory properties (25,26,29). Colony formation in both E11 and E11-NMT cells is suppressed 10 to 20%, whereas the relative colony formation following p21 (mda-6) and mda-7 transfection is decreased by 40 to 58% (FIG. 6 and data not shown). Colony formation is also reduced by 10 to 20% when PEG-3 is transfected into CREF, normal human breast (HBL-100) and human breast carcinoma (MCF-7 and T47D) cell lines (data not shown). Although the gadd and MyD genes were not tested for growth inhibition in E11 or E11-NMT cells, previous studies indicate colony formation reductions of >50 to 75% in several cell types transfected with gadd34, gadd45, gadd153, MyD116 or MyD118 (24,37). The lack of dramatic growth suppressing effects of PEG-3 and its direct association with the progression state suggest that this gene may represent a unique member of this acidic protein gene family that directly functions in regulating progression. This may occur by constitutively inducing signals that would normally only be generated during genomic stress. In this context, PEG-3 might function to alter genomic stability and facilitate tumor progression. This hypothesis is amenable to experimental confirmation.

PEG-3 Induces a Progression Phenotype in Ad5-Transformed RE Cells.

Figure 7:
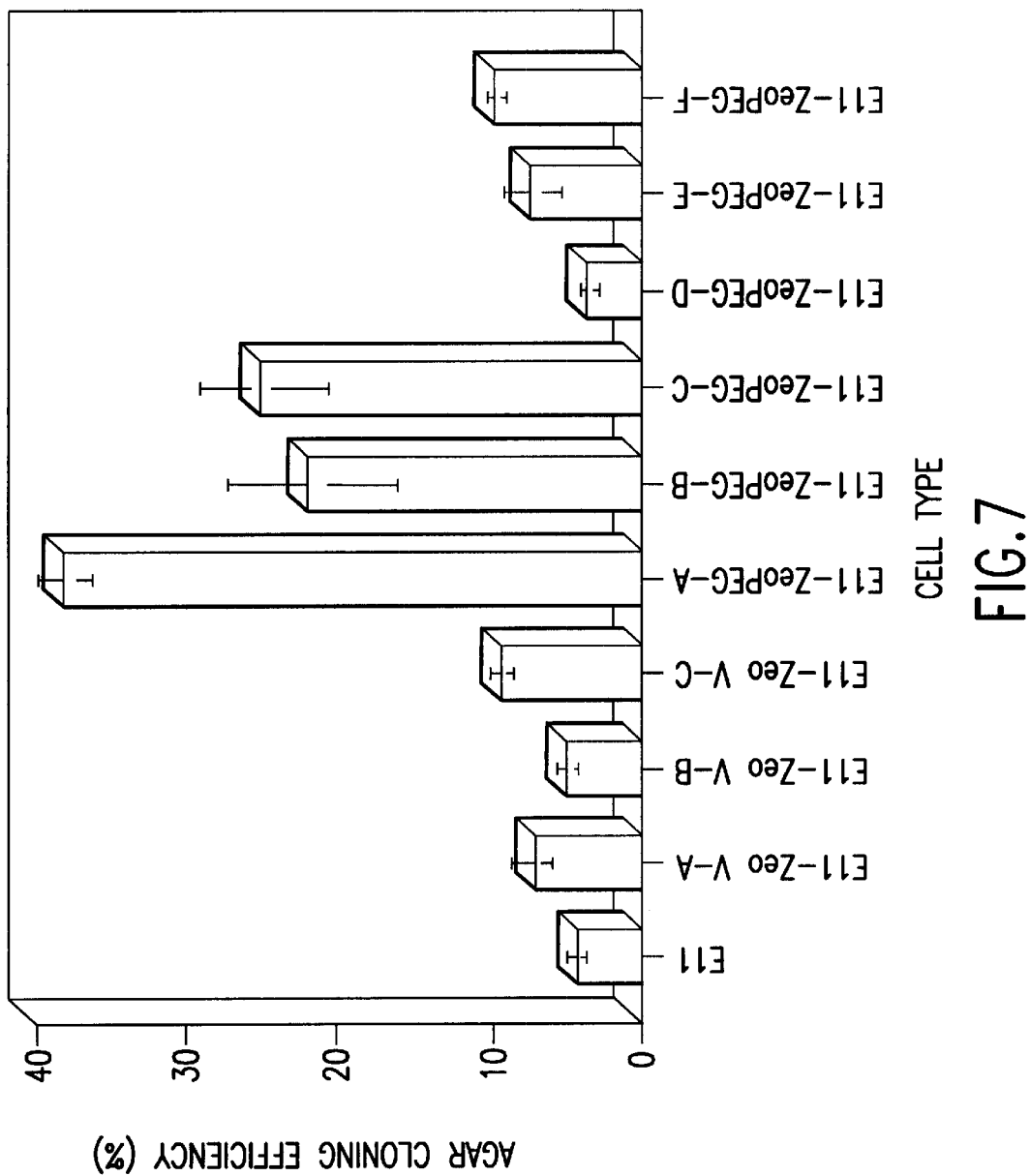
FIG. 7: Histogram illustrating the effect of stable PEG-3 expression on anchorageindependent growth of E11 cells. Agar cloning efficiency of E11, Zeocin resistant pZeoV (vector) transfected E11 and Zeocin resistant pZeoPEG transfected E11 cells. Average number of colonies developing in 4 replicate plates±S.D.
Figure 8:
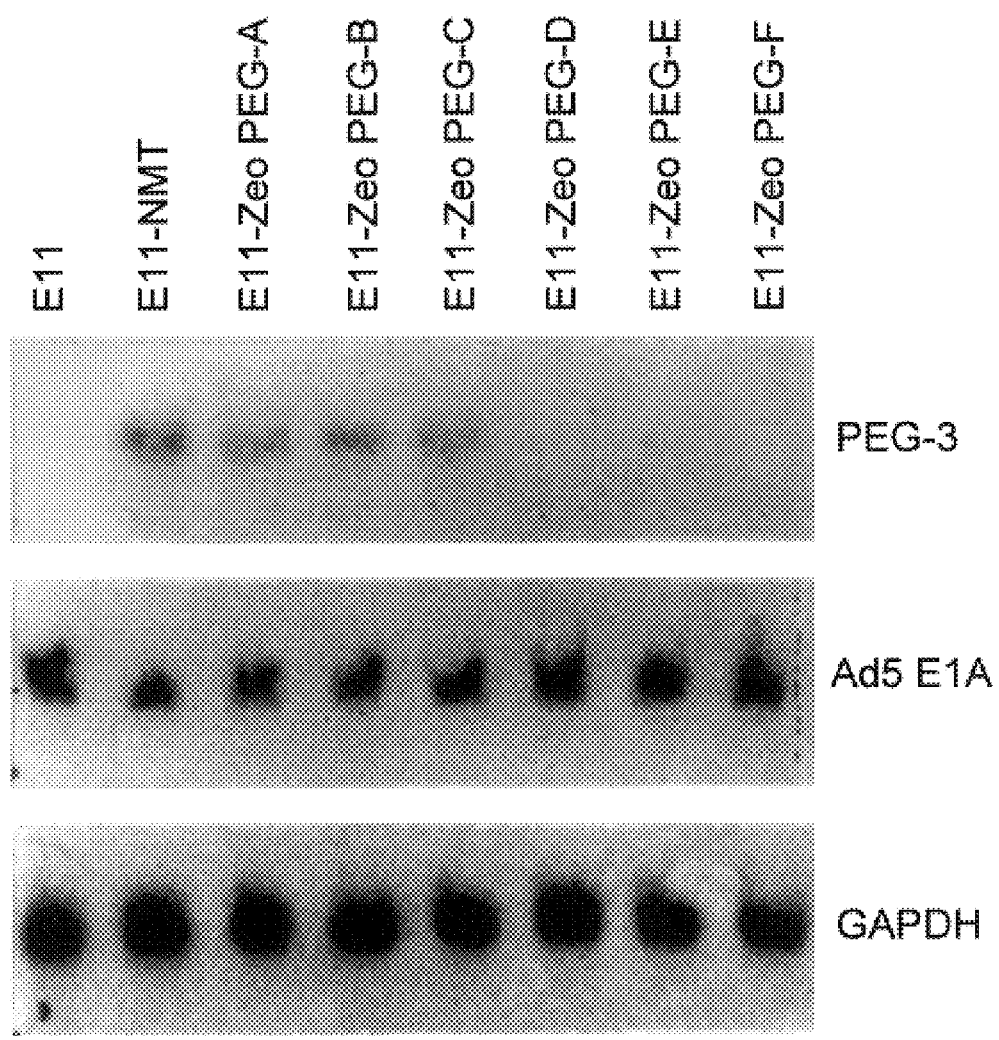
FIG. 8: Autoradiogram illustrating the expression of PEG-3, Ad$^5$ E1A and GAPDH RNA in pZeoPEG transfected E11 cells. The experimental procedure was as described in the legend to FIG. 1. Blots were probed sequentially with PEG-3 (top), Ad$^5$ E1A (middle) and GAPDH (bottom). The E11-ZeoPEG clones are the same clones analyzed for anchorage-independence in FIG. 7.

An important question is whether PEG-3 expression simply correlates with transformation progression or whether it can directly contribute to this process. To distinguish between these two possibilities we have determined the effect of stable elevated expression of PEG-3 on expression of the progression phenotype in E11 cells. E11 cells were transfected with a Zeocin expression vector either containing or lacking the PEG-3 gene and random colonies were isolated and evaluated for anchorage independent growth (FIG. 7). A number of clones were identified that display a 5- to 9-fold increase in agar cloning efficiency in comparison with E11 and E11-Zeocin vector transformed clones. To confirm that this effect was indeed the result of elevated PEG-3 expression, independent Zeocin resistant E11 clones either expressing or not expressing the progression phenotype were analyzed for PEG-3 mRNA expression (FIG. 8). This analysis indicates that elevated anchorage-independence in the E11 clones correlates directly with increased PEG-3 expression. In contrast, no change in Ad5 E1A or GAPDH mRNA expression is detected in the different clones. These findings demonstrate that PEG-3 can directly induce a progression phenotype without altering expression of the Ad5 E1A transforming gene. Further studies are required to define the precise mechanism by which PEG-3 elicits this effect.

Cancer is a progressive disease characterized by the accumulation of genetic alterations in an evolving tumor (1–6). Recent studies provide compelling evidence that mutations in genes involved in maintaining genomic stability, including DNA repair, mismatch repair, DNA replication, microsattelite stability and chromosomal segregation, may mediate the development of a mutator phenotype by cancer cells, predisposing them to further mutations resulting in tumor progression (38). Identification and characterization of genes that can directly modify genomic stability and induce tumor progression will provide significant insights into cancer development and evolution. This information would be of particular benefit in defining potentially novel targets for intervening in the cancer process. Although the role of PEG-3 in promoting the cancer phenotype remains to be defined, the current studies suggest a potential causal link between constitutive induction of DNA damage response pathways, that may facilitate genomic instability, and cancer progression. In this context, constitutive expression of PEG-3 in progressing tumors may directly induce genomic instability or it may induce or amplify the expression of down-stream genes involved in this process. Further studies are clearly warranted and will help delineate the role of an important gene, PEG-3, in cancer.

Conclusion

Subtraction hybridization results in the identification and cloning of a gene PEG-3 with sequence homology and DNA damage inducible properties similar to gadd34 and MyD116. However, PEG-3 expression is uniquely elevated in all cases of rodent progression analyzed to date, including spontaneous and oncogene-mediated, and overexpression of PEG-3 can induce a progression phenotype in Ad5-transformed cells. Our studies suggest that PEG-3 may represent an important gene that is both associated with (diagnostic) and causally related to cancer progression. They also provide a potential link between constitutive expression of a DNA damage response pathway and progression of the transformed phenotype.

REFERENCES FOR THE FIRST SERIES OF EXPERIMENTS

1. Fisher, P. B. (1984) in *Tumor Promotion and Cocarcinogenesis In Vitro, Mechanisms of Tumor Promotion*, ed. Slaga, T. J. (CRC Press, Boca Raton, Fla.), pp. 57–123.
2. Bishop, J. M. (1991) *Cell* 64:235–248.
3. Vogelstein, B. & Kinzler, K. W. (1991) *Trends Genet.* 9:138–141.
4. Knudson, A. G. (1993) *Proc. Natl. Acad. Sci. USA* 90:10914–10921.
5. Levine, A. J. (1993) *Annu. Rev. Biochem.* 62:623–651.
6. Hartwell, L. H. & Kastan, M. B. (1994) *Science* 266:1821–1828.
7. Fisher, P. B., Goldstein, N. I. & Weinstein, I. B. (1979) *Cancer Res.* 39:3051–3057.
8. Fisher, P. B., Dorsch-Hasler, K., Weinstein, I. B. & Ginsberg, H. S. (1979) *Nature* 281:591–594.
9. Fisher, P. B., Bozzone, J. H. & Weinstein, I. B. (1979) *Cell* 18:695–705.
10. Babiss, P. B., Zimmer, S. G. & Fisher, P. B. (1985) *Science* 228:1099–1101.
11. Duigou, G. J., Babiss, L. E., Iman, D. S., Shay J. W. & Fisher, P. B. (1990) *Mol. Cell. Biol.* 10:2027–2034.
12. Duigou, G. J., Su, Z. -z., Babiss, L. E., Driscoll, B., Fung, Y. -K. T. & Fisher, P. B. (1991) *Oncogene* 6:1813–1824.
13. Reddy, P. G., Su, Z. -z. & Fisher, P. B. (1993) in *Chromosome and Genetic Analysis, Methods in Molecular Genetics*, ed. Adolph, K. W. (Academic, Orlando, Fla.), Vol. 1, pp. 68–102.

14. Su, Z. -z., Shen, R., O'Brian, C. A. & Fisher, P. B. (1994) *Oncogene* 9:1123–1132.
15. Fidler, I. J. (1990) *Cancer Res.* 50:6130–6138.
16. Liotta, L. A., Steeg, P. G. & Stetler-Stevenson, W. G. (1991) *Cell* 64:327–336.
17. Fidler, I. J. (1995) *J. Natl. Cancer Inst.* 87:1588–1592.
18. Fisher, P. B., Babiss, L. E., Weinstein, I. B. & Ginsberg, H. S. (1982) *Proc. Natl. Acad. Sci. USA* 79: 3527–3531.
19. Boylon, J. F., Jackson, J., Steiner, M., Shih, T. Y., Duigou, G. J., Roszman, T., Fisher, P. B. & Zimmer, S. G. (1990) *Anticancer Res.* 10:717–724.
20. Boylon, J. F., Shih, T. Y., Fisher, P. B. & Zimmer, S. G. (1992) *Mol. Carcinog.* 3:309–318.
21. Su, Z. -z., Austin, V. N., Zimmer, S. G. & Fisher, P. B. (1993) *Oncogene* 8:309–318.
22. Su, Z. -z., Yemul, S., Estabrook, A., Friedman, R. M., Zimmer, S. G. & Fisher, P. B. (1995) *Intl. J. Oncology* 7:1279–1284.
23. Jiang, H. & Fisher, P. B. (1993) *Mol. Cell. Different.* 1:285–299.
24. Zhan, Q., Lord, K. A., Alamo, I., Jr., Hollander, M. C., Carrier, F., Ron, D., Kohn, K. W., Hoffman, B., Liebermann, D. A. & Fornace, A. J., Jr. (1994) *Mol. Cell. Biol.* 14:2361–2371.
25. Jiang, H., Lin, J., Su, Z. -z., Kerbel, R. S., Herlyn, M., Weissman, R. B., Welch, D. R. & Fisher, P. B. (1995) *Oncogene* 10:1855–1864.
26. Jiang, H., Lin, J. J., Su, Z. -z., Goldstein, N. I. & Fisher, P. B. (1995) *Oncogene* 11:2477–2486.
27. Su, Z. -z., Leon, J. A., Jiang, H., Austin, V. A., Zimmer, S. G. & Fisher, P. B. (1993) *Cancer Res.* 53: 1929–1938.
28. Jiang, H., Su, Z. -z., Datta, S., Guarini, L., Waxman, S. & Fisher, P. B.(1992) *Intl. J. Oncol.* 1:227–239.
29. Jiang, H., Su, Z. -z., Lin, J. J., Goldstein, N. I., Young, C. S. H. & Fisher, P. B. (1996) *Proc. Natl. Acad. Sci. USA* 93:9160–9165.
30. Su, Z. -z., Grunberger, D. & Fisher, P. B. (1991). *Mol. Carcinog* 4:231–242.
31. Fisher, P. B., Weinstein, I. B., Eisenberg, D. & Ginsberg, H. S. (1978) *Proc. Natl. Acad. Sci. USA* 75:2311–2314.
32. Fornace, A. J., Jr., Alamo, I., Jr. & Hollander, M. C. (1988) *Proc. Natl. Acad. Sci. USA* 85:8800–8804.
33. Lord, K. A., Hoffman-Liebermann, B. & Liebermann, D. A. (1990) *Oncogene* 5:387–396.
34. Lord, K. A., Hoffman-Liebermann, B. & Liebermann, D. A. (1990) *Nucleic Acids Res.* 18:2823.
35. Chou, J. & Roizman, B. (1994) *Proc. Natl. Acad. Sci. USA* 91:5247–5251.
36. He, B., Chou, J., Liebermann, D. A., Hoffman, B. & Roizman, B. (1996) *J. Virol.* 70:84–90.
37. Vairapandi, M., Balliet, A. G., Fornace, A. J., Jr., Hoffman, B. & Liebermann, D. A. (1996) *Oncogene* 11: 2579–2594.
38. Loeb, L. A. (1994) *Cancer Res.* 54:5059–5063.

Second Series of Experiments
Development of Biosensor Systems to Efficiently and Selectively Detect Agents Inducing and Inhibiting DNA Damage Pathways, Oncogenic Transformation and Cancer Progression The PEG-3 gene is induced in a p53-independent manner in E11, CREF and human melanoma cells following treatment with DNA damaging agents, such as gamma irradiation (1 and unpublished data). Nuclear run-on assays, that measure rates of gene transcription, indicate that induction of PEG-3 by DNA damage and expression of PEG-3 in cells displaying the progression phenotype (such as E11-NMT and CREF cells transformed by various oncogenes) involves elevated transcription of this gene (1). This data supports the hypothesis that the appropriate transcriptional regulating factors are inducible following DNA damage in cells and they are constitutively expressed in progressed cells. Since transcription of genes involves elements located in the promoter region of genes, current data supports the hypothesis that the promoter region of the PEG-3 gene is directly regulated as a function of genotoxic stress, oncogenic transformation and during cancer progression. This finding will be exploited by isolating the promoter of PEG-3 (as described below), linking this DNA sequence to a β-galactosidase (β-gal) reporter gene and constructing cells that either constitutively express this reporter gene (E11-NMT-β-gal, CREF-ras-β-gal and CREF-src-β-gal) or cells that contain a DNA damage inducible reporter gene (E11-β-gal and CREF-β-gal). The E11-NMT-β-gal, CREF-ras-β-gal and CREF-src-β-gal constructs can be used as sensitive and selective monitors for agents that can inhibit DNA damage and repair pathways, cancer progression and oncogene mediated transformation. Conversely, the E11-β-gal and CREF-β-gal cell constructs can be used as sensitive and selective monitors for conditions and agents that induce DNA damage and repair pathways and may also induce the progression and oncogene-mediated transformed phenotypes. The ability to modify β-gal expression, as a function of activation or suppression of the PEG-3 promoter region or factors that interact with the promoter region, can easily be assessed using the appropriate substrate (5-bromo-4-chloro-3-indolyl-beta-D-galacto-pyranoside (X-gal) that is converted into a final product (5-bromo-4-chloro-3-indole) that has a blue color. E11-NMT-β-gal cells will normally stain blue following addition of the appropriate substrate. However, should expression from the PEG-3 promoter region be suppressed this will extinguish β-gal expression thereby resulting in a loss of blue staining following addition of the substrate. These rapid, efficient and selective biosensor systems can easily be formatted for the screening of an infinite number of compounds with potential cancer progression suppression, oncogene suppression and DNA damage inhibiting functions. E11-β-gal and CREF-β-gal cells will normally not stain blue following addition of the substrate. However, should the promoter region be activated, following induction of appropriate DNA damage and repair pathways or expression of specific oncogenes, the β-gal gene will be activated resulting in a blue stain following addition of the substrate. These rapid, efficient and selective biosensor systems can easily be formatted for the screening of an infinite number of compounds with potential cancer progression, oncogene transformation and DNA damage inducing properties. These model systems will prove valuable in identifying agents and elucidating pathways involved in cancer progression, oncogenic transformation and DNA damage induction and repair. This should lead to the development of novel therapeutics to prevent genomic damage and instability, thereby inhibiting cancer progression and oncogene mediated-transformation, and the identification of new classes of agents that can prevent DNA damage and enhance DNA damage repair.

Identification and Characterization of the Promoter Region of PEG-3, Cis-Acting Regulatory Elements of the PEG-3 Promoter and Trans-Acting Regulatory Elements That Activate (or Repress) PEG-3 Expression.

Overview.

Nuclear run-on studies indicate that the PEG-3 gene is constitutively transcribed in progressed E11-NMT, CREF cells treated with methyl methanesulfonate (MMS) or gamma irradiation and in CREF-cells transformed by various oncogenes, such as Ha-ras and v-src. Studies will, therefore, be conducted to (i) clone the 5'-flanking region of the PEG-3 gene and analyze its activity in E11 and E11-NMT, CREF and DNA damaged CREF and CREF cells transformed by various oncogenes; (ii) identify cis-acting regulatory elements in the promoter region of the PEG-3 gene which are responsible for the differential induction of expression in the different cell types and under different experimental conditions; and (iii) identify and characterize trans-acting regulatory elements which activate (or repress) expression of the PEG-3 gene.

To elucidate the mechanism underlying the transcriptional regulation of the PEG-3 gene the 5'-flanking region of this gene will be analyzed. This will be important for studies determining regulatory control of the PEG-3 gene including autoregulation, developmental regulation, tissue and cell type specific expression, DNA damage induction and differential expression in cells displaying a progressed cancer phenotype. The isolation of the promoter region will also be necessary for creating a biosensor model for monitoring and analyzing factors involved in mediating DNA damage and repair and oncogenic transformation and cancer progression. Once the appropriate sequence of the PEG-3 gene regulating the initiation of transcription has been identified, studies can be conducted to determine relevant trans-acting regulatory factors that bind to specific cis-acting regulatory elements and activate or repress the expression of the PEG-3 gene. These molecules may provide important clues for understanding the pathways governing DNA damage and repair mechanisms underlying cancer progression. Ultimately, such an understanding may uncover important targets for directly modifying and intervening in these phenotypes and processes.

Cloning the Promoter Region of the PEG-3 Gene and Testing its Function.

To identify the promoter region of PEG-3 we have used a human PromoterFinder™ DNA Walking Kit (Clontech) (2,3), This PCR-based method facilitates the cloning of unknown genomic DNA sequences adjacent to a known cDNA sequence. Using this approach an ~2 kb fragment of PEG-3 that may contain the promoter region of this gene has been isolated. The putative 5' flanking-region of PEG-3 has been subcloned into the pBluescript vector and sequenced by the Sanger dideoxynucleotide procedure. To verify the transcriptional start site deduced from the cDNA, primer extension analysis will be performed (4). In case of the identification of multiple putative ATG or start sites RNase protection assays will be performed using oligonucleotides spanning the 5' end of the PEG-3 cDNA sequence (4,5). To define the boundary of the PEG-3 promoter region, a heterologous expression system containing a bacterial chloramphenicol acetyltransferase (CAT) or luciferase gene without promoter or enhancer will be employed (4,5,6). Putative promoter inserts of varying sizes will be subcloned into a CAT expression vector (6,7). Internal deletion constructs will be generated by taking advantage of either internal restriction sites or by partial digestion of internal sites if these sites are not unique. These constructs will be transfected into E11-NMT cells that display high levels of PEG-3 expression. The CAT construct with minimal 5'-flanking region showing the highest degree of expression will be identified as the PEG-3 gene promoter.

The functionality of the PEG-3 promoter will be determined in E11-NMT, CREF cells treated with MMS and gamma irradiation and CREF cells transformed by the Ha-ras and v-src oncogenes. Various CAT constructs will be transfected into these cell lines by the lipofectin method or electroporation (Gene Pulser, Bio-Rad) as previously described (4,8). To correct for DNA uptake and cell number used for each transfection experiment, the CAT constructs will be cotransfected with plasmids containing bacterial β-gal gene under the control of an Rous sarcoma virus (RSV) promoter. The CAT and β-galactosidase enzymatic activities will be determined using standard protocols (4,6, 7). Minimal 5'-flanking region displaying the highest CAT activity will be identified as the promoter region for that tissue cell type or experimental condition. If no induction of CAT activity is apparent, further subcloning and screening of cosmid or phage clones would be performed until a PEG-3 promoter of sufficient length to mediate CAT induction in E11-NMT, CREF cells treated with MMS and gamma irradiation and CREF cells transformed by the Ha-ras and v-src oncogenes is obtained.

Once the promoter of PEG-3 is identified it will be subcloned into a vector adjacent to a bacterial β-gal gene, PEG-3-Prom-β-gal fusion (4). This construct will allow activation of the β-gal gene as a function of transcription from the PEG-3 promoter. The vector construct will also contain a bacterial antibiotic resistance gene, such as the neomycin or hygromycin gene, that will permit selection of cells containing the PEG-3-Prom-β-gal fusion. This vector will be transfected into E11, E11-NMT, CREF and CREF cells transformed by Ha-ras and v-src and antibiotic resistant colonies will be selected in G418 (neomycin gene) or hygromycin (hygromycin gene) as previously described (1,8,9). Antibiotic resistant colonies will be isolated and maintained as independent cell lines. Clones constitutively expressing the PEG-3-Prom-β-gal gene (E11-NMT and CREF cells transformed by the Ha-ras and v-src oncogenes) will be identified by growth in the appropriate substrate resulting in a blue color. Similarly, clones containing an inducible PEG-3-Prom-β-gal gene (E11 and CREF cells) will be identified by treating cells with MMS or gamma irradiation, incubation in the appropriate substrate and identifying clones that develop a blue color. Clones displaying the appropriate properties will be further characterized by Southern blotting (DNA organization) and Northern blotting (RNA expression). Clones with constitutive or inducible β-gal expression will then be tested for alteration in expression as a function of culture conditions (low serum, high cell density, etc.), exposure to various DNA damaging agents, incubation in agents known to specifically inhibit or enhance oncogene and progression phenotypes (such as caffeic acid phenethyl ester, phorbol ester tumor promoters, farnesyl transferase inhibitors, etc.), chemotherapeutic agents, viral infection, etc. These studies will provide useful baseline information as to the potential use of the specific constructs as biosensor monitors for agents capable of modifying cancer progression, oncogenic transformation and DNA damage and repair pathways.

Identifying Cis-acting Elements in the PEG-3 Promoter Responsible For Expression in Progressed Cancer Cells, Oncogene Transformed CREF Cells and DNA Damaged Cells.

Once a functional PEG-3 promoter has been identified studies will be conducted to locate cis-acting elements responsible for expression of PEG-3 in E11-NMT, oncogene transformed CREF (Ha-ras and v-src) and MMS treated CREF cells. To identify cis-acting DNA sequences, the DNA fragment displaying maximal promoter function in a transient transfection assay in E11-NMT, oncogene transformed CREF and MMS treated CREF cells will be sequenced. Potential regulatory elements will be defined by comparison to previously characterized transcriptional motifs. The importance of these sequences in regulating PEG-3 expression will be determined by introducing point mutations in a specific cis element into the promoter region using previously described site-specific mutagenesis techniques (4,9–12) or with recently described PCR-based strategies, i.e., ExSite™ PCR-based site-directed mutagenesis kit and the Chameleon™, double-stranded site-directed mutagenesis kit (Stratagene, Calif.). The mutated promoter constructs will be cloned into CAT expression vectors and tested for their effects on the promoter function by transfecting into different cell types displaying CAT activity. If increased detection sensitivity is required, the various promoter region mutants will be subcloned into a luciferase reporter construct (7).

Identifying Trans-acting Nuclear Proteins That Mediate Transcriptional Enhancing Activity of the PEG-3 in Progressed Cancer Cells, Oncogene Transformed CREF Cells and in DNA Damaged CREF Cells.

The current view on regulation of eukaryotic gene expression suggests that trans-acting proteins bind to specific sites within cis-elements of a promoter region resulting in transcriptional activation (13,14). Experiments will be performed to identify trans-acting factors (nuclear proteins) and determine where these factors interact with cis-regulatory elements. To achieve this goal, two types of studies will be performed, one involving gel retardation (gel shift) assays (4,15–17) and the second involving DNase-I footprinting (methylation interference) assays (4).

Gel shift assays will be used to analyze the interactions between cis-acting elements in the PEG-3 promoter and trans-acting factors in mediating transcriptional control (4,15–17). To begin to identify the trans-acting factors, different non-labeled DNAs (including TATA, CAT, TRE, Sp-I binding site, NFKB, CREB, TRE, TBP, etc.) can be used as competitors in the gel shift assay to determine the relationship between the trans-acting factors and other previously identified transcriptional regulators. It is possible that the trans-acting factors regulating transcriptional control of the PEG-3 gene may be novel. To identify these factors extracts will be purified from E11-NMT cells by two cycles of heparin-Sepharose column chromatography, two cycles of DNA affinity chromatography and separation on SDS-polyacrylamide gels (18,19). Proteins displaying appropriate activity using gel shift assays will be digested in situ with trypsin, the peptides separated by HPLC and the peptides sequenced (20). Peptide sequences will be used to synthesize degenerate primers and RT-PCR will be used to identify putative genes encoding the trans-acting factor. These partial sequences will be used with cDNA library screening approaches and the RACE procedure, if necessary, to identify full-length cDNAs encoding the trans-acting factors (21–23). Once identified, the role of the trans-acting factors in eliciting PEG-3 induction following DNA damage in CREF and constitutive expression in E11-NMT, CREF-ras and CREF-src cells will be determined.

The functionality of positive and negative trans-acting factors will be determined by transiently and stably expressing these genes in E11 and E11-NMT cells to determine effects on the progression phenotype, CREF and CREF-ras and CREF-src cells to determine effects on oncogene transformation and in CREF and MMS treated CREF cells to determine the effects of DNA damage on PEG-3 induction. Positive effects would be indicated if overexpressing a positive trans-acting factor facilitates progression, expression of the oncogenic phenotype and/or a DNA-damage inducible response, whereas overexpressing a negative trans-acting factor inhibits progression, oncogene transformation and/or a DNA-damage inducible response.

Antisense approaches will be used to determine if blocking the expression of positive or negative trans-acting factors can directly modify progression, oncogenic transformation and/or DNA damage repair pathways. A direct effect of positive trans-acting factors in affecting cellular phenotype would be suggested if antisense inhibition of the positive acting factor partially or completely inhibits the progression and oncogene transformation phenotypes and/or DNA-damage and repair pathways. Conversely, a direct effect of negative trans-acting factors in inhibiting expression of PEG-3 and progression, oncogene transformation and/or DNA-damage and repair pathways would be suggested if antisense inhibition of the negative factor facilitates PEG-3 expression and the progression, oncogene transformation and/or DNA-damage inducible response pathways. Depending on the results obtained, cis-element knockouts could be used to further define the role of these elements in regulating PEG-3 expression.

For DNase-I footprinting assays, nuclear extracts from E11, E11-NMT, CREF, CREF-ras, CREF-src and MMS treated CREF cells will be prepared and DNase-I footprinting assays will be performed as described (4,6). The differential protection between nuclear extracts from E11-NMT and E11 and MMS treated CREF, CREF-ras and CREF-src cells will provide relevant information concerning the involvement of trans-acting factors in activation and the location of specific sequences in the cis-regulatory elements of the PEG-3 promoter mediating this activation. If differential protection is not detected using this approach, the sensitivity of the procedure can be improved by using different sized DNA fragments from the PEG-3 promoter region or by using partially purified nuclear extracts (4,6).

The studies briefly described above will result in the identification and cloning of the PEG-3 promoter region, the identification of cis-acting regulatory elements in the PEG-3 promoter and the identification of trans-acting regulatory elements that activate (or repress) expression of the PEG-3 gene in unprogressed and progressed cancer cells, untransformed and oncogene transformed cells and undamaged and DNA damaged cells. Experiments will also determine if cells containing a PEG-3-Prom-β-gal fusion gene can be used as a biosensor monitoring system for the progression, oncogene transformation and DNA damage and repair pathways. These reagents will be useful in defining the mechanism underlying the differential expression of PEG-3 in progressed and oncogene transformed cancer cells and during induction of DNA damage and repair. This information should prove valuable in designing approaches for selectively inhibiting PEG-3 expression, and therefore potentially modifying cancer and DNA damage resulting from treatment with physical and chemical carcinogens.

Identifying a Human Homologue of the Rat PEG-3 Gene and Defining the Genomic Structure and the Pattern of Expression of the PEG-3 Gene.

Figure 9:
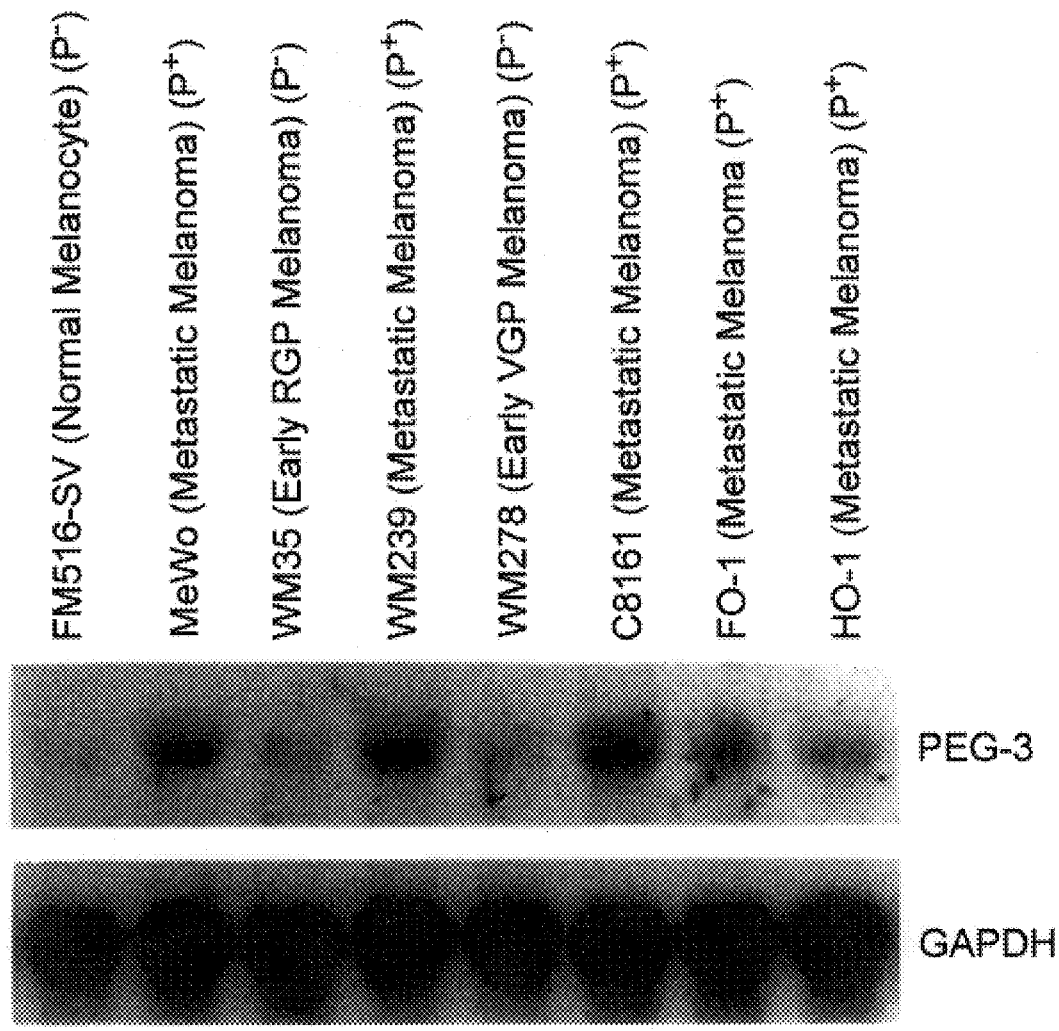
FIG. 9: Autoradiogram showing PEG-3 expression in normal human melanocyte and melanoma cell lines. Fifteen μg of cellular RNA isolated from the indicated cell types, were electrophoresed, transferred to nylon membranes and hybridized with an ~700 bp 3' region of the PEG-3 gene (top) and then stripped and probed with GAPDH (bottom). Cell types include: FM516-SV, normal human melanocyte immortalized with the SV40 T-antigen; MeWo, WM239, C8161, FO-1 and Ho-1, metastatic human melanoma; WM35, early radial growth phase (RGP) primary human melanoma; and WM278, early vertical growth phase (VGP) primary human melanoma.
Figure 10:
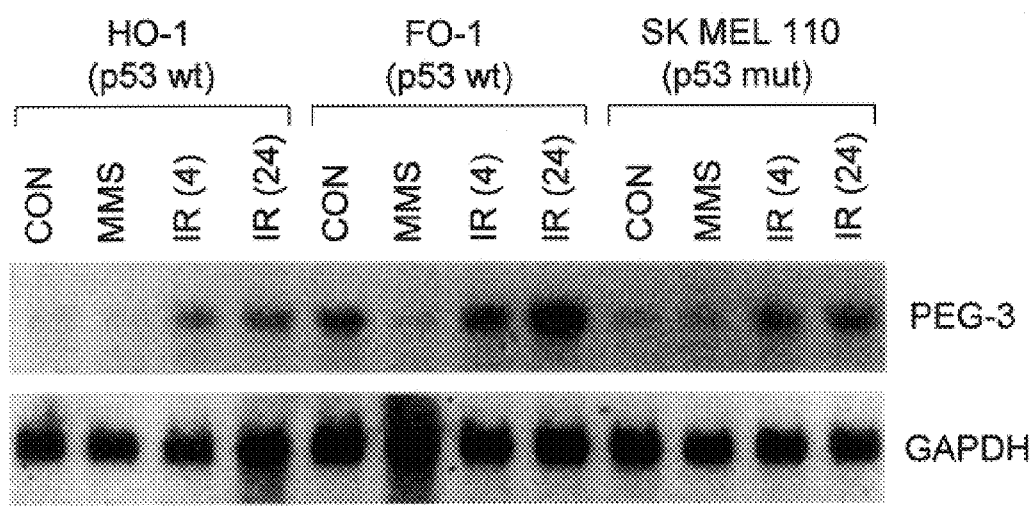
FIG. 10: Autoradiogram showing the effect of treatment with DNA damaging agents on PEG-3 expression in human melanoma cells. The indicated cell type was exposed to methyl methanesulfonate (MMS) (100 μg/ml for 2 hr and then grown in medium lacking MMS for 2 hr) or gamma irradiation (JR) (10 gy and cells were grown for 4 or 24 hr in medium) prior to RNA isolation. Fifteen μg of cellular RNA isolated from the indicated cell types and conditions, were electrophoresed, transferred to nylon membranes and hybridized with an ~700 bp 3' region of the PEG-3 gene (top) and then stripped and probed with GAPDH (bottom). HO-1 and FO-1 cells express wild-type p53 protein (p53 wt) and SK MEL 110 expresses a mutant p53 (p53 mut).

Probing Northern blots containing total cytoplasmic RNA from human melanoma cells displaying different stages of cancer progression, i.e., normal melanocytes, early radial growth phase (RGP) primary human melanoma, early and late vertical growth phase (VGP) primary human melanoma and metastatic human melanoma cells, indicate that PEG-3 expression is highest in more advanced metastatic human melanoma (FIG. 9). Treatment of human melanoma cells, containing a wild-type p53 or a mutant p53 gene, with gamma irradiation results in enhanced PEG-3 expression (FIG. 10). These results suggest that a human homologue of rat PEG-3 is present in human melanoma cells and induction of this gene correlates with cancer progression and DNA damage. Human genomic clones of PEG-3 will be isolated by screening a human melanoma genomic lambda library with sequences corresponding to the carboxyl terminus of PEG-3 (that is significantly different from gadd34 and MyD116) and by PCR based genomic DNA amplification procedures (4) The isolated positive clones will be characterized by restriction mapping, and suitable restriction fragments will be subcloned into the pBluescript vector (Strategene) (24). Exons will be identified by hybridization of the genomic fragments of a panel of PEG-3 clones and subsequent comparison of the genomic DNA sequences to that of the cDNA (25,26). A given intron/exon boundary will be indicated when the sequence from the genomic clones diverges from that of the cDNA. The size of each intron will be estimated by restriction mapping (4,25,26). An alternative approach for identifying intron/exon junctions will use a set of different restriction endonucleases to digest the human genomic DNAs. Restriction fragments resulting from this digestion will be ligated with appropriate cDNA sequences and the other specific primer to the linker sequences. By using a panel of PEG-3 cDNA oligonucleotides as primers, PCR products will be generated, that contain most, if not all, uncloned genomic DNA adjacent to PEG-3 exon sequence (25,26). The PCR products obtained will be cloned and sequenced to deduce the intron/exon boundaries of the PEG-3 gene.

Having a human genomic clone of PEG-3 will permit a direct determination of possible structural alterations and mutations in the PEG-3 gene (or its promoter) in human cancers. Tumor and normal tissue samples will be collected in pairs from patients. Genomic DNAs will be extracted from these samples (4) and analyzed by Southern blotting with appropriate restriction enzymes for possible heterozygous deletions, homozygous deletions, insertions and/or rearrangements (27,28). To detect point mutations, pairs of oligonucleotide primers for the exons will be designed for single-strand conformation polymorphism (SSCP) analysis (27,28).

The studies briefly described above will delineate the structure of the human PEG-3 gene and identify structural changes in the PEG-3 gene (or its promoter) in cancer versus normal tissue. A high frequency of structural alterations and mutations, especially those that can potentially alter the expression and functionality of the PEG-3 protein, in normal versus cancer tissue or in early versus late stage cancers, would suggest that these alterations in the PEG-3 gene may be involved in initiation and/or progression of this cancer. Additionally, experiments to determine the state of methylation of the PEG-3 promoter region should prove informative (29).

If specific mutations in PEG-3 (or its promoter) are found to correlate with cancer development and/or evolution, the effect of such mutations on the in vitro and in vivo biological properties of cells can be determined. Mutations will be introduced that alter the normal PEG-3 gene to generate a progression specific PEG-3 gene product. To achieve these goals, the PEG-3 gene will be mutagenized at specific sites, using the ExSite™ PCR-based site-directed mutagenesis kit and the Chameleon™ double-stranded site-directed mutagenesis kit (Stratagene, La Jolla, Calif.). We have documented experience in introducing mutations in defined regions of the adenovirus genome and characterizing these genetic changes (9–12). Once identified and characterized, mutant constructs of the PEG-3 gene will be transfected into appropriate target cells to determine the effects of specific mutations in PEG-3 on cellular phenotype.

REFERENCES FOR THE SECOND SERIES OF EXPERIEMENTS

1. Su Z-z, Shi Y & Fisher P B (1994) *Proc Natl Acad Sci USA*, in submission.
2. Siebert P, Chen S & Kellogg D (1995) *CLONTECHniques, X* (2)L: 1–3.
3. Siebert P, Chenchik A, Kellogg D E, Lukyanov K A & Lukyanov S A (1995) *Nucleic Acids Res,* 23: 1087–1088.
4. Sambrook J, Fritsch E F & Maniatis T. In: *Molecular Cloning: A Laboratory Manual,* 2nd edition, Cold Spring Harbor Laboratories Press, Cold Spring Harbor, N.Y., 1989.
5. Duigou G J, Su Z-z, Babiss L E, Driscoll B, Fung Y-K T & Fisher P B. (1991) *Oncogene* 6:1813–1824.
6. Shen R, Goswami S K, Mascareno E, Kumar A & Siddiqui M A Q. (1991) *Mol Cell Biol* 11: 1676–1685.
7. Fisher A L, Ohsako S & Caudy M. (1996) *Mol Cell Biol* 16:2670–2677.
8. Jiang H, Lin J J, Su Z-z, Goldstein N I & Fisher P B (1995) *Oncogene* 11:2477–2486.
9. Babiss L E, Fisher P B & Ginsberg H S. (1984) *J Virol* 49:731–740.
10. Babiss L E, Fisher P B & Ginsberg H S. (1984) *J Virol* 52: 389–395.
11. Herbst R S, Hermo H Jr, Fisher P B & Babiss L E. (1988) *J Virol* 62:4634–4643.
12. Su Z-z, Shen R, Young C S H & Fisher P B. (1993) *Mol Carcinog* 8:155–166.
13. Maniatis T, Goodbourn S & Fischer A. (1987) *Science* 236:1237–1244.
14. Ptashne M. (1988) *Nature* 335:683–689.
15. Su Z-z, Yemul S, Stein C A & Fisher P B. (1995) *Oncogene* 10:2037–2049.
16. Jiang H, Lin J, Young S-m, Goldstein N I, Waxman S, Davila V, Chellappan S P & Fisher P B. (1995) *Oncogene* 11:1179–1189.
17. Su Z-z, Shen R. O'Brian C A & Fisher P B. (1994) *Oncogene* 9:1123–1132.
18. Kamat J P, Basu K, Satyamoorthy L, Showe L & Howe C C (1995) *Mol Rep Dev* 41:8–15.
19. Basu A, Dong B, Krainer A R & Howe C C (1997) *Mol Cell Biol* 17:677–686.
20. Aebersold R H, Leavitt R A, Saavedra R A, Hood L E & Kent S B H (1987) *Proc Natl Acad Sci USA* 84:6970–6974.
21. Jiang H, Lin J, Su Z-z, Kerbel R S, Herlyn M, Weissman R B, Welch D R & Fisher P B. (1995) *Oncogene* 10: 1855–1864.
22. Jiang H, Lin J J, Su Z-z, Goldstein N I & Fisher P B (1995) *Oncogene* 11:2477–2486.
23. Lin J J, Jiang H & Fisher P B (1996) *Mol Cell Different* 4:317–333.
24. Reddy P G, Su Z-z & Fisher P B *Methods in Molecular Genetics,* vol. 1, K W Adolph, Ed, Academic Press, Inc, Orlando, Fla., pp 68–102, 1993.
25. Hong F D, Huang H-S, To H, Young L-J H S, Oro A, Bookstein R, Lee E Y-H P & Lee W H (1989) *Proc Natl Acad Sci USA* 86:5502–5506.
26. Sun J, Rose J B & Bird P (1995) *J Biol Chem* 270:16089–16096.
27. Puffenberger E G, Hosoda K, Washington S S, Nakao K, dewit D, Yanagisawa M and Charkravarti A. (1994) *Cell* 79:1257–1266.
28. Washimi 0, Nagatake M, Osada H, Ueda R, Koshikawa T, Seki T, Takahashi T and Takahashi T (1995) *Cancer Res* 55:514–517.
29. Babiss L E, Zimmer S G & Fisher P B (1985) *Science* 228:1099–1101.

Third Series of Experiments

Expression of PEG-3 in Human Melanoma Cells.

Studies were also performed to evaluate PEG-3 expression in human melanoma cells and to determine whether induction or increased expression occurs during DNA damage. PEG-3 is expressed de novo in advanced stage tumorigenic and metastatic human melanoma cell lines (MeWo, WM239, C8161, FO-1 and HO-1), whereas expression is reduced in immortalized normal human melanocyte (FM516-SV) and RGP (WM35) and early VGP (WM278) primary melanomas (FIG. 9). Moreover, PEG-3 expression is enhanced following exposure to gamma irradiation, but is not elevated following a similar dose of MMS (100 mg/ml) inducing PEG-3 expression in CREF cells (FIG. 10). Using a p53 mutant and p53 wild-type human melanoma cell lines, it is apparent that PEG-3 induction by gamma irradiation in human melanoma can occur by a wild-type p53 independent pathway (FIG. 10). These results indicate that the PEG-3 response is not restricted to rodent cells treated with specific DNA damaging agents, but insteiad is a more general response in mammalian cells. Furthermore, there appears to be a direct relationship between PEG-3 expression and human melanoma progression.

Clarifying the Role of PEG-3 in Human Cancer Progression.

To define the role of the PEG-3 gene in human cancer progression it will be essential to obtain a human homologue of this gene. This will be achieved by low stringency hybridization screening of a human melanoma cDNA library (1) and by PCR-based approaches using primers designed from the rat PEG-3 sequences that are highly homologous with gadd34 and MyD116 (4,5). Once a full-length PEG-3 (Hu) cDNA is obtained it will be sequenced and in vitro translated to insure production of the appropriate sized protein (3–5). This gene can then be used to define patterns of expression, by Northern blotting analysis, in normal, benign and metastatic human tumor cell lines and primary patient-derived samples (2–5). This survey will indicate the level of coordinate expression between PEG-3 and human cancer progression. Clearly, if PEG-3 is shown to be a regulator of the progression phenotype in human malignancies, a large number of interesting and important experiments could be conducted to amplify on this observation. However, these studies would not be in the current scope of this grant because of limited personnel and resources. The types of studies that could and should be conducted include: (a) production of monoclonal antibodies interacting with PEG-3 (Hu) and evaluation of these reagents for cancer diagnostic purposes; (b) cellular localization studies with PEG-3 (Hu) monoclonal antibodies to define potential targets for activity; (c) mapping the chromosomal location of PEG-3 (Hu) in the genome to determine any association between previously identified regions associated with cancer; (d) identification and characterization of the genomic structure of PEG-3 (Hu) and determining if alterations in structure correlate with cancer progression; (e) determine by nuclear run-on and mRNA degradation assays if PEG-3 (Hu) expression is controlled at a transcriptional or postranscriptional level; (f) identification and characterization, if PEG-3 expression is regulated transcriptionally, of the promoter region of PEG-3 (Hu) to define the mechanism of regulation of this gene in progressed cancer cells; (g) the identification and characterization of cis-acting elements and trans-regulating factors (nuclear proteins) regulating PEG-3 (Hu) expression; (h) defining the role of PEG-3 expression in vivo by creating knockout mice and tissue specific knockout mice; and (i) determining, using transgenic mice and the tyrosinase promoter, the role of overexpression of PEG-3 in normal melanocyte development. These studies would provide important information about a potentially exciting and novel gene with direct relevance to human cancer progression.

REFERENCES FOR THE THIRD SERIES OF EXPERIMENTS

1. Jiang, H. and P. Fisher Use of a sensitive and efficient subtraction hybridization protocol for the identification of genes differentially regulated during the induction of differentiation in human melanoma cells. *Mol Cell Different.* 1: 285–299, 1993.
2. Jiang, H., et al. The melanoma differentiation associated gene mda-6, which encodes the cyclin-dependent kinase inhibitor p21 is differentially expressed during growth, differentiation and progression in human melanoma cells. *Oncogene* 10: 1855–1864, 1995.
3. Jiang, H., et al. Subtraction hybridization identifies a novel melanoma differentiation associated gene, mda-7, modulated during human melanoma differentiation, growth and progression. *Oncogene,* 11: 2477–2486, 1995.
4. Shen, R., et al. Identification of the human prostatic carcinoma oncogene PTI-1 by rapid expression cloning and differential RNA display. *PNAS, USA* 92: 6778–6782, 1995.
5. Su, Z—Z, et al. Surface-epitope masking and expression cloning identifies the human prostate carcinoma tumor antigen gene PCTA-1 a member of the galectin gene family. *PNAS, USA,* 93:7252–7257, 1996.

Fourth Series of Experiments

The present invention is based, in part, on the identification of certain cDNA molecules that correspond to progression-associated mRNA molecules. As used herein, a progression-associated mRNA is a mRNA whose expression correlates with tumor cell progression (i.e., the level of RNA is at least 2-fold higher in progressing tumor cells). A progression-associated cDNA molecule comprises the sequence of a progression-associated mRNA (and/or a complementary sequence). Similarly, a progression-associated protein or polypeptide comprises a sequence encoded by a progression-associated mRNA, where the level of protein or polypeptide correlates with tumor cell progression (i.e., the level of protein is at least 2-fold higher in progressing tumor cells). Progression-associated sequences described herein are also called "progression elevated" genes (PEG).

Progression-Associated Polynucleotides.

Any polynucleotide that encodes a progression-associated polypeptide, or a portion or variant thereof as described herein, is encompassed by the present invention. Such polynucleotides may be single-stranded (coding or antisense) or double-stranded, and may be DNA (genomic, cDNA or synthetic) or RNA molecules. Additional non-coding sequences may, but need not, be present within a polynucleotide of the present invention, and a polynucleotide may, but need not, be linked to other molecules and/or support materials.

Progression-associated polynucleotides may be prepared using any of a variety of techniques. For example, such a polynucleotide may be amplified from human genomic DNA, from tumor cDNA or from cDNA prepared from any of a variety of tumor-derived cell lines (typically cell lines characterized by a progression phenotype), via polymerase chain reaction (PCR). For this approach, sequence-specific primers may be designed based on the sequences provided herein, and may be purchased or synthesized. An amplified portion may then be used to isolate a full length gene from a human genomic DNA library or from a tumor cDNA library, using well known techniques, as described below. Alternatively, a full length gene can be constructed from multiple PCR fragments.

cDNA molecules encoding a native progression-associated protein, or a portion thereof, may also be prepared by screening a cDNA library prepared from mRNA of a cell that is in progression, such as E11-NMT or MCF-7 cells, as described herein. Such libraries may be commercially available, or may be prepared using standard techniques (see Sambrook et al., *Molecular Cloning: A Laboratory Manual*, Cold Spring Harbor Laboratories, Cold Spring Harbor, N.Y., 1989, and references cited therein). A library may be a cDNA expression library and may, but need not, be subtracted using well known subtractive hybridization techniques.

There are many types of screens that may be employed, including any of a variety of standard hybridization methods. For initial screens, conventional subtractive hybridization techniques may be used.

A progression-associated cDNA molecule may be sequenced using well known techniques employing such enzymes as Klenow fragment of DNA polymerase I, Sequenase® (US Biochemical Corp., Cleveland Ohio) Taq polymerase (Perkin Elmer, Foster City Calif.), thermostable T7 polymerase (Amersham, Chicago, Ill.) or combinations of recombinant polymerases and proofreading exonucleases such as the ELONGASE Amplification System (Gibco BRL, Gaithersburg, Md). An automated sequencing system may be used, using instruments available from commercial suppliers such as Perkin Elmer and Pharmacia.

The sequence of a partial cDNA may be used to identify a polynucleotide sequence that encodes a full length progression-associated protein using any of a variety of standard techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequence.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequenced may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. In an embodiment, amplification is performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991), walking PCR (Parker et al., *Nucl. Acids. Res.* 19:3055–60,1991) and rapid amplification of cDNA end (RACE) procedures (see Jiang et al., *Oncogene* 10:1855–1864, 1995; Jiang et al., *Oncogene* 11:2477–2486, 1995). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. In an embodiment, searches for overlapping ESTs may be performed using well known programs (e.g., NCBI BLAST searches), and such ESTs may be used to generate a contiguous full length sequence It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

As noted above, antisense polynucleotides and portions of any of the above sequences are also contemplated by the present invention. In an embodiment, such polynucleotides may be prepared by any method known in the art, including chemical synthesis by, for example, solid phase phosphoramidite chemical synthesis. Alternatively, RNA molecules may be generated by in vitro or in vivo transcription of DNA sequences encoding a progression-associated protein, or a portion thereof, provided that the DNA is incorporated into a vector downstream of a suitable RNA polymerase promoter (such as T3, T7 or SP6). Large amounts of RNA probe may be produced by incubating labeled nucleotides with a linearized Progression Elevated Gene-3 fragment downstream of such a promoter in the presence of the appropriate RNA polymerase. Certain portions of a PEG-3 polynucleotide may be used to prepare an encoded polypeptide, as described herein. In addition, or alternatively, a portion may function as a probe (e.g., for diagnostic purposes, such as to monitor or study the progression of cancer), and may be labeled by a variety of reporter groups, such as radionuclides, fluorescent dyes and enzymes. Such portions are preferably at least 10 nucleotides in length, more preferably at least 12 nucleotides in length and still more preferably at least 15 nucleotides in length. Within certain preferred embodiments, a portion for use as a probe comprises a sequence that is unique to a PEG-3 gene. A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In an embodiment, a vector will contain an origin of replication functional in at least one organism, convenient restriction endonuclease sites and one or more selectable markers. Additional initial, terminal and/or intermediate DNA sequences that, for example, facilitate construction of readily expressed vectors may also be present. For example, regulatory elements required for expression include promoter sequences to bind RNA polymerase and transcription initiation sequences for ribosome binding. A bacterial expression vector may include a promoter such as the lac promoter and for transcription initiation the ShineDalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example, the methods described above for constructing vectors. Other elements that may be present in a vector will depend upon the desired use, and will be apparent to those of ordinary skill in the art.

For example, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

In one embodiment, a rat PEG-3 sequence is cloned in the EcoRI site of a pZeoSV vector. The resulting plasmid, designated pPEG-3, was deposited on Mar. 6, 1997 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. The plasmid, pPEG-3, was accorded ATCC Accession Number 97911.

Vectors as described herein may be transfected into a suitable host cell, such as a mammalian cell, by methods well-known in the art. Such methods include calcium phosphate precipitation, electroporation and microinjection.

Progression-Associated Polypeptides.

Polypeptides within the scope of the present invention comprise at least a portion of a progression-associated protein or variant thereof, where the portion is immunologically and/or biologically active. A polypeptide may further comprise additional sequences, which may or may not be derived from a native progression-associated protein. Such sequences may (but need not) possess immunogenic or antigenic properties and/or a biological activity.

As used herein, immunologically active polypeptides include, but are not limited to, a polypeptide that is recognized (i.e., specifically bound) by a B-cell and/or T-cell surface antigen receptor. In an embodiment, immunological activity may be assessed using well known techniques, such as those summarized in Paul, *Fundamental Immunology*, 3rd ed., 243–247 (Raven Press, 1993) and references cited therein. Such techniques include screening polypeptides derived from the native polypeptide for the ability to react with antigen-specific antisera and/or T-cell lines or clones, which may be prepared using well known techniques. An immunologically active portion of a progression-associated protein reacts with such antisera and/or T-cells at a level that is not substantially lower than the reactivity of the full length polypeptide (e.g., in an ELISA and/or T-cell reactivity assay). In an embodiment, such screens may be performed using methods well known to those of ordinary skill in the art, such as those described in Harlow and Lane, *Antibodies: A Laboratory Manual*, Cold Spring Harbor Laboratory, 1988. B-cell and T-cell epitopes may also be predicted via computer analysis.

Biologically active polypeptides include, but are not limited to, polypeptides that possesses one or more structural, regulatory and/or biochemical functions of the native progression-associated protein. For example, a polypeptide may induce progression in cells at levels comparable to the level of native protein. Appropriate assays designed to evaluate the activity may then be designed based on existing assays known in the art, and on the assays provided herein.

As noted above, polypeptides may comprise one or more portions of a variant of an endogenous protein, where the portion is immunologically and/or biologically active (i.e., the portion exhibits one or more antigenic, immunogenic and/or biological properties characteristic of the full length protein). Preferably, such a portion is at least as active as the full length protein within one or more assays to detect such properties. A polypeptide variant as used herein includes, but is not limited to, a polypeptide that differs from a native protein in substitutions, insertions, deletions and/or amino acid modifications, such that the antigenic, immunogenic and/or biological properties of the native protein are not substantially diminished. In an emboidment, a variant retains at least 80% sequence identity to a native sequence. In another emboidment, a variant retains at least 90% sequence identity to a native sequence. In another emboidment, a variant retains at least 95% sequence identity to a native sequence. Guidance in determining which and how many amino acid residues may be substituted, inserted, deleted and/or modified without diminishing immunological and/or biological activity may be found using any of a variety of computer programs known in the art, such as DNAStar software. In an embodiment, properties of a variant may be evaluated by assaying the reactivity of the variant with antisera and/or T-cells as described above and/or evaluating a biological property characteristic of the native protein.

In an embodiment, a variant contains conservative substitutions. A conservative substitution comprises a substitution wherein an amino acid is substituted for another amino acid that has similar properties, such that one skilled in the art of peptide chemistry would expect the secondary structure and hydropathic nature of the polypeptide to be substantially unchanged. In an embodiment, amino acid substitutions may be made on the basis of similarity on polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes.

Variants within the scope of this invention also include polypeptides in which the primary amino acid structure of a native protein is modified by forming covalent or aggregative conjugates with other polypeptides or chemical moieties such as glycosyl groups, lipids, phosphate, acetyl groups and the like. Covalent derivatives may be prepared, for example, by linking particular functional groups to amino acid side chains or at the N- or C-termini.

The present invention also includes polypeptides with or without associated native-pattern glycosylation. Polypeptides expressed in yeast or mammalian expression systems may be similar to or slightly different in molecular weight and glycosylation pattern than the native molecules, depending upon the expression system. Expression of DNA in bacteria such as $E.\ coli$ provides non-glycosylated molecules. In an embodiment, N-glycosylation sites of eukaryotic proteins are characterized by the amino acid triplet Asn-$A_1$-Z, where $A_1$ is any amino acid except Pro, and Z is Ser or Thr. Variants having inactivated N-glycosylation sites can be produced by techniques known to those of ordinary skill in the art, such as oligonucleotide synthesis and ligation or site-specific mutagenesis techniques, and are within the scope of this invention. Alternatively, N-linked glycosylation sites can be added to a polypeptide.

As noted above, polypeptides may further comprise sequences that are not related to an endogenous progression-associated protein. For example, an N-terminal signal (or leader) sequence may be present, which co-translationally or post-translationally directs transfer of the polypeptide from its site of synthesis to a site inside or outside of the cell membrane or wall (e.g., the yeast α-factor leader). The polypeptide may also comprise a linker or other sequence for ease of synthesis, purification or identification of the polypeptide (e.g., poly-His or hemagglutinin), or to enhance binding of the polypeptide to a solid support. Fusion proteins capped with such peptides may also be resistant to intracellular degradation in $E.\ coli$. Protein fusions encompassed by this invention further include, for example, polypeptides conjugated to an immunoglobulin Fc region or a leucine zipper domain as described, for example, in published PCT Application Wo 94/10308. Polypeptides comprising leucine zippers may, for example, be oligomeric, dimeric or trimeric. All of the above protein fusions may be prepared by chemical linkage or as fusion proteins, as described below.

Also included within the present invention are alleles of a progression-associated protein. Alleles are alternative forms of a native protein resulting from one or more genetic mutations (which may be amino acid deletions, additions and/or substitutions), resulting in an altered mRNA. Allelic proteins may differ in sequence, but overall structure and function are substantially similar.

Progression-associated polypeptides, variants and portions thereof may be prepared from nucleic acid encoding the desired polypeptide using well known techniques. To prepare an endogenous protein, an isolated cDNA may be used. To prepare a variant polypeptide, standard mutagenesis techniques, such as oligonucleotide-directed site-specific mutagenesis may be used, and sections of the DNA sequence may be removed to permit preparation of truncated polypeptides. Briefly, host cells of a vector system containing a PEG-3 sequence under suitable conditions permitting production of the polypeptide may be grown, and the polypeptide so produced may then be recovered.

Any of a variety of expression vectors known to those of ordinary skill in the art may be employed to express recombinant polypeptides of this invention. Expression may be achieved in any appropriate host cell that has been transformed or transfected with an expression vector containing a DNA sequence that encodes a recombinant polypeptide. Suitable host cells include prokaryotes, yeast, insect cells and animal cells. In an embodiment, the host cells employed are $E.\ coli$, yeast, primary mammalian cells or a mammalian cell line such as COS, Vero, HeLa, fibroblast NIH3T3, CHO, Ltk$^-$ or CV1. Following expression, supernatants from host/vector systems which secrete recombinant protein or polypeptide into culture media may be first concentrated using a commercially available filter. Following concentration, the concentrate may be applied to a suitable purification matrix such as an affinity matrix or an ion exchange resin. One or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Various modified solid phase techniques are also available (e.g., the method of Roberge et al., Science 269:202–204, 1995). Equipment for automated synthesis of polypeptides is commercially available from suppliers such as Applied BioSystems, Inc. (Foster City, Calif.), and may be operated according to the manufacturer's instructions.

In an embodiment, an isolated polypeptide or polynucleotide is one that is removed from its original environment. For example, a naturally-occurring protein is isolated if it is separated from some or all of the coexisting materials in the natural system. A polynucleotide is considered to be isolated if, for example, it is cloned into a vector that is not a part of the natural environment.

Antibodies and Fragments Thereof.

The present invention further provides antibodies, and antigen-binding fragments thereof, that specifically bind to a progression-associated protein. In an embodiment, an antibody, or antigen-binding fragment specifically binds to a progression-associated protein if it reacts at a detectable level (within, for example, an ELISA) with a progression-associated protein or a portion or variant thereof, and does not react detectably with unrelated proteins. In certain embodiments, antibodies that inhibit PEG-3 induced progression are used.

Antibodies may be prepared by any of a variety of techniques known to those of ordinary skill in the art. See, e.g., Harlow and Lane, *Antibodies: A Laboratory Manual*, Cold Spring Harbor Laboratory, 1988. In an embodiment, antibodies can be produced by cell culture techniques, including the generation of monoclonal antibodies as described herein, or via transfection of antibody genes into suitable bacterial or mammalian cell hosts, in order to allow for the production of recombinant antibodies. In an embodiment, monoclonal antibodies may be produced by in vitro techniques known to a person of ordinary skill in the art.

Polypeptides comprising specific portions of a PEG-3 protein may be selected for the generation of antibodies using methods well known in the art. In general, hydrophilic regions are more immunogenic than the hydrophobic regions. In an embodiment, hydrophilic portions are used for the generation of antibodies.

In one such technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. In an embodiment, the selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The antibodies of this invention may be used in the purification process in, for example, an affinity chromatography step. Antibodies with a high degree of specificity for PEG-3 may then be selected. Such antibodies may be used, for example, to detect the expression of PEG-3 in living animals, in humans, or in biological tissues or fluids isolated from animals or humans.

In certain embodiments, antigen-binding fragments of antibodies are used. Such fragments include Fab fragments, which may be prepared using standard techniques. In an embodiment, immunoglobulins are purified from rabbit serum by affinity chromatography on Protein A bead columns (Harlow and Lane, *Antibodies: A Laboratory Manual, Cold Spring Harbor Laboratory,* 1988) and digested by papain to yield Fab and Fc fragments. The Fab and Fc fragments may be separated by affinity chromatography on protein A bead columns.

Methods for Identifying Binding Agents and Modulating Agents.

The present invention further provides methods for identifying compounds that bind to and/or modulate the activity of a progression-associated protein. Such agents may be identified by contacting a polypeptide as provided herein with a candidate compound or agent under conditions and for a time sufficient to allow interaction with the polypeptide. Any of a variety of well known binding assays may then be performed to assess the ability of the candidate compound to bind to the polypeptide, and assays for a biological activity of the polypeptide may be performed to identify agents that modulate (i.e., enhance or inhibit) the biological activity of the protein. Depending on the design of the assay, a polypeptide may be free in solution, affixed to a solid support, present on a cell surface or located intracellularly. Large scale screens may be performed using automation.

Alternatively, compounds may be screened for the ability to modulate expression (e.g., transcription) of PEG-3. For such assays a promoter for PEG-3 may be isolated using standard techniques. The present invention provides nucleic acid molecules comprising such a promoter or a cis- or trans-acting regulatory element thereof. Such regulatory elements may activate or suppress expression of PEG-3.

One method for identifying a promoter region uses a PCR-based method to clone unknown genomic DNA sequences adjacent to a known cDNA sequence (e.g., a human PromoterFinder™ DNA Walking Kit, available from Clontech). This approach may generate a 5' flanking region, which may be subcloned and sequenced using standard methods. Primer extension and/or RNase protection analyses may be used to verify the transcriptional start site deduced from the cDNA.

To define the boundary of the promoter region, putative promoter inserts of varying sizes may be subcloned into a heterologous expression system containing a suitable reporter gene without a promoter or enhancer may be employed. Suitable reporter genes may include genes encoding luciferase, beta-galactosidase, chloramphenicol acetyl transferase, secreted alkaline phosphatase or the Green Fluorescent Protein gene, and may be generated using well known techniques Internal deletion constructs may be generated using unique internal restriction sites or by partial digestion of non-unique restriction sites. Constructs may then be transfected into cells that display high levels of PEG-3 expression (e.g., E11-NMT). In an embodiment, the construct with the minimal 5' flanking region showing the highest level of expression of reporter gene is identified as the PEG-3 gene promoter.

Once a functional PEG-3 promoter is identified, cis- and trans-acting elements may be located. In an embodiment, cis-acting sequences may be identified based on homology to previously characterized transcriptional motifs. Point mutations may then be generated within the identified sequences to evaluate the regulatory role of such sequences. Such mutations may be generated using site-specific mutagenesis techniques or a PCR-based strategy. The altered promoter is then cloned into a reporter gene expression vector, as described above, and the effect of the mutation on reporter gene expression is evaluated. Trans-acting factors that bind to cis-acting sequences may be identified using assays such as gel shift assays. Proteins displaying binding activity within such assays may be partially digested, and the resulting peptides separated and sequenced. Peptide sequences may be used to design degenerate primers for use within RT-PCR to identify cDNAs encoding the trans-acting factors.

To evaluate the effect of a candidate agent on PEG-3 expression, a promoter or regulatory element thereof may be operatively linked to a reporter gene as described above. Such a construct may be transfected into a suitable host cell, such as E11-NMT or transfected forms of CREF Trans 6, including CREF-Trans 6:4NMT (expressing PTI-1), T24 (expressing ras), CREF-src (expressing src) and CREF-HPV (expressing HPV). It has been found, within the context of the present invention, that the PEG-3 promoter is constitutively expressed in tumor cell lines, but not in normal cells. Clones that constitutively express high levels of reporter protein may be selected and used within a variety of screens. Such clones are encompassed by the present invention.

In an embodiment, cells may be used to screen a combinatorial small molecule library. Briefly, cells are incubated with the library (e.g., overnight). Cells are then lysed and the supernatant is analyzed for reporter gene activity according to standard protocols. Compounds that result in a decrease in reporter gene activity are inhibitors of PEG-3 transcription, and may be used to inhibit DNA damage and repair pathways, cancer progression and/or oncogene mediated transformation.

This invention further provides methods for identifying agents capable of inducing DNA damage and repair pathways, cancer progression and/or oncogene mediated transformation. Briefly, candidate compounds may be tested as described above, except that the cells employed (which comprise a PEG-3 promoter or regulatory element thereof operatively linked to a reporter gene) are not in progression. For example, CREF-Trans 6 cells may be employed. Within such assays, an increase in expression of the reporter gene after the contact indicates that the compound is capable of inducing DNA damage and repair pathways, cancer progression or oncogene mediated transformation.

Within other embodiments, cells may comprise one or more exogenous suicidal genes under the control of a promoter or regulatory element of PEG-3. Such suicidal genes disrupt the normal progress of the cell following transcription from the promoter. Preferably, the switching on of the suicidal gene will lead to cell death or halt in cell growth. Example of such genes are genes which lead to apoptosis.

Pharmaceutical Compositions and Vaccines.

Within certain aspects, compounds such as polypeptides, antibodies, nucleic acid molecules and/or other agents that modulate PEG-3 expression or activity may be incorporated into pharmaceutical compositions or vaccines. In an embodiment, pharmaceutical compositions comprise one or more such compounds and a physiologically acceptable carrier. In an embodiment, certain vaccines may comprise one or more polypeptides and an immune response enhancer, such as an adjuvant or a liposome (into which the compound is incorporated). Pharmaceutical compositions and vaccines may additionally contain a delivery system, such as biodegradable microspheres which are disclosed, for example, in U.S. Pat. Nos. 4,897,268 and 5,075,109. Pharmaceutical compositions and vaccines within the scope of the present invention may also contain other compounds, which may be biologically active or inactive.

A pharmaceutical composition or vaccine may contain DNA encoding an antisense polynucleotide or a polypeptides as described above, such that the polynucleotide or polypeptide is generated in situ. The DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., Science 259:1745–1749, 1993 and reviewed by Cohen, Science 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Such carriers include, but are not limited to, aqueous or non-aqueous solutions, suspensions, and emulsions. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, saline and buffered media.

Compositions of the present invention may be formulated for any appropriate manner of administration, including for example, topical, oral, nasal, intravenous, intracranial, intraperitoneal, subcutaneous or intramuscular administration. Intravenous vehicles include fluid and nutrient replenishers, electrolyte replenishers such as those based on Ringer's dextrose, and the like. For parenteral administration. such as subcutaneous injection, the carrier preferably comprises water, saline, alcohol, Ringer's dextrose, dextrose and sodium chloride, lactated Ringer's, a fixed oil, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. For certain topical applications, formulation as a cream or lotion, using well known components, is preferred.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Preservatives and other additives may also be present, such as, for example, antimicrobials, antioxidants, chelating agents, inert gases and the like. Compositions of the present invention may also be formulated as a lyophilizate. Compounds may also be encapsulated within liposomes using well known technology.

Any of a variety of adjuvants may be employed in the vaccines of this invention to nonspecifically enhance the immune response. In an embodiment, the adjuvant contains a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2,-7, or -12, may also be used as adjuvants.

The compositions described herein may be administered as part of a sustained release formulation (i.e., a formulation such as a capsule or sponge that effects a slow release of compound following administration). In an embodiment, such formulations may be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of cyclic peptide release. The amount of active compound contained within a sustained release formulation depends upon the site of implantation, the rate and expected duration of release and the nature of the condition to be treated or prevented.

Cancer Therapy.

In further aspects of the present invention, the compounds described herein may be used for therapy of cancer. Within such aspects, the compounds (which may be polypeptides, antibodies, nucleic acid molecules or other modulating agents) are preferably incorporated into pharmaceutical compositions or vaccines, as described above. Suitable patients for therapy may be any warm-blooded animal, preferably a human. A patient may or may not be afflicted with cancer, as determined by standard diagnostic methods. Accordingly, the above pharmaceutical compositions and vaccines may be used to prevent the development of cancer or to treat a patient afflicted with cancer.

Within certain aspects, cells may be protected from therapeutic damage (e.g., due to chemotherapy or a physical agent such as gamma-irradiation) and/or rendered resistant to progression by inhibiting or eliminating the expression and/or activity of PEG-3 in the cells. One method for inhibiting the expression of PEG-3 comprises providing an effective amount of antisense RNA in the cell. In an embodiment, such antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994). Alternatively, an antisense molecule may be designed to hybridize with a control region of a gene (e.g., promoter, enhancer or transcription initiation site), and block transcription of the gene; or to block translation by inhibiting binding of a transcript to ribosomes. In an embodiment, the expression of PEG-3 may be eliminated by deleting the gene or introducing mutation (s) into the gene.

Pharmaceutical compositions of the present invention may be administered in a manner appropriate to the disease to be treated (or prevented). The route, duration and frequency of administration will be determined by such factors as the condition of the patient, the type and severity of the patient's disease and the method of administration. Routes and frequency of administration may vary from individual to individual, and may be readily established using standard techniques. In an embodiment, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients.

In an embodiment, an appropriate dosage and treatment regimen provides the active compound(s) in an amount sufficient to provide therapeutic and/or prophylactic benefit. Such a benefit should results in an improved clinical outcome (e.g., more frequent remissions, complete or partial, or longer disease-free survival) in treated patients as compared to non-treated patients.

Appropriate dosages of polypeptides, polynucleotides, antibodies and modulating agents may be determined using experimental models and/or clinical trials. In an embodiment, the use of the minimum dosage that is sufficient to provide effective therapy is used. In an embodiment, patients may be monitored for therapeutic effectiveness using assays suitable for the condition being treated or prevented, which will be familiar to those of ordinary skill in the art. Suitable dose sizes will vary with the size of the patient, but will typically range from about 0.1 mL to about 5 mL.

Cancer Detection, Diagnosis and Monitoring.

Polypeptides, polynucleotides and antibodies, as described herein, may be used within a variety of methods for detecting a cancer, determining whether a cancer is in progression, and monitoring the progression and/or treatment of a cancer in a patient. Within such methods, any of a variety of methods may be used to detect PEG-3 activity or the level of PEG-3 mRNA or protein in a sample. Suitable biological samples include tumor or normal tissue biopsy, mastectomy, blood, lymph node, serum or urine samples, or other tissue, homogenate or extract thereof obtained from a patient.

Methods involving the use of an antibody may detect the presence or absence of PEG-3 in any suitable biological sample. There are a variety of assay formats known to those of ordinary skill in the art for using an antibody to detect polypeptide markers in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the polypeptide and remove it from the remainder of the sample. The bound polypeptide may then be detected using a second antibody or reagent that contains a reporter group. Alternatively, a competitive assay may be utilized, in which a polypeptide is labeled with a reporter group and allowed to bind to the immobilized antibody after incubation of the antibody with the sample. The extent to which components of the sample inhibit the binding of the labeled polypeptide to the antibody is indicative of the reactivity of the sample with the immobilized antibody, and as a result, indicative of the concentration of polypeptide in the sample.

The solid support may be any material known to those of ordinary skill in the art to which the antibody may be attached. For example, the solid support may be a test well in a microtiter plate or a nitrocellulose filter or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The antibody may be immobilized on the solid support using a variety of techniques known to those in the art, which are amply described in the patent and scientific literature. In the context of the present invention, immobilization includes both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the antibody, in a suitable buffer, with the solid support for a suitable amount of time. The contact time varies with temperature, but is typically between about 1 hour and 1 day. In an embodiment, contacting a well of a plastic microtiter plate (such as polystyrene or polyvinylchloride) with an amount of antibody ranging from about 10 ng to about 1 µg, and preferably about 100–200 ng, is sufficient to immobilize an adequate amount of polypeptide.

Covalent attachment of antibody to a solid support may also be achieved by first reacting the support with a bifunctional reagent that will react with both the support and a functional group, such as a hydroxyl or amino group, on the antibody. For example, the antibody may be covalently attached to supports having an appropriate polymer coating using benzoquinone or by condensation of an aldehyde group on the support with an amine and an active hydrogen on the binding partner using well known techniques.

In certain embodiments, the assay for detection of polypeptide in a sample is a two-antibody sandwich assay. This assay may be performed by first contacting an antibody that has been immobilized on a solid support, commonly the well of a microtiter plate, with the biological sample, such that the polypeptide within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In an embodiment, an appropriate contact time (i.e., incubation time) is that period of time that is sufficient to detect the presence of polypeptide within a sample obtained from an individual with cancer. Preferably, the contact time is sufficient to achieve a level of binding that is at least 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may be detected by the addition of substrate (i.e. for a specific period of time), followed by spectroscopic or other analysis of the reaction products.

To determine whether cells are in progression, expression of PEG-3 in the cells is evaluated and compared with the level of expression in cells that are not in progression.

In an embodiment, the signal detected from the reporter group that remains bound to the solid support is compared to a signal that corresponds to a predetermined cut-off value established from cells that are not in progression. In an embodiment, the cut-off value is the average mean signal obtained when the immobilized antibody is incubated with samples from cells that are not in progression. In an embodiment, a sample generating a signal that is three standard deviations above the predetermined cut-off value may be considered positive for progression. In an embodiment, the cut-off value is determined using a Receiver Operator Curve, according to the method of Sackett et al., *Clinical Epidemiology: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In an embodiment, a sample generating a signal that is higher than the cut-off value determined by this method is considered positive for progression.

In a related embodiment, the assay is performed in a flow-through or strip test format, wherein the antibody is immobilized on a membrane, such as nitrocellulose. In the flow-through test, the polypeptide within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of cells in progression. Typically, the concentration of second antibody at that site generates a pattern, such as a line, that can be read visually. The absence of such a pattern indicates a negative result. In an embodiment, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 $\mu$g, and more preferably from about 50 ng to about 1 $\mu$g. Such tests can typically be performed with a very small amount of biological sample.

The presence or absence of cells in progression in a patient may also be determined by evaluating the level of mRNA encoding PEG-3 within the biological sample (e.g., a biopsy, mastectomy and/or blood sample from a patient) relative to a predetermined cut-off value. Such an evaluation may be achieved using any of a variety of methods known to those of ordinary skill in the art such as, for example, in situ hybridization and amplification by polymerase chain reaction. In an embodiment, probes and primers for use within such assays may be designed based on the sequences provided herein, or on similar sequences identified in other individuals. Probes may be used within well known hybridization techniques, and may be labeled with a detection reagent to facilitate detection of the probe. Such reagents include, but are not limited to, radionuclides, fluorescent dyes and enzymes capable of catalyzing the formation of a detectable product.

Primers may be used within detection methods involving polymerase chain reaction (PCR), such as RT-PCR, in which PCR is applied in conjunction with reverse transcription. Typically, RNA is extracted from a sample tissue and is reverse transcribed to produce cDNA molecules. PCR amplification using specific primers generates a progression-associated cDNA molecule, which may be separated and visualized using, for example, gel electrophoresis. Amplification is typically performed on samples obtained from matched pairs of tissue (tumor and non-tumor tissue from the same individual) or from unmatched pairs of tissue (tumor and non-tumor tissue from different individuals). The amplification reaction may be performed on several dilutions of cDNA spanning two orders of magnitude. A two-fold or greater increase in expression in several dilutions of the tumor sample as compared to the same dilutions of the non-tumor sample is typically considered positive.

Within certain specific embodiments, expression of PEG-3 may be detected in a sample that contains cells by: (a) obtaining RNA from the cells; (b) contacting the RNA so obtained with a labeled (e.g., radioactively) probe of PEG-3 under hybridizing conditions permitting specific hybridization of the probe and the RNA; and (c) determining the presence of RNA hybridized to the molecule. As noted above, mRNA may be isolated and hybridized using any of a variety of procedures well-known to a person of ordinary skill in the art. The presence of mRNA hybridized to the probe may be determined by gel electrophoresis or other methods known in the art. By measuring the amount of the hybrid formed, the expression of the PEG-3 protein by the cell can be determined. Alternatively, RNA obtained from the cells may be amplified by polymerase chain reaction (PCR) with appropriate primers derived from a known PEG-3 sequence. The presence of specific amplified DNA following PCR is an indicative of PEG-3 expression in the cells.

Certain in vivo diagnostic assays may be performed directly on the tumor. One such assay involves contacting tumor cells with an antibody or fragment thereof that binds to a progression-associated protein. The bound antibody or fragment may then be detected directly or indirectly via a reporter group. Such antibodies may also be used in histological applications.

Within related aspects, the present invention provides methods for diagnosing the aggressiveness of cancer cells. Such methods are performed as described above, wherein an increase in the amount of the expression indicates that a cancer cell is more aggressive.

In other aspects of the present invention, the progression and/or response to treatment of a cancer may be monitored by performing any of the above assays over a period of time, and evaluating the change in the level of the response (i.e., the amount of polypeptide or mRNA detected). For example, the assays may be performed every month to every other month for a period of 1 to 2 years.

In an embodiment, a cancer is progressing in those patients in whom the level of the response increases over time. In contrast, a cancer is not progressing when the signal detected either remains constant or decreases with time.

The present invention further provides kits for use within any of the above diagnostic methods. Such kits typically comprise two or more components necessary for performing the assay. Such components may be compounds, reagents and/or containers or equipment. For example, one container within a kit may contain a monoclonal antibody or fragment thereof that specifically binds to a progression-associated polypeptide. Such antibodies or fragments may be provided attached to a support material, as described above. One or more additional containers may enclose elements, such as reagents or buffers, to be used in the assay. Such kits may also contain a detection reagent (e.g., an antibody) that contains a reporter group suitable for direct or indirect detection of antibody binding.

Transgenic Organisms.

The present invention also provides transgenic nonhuman living organism expressing PEG-3 protein. In an embodiment, the living organism is animal.

One means available for producing a transgenic animal, with a mouse as an example, is as follows: Female mice are mated, and the resulting fertilized eggs are dissected out of their oviducts. The eggs are stored in an appropriate medium. PEG-3 DNA or cDNA is purified from a vector by methods well-known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipes puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

EXAMPLE

Identification of Human PEG-3.

This Example illustrates the identification of a human PEG-3 cDNA molecule. Initially, PEG-3 gene expression was examined in various human tumor cell lines using a rat PEG-3 cDNA 3'-end fragment as a probe under low stringency conditions. Hybridization was performed at 65° C. overnight in the following solution: 800 μl of 5M NaCl, 80 μl of 0.5M EDTA, 2 ml of 1M Na(PO$_4$) (pH 6.4), 10 ml 10% SDS, 23.12 ml H20, for a total of 40 ml. Following hybridization, washing was performed in 1×SSC, 0.1%SDS at room temperature for 15 minutes, and then twice at 65° C. for 30 minutes. Overnight exposures indicated that the MCF-7 cell line highly expresses a human PEG-3 homolog and MCF-7 was used to provide mRNA resources for the establishment of a cDNA library.

To establish an MCF-7 cDNA library, poly (A$^+$) RNA was extracted and purified of from MCF-7 cells, and cDNA was generated using oligo (dT) as a primer through reverse transcription. λBk-MCV was used as a vector to generate cDNA library. The original MCF-7 cDNA library was generated with 1×10$^6$ pfu and insert size was about 0.4 Kb –4 Kb.

The MCF-7 cDNA library was screened using a 600 bp rat PEG-3 cDNA 3'-end fragment as a probe at low stringency. Prehybridization and hybridization were performed in the following solution:

| | |
|---|---|
| 100% Formamide | 50 ml |
| 20X SSC | 25 ml |
| 50X Denhardt's | 10 ml |
| 1 m Na(PO$_4$) (pH 6.8) | 5 ml |
| 100 mg/ml SSDNA | 1 ml |
| 10% SDS | 1 ml |
| H$_2$O | 8 ml |
| | 100 ml |

Hybridization was performed at 42° C. overnight. Washing was performed in 1×SSC, 0.1% SDS at room temperature for 15 minutes, and then twice at 65° C. for 30 minutes. Exposures were performed overnight.

Twenty-five positive clones were isolated from the MCF-7 cDNA library using the above condition through primary screening, secondary screening, and third screening. After restriction mapping and sequencing, all 25 positive clones were confirmed to have an insert of human PEG-3 cDNA 3'-end. The size for all these inserts was about 400–500 bp.

Northern blots were performed to evaluate the human PEG-3 gene expression pattern in normal human tissues and human tumor cell lines, using a 400 bp human PEG-3 cDNA 3'-end fragment as a probe.

Hybridization was performed at 65° C. overnight in the following solution: 800 μl of 5M NaCl, 80 μl of 0.5M EDTA, 2 ml of 1M Na (PO$_4$) (pH 6.4), 10 ml 10% SDS, 23.12 ml H20, for a total of 40 ml. Following hybridization, washing was performed in 1×SSC, 0.1%SDS at room temperature for 15 minutes, and then twice at 65° C. for 30 minutes. Overnight exposures indicated 2 mRNA species of human PEG-3 gene that express in a high level in most human tumor cell lines. These two mRNA species are about 1.5 and 2.8 Kb in size. No expression of PEG-3 gene was detected in all normal tissues except skeletal muscle which expresses 1.5 Kb species of human PEG-3 mRNAs in a low level.

5' RACE was used to generate the full length human PEG-3 cDNA, using poly (A$^+$) RNA extracted from MCF-7 cells as the template. PEG gene specific primers were designed from the human PEG-3 cDNA 400 bp fragment, including primer A (CTAAGGCGTGTCCATGCTCTGGCC) (SEQ ID NO: 9), primer B (CTCCTCTGCCTGGGCAATG) (SEQ ID NO: 10) and primer C (CGAGCAAAGCGGCTTCGATC) (SEQ ID NO: 11). First strand cDNA synthesis was carried out using human PEG-3 gene specific primer A or B through reverse transcription. cDNA was purified by GlassMax DNA isolation spin cartridge purification and TdT tailed. PCR of dc-tailed cDNA was carried out using nested primer B or primer C. After PCR, the PCR products were separated using 1% agarose at 100 voltages for 1 hour. Two dominant fragments (1.7 Kb and 0.9 Kb) were observed after electrophoresis and cut for subcloning using AT cloning vector. After sequencing some subclones, the 1.7 Kb fragment was confirmed to cover all coding regions of the human PEG-3 cDNA, and 0.9 Kb fragment was a truncated product of the human PEG-3 cDNA with a start at the first internal repeat of PEG-3 cDNA and also had a 25 bp unique sequence at the 5'-end. The 5' and 3' sequences of the 1.7 kb fragment are shown in FIG. 13.

The human PEG-3 gene also was found to express in human primary tumor samples using the RT-PCR method. Total RNAs extracted from primary human tumor sample were used as template, with an oligo (dT) primer. Reverse transcription was carried out in 42° C. for one hour. For PCR, First strand cDNA generated from reverse transcription was used as the template, and the primers were the human PEG-3 gene specific primers designed from the human PEG-3 gene cDNA 3'-end. PCR conditions were as follows:

| | | |
|---|---|---|
| Denaturation | 94° C. - 5' | 1 cycle |
| Denaturation | 94° C. - 30" | |
| Annealing of primers | 60° C. - 30' | 35 cycles |
| Primer extension | 72° C. - 2' | |
| Followed by | | |
| Final extension | 72° C. - 7' | |
| Indefinite hold | 4° C., until samples are removed | |

Electrophoresis was used to separate PCR products of all tested samples, in a 1.5% agarose gel, for 1 hour at 100 V.

Fifth Series of Experiments

Cancer is often a multistep process in which a tumor cell either develops qualitatively new phenotypes or an enhanced expression of transformation related properties. Defining the molecular determinants of progression should lead to improved cancer diagnosis and strategies for therapy. Subtraction hybridization identified a novel gene associated with induction of transformation progression in virus and oncogene transformed rat embryo cells, progression elevated gene-3 (PEG-3). PEG-3 expression correlates directly with the progression phenotype in rodent cells. Ectopic expression of PEG-3 in transformed rodent cells elicits an aggressive oncogenic phenotype, whereas antisense inhibition of PEG-3 expression eliminates cancer aggressiveness. PEG-3 has sequence homology to the growth arrest and DNA damage inducible hamster gene gadd34, implicating DNA damage and repair processes in progression. A working hypothesis is that PEG-3 expression is a downstream event in oncogenic transformation and progression and activation of PEG-3 may directly alter the expression of genes involved in cancer progression, including genes associated with tumorigenesis, metastasis and angiogenesis. Studies are evaluating the effect of transient and stable expression of sense and antisense PEG-3 constructs in transformed cells on transformation progression in vitro and in vivo. Since induction of PEG-3 during progression and as a consequence of DNA damage involves transcriptional activation, the promoter region of the PEG-3 gene has been isolated and will be investigated to identify and characterize cis-acting and trans-acting regulatory elements which control gene expression. Using the PEG-3 promoter, sensitive indicator cell lines have been developed for identifying compounds capable of inducing and inhibiting cancer progression.

These studies are providing important insights into a novel progression gene with potential relevance to cancer development and evolution. The PEG-3 gene may serve as a target for selectively intervening in the progression process, thereby preventing cancer aggressiveness and metastasis.

Cancer is a progressive process with defined temporal stages culminating in metastatic potential by evolving tumor cells. Although extensively scrutinized the molecular determinants of cancer progression remain unclear. Well-characterized cell culture systems are valuable experimental tools for defining the biochemical and molecular basis of progression. Two rodent model systems are providing insights into the genes and processes regulating malignant progression of the transformed cell.

In adenovirus type 5 (Ad5) transformed rat embryo (RE) cells, progression can occur spontaneously by tumor formation in nude mice or by ectopic expression of oncogenes and signal transducing growth-regulating genes. In all contexts of progression, the demethylating agent 5-azacytidine (AZA) can reverse this process resulting in an unprogressed phenotype in >95% of treated clones. Inhibition of progression also occurs in this system after forming somatic cell hybrids between progressed and unprogressed cells. Using an immortal cloned rat embryo fibroblast (CREF) cell culture system, progression to metastasis and reversion of progression can be regulated by appropriate genetic manipulation using the Ha-ras oncogene and the Krev-1 suppressor gene. These experimental findings support the hypothesis that progression may involve the selective inactivation of genes that suppress progression (progression suppressing genes) and/or the induction of genes that promote progression (progression enhancing genes). Identification and characterization of both types of genetic elements would prove of immense value for defining this important component of the cancer process and could provide useful target molecules for intervening in the neoplastic process.

To elucidate the molecular basis of progression we are using a subtraction hybridization approach. Subtraction hybridization between progressed and unprogressed Ad5-transformed RE cells resulted in the cloning of progression elevated gene-3, PEG-3, that displays coordinate expression with the progression and transformation phenotypes in Ad5 and oncogene transformed rat embryo cultures. PEG-3 is a novel gene sharing nucleotide (~73 and ~68%) and amino acid (~59 and ~72%) sequence homology with the hamster growth arrest and DNA damage inducible gene gadd34 and a homologous murine gene, MyD116, that is induced during induction of differentiation by IL6 in murine myeloid leukemia cells. It is hypothesized that overexpression of PEG-3 in transformed and progressed tumor cells may facilitate progression by regulating the expression of genes that control the cancer process, including genes directly promoting tumorigenesis, metastasis and/or angiogenesis. Our research is providing important information relative to the role of a novel DNA damage-inducible gene, PEG-3, in cancer development and progression. This information should be valuable in designing refined and sensitive techniques for cancer detection and for identifying cancer preventing compounds. It may also provide a platform for developing new and improved cancer therapeutics.

The carcinogenic process involves a series of sequential changes in the phenotype of a cell resulting in the acquisition of new properties or a further elaboration of transformation-associated traits by the evolving tumor cell (1–4). Although extensively studied, the precise genetic mechanisms underlying tumor cell progression during the development of most human cancers remain unknown. Possible factors contributing to transformation progression, include: activation of cellular genes that promote the cancer cell phenotype, i.e., oncogenes; activation of genes that regulate genomic stability, i.e., DNA repair genes; activation of genes that mediate cancer aggressiveness and angiogenesis, i.e., progression elevated genes; loss or inactivation of cellular genes that function as inhibitors of the cancer cell phenotype, i.e., tumor and progression suppressor genes; and/or combinations of these genetic changes in the same tumor cell (1–6). A useful model for defining the genetic and biochemical changes mediating tumor progression is the Ad5/early passage RE cell culture system (1,7–15). Transformation of secondary RE cells by Ad5 is often a sequential process resulting in the acquisition of and further elaboration of specific phenotypes by the transformed cell (7–10). Progression in the Ad5-transformation model is characterized by the development of enhanced anchorage-independence and tumorigenic capacity (as indicated by a reduced latency time for tumor formation in nude mice) by progressed cells (1,10). The progression phenotype in Ad5-transformed rat embryo cells can be induced by selection for growth in agar or tumor formation in nude mice (7–10), referred to as spontaneous-progression, by transfection with oncogenes (11,14), such as Ha-ras, v-src, v-raf or E6/E7 region of human papilloma virus type-18 (HPV-18), referred to as oncogene-mediated progression, or by transfection with specific signal transducing genes (15), such as protein kinase C (PKC), referred to as growth factor-related, gene-induced progression.

Progression, induced spontaneously or after gene transfer, is a stable cellular trait that remains undiminished in Ad5-transformed RE cells even after extensive passage (>100) in monolayer culture (1,10,14). However, a single-treatment with the demethylating agent AZA results in a stable reversion in transformation progression in >95% of cellular clones (1,10,11,14,15). The progression phenotype is also suppressed in somatic cell hybrids formed between normal or unprogressed transformed cells and progressed cells (12–14). These findings suggest that progression may result from the activation of specific progression-promoting (progression elevated) genes or the selective inhibition of progression-suppressing genes, or possibly a combination of both processes. To identify potential progression inducing genes with elevated expression in progressed versus unprogressed Ad5-transformed cells we are using subtraction hybridization (14,16,17). The subtraction hybridization approach resulted in cloning of PEG-3 displaying elevated expression in progressed cells (spontaneous, oncogene-induced and growth factor-related, gene-induced) than in unprogressed cells (parental Ad5-transformed, AZA-suppressed, and suppressed somatic cell hybrids) (17). These findings document a direct correlation between expression of PEG-3 and the progression phenotype in this rat embryo model system.

The nucleotide sequence of PEG-3 is ~73 and ~68% and the amino acid sequence is ~59 and 72% homologous to gadd34 (18) and MyD116 (19,20), respectively (17). The sequence homologies between PEG-3 and gadd34/MyD116 are highest in the amino terminal region of their encoded proteins, i.e., ~69 and ~76% homology with gadd34 and MyD116 respectively, in the first 279 aa (17). In contrast, the sequence of the carboxyl terminus of PEG-3 significantly diverges from gadd34/MyD116, i.e., only ~28 and ~49% homology in the carboxyl 88 aa (17). The specific function of the gadd34/MyD116 gene is not known. Like hamster gadd34 and its murine homologue MyD116, PEG-3 expression is induced in CREF cells by MMS and gamma irradiation (17). The gadd34/MyD116 gene, as well as the gadd45, MyD118 and gadd153 genes, encode acidic proteins with very similar and unusual charge characteristics (21). PEG-3 also encodes a putative protein with acidic properties similar to the gadd and MyD genes. The carboxyl-terminal domain of the murine MyD116 protein is homologous to the corresponding domain of the herpes simplex virus 1 $\gamma_1 34.5$ protein, that prevents the premature shutoff of total protein synthesis in infected human cells (22,23). Replacement of the carboxyl-terminal domain of $\gamma_1 34.5$ with the homologous region from MyD116 results in a restoration of function to the herpes viral genome, i.e., prevention of early host shutoff of protein synthesis (23). Although further studies are necessary, preliminary results indicate that expression of a carboxyl terminus region of MyD116 results in nuclear localization (23). Similarly, both gadd153 and gadd45 gene products are nuclear proteins (21). When transiently expressed in various human tumor cell lines, gadd34/MyD116 is growth inhibitory and this gene can synergize with gadd45 or gadd153 in suppressing cell growth (21). In contrast, ectopic expression of PEG-3 in normal CREF (cloned rat embryo fibroblast) and HBL-100 (normal breast epithelial) cells and cancer (E11 and E11-NMT (Ad5-transformed rat embryo) and MCF-7 and T47D (human breast carcinoma) cells does not significantly inhibit cell growth or colony formation (17) (unpublished data). These results suggest that gadd34/MyD116, gadd45, gadd153 and MyD118, represent a novel class of mammalian genes encoding acidic proteins that are regulated during DNA damage and stress and involved in controlling cell growth. In this context, PEG-3 would appear to represent an enigma, since it is not growth suppressive and its expression is elevated in cells displaying an in vivo proliferative advantage and a progressed transformed and tumorigenic phenotype (17). PEG-3 may represent a unique member of this acidic protein gene family that directly functions in regulating progression, perhaps by constitutively inducing signals that would normally only be induced during genomic stress. Additionally, PEG-3 may modify the expression of down-stream genes involved in mediating cancer aggressiveness, i.e., tumor- and metastasis-mediating genes and genes involved in tumor angiogenesis. In these contexts, PEG-3 could function to modify specific programs of gene expression and alter genomic stability, thereby facilitating tumor progression. This hypothesis is amenable to experimental confirmation.

The final stage in tumor progression is the acquisition by transformed cells of the ability to invade local tissue, survive in the circulation and recolonize in a new area of the body, i.e., metastasis (24,25). Transfection of a Ha-ras oncogene into CREF cells (26) results in morphological transformation, anchorage-independence and acquisition of tumorigenic and metastatic potential (27–29). Ha-ras-transformed CREF cells exhibit profound changes in the transcription and steady-state levels of genes involved in suppression and induction of oncogenesis (29,30). Simultaneous overexpression of the Ha-ras suppressor gene Krev-1 in Ha-ras-transformed CREF cells results in morphological reversion, suppression of agar growth capacity and a delay in in vivo oncogenesis (29). Reversion of transformation in Ha-ras+Krev-1 transformed CREF cells correlates with a return in the transcriptional and steady-state mRNA profile to that of nontransformed CREF cells (29,30). Following long latency times, Ha-ras+Krev-1 transformed CREF cells form both tumors and metastases in athymic nude mice (29). The patterns of gene expression changes observed during progression, progression suppression and escape from progression suppression supports the concept of transcriptional switching as a major component of Ha-ras-induced transformation (29,30).

Analysis of PEG-3 expression in CREF cells and various oncogene-transformed and suppressor gene-reverted CREF cells indicates a direct relationship between PEG-3 expression and transformation and oncogenic progression (17). Northern blotting indicates that CREF cells do not express PEG-3, whereas PEG-3 expression occurs in CREF cells transformed by several diverse-acting oncogenes, including Ha-ras, v-src, HPV 18 and mutant Ad5 (H5hr1) (17). Suppression of Ha-ras-induced transformation by Krev-1 results in suppression of PEG-3 expression. However, both tumor-derived and metastasis-derived Krev-1 Ha-ras-transformed CREF cells express PEG-3. The highest relative levels of PEG-3 mRNA are consistently found in the metastasis-derived Ha-ras+Krev-1 transformed CREF cells. These results indicate a direct relationship between PEG-3 expression and the transformed and oncogenic capacity of CREF cells. In addition, PEG-3 expression directly correlates with human melanoma progression, with the highest levels of expression found in metastatic human melanoma and reduced levels observed in normal human melanocytes, radial growth phase (RGP) primary melanomas and early vertical growth phase (VGP) primary melanomas (unpublished data). Although further studies with increased samples are required, these intriguing results suggest that PEG-3 may be relevant in human as well as rodent cancers.

A fundamentally important question is the role of PEG-3 in cancer progression. PEG-3 could simply correlate with transformation progression or alternatively it could directly regulate this process. To distinguish between these possibilities, E11 cells (not expressing PEG-3) were genetically engineered to express PEG-3 (17). When assayed for growth in agar or aggressiveness in vivo in nude mice, E11-PEG-3 cells display a progression phenotype akin to that seen in E11-NMT cells (17,31). Moreover, antisense inhibition of PEG-3 in E11-NMT (normally expressing PEG-3) results in suppression of the progression phenotype in vitro and in vivo (31). Although the mechanism by which PEG-3 affects cancer progression in vivo remains to be determined, a potential role for induction of angiogenesis by PEG-3 is suggested (31). Tumors isolated from nude mice infected with E11-NMT and E11-PEG-3 clones are highly vascularized and they contain large numbers of blood vessels, whereas E11 and E11-NMT-PEG-3 AS tumors grow slower and they remain compact without extensive blood vessel involvement (31). Further studies are necessary to determine the mechanism by which PEG-3 expression modifies angiogenesis.

Experimental Studies

Model System For Analyzing Progression and Suppression of the Transformed Phenotype: Oncogene-transformed and Signal Transduction Gene-transformed Early Passage Rat Embryo (RE) Cell Cultures.

Transformation of early passage RE cells with Ad5 or mutants of Ad5 is a multistep process involving temporal acquisition of enhanced transformation-related phenotypes by the evolving transformed cells, i.e., progression. The progression process can be accelerated by selecting cells for increased anchorage-independence in vitro, injecting Ad5-transformed cells into nude mice and isolating tumor-derived clonal cell lines or by transfection with specific oncogenes (including Ha-ras, V-src, V-raf and E6/E7 of HPV-18) or with signal transducing genes (including the $\beta_1$ isoform of PKC (7–15,16). In early passage RE cells transformed by the mutant Ad5, H5ts125, the progression phenotype, induced spontaneously by nude mouse tumor formation or by transfection with the Ha-ras oncogene or the $\beta_1$ PKC gene, can be reversed by treating cells with AZA (10,11,15). Suppression of the progression phenotype also occurs in intraspecific somatic cell hybrids formed between normal CREF and E11-NMT (spontaneously progressed nude-mouse tumor derived H5ts125transformed RE) cells or between E11(non-progressed H5ts125-transformed RE) and E11-NMT cells (12,14). These findings indicate that progression in Ad5-transformed, Ad5+oncogene (Ha-ras) transformed or Ad5+signal transducing gene ($\beta_1$ PKC) transformed cells is a reversible process that behaves genetically as a recessive phenotype. Progression may, therefore, involve the selective inactivation of progression-suppression genes and/or the activation of progression-inducing genes.

Identification and Cloning Genes Associated with Cancer Progression.

Figure 15:
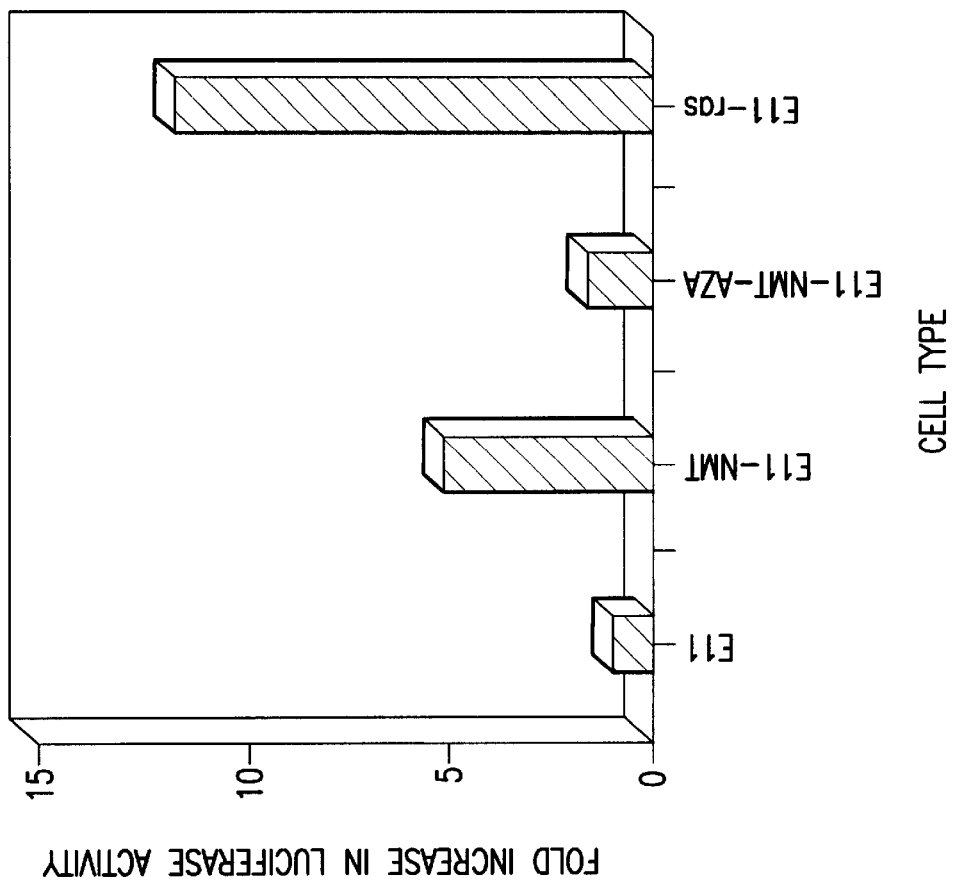
FIG. 15: Relative PEG-3 promoter luciferase activity in unprogressed (E11 and E11-NMT-AZA) and progressed (E11-NMT and E11-ras) transformed rodent cells.

To identify genes expressed at elevated levels in progressed E11-NMT versus unprogressed E11 cells we are using a subtraction hybridization approach developed in our laboratory (16,17). For the subtraction hybridization approach, tester (E11-NMT) and driver (E11) cDNA libraries were directionally cloned into the commercially available $\lambda$ Uni-ZAP phage vector and subtraction hybridization was then performed between double-stranded tester DNA (E11-NMT) and single-stranded driver DNA (E11) prepared by mass excision of the libraries. The subtracted cDNAs were then cloned into the $\lambda$ Uni-ZAP phage vector and used to probe Northern blots initially containing E11-NMT and E11RNAs. cDNAs displaying elevated expression in E11-NMT versus E11 cells were identified, used to screen additional RNA samples and appropriate clones were sequenced. One cDNA clone, PEG-3, displays the predicted association with expression of the progression phenotype (17). Expression of PEG-3 is apparent in a wide and diverse spectrum of progressed transformed RE clones, including spontaneously progressed (E11-NMT), progressed CREF X E11-NMT somatic cell hybrids (R1 and R2), a progressed E11X E11-NMT somatic cell hybrid (IIa), progressed tumor-derived E11X E11-NMT somatic cell hybrids (A6-TD and IIId-TD), an HPV 18 progressed clone (E11-E6/E7), a Ha-ras progressed clone (E11-Ras-12) and a $\beta_1$ protein kinase C progressed clone (E11-PKC B1) (16). In contrast, PEG-3 expression is not detected or is apparent at reduced levels in the same series of cell lines that do not express the progression phenotype, including unprogressed E11, unprogressed CREF X E11-NMT somatic cell hybrid clones (F1 and F2), unprogressed E11X E11-NMT somatic cell hybrid clones (IIId, A6 and 3b), and unprogressed E11-NMT subclones isolated after AZA treatment (E11-NMT-AZA clone C1, B1 and C2) (FIG. 15). These results document a direct correlation between expression of progression and PEG-3 in RE cells displaying specific stages of cancer progression (17).

Model System to Analyze Progression and Suppression of the Transformed, Tumorigenic and Metastatic Phenotype: Ha-ras-Transformed and Ha-ras+Krev-1-transformed CREF Cells.

A second rodent model used to study the process of cancer progression employs a specific clone of Fischer rat embryo fibroblast cells, CREF, modified by transfection to express dominant acting oncogenes (such as Ha-ras, v-src, v-raf, and HPV 18) and tumor suppressor genes (such as Krev-1, RB and p53) (27–30,32–34). In this model system, Ha-ras-transformed CREF cells are morphologically transformed, anchorage-independent and induce both tumors and lung metastases in syngeneic rats and athymic nude mice (27–30). The Krev-1 (Ha-ras) suppressor gene reverses the in vitro and in vivo properties in Ha-ras transformed cells (29,30). Although suppression is stable in vitro, Ha-ras/Krev-1 CREF cells induce both tumors and metastases after extended latency times in nude mice (29). CREF cells, as well as Ha-ras/Krev-1 reverted cells, contain RNA transcripts and steady-state mRNA for several cancer suppressing genes, whereas these cells do not express transcripts or mRNAs for several cancer promoting genes (29). During the processes of transformation suppression and escape from transformation suppression changes in the transcription and steady state RNA levels of defined genes are observed (29,30).

Expression of PEG-3 occurs in tumorigenic CREF cells transformed by v-src, HPV-18, H5hr1 (mutant of Ad5) and Ha-ras (17). Suppression of Ha-ras induced transformation by Krev-1 inhibits PEG-3 expression. However, when Ha-ras/Krev-1 cells escape tumor suppression and form tumors and metastases in nude mice, PEG-3 expression reappears. Treatment of CREF cells with gamma irradiation and MMS results in PEG-3 expression by 4 hr and continued expression at 24 hr (17 and data not shown). These results indicate that PEG-3 expression is inducible by DNA damage and suggests a direct association between PEG-3 expression and oncogenic transformation and tumor progression.

Analysis of PEG-3 in Rodent Progression Models.

(1) PEG-3 is a DNA Damage-inducible Gene.

To define the level of regulation of PEG-3 in normal and transformed cells nuclear run-on assays were performed (17). These studies document that PEG-3 is transcriptionally induced in CREF cells as a function of DNA damage, resulting from gamma irradiation or MMS treatment. The same DNA-damage induction protocol also induces MyD116 and gadd34 transcription in CREF cells. In contrast, analysis of transformed CREF cells (Ha-ras), unprogressed rodent cells (E11, E11-NMT AZA C1 and E11X E11-NMT 3b) and progressed rodent cells (E11-NMT and E11 X E11-NMT IIa) indicate that PEG-3, but not MyD116 or gadd34, is transcribed as a consequence of transformation progression (17). These results document that PEG-3 is a DNA damage inducible gene that is constitutively expressed in transformed and progressed cells. They further demonstrate that a primary level of regulation of PEG-3 occurs at a transcriptional level.

(2) PEG-3 Lacks Growth Inhibitory and Oncogenic Transformation Inducing Properties.

An attribute shared by the gadd and MyD genes is their ability to markedly suppress growth when expressed in human and murine cells (21,35). When transiently expressed in various human and murine cell lines, gadd34/MyD116 is growth inhibitory and this gene can synergize with gadd45 or gadd153 in suppressing cell growth (21). To determine the effect of PEG-3 on growth, E11 and E11-NMT cells were transfected with the protein coding region of the PEG-3 gene cloned into a Zeocin expression vector, pZeoSV (17). This construct permits an evaluation of growth in Zeocin in the presence and absence of PEG-3 expression. E11 and E11-NMT cells were also transfected with the p21 (mda-6) and mda-7 genes, previously shown to display growth inhibitory properties (36–38). Colony formation in both E11 and E11-NMT cells is suppressed 10–20% by PEG-3, whereas the relative colony formation following p21 (mda-6) and mda-7 transfection is decreased by 40–58% (17 and data not shown). Colony formation is also reduced by 10–20% when PEG-3 is transfected into CREF, normal human breast (HBL-100), and human breast carcinoma (MCF-7 and T47D) cell lines (data not shown). These results document that PEG-3 is distinct from the gadd and MyD genes since it does not significantly alter growth when expressed in various human and rodent cell lines. To determine if PEG-3 has transforming ability or if it can elicit an oncogenic phenotype in rodent cells, CREF-Trans 6 cells (39,40) were transfected with the PEG-3 gene in a pZeoSV vector and analyzed for transformation in monolayer culture, growth in agar and tumor formation in athymic nude mice. PEG-3 did not induce morphological transformation or growth in agar and pooled Zeocin resistant PEG-3 expressing CREF-Trans 6 cells did not produce tumors in nude mice (data not shown) These results indicate that PEG-3 does not have transforming or oncogenic potential when expressed in normal rodent cells.

(3) PEG-3 Controls the Progression Phenotype in Ad5-transformed RE Cells.

A consequential question is whether PEG-3 expression simply correlates with transformation progression or whether it can directly contribute or regulate this process. To distinguish between these possibilities we have determined the effect of stable elevated expression of PEG-3 on expression of the progression phenotype in E11 cells. E11 cells were transfected with a Zeocin expression vector either containing or lacking the PEG-3 gene, and random colonies were isolated and evaluated for anchorage independent growth (17). A number of clones were identified that displayed a 5- to 9-fold increase in agar cloning efficiency in comparison with E11 and E11-Zeocin vector-transformed clones. Only the three PEG-3-transfected E11 clones displaying elevated agar growth, i.e., E11-ZeoPEG-A, E11-ZeoPEG-B and E11-ZeoPEG-C, expressed PEG-3 mRNA (17). These findings demonstrate that PEG-3 can directly induce a progression phenotype, as monitored by anchorage independence, in H5ts125-transformed E11 cells.

(4) PEG-3 Expression Correlates with Cancer Aggressiveness and Angiogenesis in Ad5-transformed RE Cells.

Studies were conducted to determine the effect of forced PEG-3 expression in E11 cells and the consequence of antisense inhibition of expression of PEG-3 in E11-NMT cells on tumorigenesis in nude mice. When injected subcutaneously into nude mice, stable PEG-3 expressing E11 induced tumors in 100% of animals (n=10) with a shorter latency time than observed with E11 and even E11-NMT cells (data not shown). In contrast, E11-NMT cells containing an antisense PEG-3 gene display a reduction in agar colony formation (data not shown) and an extension of tumor latency time in comparison with E11-NMT cells (data not shown). Tumors that developed were analyzed and found to be significantly larger and highly vascularized in E11-PEG-3 and E11-NMT cells as compared to E11 and E11-NMT AS PEG-3 cells (data not shown). Sectioning of tumors indicate extensive blood vessel formation in E11-PEG-3 and E11-NMT cells but not in E11 parental cells or AS PEG-3 expressing E11-NMT cells (data not shown). These results indicate that modifying PEG-3 expression in E11 and E11-NMT cells can directly effect tumorigenesis and blood vessel formation (angiogenesis).

(5) Isolation and Initial Characterization of the PEG-3 Promoter.

Figure 16:
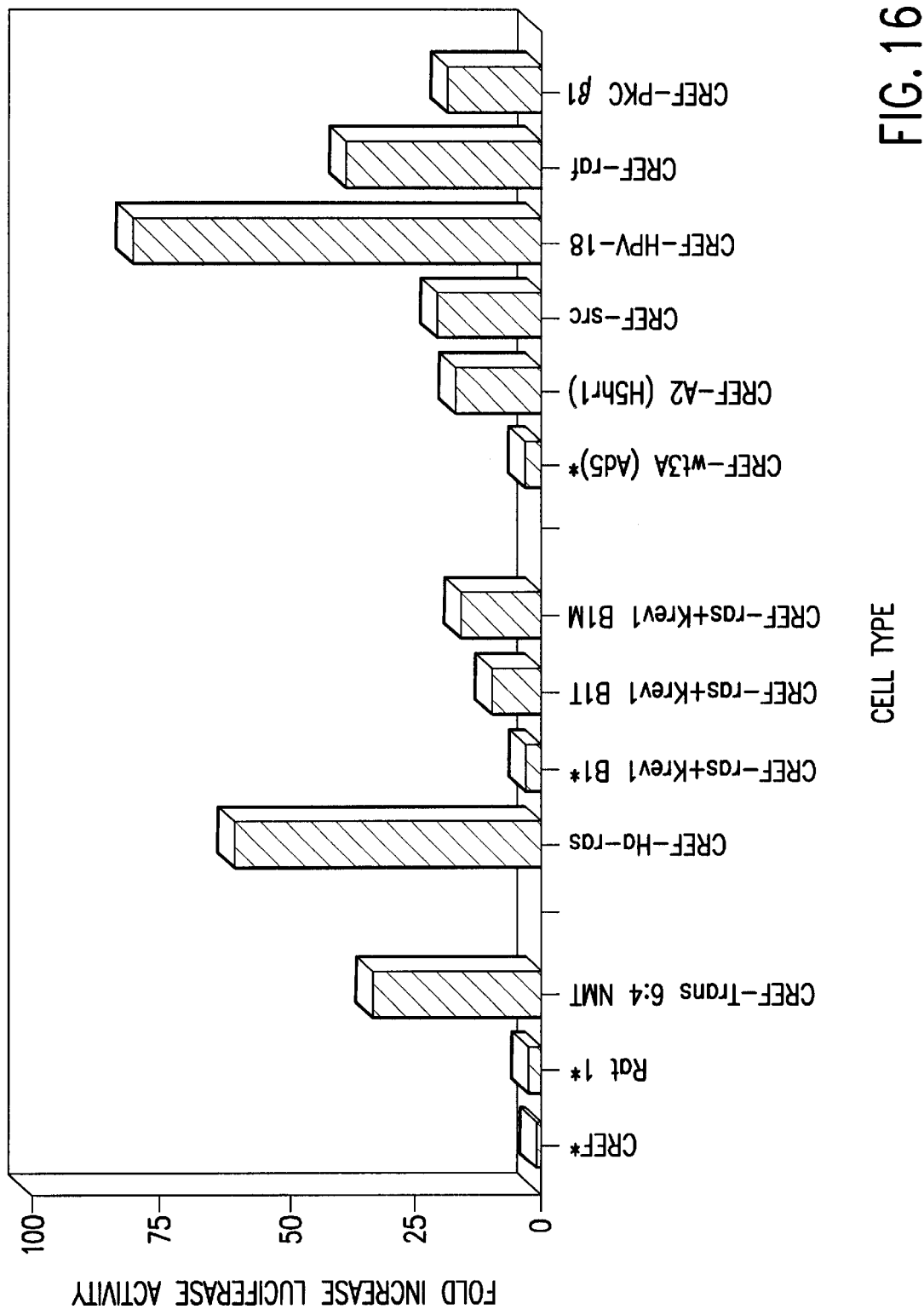
FIG. 16: Relative PEG-3 promoter luciferase activity in normal and transformed CREF cells. These include unprogressed and non-tumorigenic (CREF, Rat 1, CREF-ras+Krev-1 B1, and CREF-wt3A (Ad5) and progressed and oncogenic (CREF-Trans 6:4 NMT, CFEF-Ha-ras, CREF-ras+Krev-1 B1T, CREF-ras+Krev-1 B1M, CREF-A2 (H5hr1), CREF-src, CREF-HPV-18, CREF-raf and CREF-PKC B1) cells. * Indicates non-tumorigenic cell type.
Figure 17:
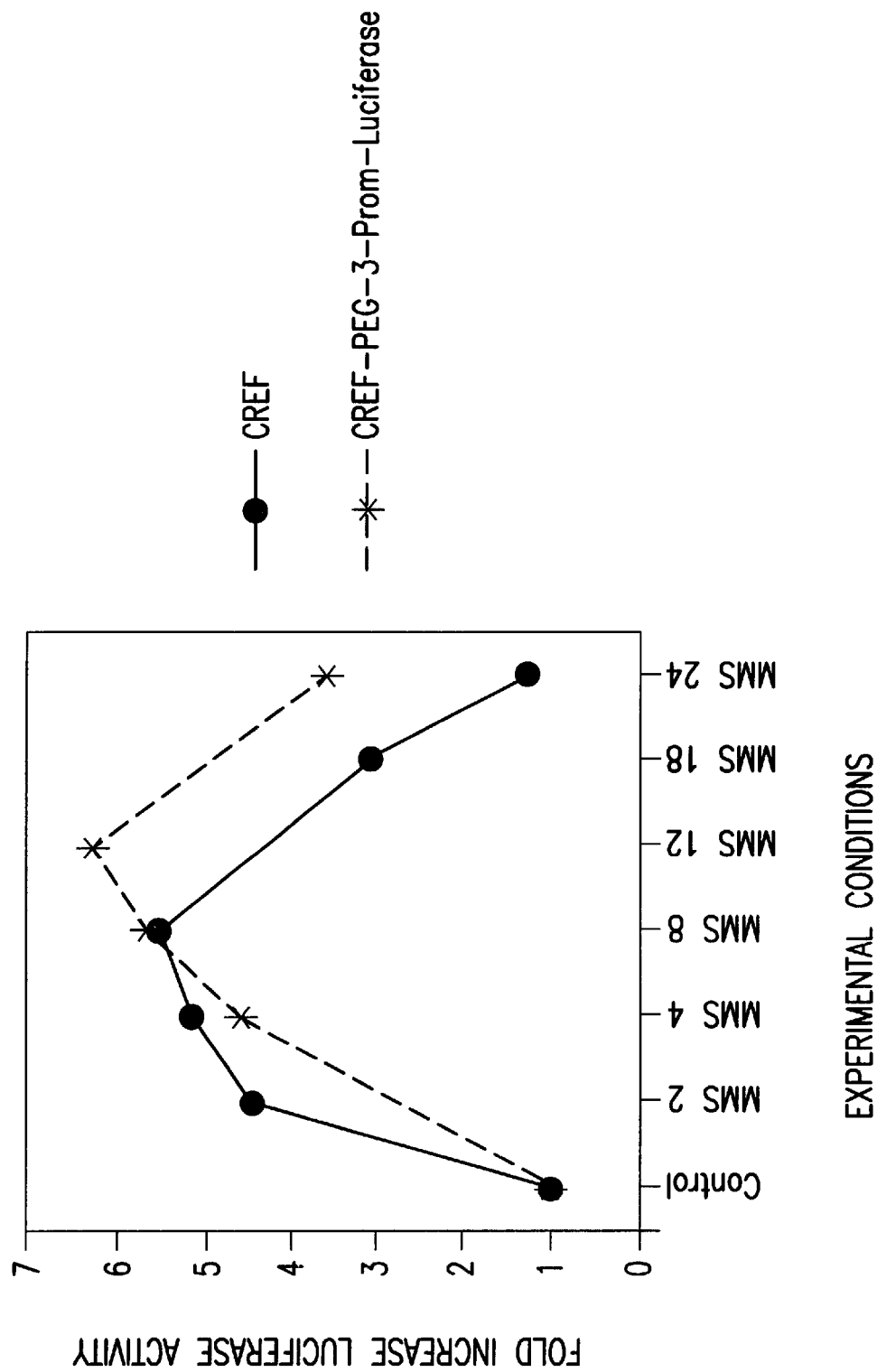
FIG. 17: Induction of PEG-3 promoter luciferase activity in CREF and CREF-PEG-Luc cells after MMS (100 µg/ml) treatment. CREF (o) and CREF-PEG-Luc (X).

To begin to define the mechanism by which DNA damage and progression transcriptionally induce PEG-3 expression we have identified a putative region of genomic DNA that contains the promoter of this gene. This was achieved using the GenomeWalker™ Kit from CLONTECH (Palo Alto, Calif.) that relies on an approach described by Siebert et al. (41,42). Using this methodology a rat genomic DNA fragment upstream of the 5' untranslated region of the PEG-3 cDNA has been isolated and cloned. The size of this DNA fragment is ~2.1 kb and its sequence is shown in FIG. 14. This promoter has been linked to a luciferase reporter construct and evaluated for expression in different cell types. Additionally, PEG-Luc reporter constructs have been stably integrated into CREF-Trans 6, human prostate cancer DNA transformed CREF-Trans 6 (CREF-Trans 6:4 NMT, 4NMT), Ha-ras-transformed CREF (CREF-Ha-ras), V-src-transformed CREF (CREF-src) and human papilloma virus 18-transformed CREF (CREF-HPV-18) cells. In these stable transfectants, luciferase is inducible by DNA damage (CREF-PEG-Luc) or constitutively expressed (4NMT-PEG-Luc, CREF-Ha-ras-Luc, CREF-src-Luc and CREF-HPV-18-Luc). Using a PEG-Luc reporter construct and transient transfection assays we demonstrate enhanced expression in progressed E11-NMT and E11-Ha-ras cells versus unprogressed E11 and E11-NMT-AZA cells (FIG. 15). In this system, the PEG-3 promoter is constitutively active in unprogressed cells and a relative increase of 5- to 10-fold is apparent in the progressed cells. Studies were also performed to determine if a relationship exists between oncogenic transformation induced by diverse oncogenes in CREF and CREF-Trans 6 cells and expression of the PEG-3 promoter (FIG. 16). In all cases of progression to an oncogenic phenotype the PEG-3 promoter is more active than in CREF or transformed CREF cells not displaying an oncogenic phenotype. The relative fold-induction of luciferase is higher in the CREF series than in the E11/E11-NMT series, whereas the absolute levels of luciferase activity are lower in the CREF series. This reflects a lower de novo (essentially null) expression of PEG-3 in CREF and CREF-Trans 6 cells. The final test for promoter activity employed CREF-Trans 6 cells and CREF-Trans 6 cells containing a stable PEG-Luciferase gene (CREF-PEG-Luc cl 1). Using these cells we demonstrate induction of luciferase activity in a temporal manner as a function of DNA damage induced by treatment with MMS (100 $\mu$g/ml) (FIG. 17). In the DNA damaged CREF cells the absolute levels of luciferase that are induced are lower than found in oncogenically transformed CREF cells, thereby accounting for the lower relative fold increase apparent in luciferase activity. These results indicate that we have identified rat genomic sequences containing the promoter region of the PEG-3 gene that contains all of the elements necessary for responsiveness to cellular alterations occurring during cancer progression, oncogenic transformation and DNA damage.

Experimental Assay Protocols for Monitoring Luciferase Activity:

Data presented in FIGS. 15 and 16. Cells were seeded at $2\times10^5$/35-mm plate, ~24 hr later cells were treated with lipofectin containing 4 µg of PEG-Luc plus a β-Gal control plasmid for 7 to 8 hr and the plates were washed and incubated in complete medium for 48 hr. Cells were lysed in cell lysate buffer E3971 (Promega), added to luciferase substrate E1500 (Promega) and luciferase activity was determined using a luminometer. In FIG. 15, data reflects fold-change in luciferase activity versus E11 cells. In FIG. 16, data reflects fold-change in luciferase activity of transformed cells versus CREF cells. FIG. 17: CREF cells were treated as described above for 48 hr and then exposed to 100 µg/ml of MMS for 24, 18, 8, 4 and 2 hr prior to lysate preparation and assaying for luciferase activity. Untransfected CREF-PEG-Luc (containing an integrated PEG-Luc gene) were treated with 100 µg/ml of MMS for 24, 12, 8 and 4 hr prior to lysate preparation and assaying for luciferase activity. Data reflects fold-change in luciferase activity versus CREF or CREF-PEG-Luc, respectively. All luciferase activities were normalized to β-Gal activities.

Defining the Mechanism Underlying the Differential Expression of PEG-3 as a Function of Cancer Progression, Oncogenic Transformation and DNA Damage.

Nuclear run-on assays indicate that PEG-3 expression directly correlates with an increase in the rate of RNA transcription (17). This association is supported by the isolation of a genomic fragment upstream of the 5' untranslated region of the PEG-3 cDNA and demonstration that this sequence linked to a luciferase reporter gene is activated as a function of cancer progression, oncogenic transformation and DNA damage (FIGS. 15, 16 & 17). Additionally, changes in the stability of PEG-3 mRNA may also contribute to differential expression of this gene as a function of cancer progression, oncogene expression and DNA damage. To address this issue mRNA stability (RNA degradation) assays will be performed as described in detail previously (43). Our analysis focuses on the effect of cancer progression (E11-NMT, R1 and R2 cells), oncogenic transformation (Ha-ras, V-src, H5hr1 and HPV-18 transformed CREF cells) and DNA damage (gamma irradiation and MMS-treatment of CREF cells). Appropriate controls, E11, untransformed CREF cells and CREF cells not treated with DNA damaging agents, respectively, and experimental samples will be incubated without additions or in the presence of 5 mg/ml of actinomycin D (in the dark), and 30, 60 and 120 min later, total cellular RNA will be isolated and analyzed for gene expression using Northern hybridization. RNA blots will be quantitated by densitometric analysis using a Molecular Dynamics densitometer (Sunnyvale, Calif.). These straight forward experiments will indicate if the stability of PEG-3 is altered in cells as a direct consequence of spontaneous progression, expression of defined oncogenes or as a consequence of DNA damage.

Most eukaryotic genes are regulated at the level of initiation of gene transcription. Detailed characterization of many different eukaryotic transcriptional units has led to the general concept that specific interactions of short DNA sequences, usually located at the 5'-flanking region of the corresponding genes (cis-acting elements), with certain cellular proteins (trans-acting elements) play a major role in determining the rate of initiation of gene transcription. To elucidate the mechanism underlying the transcriptional regulation of the PEG-3 gene the 5'-flanking region of this gene will be analyzed. This will be important for determining regulatory control of the PEG-3 gene including autoregulation, developmental regulation, tissue and cell type specific expression and differential expression in progressed versus unprogressed cells, enhanced expression as a function of oncogenic transformation and induction of expression as a consequence of DNA damage. Once the appropriate regions of the PEG-3 gene regulating the initiation of transcription has been confirmed, studies will be conducted to determine the relevant trans-acting regulatory factors that bind to specific cis-acting regulatory elements and activate or repress expression of the PEG-3 gene. The experiments outlined below are designed to: [1] define the 5'-flanking regions of the PEG-3 gene involved in mediating differential activity of PEG-3 in progressed, oncogenically transformed and DNA damaged cells; [2] identify cis-acting regulatory elements in the promoter region of the PEG-3 gene which are responsible for the differential induction of PEG-3 expression; and [3] identify and characterize trans-acting regulatory elements that activate (or repress) expression of the PEG-3 gene.

(1) Primary Analysis of the Functional Regions of the PEG-3 Promoter.

Using a genomic walking strategy we have identified a 5'-flanking promoter region of the PEG-3 gene that appears to encompass a functionally complete PEG-3 promoter (FIG. 14). To define important transcriptional regulatory regions of the PEG-3 promoter, a heterologous expression system containing a luciferase gene without promoter or enhancer has been developed using the full-length promoter construct (44–46). Internal deletion mutations will be generated either by taking advantage of internal restriction sites or by a nested exonuclease III base deletion strategy. These constructs will be transfected into E11 and E11-NMT, untransformed and transformed CREF (H5hr1, Ha-ras, v-src and HPV-18) and control CREF and gamma irradiation or MMS treated CREF cells. On the basis of transfection analyses of various deletion and point mutations it will be possible to define elements responsible for induction of PEG-3 as a consequence of cancer progression, specific transformation pathways or DNA damage response.

Transcription of PEG-3 in E11-NMT cells, as determined by nuclear run-on assays, is >20-fold higher than in E11 cells, whereas transient transfection of the PEG-3 promoter-luciferase gene into these two cell types indicates only an ~5-fold increase in activity in E11-NMT versus E11 cells. This could indicate that the PEG-3 gene is repressed in non-expressing cells (such as E11) through a cis-acting mechanism that is non-functional on transiently transfected promoters. Various luciferase constructs will be transfected into the different cell types by the lipofectamine method or electroporation (Gene Pulser, Bio-Rad) as previously described (44,47). To correct for DNA uptake and cell number used for each transfection experiment, the luciferase constructs will be transfected with plasmids containing bacterial β-galactosidase gene under the control of an Rous sarcoma virus (RSV) promoter (44–46). Studies will be conducted using multiple adult rat tissue Northern blots (CLONTECH) containing poly $A^+$ RNA and probing with PEG-3 (as well as gadd34 and MyD116) to define which rat tissue normally express PEG-3. Previous studies document that genes expressing in more than one tissue often require different sequences flanking the 5'-end of the gene. It is possible that PEG-3 expression in any normal tissue or under different circumstances in rat cells, i.e., progression, oncogenic transformation or DNA damage, may be regulated by different 5'-sequences. In that case, we will obtain variable luciferase activities for different luciferase constructs in the various cell lines. Transcription motifs contributing to PEG-3 regulation in a tissue, cell type or specific progression, transformation or DNA damage pathway will thus be identified.

(2) Identifying cis-acting elements in the PEG-3 promoter responsible for expression during cancer progression, oncogenic transformation and DNA damage. On the basis of the deletion studies described above, the potential location of cis-acting elements responsible for expression of PEG-3 during cancer progression, oncogenic transformation and DNA damage will be identified. The ~2.1 kb PEG-3 promoter has been sequenced and potential regulatory elements have been identified by comparison to previously characterized transcriptional motifs. The PEG-3 promoter contains a number of potentially important transcriptional motifs including PEA3 (AGGAAA), E2A (GCAGGTG), GRE (TGTTCT), E2F (TTTTGGCCG), TRE (GGTCA), acute phase reactive regulating element (GTGGGA), SP1 (GGGCGG), AP1 (TGACTCA), AP2 (TCCCCAACCC) (SEQ ID NO:12) and NF1 (TGGATTTGAGCCA). The importance of these sequences in regulating PEG-3 expression during cancer progression, oncogenic transformation and DNA damage will be determined by introducing point mutations in a specific cis element into the promoter region using previously described site-specific mutagenesis techniques (44,47–50) or with recently described PCR-based strategies, i.e., ExSite™ PCR-based site-directed mutagenesis kit and the Chameleon™ double-stranded site-directed mutagenesis kit (Stratagene, Calif.). The mutated promoter constructs will be cloned into luciferase expression vectors and tested for their effects on the promoter function by transfection into different cell types and monitoring luciferase activity. Since the promoter region for the PEG-3 gene is located in front of the luciferase reporter gene in the various pPEG-Luciferase constructs, the change in luciferase activity for each construct will permit a direct comparison of the activity of the mutant promoter to that of the unmodified PEG-3 promoter.

After the regulatory regions of the PEG-3 promoter are confirmed experiments will be conducted to address a number of important questions relative to cancer progression, oncogenic transformation and DNA damage induction of PEG-3 expression. (i) Nuclear run-on and transient transfection assays with pPEG-Luciferase constructs will be used to determine the effect of changes in DNA methylation (AZA and phenyl butyrate treatment) on PEG-3 expression in E11-NMT cells, treatment with different classes of DNA damaging and cancer modulating agents (such as TPA, retinoids, UV-C, gamma irradiation, methylating carcinogens, topoisomerase inhibitors, okadaic acid, etc.) on PEG-3 expression in CREF and CREF-PEG-Luc cl 1 cells (PEG-Luciferase stably transformed CREF clone) and exposure to cancer modulating agents (such as the Krev-1 gene, dominant negative inhibitors of specific oncogenes, chemicals such as CAPE, retinoids, sodium butyrate, interferon, TNF-α and additional progression modulating agents) on PEG-3 expression in oncogenically transformed CREF cells (1,8-10,18,21,28,29,32,33,51); (ii) The level of PEG-3 transcription in cells displaying different stages of cancer progression and oncogenic transformation, including rodent model systems of cancer progression (such as the Dunning rat prostate model, metastatic murine melanoma variants, etc.) and additional rodent cells transformed by various oncogenes. These studies will indicate if expression of PEG-3 occurs in additional pathways of progression and transformation. (iii) Transfection of varying lengths of the 5' flanking region and internal deletion luciferase constructs into rodent cells displaying different stages of progression, transformed by different classes of oncogenes and treated with various DNA damaging and cancer promoting and inhibiting agents. These regulatory elements will be sequenced and compared with previously characterized transcriptional motifs to identify potential positive and negative regulatory elements; (iv) In addition to mutagenesis studies (to define functional motifs regulating transcriptional regulation of the PEG-3 promoter), cotransfection studies will be conducted with cDNAs containing putative positive acting regulatory elements and a minimal PEG-3 promoter-Luciferase construct into unprogressed and progressed rodent cells, untransformed CREF and oncogenically transformed CREF and untreated and DNA damage treated CREF cells. These studies will indicate if the introduction of specific putative positive acting regulatory elements can enhance PEG-3 expression in cells cotransfected with a minimal PEG-3 promoter region. The potential role of putative cis-acting negative regulatory elements will be addressed by cotransfection with a complete PEG-3 promoter region into the same target cells. These studies will provide relevant information about the potential role of inhibitory elements in regulating PEG-3 expression. (v) Experiments will also be performed to evaluate the status of the endogenous PEG-3 gene during cancer progression, oncogenic transformation and DNA damage. This will be approached by using DNase hypersensitivity assays to look for structural changes in this gene (44). Although not within the scope of the present studies, future studies could involve the identification of a human PEG-3 cDNA, elucidation of the human PEG-3 promoter and analysis of the level of PEG-3 expression in human progression model systems. These studies would be quite informative in providing a potential link between PEG-3 expression and cancer progression in human cells.

(3) Identifying Trans-acting Nuclear Proteins that Mediate Transcriptional Enhancing Activity of the PEG-3 Gene During Cancer Progression, Oncogenic Transformation and DNA Damage.

The current view on regulation of eukaryotic gene expression suggests that trans-acting proteins bind to specific sites within cis-elements of a promoter region resulting in transcriptional activation (52,53). Experiments will be performed to identify trans-acting factors (nuclear proteins) and determine where these factors interact with cis-regulatory elements. To achieve this goal, two types of studies will be performed, one involving gel retardation (gel shift) assays (15,44,54,55) and the second involving DNase-I footprinting (methylation interference) assays (44,56,57).

Gel shift assays will be used to analyze the interactions between cis-acting elements in the PEG-3 promoter and trans-acting factors in mediating transcriptional control (15, 54,55). For this assay, $^{32}$P-labeled cis-elements will be incubated with nuclear extracts from E11 and E11-NMT, CREF and transformed CREF (Ha-ras, v-src, H5hr1 and HPV-18) and untreated CREF and CREF treated with MMS (100 µg/ml for 8 hr) or gamma irradiation (10 Gy for 4 hr) and reaction mixtures will be resolved on 5 or 8% polyacrylamide gels. After autoradiography, the pattern of retarded DNAs on the gel will provide information concerning the interaction between trans-acting factors and specific regions of the cis-acting elements in the PEG-3 promoter. Non-labeled cis-acting elements (self-competition) will be added as a competitor to duplicate samples to eliminate the possibility of non-specific binding and to confirm that the interaction is really conferred by the trans-acting factor. To begin to identify the transacting factors, different non-labeled DNAs (including those corresponding to sequences identified in the PEG-3 promoter, such as TATA, PEA3, E2A, GRE, E2F, TRE, acute phase reactive regulating element, SP1, AP1, AP2 and NFi) can be used as competitors in the gel shift assay to determine the relationship between the trans-acting factors and previously identified transcriptional regulators. It is possible that the trans-acting factors regulating transcriptional control of the PEG-3 promoter may be novel. To identify these factors extracts will be purified from E11 and E11-NMT, CREF and transformed CREF and untreated and DNA damaged CREF cells by two cycles of heparin-Sepharose column chromatography, two cycles of DNA affinity chromatography and separation on SDS-polyacrylamide gels (58,59). Proteins displaying appropriate activity using gel shift assays will be digested in situ with trypsin, the peptides separated by HPLC and the peptides sequenced (60). Peptide sequences will be used to synthesize degenerate primers and RT-PCR will be used to identify putative genes encoding the trans-acting factor. These partial sequences will be used with cDNA library screening approaches and the RACE procedure, if necessary, to identify full-length cDNAs encoding the trans-acting factors (17,47,61,62). Once identified, the role of the trans-acting factors in eliciting cancer progression will be analyzed. (i) The functionality of positive and negative trans-acting factors will be determined by transiently and stably expressing these genes in E11 and E11-NMT cells to determine effects on anchorage independence and tumorigenic potential in nude mice (stable expression). Positive effects would be indicated if overexpressing a positive trans-acting factor facilitates the progression phenotype, whereas overexpressing a negative trans-acting factor inhibits the progression phenotype. (ii) Antisense approaches will be used to determine if blocking the expression of positive or negative trans-acting factors can directly modify the progression state. A direct effect of a positive trans-acting factor in affecting progression would be suggested if antisense inhibition of the positive factor partially or completely inhibits the progression phenotype in E11-NMT, i.e., growth in agar is reduced and tumor latency time is extended. Conversely, a direct effect of negative trans-acting factors in inhibiting progression would be suggested if antisense inhibition of the negative factor enhances the ability of E11 to grow in agar and reduces tumor latency time. A potential problem with these types of studies would be encountered if the factors are involved in the regulation of many genes, e.g., Fos/Jun, and the antisense effects may, therefore, be non-specific. Although not within the scope of the present proposal, depending on the results obtained, cis-element knockouts could be used to further define the role of these elements in regulating PEG-3 expression.

For DNase-I footprinting assays, nuclear extracts from E11 and E11-NMT, CREF and transformed CREF and untreated CREF and DNA damaged (MMS and gamma irradiation) CREF cells will be prepared and DNase-I footprinting assays will be performed as described (44,63,64). The promoter necessary for PEG-3 expression, identified from the experiments described above, will be terminally labeled with $^{32}P$ and incubated with crude nuclear extracts from the different cell types and experimental conditions described above using established protocols (44,63,64). The reaction mixture that has been digested with DNase-I enzyme will be terminated and the digested products will be analyzed on an 8% sequencing gel. The differential protection between nuclear extracts from progressed versus unprogressed, untransformed and oncogenically transformed and undamaged and DNA damaged cells will provide relevant information concerning the involvement of trans-acting factors in activation and the location of specific sequences in the cis-regulatory elements of the PEG-3 promoter mediating this activation. If differential protection is not detected using this approach, the sensitivity of the procedure can be improved by using different sized DNA fragments from the PEG-3 promoter region or by using partially purified nuclear extracts (44,63,64).

The studies described above will result in the characterization of the PEG-3 promoter region, the identification of cis-acting regulatory elements in the PEG-3 promoter and the identification of trans-acting regulatory elements that activate (or repress) expression of the PEG-3 gene as a function of cancer progression, oncogenic transformation and DNA damage. This information could prove valuable in designing approaches for selectively inhibiting PEG-3 expression, and therefore modifying cellular phenotypes related to cancer progression and response to DNA damage. The PEG-3 Promoter as a Sensitive Biosensor Monitoring System For Identifying Compounds with the Capacity to Modulate Cancer Progression and Oncogenic Transformation.

Figure 18:
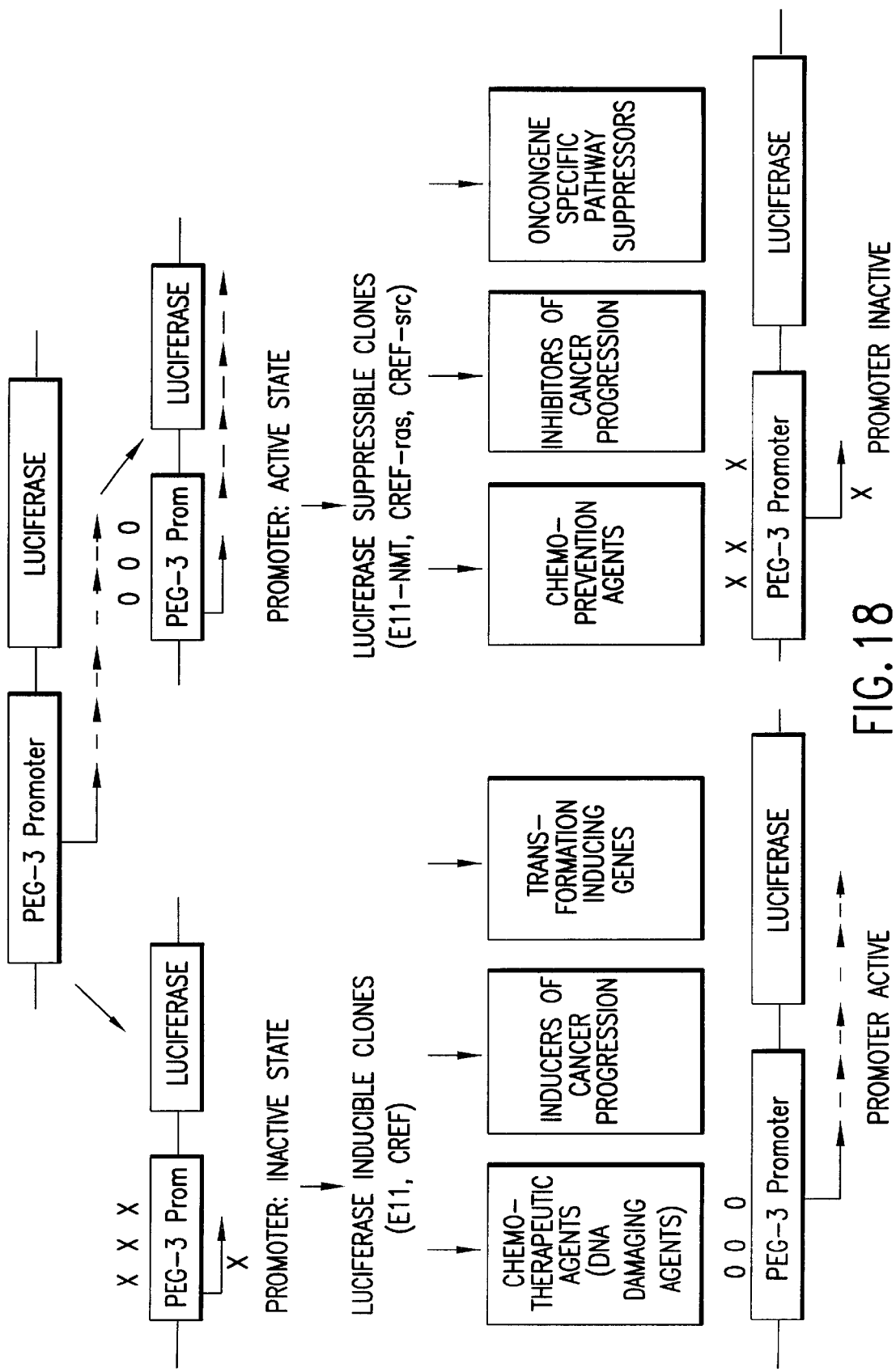
FIG. 18: The Rapid Promoter Screening (RPS) assay system for identifying compounds and experimental conditions regulating important physiological processes. The systems outlined above represent sensitive biosensor monitoring approaches for defining conditions and compounds that can regulate cellular phenotype, thereby altering the functionality of the PEG-3 promoter. Briefly, the PEG-3 promoter is linked to a reporter gene, such as luciferase, and stable cell clones are generated that contain either an inducible PEG-Luc gene (CREF) or a suppressible PEG-Luc gene (E11-NMT or various transformed CREF cells, including 4NMT, CREF-ras, CREF-src, CREF-HPV etc.). The PEG-3-Luc containing clones can then be used as sensitive indicators of alterations in cellular physiology resulting from DNA damage, induction of cancer progression, induction of oncogenic transformation, treatment with chemoprevention agents, inhibitors of cancer progression, inhibitors of angiogenesis and agents specifically involved in regulating defined oncogenic pathways. The RPS approach can be adapted for manual or rapid automated screening.
Figure 19:
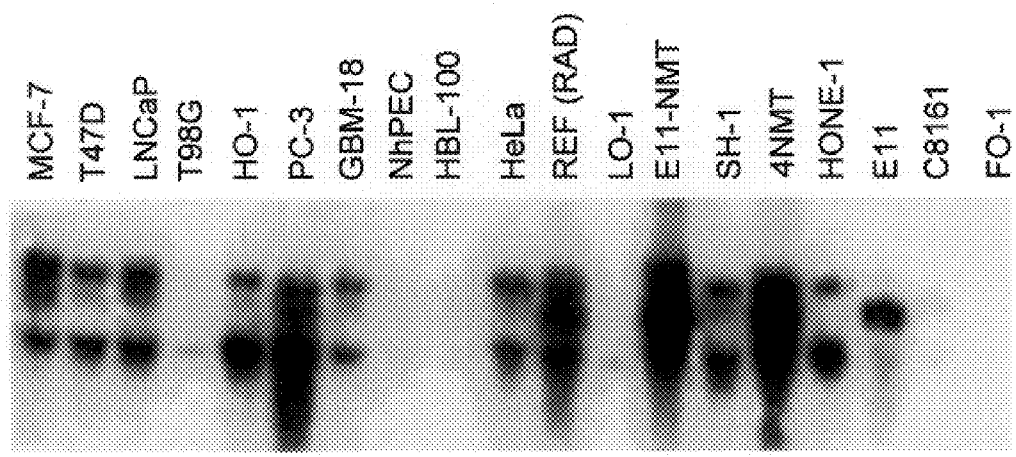
FIG. 19: Northern blot analysis of human PEG-3. A 500 bp probe from the 3' end of the human PEG-3 gene was used to probe a Northern blot containing the following tumor and normal cell lines.

As documented in this grant proposal, PEG-3 expression is elevated as a function of cancer progression, oncogenic transformation and DNA damage (17). Moreover, the PEG-3 promoter displays increased activity in cells displaying these different phenotypes (FIGS. 15, 16 & 17). These observations suggest that cell cultures stably expressing PEG-3 may prove effective as biosensor monitoring systems for identifying compounds and experimental conditions that can regulate important physiological processes, including cancer progression, oncogenic transformation, DNA damage and angiogenesis. This approach is called the Rapid Promoter Screening (RPS) assay system (FIG. 18). This strategy uses stable cell lines containing a PEG-Luciferase transgene for evaluating the activation or suppression of transcription from the PEG-3 promoter. Stable expression systems are preferable to transfection of the PEG-Luciferase gene into target cells since they are not dependent on variable transfection efficiencies or affected by cellular heterogeneity. Moreover, cells containing a stable PEG-Luciferase transgene can be used to develop a high throughput RPS assay system with the capacity to evaluate large numbers of compounds in a simple manual or automated assay. Initial proof-of-principle for the RPS assay system has now been obtained. CREF and 4NMT clones have been established that stably express a PEG-Luciferase transgene (FIG. 17). Treatment of CREF-PEG-Luc clones with the DNA damaging agent MMS (100 μg/ml) results in a temporal induction of luciferase activity (FIG. 17). Similarly, MMS treatment of parental CREF cells transiently transfected with a PEG-Luciferase construct results in similar kinetics of luciferase induction. Stable PEG-Luciferase expressing clones of 4NMT cells, tumorigenic CREF-Trans 6 cells transformed with human LNCaP DNA and expressing the PTI-1 oncogene (65), results in 4NMT-PEG-Luc clones constitutively expressing luciferase activity (unpublished data). When treated with an antisense phosphorothioate oligonucleotide that modifies the transformed state by suppressing PTI-1 expression, the level of luciferase expression is inhibited (unpublished data). These results support the suggestion that this approach will prove amenable for developing an RPS biosensor monitoring assay system to detect agents inducing DNA damage, enhancing cancer progression, inducing oncogenic transformation pathways and regulating anglogenesis (CREF-PEG-Luc) or agents inhibiting these processes (4NMT-PEG-Luc).

Initial studies will focus on the CREF-PEG-Luc and 4NMT-PEG-Luc assay systems. These cells will be used to test the utility of the RPS biosensor monitoring system with well characterized reagents capable of modifying specific physiological pathways. The two cell types will be treated with various agents, including DNA damaging (a spectrum of compounds that elicit different DNA repair pathways, used alone and in combination with agents that directly modify DNA repair processes), oncogenic transformation pathway inducing (such as phorbol ester tumor promoters, tyrosine kinase pathway modifiers and compounds affecting DNA methylation) and angiogenesis inducing and inhibiting agents (such as TNF-$\alpha$, bFGF, alpha interferon, beta interferon, thrombospondin and pleiotropin) and then monitored for luciferase activity. If these studies are successful, i.e., the assay systems can identify agents that have an impact on specific biological pathways, they would provide the basis for future expanded studies using this strategy. These studies would include: (i) Screening small molecules, produced by recombinatorial chemistry, to identify potentially important and clinically useful modulators of DNA damage and repair, cancer progression, oncogenic transformation and angiogenesis; (ii) Evaluating stable CREF-ras-PEG-Luc, CREF-src-PEG-Luc, CREF-HPV-PEG-Luc and additional PEG-Luc transformed cell lines. These luciferase expressing cells could be used to directly identify inhibitory molecules suppressing specific oncogenic transformation pathways. (iii) CREF-PEG-Luc or CREF-PEG-$\beta$-Gal (beta galactosidase) containing cells could be used to identify transforming cDNAs capable of initiating cellular transformation and consequently inducing PEG transcription. The human tumor cDNA containing CREF-PEG-Luc or CREF-PEG-$\beta$-Gal expressing clones could then be used to identify the putative transforming human tumor cDNAs. (iv) Transfection of normal cDNAs into transformed CREF-PEG or CREF-$\beta$-Gal expressing cells could be used to identify potentially novel cancer suppressor genes, by their ability to inhibit PEG transcription. Appropriately modified cells could then be used to clone the putative human tumor suppressor cDNA. (v) A PEG-$\beta$-Gal transgene could be inserted into mouse ovum to create transgenic mice harboring this gene. These animals could then be used as a sensitive in vivo indicator for evaluating DNA damage resulting from exposure to chemotherapeutic agents, evaluating gene regulation leading to cancer formation and identifying early stages in the conversion of a normal cell into a cancer cell.

PEG-3 Promoter-Luciferase Biosensor Monitoring Assay System:

The basic protocol for this assay will involve incubating target cells for varying times with compounds or growing cells under experimental conditions that either induce (CREF-PEG-Luc) or inhibit (4NMT-PEG-Luc) luciferase activity and assaying for such activity. As part of the experimental procedures, appropriate control reagents will be used. These will include MMS for the CREF-PEG-Luc cell culture system and PTI-1 antisense phosphorothioate oligonucleotide bridge primers for the 4NMT-PEG-LUC cell culture system. Two formats can be used for assaying compounds, one employing cells plated in 35 mm-tissue culture plates and the other employing cells plated in 96-well microtiter plates. The former approach will be used to evaluate small numbers of compounds or experimental conditions (maximum of 60 plates (20 agents tested in triplicate) in a single assay), and the latter approach can be adapted for screening large numbers of compounds in an automated fashion (96 agents tested per assay block, using multiple assay blocks). After incubating cells for different times with test reagents, growth medium will be removed, the cells will be washed with serum-free growth medium and the cells will be lysed using Reporter Lysis Buffer (Promega, Cat # E4531). Samples (placed in microcentrifuge tubes) or plates (96-well microtiter format) can be stored at −70° C. (to be assayed within 24-hr or stored for several weeks with samples remaining stable through several freeze-thaw cycles). Samples or plates are centrifuged to remove debris and a 10 $\mu$l aliquot is removed for monitoring luciferase assay using a luminometer.

REFERENCES FOR THE FIFTH SERIES OF EXPERIMENTS

1. Fisher P B. Enhancement of viral transformation and expression of the transformed phenotype by tumor promoters. In: T J Slaga (ed), *Tumor Promotion and Cocarcinogenesis In Vitro, Mechanisms of Tumor Promotion*, CRC Press, Inc, Florida, pp. 57–123, 1984.
2. Bishop J M. Molecular themes in oncogenesis. Cell, 64: 235–248, 1991.
3. Vogelstein B & Kinzler K W. The multistep nature of cancer. *Trends Genet*, 9: 138–141, 1991.
4. Knudson A G. Antioncogenes and human cancer. *Proc Natl Acad Sci USA*, 90: 10914–10921, 1993.
5. Levine A J. The tumor suppressor genes. *Annu Rev Biochem*, 62: 623–651, 1993.
6. Hartwell L H & Kastan M B. Cell cycle control and cancer. *Science*, 266: 1821–1828, 1994.
7. Fisher P B, Goldstein N I & Weinstein I B. Phenotypic properties and tumor promoter induced alterations in rat embryo cells transformed by adenovirus. *Cancer Res*, 39: 3051–3057, 1979.
8. Fisher P B, Dorsch-Hasler K, Weinstein I B & Ginsberg H S. Tumor promoters enhance anchorage-independent growth of adenovirus-transformed cells without altering the integration pattern of viral sequences. *Nature*, 281: 591–594, 1979.
9. Fisher P B, Bozzone J H & Weinstein I B. Tumor promoters and epidermal growth factor stimulate anchorage-independent growth of adenovirus transformed rat embryo cells. *Cell*, 18: 695–705, 1979.
10. Babiss L E, Zimmer S G & Fisher P B. Reversibility of progression of the transformed phenotype in Ad5transformed rat embryo cells. *Science*, 228: 1099–1101, 1985.
11. Duigou G J, Babiss L E & Fisher P B. Suppression of the progression phenotype by 5-azacytidine in rat embryo cells doubly transformed by type 5 adenovirus and the Ha-ras oncogene. *N.Y. Acad Sci*, 567: 302–306, 1989.
12. Duigou G J, Babiss L E, Iman D S, Shay J W & Fisher P B. Suppression of the progression phenotype in somatic cell hybrids occurs in the absence of altered type 5 adenovirus gene expression. *Mol Cell Biol*, 10: 2027–2034, 1990.
13. Duigou G J, Su Z-z, Babiss L E, Driscoll B, Fung Y-K T & Fisher P B. Analysis of viral and cellular gene expression during progression and suppression of the transformed phenotype in type 5 adenovirus transformed rat embryo cells. *Oncogene*, 6: 1813–1824, 1991.
14. Reddy P G, Su Z-z & Fisher P B. Identification and cloning of genes involved in progression of transformed phenotype. In: *Chromosome and Genetic Analysis, Meth-* ods in *Molecular Genetics,* vol. I, K W Adolph, Ed, Academic Press, Inc., Orlando, Fla., vol 1, pp 68–102, 1993.
15. Su Z-z, Shen R, O'Brian C A & Fisher P B. Induction of a progression phenotype in type 5 adenovirus-transformed rat embryo cells by the protein kinase C b gene and its reversal by 5-azacytidine. *Oncogene,* 9: 1123–1132, 1994.
16. Jiang H & Fisher P B. Use of a sensitive and efficient subtraction hybridization protocol for the identification of genes differentially regulated during the induction of differentiation in human melanoma cells. *Mol Cell Different,* 1 (3): 285–299, 1993.
17. Su Z-z, Shi Y & Fisher P B. Subtraction hybridization identifies a transformation progression elevated gene PEG-3 with sequence homology to a growth arrest and DNA damage inducible gene. *Proc Natl Acad Sci USA,* 94: 9125–9130, 1997.
18. Fornace A J Jr, Alamo I Jr & Hollander M C. DNA damage-inducible transcripts in mammalian cells. *Proc Natl Acad Sci USA,* 85: 8800–8804, 1988.
19. Lord K A, Hoffman-Liebermann B & Liebermann D A. Complexity of the immediate early response of myeloid cells to terminal differentiation and growth arrest includes ICAM-1, Jun-B and histone variants. *Oncogene,* 5: 387–396, 1990.
20. Lord K A, Hoffman-Liebermann B & Liebermann D A. Sequence of MyD116 cDNA: a novel myeloid differentiation primary response gene induced by IL6. *Nucleic Acids Res,* 18: 2823, 1990.
21. Zhan Q, Lord K A, Alamo I Jr, Hollander M C, Carrier F, Ron D, Kohn K W, Hoffman B, Liebermann D A & Fornace A J Jr. The gadd and MyD genes define a novel set of mammalian genes encoding acidic proteins that synergistically suppress cell growth. *Mol Cell Biol,* 14: 2361–2371, 1994.
22. Chou J & Roizman B. Herpes simplex virus 1 $\gamma_1 34.5$ gene function, which blocks the host response to infection, maps in the homologous domain of the genes expressed during growth arrest and DNA damage. *Proc Natl Acad Sci USA,* 91: 5247–5251, 1994.
23. He B, Chou J, Liebermann D A, Hoffman B & Roizman B. The carboxyl terminus of the murine MyD116 gene substitutes for the corresponding domain of the $\gamma_1 34.5$ gene of herpes simplex virus to preclude the premature shutoff of total protein synthesis in infected human cells. *J Virol,* 70: 84–90, 1996.
24. Liotta L A, Steeg P G & Stetler-Stevenson W G. Cancer metastasis and angiogenesis: an imbalance of positive and negative regulation. *Cell,* 64: 327–336, 1991.
25. Khosravi-Far R & Der C J. The Ras signal transduction pathway. *Cancer Metastasis Rev,* 13: 67–89, 1994.
26. Fisher P B, Babiss L E, Weinstein I B & Ginsberg H S. Analysis of type 5 adenovirus transformation with a cloned rat embryo cell line (CREF). *Proc Natl Acad Sci USA,* 79: 3527–3531, 1982.
27. Boylon J F, Jackson J, Steiner M, Shih T Y, Duigou G J, Roszman T, Fisher P B & Zimmer S G. Role of Ha-ras (rasH) oncogene in mediating progression of the tumor cell phenotype (review). *Anticancer Res,* 10: 717–724, 1990.
28. Boylon J F, Shih T Y, Fisher P B & Zimmer S G. Induction and progression of the transformed phenotype in cloned rat embryo fibroblast cells: studies employing type 5 adenovirus and wild-type and mutant Ha-ras oncogenes. *Mol Carcinog,* 3: 309–318, 1992.
29. Su Z-z, Austin V N, Zimmer S G & Fisher P B. Defining the critical gene expression changes associated with expression and suppression of the tumorigenic and metastatic phenotype in Ha-ras-transformed cloned rat embryo fibroblast cells. *Oncogene,* 8: 1211–1219, 1993.
30. Su Z-z, Yemul S. Estabrook A, Friedman R M, Zimmer S G & Fisher P B. Transcriptional switching model for the regulation of tumorigenesis and metastasis by the Ha-ras oncogene: transcriptional changes in the Ha-ras tumor suppressor gene lysyl oxidase. *Intl J Oncol,* 7: 1279–1284, 1995.
31. Su Z-z, Zhang N, Wang M-N, Goldstein N I & Fisher P B. Progression elevated gene-3 is a positive regulator of cancer aggressiveness and angiogenesis. Manuscript in preparation, 1998.
32. Lin J, Su Z-z, Grunberger D, Zimmer S G & Fisher P B. Expression of the transformed phenotype induced by diverse acting viral oncogenes mediates sensitivity to growth suppression induced by caffeic acid phenethyl ester (CAPE). *Intl J Oncol,* 5: 5–15, 1994.
33. Su Z-z, Lin J, Prewett M, Goldstein N I & Fisher P B. Apoptosis mediates the selective toxicity of caffeic acid phenethyl ester (CAPE) toward oncogene-transformed rat embryo fibroblast cells. *Anticancer Res,* 15: 1841–1848, 1995.
34. Santos C, Chandler K, Zimmer S, Fisher P B, Gunthert U & Ward-Anderson K. Detachment of transformed cells: role of CD44 variant. *Cellular Biophysics,* 26: 1–19, 1995.
35. Vairapandi M, Balliet A G, Fornace A J Jr, Hoffman B & Liebermann D A. The differentiation primary response gene MyD118, related to GADD45, encodes for a nuclear protein which interacts with PCNA and p21 WAF1/CIP1. *Oncogene,* 12: 2579–2594, 1996.
36. Jiang H, Lin J, Su Z-z, Kerbel R S, Herlyn M, Weissman R B, Welch D R & Fisher P B. The melanoma differentiation associated gene mda-6, which encodes the cyclin-dependent kinase inhibitor p21, is differentially expressed during growth, differentiation and progression in human melanoma cells. *Oncogene,* 10: 1855–1864, 1995.
37. Jiang H, Lin J & Fisher P B. A molecular definition of terminal cell differentiation in human melanoma cells. *Mol Cell Different,* 2 (3): 221–239, 1994.
38. Jiang H, Su Z-z, Lin J J, Goldstein N I, Young C S H & Fisher P B. The melanoma differentiation associated gene mda-7 suppresses cancer cell growth. *Proc Natl Acad Sci USA,* 93: 9160–9165, 1996.
39. Su Z—Z, Olsson C A, Zimmer S G & Fisher P B. Transfer of a dominant-acting tumor-inducing oncogene from human prostatic carcinoma cells to cloned rat embryo fibroblast cells by DNA-transfection. *Anticancer Res,* 12: 297–304, 1992.
40. Shen R, Su Z—Z, C.A. Olsson and P.B. Fisher. Identification of the human prostatic carcinoma oncogene PTI-1 by rapid expression cloning and differential RNA display. *Proc Natl Acad Sci USA,* 92: 6778–6782, 1995.
41. Siebert P, Chen S & Kellogg D. The Human Promoter-Finder™ DNA Walking Kit: a new PCR method for walking in uncloned genomic DNA. *CLONTECHniques, X* (2): 1–3, 1995.
42. Siebert P, Chenchik A, Kellogg D E, Lukyanov K A & Lukyanov S A. An improved PCR method for walking in uncloned genomic DNA. *Nucleic Acids Res,* 23 (6): 1087–1088, 1995.
43. Jiang H, Waxman S & Fisher P B. Regulation of c-fos, c-jun and jun-B gene expression in human melanoma cells induced to terminally differentiate. *Mol Cell Different,* 1 (2): 197–214, 1993.
44. Sambrook J, Fritsch E F & Maniatis T. In: *Molecular Cloning: A Laboratory Manual,* 2nd edition, Cold Spring Harbor Laboratories Press, Cold Spring Harbor, N.Y., 1989.

45. Johansen F-E & Prywes R. Two pathways for serum regulation of the c-fos serum response element require specific sequence elements and a minimal domain of serum response factor. *Mol Cell Biol* 14: 5920–5928, 1994.
46. Albanese C, Johnson J, Watanabe G, Eklund D, Vu D, Arnold A & Pestell R G. Transforming p21ras mutants and c-Ets-2 activate the cyclin D1 promoter through distinguishable regions. *J Biol Chem* 270: 23589–23597, 1995.
47. Jiang H, Lin J J, Su Z-z, Goldstein N I & Fisher P B. Subtraction hybridization identifies a novel melanoma differentiation associated gene, mda-7, modulated during human melanoma differentiation, growth and progression. *Oncogene,* 11: 2477–2486, 1995.
48. Babiss L E, Fisher P B & Ginsberg H S. Deletion and insertion mutations in early region 1a of type 5 adenovirus producing cold-sensitive or defective phenotypes for transformation. *J Virol,* 49: 731–740, 1984.
49. Herbst R S, Hermo H Jr, Fisher P B & Babiss L E. Regulation of adenovirus and cellular gene expression and cellular transformation by the E1B-encoded 175R protein. *J Virol,* 62: 4634–4643, 1988.
50. Su Z-z, Shen R, Young C S H & Fisher P B. Genetic analysis of carcinogen enhancement of type 5 adenovirus transformation oc cloned Fischer rat embryo fibroblast cells. *Mol Carcinog,* 8: 155–166, 1993.
51. Gorospe M, Martindale J L, Sheikh M S, Fornace A J Jr & Holbrook N J. Regulation of $p_{21}^{CIP1/WAF1}$ expression by cellular stress: p53-dependent and p53-independent mechanisms. *Mol Cell Different,* 4 (1): 47–65, 1996.
52. Maniatis T, Goodbourn S & Fischer A. Regulation of inducible and tissue-specific gene expression. *Science,* 236: 1237–1244, 1987.
53. Ptashne M. How eukaryotic transcriptional activators work. *Nature,* 335: 683–689, 1988.
54. Su Z-z, Yemul S, Stein C A & Fisher P B. c-fos is a positive regulator of carcinogen enhancement of adenovirus transformation. *Oncogene,* 10: 2037–2049, 1995.
55. Jiang H, Lin J, Young S-m, Goldstein N I, Waxman S, Davila V, Chellappan S P & Fisher P B. Cell cycle gene expression and E2F transcription factor complexes in human melanoma cells induced to terminally differentiate. *Oncogene,* 11: 1179–1189, 1995.
56. Thanos D & Maniatis T. The high mobility group protein HMGI(Y) is required for NF-KB dependent virus induction of the human IFN-b gene. *Cell,* 71: 777–789, 1992.
57. Weber J A & Gilmour D S. Genomic footprinting of the hsp70 and histone H3 promoters in Drosophila embryos reveal novel protein-DNA interactions. *Nucleic Acids Res,* 23: 3327–3334, 1995.
58. Kamat J P, Basu K, Satyamoorthy L, Showe L & Howe C C. IPEB transcription factor regulating intracisternal A particle during F9 cell differentiation is expressed at sites of lymphoid development. *Mol Rep Dev,* 41: 8–15, 1995.
59. Basu A, Dong B, Krainer A R & Howe C C. The intracisternal A-particle proximal enhancer-binding protein activates transcription and iss identical to the RNA- and DNA-binding protein p54nrb/NonO. *Mol Cell Biol,* 17: 677–686, 1997.
60. Aebersold R H, Leavitt R A, Saavedra R A, Hood L E & Kent S B H. Internal amino acid sequence analysis of proteins separated by one- or two-dimensional gel electrophoresis after in situ protease digestion on nitrocellulose. *Proc Natl Acad Sci USA,* 84: 6970–6974, 1987.
61. Lin J J, Jiang H & Fisher P B. Characterization of a novel melanoma differentiation associated gene, mda-9, that is down-regulated during terminal cell differentiation. *Mol Cell Different,* 4 (4): 317–333, 1996.
62. Lin J J, Jiang H & Fisher P B. Melanoma differentiation associated gene-9, mda-9, is a human gamma interferon responsive gene. *Gene,* in press, 1997.
63. Shen R, Goswami S K, Mascareno E, Kumar A & Siddiqui M A Q. Tissue-specific transcription of the cardiac myosin light-chain 2 gene is regulated by an upstream repressor element. *Mol Cell Biol,* 11: 1676–1685, 1991.
64. Fisher A L, Ohsako S & Caudy M. The WRPW motif of the hairy-related basic helix-loop-helix repressor proteins acts as a 4-amino-acid transcription repression and protein-protein interaction domain. *Mol Cell Biol,* 16: 2670–2677, 1996.
65. Su Z-z, Goldstein N I & Fisher P B. Antisense inhibition of the PTI-1 oncogene reverses cancer phenotypes. *Proc Natl Acad Sci USA,* 95: 1764–1769, 1998.

Sixth Series of Experiments

PEG-3 Promoter/PTI-1 System

Rationale:

Cancer is a progressive, multigenic disorder characterized by changes in the transformed phenotype that culminates in metastatic disease. Through the use of subtraction hybridization, a novel gene associated with transformation progression in virus- and oncogene-transformed rat embryo cells was cloned. The gene, designated PEG-3, shares significant nucleotide and amino acid sequence homology with the hamster growth arrest and DNA-damage inducible gene gadd34 and a homologous murine gene, MyD116, that is induced during induction of terminal differentiation by IL-6 in murine myeloid leukemia cells. PEG-3 expression is elevated in rodent cells displaying a progressed-transformed phenotype and in rodent cells transformed by various oncogenes including Ha-ras, v-src, mutant type 5 adenovirus, and human papilloma virus type 18 (HPV). PEG-3 is transcriptionally activated in rodent cells, as is gadd34 and MyD116, after treatment with DNA damaging agents. However, only PEG-3 is active in rodent cells displaying a transformed progressed phenotype. PEG-3 has been shown to be upregulated in ras, src, HPV, and PTI-1 transformed CREF-Trans 6 cells but not in CREF-Trans 6 itself. In addition, the gene is also expressed in various human tumor lines but not in normal cell lines.

Recently, the PEG-3 promoter has been isolated and linked to a luciferase reporter gene. Transient transfection of the promoter/reporter construct into cell lines of both tumor and normal origin has demonstrated that the promoter is constitutively expressed in the tumor cell lines but not in normal cells. We have stably transfected the PEG-3/luciferase construct into various transformed derivatives of CREF-Trans 6 containing the oncogenes PTI-1, ras, and src, as well cells transformed by HPV. These cell lines are used as targets for our small molecule combinatorial libraries.

The PEG-3 Promoter Assay. Cell Lines: Stable transfectants expressing a PEG-3 promoter/luciferase construct were prepared in CREF-Trans 6:4NMT (PTI-1 positive), T24 (ras positive); CREF-src, and CREF-HPV. Clones were isolated that constitutively expressed high levels of luciferase. These clones are currently being used as targets in GenQuest's small molecule screening assays.

The following protocol is being used to screen small molecule libraries:

a. Cells (e.g., 4NMT; PTI-1 positive) are plated in 96 well opaque microtiter plates at a cell concentration of $1-2 \times 10^4$ cells/well in 100 ul of growth medium.
b. A stock solution of the combinatorial library is prepared in DMSO (final concentration=1 mM) Further dilutions are made in growth medium to final concentrations of 20 uM, 2 uM, and 0.2 uM.

c. 100 ul/well of each sample is added to the cells. The final concentrations are 10, 1, and 0.1 uM.

d. Growth medium alone is added to the first two wells (Row A, wells 1 and 2) of each plate; a positive control is added to the next two wells (Row A, wells 3 and 4). In the case of PTI-1, an antisense oligonucleotide to the bridge region has been shown to down-regulate luciferase activity within 24 hours.

e. Plates are incubated overnight at 37C. Medium is removed and cells are washed with PBS. Cells are lysed using Reporter Lysis Buffer supplied by the kit manufacturer (Luciferase Reporter Gene Assay kit; Boehringer Mannheim, cat. #1 669 893).

f. Plates are placed −70C. overnight. Alternatively, the plates can be stored for several weeks (the manufacturer notes that luciferase is stable in their Reporter Lysis Buffer) over several freeze thaw cycles).

g. Plates are thawed and 50 ul of the luciferase reaction mixture is added. Plates are immediately read in a 96 well luminometer (Tropix TR717 microplate luminometer).

h. A hit is defined as the decrease in luciferase activity compared to control.

This assay can be completed in 48 hours:

i. Overnight incubation with library ii. Luciferase assay: 4 hours

For viability assays.

a. Plates are set up as above except in transparent 96 well microtiter plates.

b. After a 24 hour incubation, 10 ul of WST-1 (Cell Proliferation Reagent; Boehringer Mannheim 1 544 807) is added to each well.

c. Plates are read at 30, 60, 120, and 180 minutes in an ELISA reader at 450 nM).

d. Viability is calculated as a percentage of the untreated cells.

Deletion Analysis of the Rat PEG-3 Promoter

A series of deletion mutants have been produced by mutagenesis (Erase-a-Base System, Promega), linked to a luciferase reporter gene and transfected into different cell types to define the regions of the PEG-3 promoter that mediate differential expression in progressed versus unprogressed, oncogenically transformed versus nontransformed and DNA damaged versus undamaged cells. The mutagenesis procedure was performed as described by Promega. The position of the various deletion mutants (determined by sequence analysis) relative to the promoter are shown in FIG. 24. The various deletion clones are indicated by numbers ranging from 2 to 11, with 1 being the complete PEG-3 promoter, and the clone designations are indicated in brackets. These include: 1 (46): intact rat PEG-3 promoter; 2 (22): missing 223 nt from the 5' region of the rat PEG-3 promoter; 3 (33): missing 386 nt from the 5' region of the rat PEG-3 promoter; 4 (42): missing 507 nt from the 5' region of the rat PEG-3 promoter; 5 (14): missing 784 nt from the 5' region of the rat PEG-3 promoter; 6 (8): missing 809 nt from the 5' region of the rat PEG-3 promoter; 7 (65): missing 853 nt from the 5' region of the rat PEG-3 promoter; 8 (74): missing 1190 nt from the 5' region of the rat PEG-3 promoter; 9 (17): missing 1215 nt from the 5' region of the rat PEG-3 promoter; 10 (114): missing 1511 nt from the 5' region of the rat PEG-3 promoter; and 11 (20): missing 1737 nt from the 5' region of the rat PEG-3 promoter. The different deletion mutants are being used to define the regions of the PEG-3 promoter that can enhance or suppress expression of the PEG-3 gene. These constructs can now be used to determine the regulatory control of the PEG-3 gene including autoregulation, developmental regulation, tissue and cell type specific expression and differential expression in progressed versus unprogressed, enhanced expression as a function of oncogenic transformation and induction of expression as a consequence of DNA damage.

Expression of the intact PEG-3 promoter and various deletion mutants of the PEG-3 promoter in the different cell types is shown in FIGS. 25 to 31. The different cell types include: E11(FIG. 12), E11-NMT (FIG. 26), a comparison of E11 versus E11-NMT (FIG. 14), E11-PKC (FIG. 28), CREF-HPV (FIG. 29), CREF-ras (FIG. 30) and CREF-Trans 6:4 NMT (FIG. 31).

Seventh Series of Experiments

CURE (Cancer Utilized Reporter Execution):

A Strategy for Selectively Inhibiting the Growth and/or Killing of Cancer Cells

Use of CIRAs (Cancer Inhibitory Recombinant Adenoviruses) in CURE.

Cancer is a progressive process with defined temporal stages culminating in metastatic potential by evolving tumor cells. Although extensively scrutinized the molecular determinants of cancer progression remain unclear. Well-characterized cell culture systems are valuable experimental tools for defining the biochemical and molecular basis of progression. Two rodent model systems are providing insights into the genes and processes regulating malignant progression of the transformed cell.

In adenovirus type 5 (Ad5) transformed rat embryo (RE) cells, progression can occur spontaneously by tumor formation in nude mice or by ectopic expression of oncogenes and signal transducing growth-regulating genes. In all contexts of progression, the demethylating agent 5-azacytidine (AZA) can reverse this process resulting in an unprogressed phenotype in >95% of treated clones. Inhibition of progression also occurs in this system after forming somatic cell hybrids between progressed and unprogressed cells. Using an immortal cloned rat embryo fibroblast (CREF) cell culture system, progression to metastasis and reversion of progression can be regulated by appropriate genetic manipulation using the Ha-ras oncogene and the Krev-1 suppressor gene. These experimental findings support the hypothesis that progression may involve the selective inactivation of genes that suppress progression (progression suppressing genes) and/or the induction of genes that promote progression (progression enhancing genes). Identification and characterization of these genetic elements would prove of immense value for defining this significant and defining component of the cancer process and could provide useful target molecules for intervening in the neoplastic process.

To elucidate the molecular basis of progression we are using a subtraction hybridization approach. Subtraction hybridization between progressed and unprogressed Ad5-transformed RE cells resulted in the cloning of progression elevated gene-3, PEG-3, that displays coordinate expression with the progression and transformation phenotypes in Ad5 and oncogene transformed rat embryo cultures. PEG-3 is a novel gene sharing nucleotide (~73 and ~68%) and amino acid (~59 and ~72%) sequence homology with the hamster growth arrest and DNA damage inducible gene gadd34 and a homologous murine gene, MyD116, that is induced during induction of differentiation by IL6 in murine myeloid leukemia cells. Like gadd34 and MyD116, PEG-3 expression is induced by DNA damage. Induction following DNA damage results from increased RNA transcription and elevated steady-state levels of the PEG-3 gene. PEG-3 expression is also elevated in temperature sensitive mutant adenovirus transformed Sprgaue-Dawley rat embryo cells as a consequence of increased expession of the transformed phenotype, i.e., elevated cancer progression. Additionally, PEG-3 expression increases in CREF cells as a consequence of oncogenic transformation by diverse acting oncogenes, including Ha-ras, v-src, human papilloma virus type 18, v-raf, mutant type 5 adenovirus (H5hr1) and prostate tumor inducing gene-1 (PTI-1). These experimental results support the hypothesis that PEG-3 expression is regulated by cancer progression, oncogenic transformation and DNA damage.

To define the mode of action of PEG-3 a 5' DNA sequence containing the promoter region of this gene has been isolated and analyzed. The PEG-3-Promoter (PEG-Prom) (~2.1 kb) has been linked to a luciferase reporter gene (PEG-Prom-Luc) and evaluated for expression in various cell types. Elevated levels of PEG-Prom-Luc activity are apparent in transformed rodent cells displaying a progressed transformed phenotype, DNA damaged rodent and human cells, oncogenically transformed rodent cells and histologically distinct human cancer cells (including metastatic melanoma, glioblastoma multiforme and carcinomas of the breast, cervix, colon, lung, nasopharyngx and prostate). On the basis of the selective activity of the PEG-Prom for cancer cells, genetic vectors are being constructed that display targeted expression of growth arresting and apoptosis-inducing genes or genes encoding an enzyme permitting activation of a toxic product in cancer cells. Additionally, genetic vectors can be constructed using the CURE protocol that target the expression of molecules on the surface of only cancer cells permitting the directed therapy of cancer using immunological reagents (monoclonal antibodies, cytotoxic T-cells, TILs, etc.) or toxic chemicals. These novel vectors are the basis for the CURE (Cancer Utilized Reporter Execution) protocol (FIG. 32). As one application of CURE, recombinant adenoviruses are being constructed that permit the efficient delivery of CURE vectors into cells. These vectors are designed as CIRAs (Cancer Inhibitory Recombinant Adenoviruses) and they contain the PEG-Prom driving expression of target genes, including wild-type p53 (wt p53), melanoma differentiation associated gene-7 (mda-7), adenovirus E1A and E1B (Ad E1A and E1B) or herpes simplex type 1 thymidine kinase gene (HSV TK) (FIG. 32). When cancer cells are infected with the CIRAs, the appropriate genes are activated resulting in a direct growth inhibition or apoptosis (wt p53 or mda-7), cell death following adenovirus replication (Ad E1A and E1B) or cell death following administration of gangcyclovir (HSV TK).

The carcinogenic process involves a series of sequential changes in the phenotype of a cell resulting in the acquisition of new properties or a further elaboration of transformation-associated traits by the evolving tumor cell (rev 1–4). Although extensively studied, the precise genetic mechanisms underlying tumor cell progression during the development of most human cancers remain unknown. Possible factors contributing to transformation progression, include: activation of cellular genes that promote the cancer cell phenotype, i.e., oncogenes; activation of genes that regulate genomic stability, i.e., DNA repair genes; activation of genes that mediate cancer aggressiveness and angiogenesis, i.e., progression elevated genes; loss or inactivation of cellular genes that function as inhibitors of the cancer cell phenotype, i.e., tumor and progression suppressor genes; and/or combinations of these genetic changes in the same tumor cell (rev 1–6). A useful model for defining the genetic and biochemical changes mediating tumor progression is the Ad5/early passage RE cell culture system (1,7–15). Transformation of secondary RE cells by Ad5 is often a sequential process resulting in the acquisition of and further elaboration of specific phenotypes by the transformed cell (7–10). Progression in the Ad5-transformation model is characterized by the development of enhanced anchorage-independence and tumorigenic capacity (as indicated by a reduced latency time for tumor formation in nude mice) by progressed cells (1,10). The progression phenotype in Ad5-transformed rat embryo cells can be induced by selection for growth in agar or tumor formation in nude mice (7–10), referred to as spontaneous-progression, by transfection with oncogenes (11,14), such as Ha-ras, v-src, v-raf or E6/E7 region of human papilloma virus type-18 (HPV-18), referred to as oncogene-mediated progression, or by transfection with specific signal transducing genes (15), such as protein kinase C (PKC), referred to as growth factor-related, gene-induced progression.

Progression, induced spontaneously or after gene transfer, is a stable cellular trait that remains undiminished in Ad5-transformed RE cells even after extensive passage (>100) in monolayer culture (1,10,14). However, a single-treatment with the demethylating agent AZA results in a stable reversion in transformation progression in >95% of cellular clones (1,10,11,14,15). The progression phenotype is also suppressed in somatic cell hybrids formed between normal or unprogressed transformed cells and progressed cells (12–14). These findings suggest that progression may result from the activation of specific progression-promoting (progression elevated) genes or the selective inhibition of progression-suppressing genes, or possibly a combination of both processes. To identify potential progression inducing genes with elevated expression in progressed versus unprogressed Ad5-transformed cells we are using a subtraction approach (14,16,17). The subtraction hybridization approach resulted in cloning of PEG-3 displaying elevated expression in progressed cells (spontaneous, oncogene-induced and growth factor-related, gene-induced) than in unprogressed cells (parental Ad5-transformed, AZA-suppressed, and suppressed somatic cell hybrids) (17). These findings document a direct correlation between expression of PEG-3 and the progression phenotype in this rat embryo model system.

The nucleotide sequence of PEG-3 is ~73 and ~68% and the amino acid sequence is ~59 and 72% homologous to gadd34 (18) and MyD116 (19,20), respectively (17). The sequence homologies between PEG-3 and gadd34/MyD116 are highest in the amino terminal region of their encoded proteins, i.e., ~69 and ~76% homology with gadd34 and MyD116 respectively, in the first 279 aa (17). In contrast, the sequence of the carboxyl terminus of PEG-3 significantly diverges from gadd34/MyD116, i.e., only ~28 and ~49% homology in the carboxyl 88 aa (17). The specific function of the gadd34/MyD116 gene is not known. Like hamster gadd34 and its murine homologue MyD116, PEG-3 expression is induced in CREF cells by MMS and gamma irradiation (17). The gadd34/MyD116 gene, as well as the gadd45, MyD118 and gadd153 genes, encode acidic proteins with very similar and unusual charge characteristics (21). PEG-3 also encodes a putative protein with acidic properties similar to the gadd and MyD genes. The carboxyl-terminal domain of the murine MyD116 protein is homologous to the corresponding domain of the herpes simplex virus 1 $\gamma_1 34.5$ protein, that prevents the premature shutoff of total protein synthesis in infected human cells (22,23). Replacement of the carboxyl-terminal domain of $\gamma_1 34.5$ with the homologous region from MyD116 results in a restoration of function to the herpes viral genome, i.e., prevention of early host shutoff of protein synthesis (23). Although further studies are necessary, preliminary results indicate that expression of a carboxyl terminus region of MyD116 results in nuclear localization (23). Similarly, both gadd153 and gadd45 gene products are nuclear proteins (21). When transiently expressed in various human tumor cell lines, gadd34/MyD116 is growth inhibitory and this gene can synergize with gadd45 or gadd153 in suppressing cell growth (21). In contrast, ectopic expression of PEG-3 in normal CREF (cloned rat embryo fibroblast) and HBL-100 (normal breast epithelial) cells and cancer (E11 and E11-NMT (Ad5-transformed rat embryo) and MCF-7 and T47D (human breast carcinoma) cells does not significantly inhibit cell growth or colony formation (17). These results suggest that gadd34/MyD116, gadd45, gadd153 and MyD118, represent a novel class of mammalian genes encoding acidic proteins that are regulated during DNA damage and stress and involved in controlling cell growth. In this context, PEG-3 would appear to represent an enigma, since it is not growth suppressive and its expression is elevated in cells displaying an in vivo proliferative advantage and a progressed transformed and tumorigenic phenotype (17). PEG-3 may represent a unique member of this acidic protein gene family that directly functions in regulating progression, perhaps by constitutively inducing signals that would normally only be induced during genomic stress. Additionally, PEG-3 may modify the expression of down-stream genes involved in mediating cancer aggressiveness, i.e., tumor- and metastasis-mediating genes and genes involved in tumor angiogenesis. In these contexts, PEG-3 could function to modify specific programs of gene expression and alter genomic stability, thereby facilitating tumor progression. This hypothesis is amenable to experimental confirmation.

The final stage in tumor progression is the acquisition by transformed cells of the ability to invade local tissue, survive in the circulation and recolonize in a new area of the body, i.e., metastasis (rev. 24,25). Transfection of a Ha-ras oncogene into CREF cells (26) results in morphological transformation, anchorage-independence and acquisition of tumorigenic and metastatic potential (27–29). Ha-ras-transformed CREF cells exhibit profound changes in the transcription and steady-state levels of genes involved in suppression and induction of oncogenesis (30,31). Simultaneous overexpression of the Ha-ras suppressor gene Krev-1 in Ha-ras-transformed CREF cells results in morphological reversion, suppression of agar growth capacity and a delay in in vivo oncogenesis (30). Reversion of transformation in Ha-ras+Krev-1 transformed CREF cells correlates with a return in the transcriptional and steady-state mRNA profile to that of nontransformed CREF cells (30,31). Following long latency times, Ha-ras+Krev-1 transformed CREF cells form both tumors and metastases in athymic nude mice (30). The patterns of gene expression changes observed during progression, progression suppression and escape from progression suppression supports the concept of transcriptional switching as a major component of Ha-ras-induced transformation (30,31).

Analysis of PEG-3 expression in CREF cells and various oncogene-transformed and suppressor gene-reverted CREF cells indicates a direct relationship between PEG-3 expression and transformation and oncogenic progression (17). Northern blotting indicates that CREF cells do not express PEG-3, whereas PEG-3 expression occurs in CREF cells transformed by several diverse-acting oncogenes, including Ha-ras, v-src, HPV 18 and mutant Ad5 (H5hr1) (17). Suppression of Ha-ras-induced transformation by Krev-1 results in suppression of PEG-3 expression. However, both tumor-derived and metastasis-derived Krev-1 Ha-ras-transformed CREF cells express PEG-3. The highest relative levels of PEG-3 mRNA are consistently found in the metastasis-derived Ha-ras+Krev-1 transformed CREF cells. These results indicate a direct relationship between PEG-3 expression and the transformed and oncogenic capacity of CREF cells. In addition, PEG-3 expression directly correlates with human melanoma progression, with the highest levels of expression found in metastatic human melanoma and reduced levels observed in normal human melanocytes, radial growth phase (RGP) primary melanomas and early vertical growth phase (VGP) primary melanomas.

An important question is the role of PEG-3 in cancer progression. PEG-3 could simply correlate with transformation progression or alternatively it could directly regulate this process. To distinguish between these possibilities, E11 cells (not expressing PEG-3) were genetically engineered to express PEG-3 (17). When assayed for growth in agar or aggressiveness in vivo in nude mice, E11-PEG-3 cells display a progression phenotype akin to that seen in E11-NMT cells (17,31). Moreover, antisense inhibition of PEG-3 in E11-NMT (normally expressing PEG-3) results in suppression of the progression phenotype in vitro and in vivo (31). Although the mechanism by which PEG-3 affects cancer progression in vivo remains to be determined, a potential role for induction of angiogenesis by PEG-3 is suggested (31). Tumors isolated from nude mice infected with E11-NMT and E11-PEG-3 clones are highly vascularized and they contain large numbers of blood vessels, whereas E11 and E11-NMT-PEG-3 AS tumors grow slower and they remain compact without extensive blood vessel involvement (31). Further studies are necessary to determine the potentially important relationship between PEG-3 expression and angiogenesis.

Defining the Mechanism Underlying the Differential Expression of PEG-3 as a Function of Cancer Progression, Oncogenic Transformation and DNA Damage.

Nuclear run-on assays indicate that PEG-3 expression directly correlates with an increase in the rate of RNA transcription (17). This association is supported by the isolation of a genomic fragment upstream of the 5' untranslated region of the PEG-3 cDNA and demonstration that this sequence linked to a luciferase reporter gene is activated as a function of cancer progression, oncogenic transformation and DNA damage. Additionally, changes in the stability of PEG-3 mRNA may also contribute to differential expression of this gene as a function of cancer progression, oncogene expression and DNA damage. To address this issue mRNA stability (RNA degradation) assays will be performed as described in detail previously (32). Our analysis will focus on the effect of cancer progression (E11-NMT, R1 and R2 cells), oncogenic transformation (Ha-ras, V-src, H5hr1 and HPV-18 transformed CREF cells) and DNA damage (gamma irradiation and MMS-treatment of CREF cells). Appropriate controls, E11, untransformed CREF cells and CREF cells not treated with DNA damaging agents, respectively, and experimental samples will be incubated without additions or in the presence of 5 µg/ml of actinomycin D (in the dark), and 30, 60 and 120 min later, total cellular RNA will be isolated and analyzed for gene expression using Northern hybridization. RNA blots will be quantitated by densitometric analysis using a Molecular Dynamics densitometer (Sunnyvale, Calif.) (32). These straight forward experiments will indicate if the stability of PEG-3 is altered in cells as a direct consequence of spontaneous progression, expression of defined oncogenes or as a consequence of DNA damage.

Most eukaryotic genes are regulated at the level of initiation of gene transcription. Detailed characterization of many different eukaryotic transcriptional units has led to the general concept that specific interactions of short DNA sequences, usually located at the 5'-flanking region of the corresponding genes (cis-acting elements), with certain cellular proteins (trans-acting elements) play a major role in determining the rate of initiation of gene transcription. To elucidate the mechanism underlying the transcriptional regulation of the PEG-3 gene the 5'-flanking region of this gene is being analyzed. These experiments are important and they will determine regulatory control of the PEG-3 gene including autoregulation, developmental regulation, tissue and cell type specific expression and differential expression in progressed versus unprogressed cells, enhanced expression as a function of oncogenic transformation and induction of expression as a consequence of DNA damage. Once the appropriate regions of the PEG-3 gene regulating the initiation of transcription has been confirmed, studies will be conducted to determine the relevant trans-acting regulatory factors that bind to specific cis-acting regulatory elements and activate or repress expression of the PEG-3 gene. The experiments outlined below are designed to: [1] define the 5'-flanking regions of the PEG-3 gene involved in mediating differential activity of PEG-3 in progressed, oncogenically transformed and DNA damaged cells; [2] identify cis-acting regulatory elements in the promoter region of the PEG-3 gene which are responsible for the differential induction of PEG-3 expression; and [3] identify and characterize trans-acting regulatory elements that activate (or repress) expression of the PEG-3 gene.

Primary Analysis of the Functional Regions of the PEG-3 Promoter.

Using a genomic walking strategy we have identified a 5'-flanking promoter region of the PEG-3 gene that appears to encompass a functionally complete PEG-3 promoter. To define important transcriptional regulatory regions of the PEG-3 promoter, a heterologous expression system containing a luciferase gene without promoter or enhancer has been developed using the full-length promoter construct (33–35). Internal deletion mutations will be generated either by taking advantage of internal restriction sites or by a nested exonuclease III base deletion strategy. These constructs will be transfected into E11 and E11-NMT, untransformed and transformed CREF (H5hr1, Ha-ras, v-src and HPV-18) and control CREF and gamma irradiation or MMS treated CREF cells. On the basis of transfection analyses of various deletion and point mutations it will be possible to define elements responsible for induction of PEG-3 as a consequence of cancer progression, specific transformation pathways or DNA damage response.

Transcription of PEG-3 in E11-NMT cells, as determined by nuclear run-on assays, is >20-fold higher than in E11 cells, whereas transient transfection of the PEG-3 promoter-luciferase gene into these two cell types indicates only an ~5-fold increase in activity in E11-NMT versus E11 cells (FIG. 15). This could indicate that the PEG-3 gene is repressed in non-expressing cells (such as E11) through a cis-acting mechanism that is non-functional on transiently transfected promoters. Various luciferase constructs will be transfected into the different cell types by the lipofectamine method or electroporation (Gene Pulser, Bio-Rad) as previously described (33,36). To correct for DNA uptake and cell number used for each transfection experiment, the luciferase constructs will be transfected with plasmids containing bacterial β-galactosidase gene under the control of an Rous sarcoma virus (RSV) promoter (33–35). Studies will be conducted using multiple adult rat tissue Northern blots (CLONTECH) containing poly $A^+$RNA and probing with PEG-3 (as well as gadd34 and MyD116) to define which rat tissue normally express PEG-3. Previous studies document that genes expressing in more than one tissue often require different sequences flanking the 5'-end of the gene.

It is possible that PEG-3 expression in any normal tissue or under different circumstances in rat cells, i.e., progression, oncogenic transformation or DNA damage, may be regulated by different 5'-sequences. In that case, we will obtain variable luciferase activities for different luciferase constructs in the various cell lines. Transcription motifs contributing to PEG-3 regulation in a tissue, cell type or specific progression, transformation or DNA damage pathway will thus be identified.

Identifying cis-acting elements in the PEG-3 promoter responsible for expression during cancer progression, oncogenic transformation and DNA damage. On the basis of the deletion studies described above, the potential location of cis-acting elements responsible for expression of PEG-3 during cancer progression, oncogenic transformation and DNA damage will be identified. The ~2.1 kb PEG-3 promoter has been sequenced and potential regulatory elements have been identified by comparison to previously characterized transcriptional motifs. The PEG-3 promoter contains a number of potentially important transcriptional motifs including PEA3 (AGGAAA), E2A (GCAGGTG), GRE (TGTTCT), E2F (TTTTGGCCG), TRE (GGTCA), acute phase reactive regulating element (GTGGGA), SP1 (GGGCGG), AP1 (TGACTCA), AP2 (TCCCCAACCC) (SEQ ID NO:12) and NF1 (TGGATTTGAGCCA) (SEQ ID NO:13). The importance of these sequences in regulating PEG-3 expression during cancer progression, oncogenic transformation and DNA damage will be determined by introducing point mutations in a specific cis element into the promoter region using previously described site-specific mutagenesis techniques (33,37–40) or with recently described PCR-based strategies, i.e., ExSite™ PCR-based site-directed mutagenesis kit and the Chameleon™ double-stranded site-directed mutagenesis kit (Stratagene, Calif.). The mutated promoter constructs will be cloned into luciferase expression vectors and tested for their effects on the promoter function by transfection into different cell types and monitoring luciferase activity. Since the promoter region for the PEG-3 gene is located in front of the luciferase reporter gene in the various pPEG-Luciferase constructs, the change in luciferase activity for each construct will permit a direct comparison of the activity of the mutant promoter to that of the unmodified PEG-3 promoter.

After the regulatory regions of the PEG-3 promoter are confirmed experiments will be conducted to address a number of important questions relative to cancer progression, oncogenic transformation and DNA damage induction of PEG-3 expression. (1) Nuclear run-on and transient transfection assays with pPEG-Luciferase constructs will be used to determine the effect of changes in DNA methylation (AZA and phenyl butyrate treatment) on PEG-3 expression in E11-NMT cells, treatment with different classes of DNA damaging and cancer modulating agents (such as TPA, retinoids, Uv-C, gamma irradiation, methylating carcinogens, topoisomerase inhibitors, okadaic acid, etc.) on PEG-3 expression in CREF and CREF-PEG-Luc cl 1 cells (PEG-Luciferase stably transformed CREF clone) and exposure to cancer modulating agents (such as the Krev-1 gene, dominant negative inhibitors of specific oncogenes, chemicals such as CAPE, retinoids, sodium butyrate, interferon, TNF-α and additional progression modulating agents) on PEG-3 expression in oncogenically transformed CREF cells (1,8–10,18,21,28,29,41–43); (2) The level of PEG-3 transcription in cells displaying different stages of cancer progression and oncogenic transformation, including rodent model systems of cancer progression (such as the Dunning rat prostate model, metastatic murine melanoma variants, etc.) and additional rodent cells transformed by various oncogenes. These studies will indicate if expression of PEG-3 occurs in additional pathways of progression and transformation. (3) Transfection of varying lengths of the 5' flanking region and internal deletion luciferase constructs into rodent cells displaying different stages of progression, transformed by different classes of oncogenes and treated with various DNA damaging and cancer promoting and inhibiting agents. These regulatory elements will be sequenced and compared with previously characterized transcriptional motifs to identify potential positive and negative regulatory elements; (4) In addition to mutagenesis studies (to define functional motifs regulating transcriptional regulation of the PEG-3 promoter), cotransfection studies will be conducted with cDNAs containing putative positive acting regulatory elements and a minimal PEG-3 promoter-Luciferase construct into unprogressed and progressed rodent cells, untransformed CREF and oncogenically transformed CREF and untreated and DNA damage treated CREF cells. These studies will indicate if the introduction of specific putative positive acting regulatory elements can enhance PEG-3 expression in cells cotransfected with a minimal PEG-3 promoter region. The potential role of putative cis-acting negative regulatory elements will be addressed by cotransfection with a complete PEG-3 promoter region into the same target cells. These studies will provide relevant information about the potential role of inhibitory elements in regulating PEG-3 expression. (5) Experiments will also be performed to evaluate the status of the endogenous PEG-3 gene during cancer progression, oncogenic transformation and DNA damage. This will be approached by using DNase hypersensitivity assays to look for structural changes in this gene (33). Although not within the scope of the present studies, future studies could involve the identification of a human PEG-3 cDNA, elucidation of the human PEG-3 promoter and analysis of the level of PEG-3 expression in human progression model systems. These studies would be quite informative in providing a potential link between PEG-3 expression and cancer progression in human cells.

Identifying Trans-acting Nuclear Proteins that Mediate Transcriptional Enhancing Activity of the PEG-3 Gene During Cancer Progression, Oncogenic Transformation and DNA Damage.

The current view on regulation of eukaryotic gene expression suggests that trans-acting proteins bind to specific sites within cis-elements of a promoter region resulting in transcriptional activation (44,45). Experiments will be performed to identify trans-acting factors (nuclear proteins) and determine where these factors interact with cis-regulatory elements. To achieve this goal, two types of studies will be performed, one involving gel retardation (gel shift) assays (15,33,46,47) and the second involving DNase-I footprinting (methylation interference) assays (33,48,49).

Gel shift assays will be used to analyze the interactions between cis-acting elements in the PEG-3 promoter and trans-acting factors in mediating transcriptional control (15, 46,47). For this assay, $^{32}$P-labeled cis-elements will be incubated with nuclear extracts from E11 and E11-NMT, CREF and transformed CREF (Ha-ras, v-src, H5hr1 and HPV-18) and untreated CREF and CREF treated with MMS (100 μg/ml for 8 hr) or gamma irradiation (10 Gy for 4 hr) and reaction mixtures will be resolved on 5 or 8% polyacrylamide gels. After autoradiography, the pattern of retarded DNAs on the gel will provide information concerning the interaction between trans-acting factors and specific regions of the cis-acting elements in the PEG-3 promoter. Non-labeled cis-acting elements (self-competition) will be added as a competitor to duplicate samples to eliminate the possibility of non-specific binding and to confirm that the interaction is really conferred by the trans-acting factor. To begin to identify the transacting factors, different non-labeled DNAs (including those corresponding to sequences identified in the PEG-3 promoter, such as TATA, PEA3, E2A, GRE, E2F, TRE, acute phase reactive regulating element, SP1, AP1, AP2 and NF1) can be used as competitors in the gel shift assay to determine the relationship between the trans-acting factors and previously identified transcriptional regulators. It is possible that the trans-acting factors regulating transcriptional control of the PEG-3 promoter may be novel. To identify these factors extracts will be purified from E11 and E11-NMT, CREF and transformed CREF and untreated and DNA damaged CREF cells by two cycles of heparin-Sepharose column chromatography, two cycles of DNA affinity chromatography and separation on SDS-polyacrylamide gels (50,51). Proteins displaying appropriate activity using gel shift assays will be digested in situ with trypsin, the peptides separated by HPLC and the peptides sequenced (52). Peptide sequences will be used to synthesize degenerate primers and RT-PCR will be used to identify putative genes encoding the trans-acting factor. These partial sequences will be used with cDNA library screening approaches and the RACE procedure, if necessary, to identify full-length cDNAs encoding the trans-acting factors (17,36,51,52). Once identified, the role of the transacting factors in eliciting cancer progression will be analyzed. (1) The functionality of positive and negative trans-acting factors will be determined by transiently and stably expressing these genes in E11 and E11-NMT cells to determine effects on anchorage independence and tumorigenic potential in nude mice (stable expression). Positive effects would be indicated if overexpressing a positive trans-acting factor facilitates the progression phenotype, whereas overexpressing a negative trans-acting factor inhibits the progression phenotype. (2) Antisense approaches will be used to determine if blocking the expression of positive or negative trans-acting factors can directly modify the progression state. A direct effect of a positive trans-acting factor in affecting progression would be suggested if antisense inhibition of the positive factor partially or completely inhibits the progression phenotype in E11-NMT, i.e., growth in agar is reduced and tumor latency time is extended. Conversely, a direct effect of negative trans-acting factors in inhibiting progression would be suggested if antisense inhibition of the negative factor enhances the ability of E11 to grow in agar and reduces tumor latency time. A potential problem with these types of studies would be encountered if the factors are involved in the regulation of many genes, e.g., Fos/Jun, and the antisense effects may, therefore, be non-specific. Although not within the scope of the present proposal, depending on the results obtained, cis-element knockouts could be used to further define the role of these elements in regulating PEG-3 expression.

For DNase-I footprinting assays, nuclear extracts from E11 and E11-NMT, CREF and transformed CREF and untreated CREF and DNA damaged (MMS and gamma irradiation) CREF cells will be prepared and DNase-I footprinting assays will be performed as described (33,53,54). The promoter necessary for PEG-3 expression, identified from the experiments described above, will be terminally labeled with $^{32}P$ and incubated with crude nuclear extracts from the different cell types and experimental conditions described above using established protocols (33,53,54). The reaction mixture that has been digested with DNase-I enzyme will be terminated and the digested products will be analyzed on an 8% sequencing gel. The differential protection between nuclear extracts from progressed versus unprogressed, untransformed and oncogenically transformed and undamaged and DNA damaged cells will provide relevant information concerning the involvement of trans-acting factors in activation and the location of specific sequences in the cis-regulatory elements of the PEG-3 promoter mediating this activation. If differential protection is not detected using this approach, the sensitivity of the procedure can be improved by using different sized DNA fragments from the PEG-3 promoter region or by using partially purified nuclear extracts (33,53,54).

The studies described above will result in the characterization of the PEG-3 promoter region, the identification of cis-acting regulatory elements in the PEG-3 promoter and the identification of trans-acting regulatory elements that activate (or repress) expression of the PEG-3 gene as a function of cancer progression, oncogenic transformation and DNA damage. This information could prove valuable in designing approaches for selectively inhibiting PEG-3 expression, and therefore modifying cellular phenotypes related to cancer progression and response to DNA damage.

Isolation and initial characterization of the PEG-3 promoter.
Targeted Adenovirus Gene Delivery System For Selectively Inhibiting Proliferation or Inducing Toxicity in PEG-3 Expressing Cancer Cells: CURE (Cancer Utilized Reporter Execution) and CIRAs (Cancer Inhibitory Recombinant Adenoviruses).

Gene based therapies that exploit differences between cancer cells and normal cells represent potentially significant technologies for improved cancer therapy. This approach has been used to selectively target the replication of an E1B, 55-kDa gene-attenuated adenovirus (ONYX-015), to cancer cells containing a mutant p53 gene (55,56). Moreover, a minimal promoter/enhancer construct derived from the 5' flanking region of the human prostate specific antigen (PSA) promoter has been used to drive the expression of the Ad5 E1A gene in a replication competent Ad, thereby selectively inducing viral replication and toxicity in PSA-expressing prostate cancer cells (57). Similarly, viruses expressing the herpes simplex thymidine kinase (TK) gene have been used in combination with gancyclovir or acyclovir to target toxicity in cancer cells expressing herpes simplex viral thymidine kinase (58–61). In this context, a virus containing a gene promoter displaying restrictive or selective expression of a linked gene (with the capacity to inhibit growth or induce toxicity either directly or indirectly) would represent an extremely valuable therapeutic reagent.

As documented experimentally, the PEG-3 promoter displays elevated expression in progressed cancer cells, oncogenically transformed cancer cells and DNA damaged cells. The absolute level of induction of luciferase activity in progressed cancer cells and oncogenically transformed cells is ≧10-fold higher than in DNA damaged CREF cells. In this respect, it is anticipated that the activity of the PEG-3 promoter will be reduced and less effective in driving a linked gene in a recombinant replication competent or incompetent Ad when expressed in DNA damaged versus progressed or oncogenically transformed cells. However, it is likely that treatment with DNA damaging agents will even further augment the activity of the PEG-3 promoter in cancer cells. Moreover, preliminary experiments using a large panel of human cancer cell lines, including metastatic melanoma, glioblastoma multiforme and carcinomas of the breast, cervix, colon, lung, nasopharyngx and prostate, indicate that the PEG-3 promoter is active, whereas no activity is apparent in their normal cellular counterparts (unpublished data). On the basis of these considerations, the PEG-3 promoter would appear to be an ideal genetic tool for the construction of "cancer inhibitory recombinant adenoviruses" (CIRAs). These CIRAs could be used as part of a protocol called "cancer utilized reporter execution" (CURE) to selectively induce growth suppression, apoptosis or toxicity uniquely in cancer cells.

We propose to construct evaluate CURE using CIRAs that permit expression of a gene inhibiting growth and or inducing toxicity specifically in cancer cells using the PEG-3 promoter to control gene expression. Additionally, the PEG-3 promoter can be used to drive expression of a gene encoding an antigenic epitope that will increase the immunogenicity and killing of modified cells by the immune system (activated T-cells and/or antibodies). Several types of CIRAs will be generated and tested for biological efficacy using the CURE protocol.

1. Recombinant Ad expressing a wild-type p53 gene controlled by the PEG-3 promoter, Ad.PEG-wtp53. These viruses, using conventional cytomegalovirus promoters to drive wild-type p53 expression, are proving efficacious in treating a number of tumor types in humans (62). It is predicted that Ad.PEG-wtp53 would inhibit the growth or induce apoptosis in cancer cells containing defects in p53, which occur in a very high percentage of cancer cells (63). Moreover, even if low level PEG-3 promoter activity occurs in normal cells, the subsequent low level of p53 expression should not significantly affect cell growth or viability in normal cells.

2. Recombinant Ad expressing the novel mda-7 cancer growth suppressor gene controlled by the PEG-3 promoter, Ad.PEG-mda-7. The mda-7 gene is selectively growth suppressive in cancer versus normal cells (64). Moreover, the inhibitory effect of mda-7 in tumor cells is independent of p53 status and occurs in cancer cells with diverse genetic defects (64). This novel tumor suppressor gene would appear ideally suited for therapeutic applications (CURE) and the generation of CIRAs, since expression in normal cells (even following infection with 100 pfu/cell of Ad.mda-7 S virus) does not elicit a biological phenotype (65).

3. Recombinant Ad expressing the cyclin-dependent kinase inhibitor p21 (66) controlled by the PEG-3 promoter, Ad.PEG-D21. The p21 gene can induce growth arrest and apoptosis in specific cancer cells (67). In addition, recent studies indicate that an Ad expressing p21 can be used to inhibit tumor growth in animals (68). Since p21 can also modify growth in normal cells, the use of the PEG-3 promoter to selectively drive p21 in cancer cells would appear to be preferable vehicle for gene therapy than a virus constitutively expressing p21.

4. Recombinant replication competent Ad expressing the viral E1A gene controlled by the PEG-3 promoter, Ad.PEG-E1A. In principle, this virus should only replicate in cancer cells that allow activation of the PEG-3 promoter. The successful application of this type of virus for cancer therapy will be contingent upon sufficient E1A expression to permit switch-on of additional Ad genes permitting virus replication and cytotoxicity only in the cancer cells. A potential problem that might be encountered using this type of CIRA is minimal activity of the PEG-3 promoter resulting in low levels of Ad5 E1A expression in normal cells. This could prove problematic since previous studies have documented that even very low levels of Ad E1A can result in virus production (69). Moreover, since CREF cells are nonpermissive for Ad replication (1,27), this type of CIRA requires testing in a human cell line. This could be accomplished by using 293 cells, a human embryonic kidney cell line transformed by sheared Ad5 and constitutively expressing the Ad5 E1A and E1B genes. Preliminary studies indicate that the PEG-3 promoter is very active in 293 cells, whereas it displays no activity in normal human fibroblast or epithelial cells.

5. Recombinant virus expressing a HSV 1 TK gene controlled by the PEG-3 promoter, Ad.PEG-TK. This virus should produce viral TK in cancer cells as a result of activation of the PEG-3 promoter. By applying gancyclovir or acyclovir it would be possible to selectively kill cancer cells expressing elevated levels of viral TK. Previous studies provide precedents for the use of the HSV 1 TK gene and gancyclovir or acyclovir to selectively kill cancer cells (58–61).

6. Recombinant virus expressing an antigenic immunostimulating gene, such as GM-CSF and/or IL-2, controlled by the PEG-3 promoter, Ad.PEG-ImStim. This virus can be used to infect cells resulting in targeted expression, because of PEG-3 promoter utilization, specifically in cancer cells. The altered immunoreactivity in the tumor cells will elicit enhanced immune recognition and elimination of the tumor.

7. Recombinant virus expressing a defined antigen (with and without a co-stimulatory molecule) controlled by the PEG-3 promoter, Ad.PEG-Antigen. This virus can be used to infect cells resulting in targeted expression, because of PEG-3 promoter utilization, of the antigen (with or without the co-stimulatory molecule) specifically in cancer cells. The expression of this antigen on the surface of the cancer cells can then be used to target an antibody for immaging of tumor cells in a patient and/or inducing toxicity (by using an antibody with cytotoxic properties, an antibody conjugated with a toxin or an antibody carrying a high energy emitting radionuclide). By using appropriate vectors, all of the approaches briefly described above can also be used to treat patients with systemic tumors and metastases.

The methodologies for construction of the different CIRAs are routine and we have extensive experience in this approach (37–40,64). We therefore do not expect any problems in producing the appropriate viruses. Once the various recombinant viruses have been constructed they will be evaluated for biological efficacy using in vitro assays (64) and if active using in vivo tumor xenograft models (27–29). As initial tests for proof of practice of CURE and the CIRA approach, CREF, CREF-ras, CREF-src and CREF-HPV-18 cells will be infected with the specific recombinant virus (Ad.PEG-wtp53, Ad.PEG-mda-7, Ad.PEG-p21 or Ad.PEG-TK) or a recombinant virus not containing any gene insert (Ad.vec) and colony forming ability in monolayer culture will be determined (64). As indicated above, to test the Ad.PEG-E1A construct we will use 293 and normal human kidney cells. In the case of the Ad.PEG-TK virus system, infected cells will be cultured in the presence or absence of gancyclovir or acyclovir. A biologically relevant endpoint would be a statistically significant reduction of colony formation in transformed cells, but not in normal cells, for the CIRA versus the Ad.vec. This could be verified by monitoring expression of the transduced gene (RNA and protein levels) following viral infection. The levels of expression of the transduced gene should be significantly higher in transformed cells versus parental CREF cells (or in 293 versus normal human kidney cells). If these results occur with any or all of the CIRAs, further studies would be performed to assay for effects on tumor growth and metastasis using previously described procedures (27–29). This would include injecting tumor cells infected with recombinant virus prior to injection into animals and establishing tumors in animals followed by repeated administration (2× per week) of recombinant virus. If successful in reducing or eliminating cancer cells in vivo, the CIRA concept could ultimately prove of immense value for the targeted therapy of human cancers. Obvious extensions of this approach would be to isolate a human PEG-3 promoter and construct recombinant viruses in which this promoter drives the gene of choice. It is realized that the use of CIRAs for the therapy of human cancer depends on a number of important considerations. The rat or human PEG-3 promoter must display differential expression in human cancer versus normal human cells and the level of expression of the PEG-3 promoter must be sufficiently high in the cancer cells to allow for expression of adequate amounts of the linked gene to induce a biological effect in these cells. In preliminary studies, the rat PEG-3 promoter displays differential expression in human cancer versus normal cells suggesting that it my provide the appropriate reagent for the CURE approach using CIRAs. Moreover, the level of expression in normal tissue must be negligible, although this should not be a problem when using Ad.PEG-wtp53, Ad.PEG-mda-7 or Ad.PEG-p21.

REFERENCES FOR SEVENTH SERIES OF EXPERIMENTS

1. Fisher P B. Enhancement of viral transformation and expression of the transformed phenotype by tumor promoters. In: T J Slaga (ed), *Tumor Promotion and Cocarcinogenesis In Vitro, Mechanisms of Tumor Promotion*, CRC Press, Inc, Florida, pp 57–123, 1984.
2. Bishop J M. Molecular themes in oncogenesis. *Cell*, 64: 235–248, 1991.
3. Vogelstein B & Kinzler K W. The multistep nature of cancer. *Trends Genet*, 9: 138–141, 1991.
4. Knudson A G. Antioncogenes and human cancer. *Proc Natl Acad Sci USA*, 90: 10914–10921, 1993.
5. Levine A J. The tumor suppressor genes. *Annu Rev Biochem*, 62: 623–651, 1993.
6. Hartwell L H & Kastan M B. Cell cycle control and cancer. *Science*, 266: 1821–1828, 1994.
7. Fisher P B, Goldstein N I & Weinstein I B. Phenotypic properties and tumor promoter induced alterations in rat embryo cells transformed by adenovirus. *Cancer Res*, 39: 3051–3057, 1979.
8. Fisher P B, Dorsch-Hasler K, Weinstein I B & Ginsberg H S. Tumor promoters enhance anchorage-independent growth of adenovirus-transformed cells without altering the integration pattern of viral sequences. *Nature*, 281: 591–594, 1979.
9. Fisher P B, Bozzone J H & Weinstein I B. Tumor promoters and epidermal growth factor stimulate anchorage-independent growth of adenovirus transformed rat embryo cells. *Cell*, 18: 695–705, 1979.
10. Babiss L E, Zimmer S G & Fisher P B. Reversibility of progression of the transformed phenotype in Ad5-transformed rat embryo cells. *Science*, 228: 1099–1101, 1985.

11. Duigou G J, Babiss L E & Fisher P B. Suppression of the progression phenotype by 5-azacytidine in rat embryo cells doubly transformed by type 5 adenovirus and the Ha-ras oncogene. *N.Y. Acad Sci,* 567: 302–306, 1989.
12. Duigou G J, Babiss L E, Iman D S, Shay J W & Fisher P B. Suppression of the progression phenotype in somatic cell hybrids occurs in the absence of altered type 5 adenovirus gene expression. *Mol Cell Biol,* 10: 2027–2034, 1990.
13. Duigou G J, Su Z-z, Babiss L E, Driscoll B, Fung Y-K T & Fisher P B. Analysis of viral and cellular gene expression during progression and suppression of the transformed phenotype in type 5 adenovirus transformed rat embryo cells. *Oncogene,* 6: 1813–1824, 1991.
14. Reddy P G, Su Z-z & Fisher P B. Identification and cloning of genes involved in progression of transformed phenotype. In: *Chromosome and Genetic Analysis, Methods in Molecular Genetics,* vol. I, K W Adolph, Ed, Academic Press, Inc., Orlando, Fla., vol 1, pp 68–102, 1993.
15. Su Z-z, Shen R, O'Brian C A & Fisher P B. Induction of a progression phenotype in type 5 adenovirus-transformed rat embryo cells by the protein kinase C $\beta_1$ gene and its reversal by 5-azacytidine. *Oncogene,* 9: 1123–1132, 1994.
16. Jiang H & Fisher P B. Use of a sensitive and efficient subtraction hybridization protocol for the identification of genes differentially regulated during the induction of differentiation in human melanoma cells. *Mol Cell Different,* 1 (3): 285–299, 1993.
17. Su Z-z, Shi Y & Fisher P B. Subtraction hybridization identifies a transformation progression elevated gene PEG-3 with sequence homology to a growth arrest and DNA damage inducible gene. *Proc Natl Acad Sci USA,* 94: 9125–9130, 1997.
18. Fornace A J Jr, Alamo I Jr & Hollander M C. DNA damage-inducible transcripts in mammalian cells. *Proc Natl Acad Sci USA,* 85: 8800–8804, 1988.
19. Lord K A, Hoffman-Liebermann B & Liebermann D A. Complexity of the immediate early response of myeloid cells to terminal differentiation and growth arrest includes ICAM-1, Jun-B and histone variants. *Oncogene,* 5: 387–396, 1990.
20. Lord K A, Hoffman-Liebermann B & Liebermann D A. Sequence of MyD116 cDNA: a novel myeloid differentiation primary response gene induced by IL6. *Nucleic Acids Res,* 18: 2823, 1990.
21. Zhan Q, Lord K A, Alamo I Jr, Hollander M C, Carrier F, Ron D, Kohn K W, Hoffman B, Liebermann D A & Fornace A J Jr. The gadd and MyD genes define a novel set of mammalian genes encoding acidic proteins that synergistically suppress cell growth. *Mol Cell Biol,* 14: 2361–2371, 1994.
22. Chou J & Roizman B. Herpes simplex virus 1 $\gamma_1 34.5$ gene function, which blocks the host response to infection, maps in the homologous domain of the genes expressed during growth arrest and DNA damage. *Proc Natl Acad Sci USA,* 91: 5247–5251, 1994.
23. He B, Chou J, Liebermann D A, Hoffman B & Roizman B. The carboxyl terminus of the murine MyD116 gene substitutes for the corresponding domain of the $\gamma_1 34.5$ gene of herpes simplex virus to preclude the premature shut off of total protein synthesis in infected human cells. *J Virol,* 70: 84–90, 1996.
24. Liotta L A, Steeg P G & Stetler-Stevenson W G. Cancer metastasis and angiogenesis: an imbalance of positive and negative regulation. *Cell,* 64: 327–336, 1991.
25. Khosravi-Far R & Der C J. The Ras signal transduction pathway. *Cancer Metastasis Rev,* 13: 67–89, 1994.
26. Fisher P B, Babiss L E, Weinstein I B & Ginsberg H S. Analysis of type 5 adenovirus transformation with a cloned rat embryo cell line (CREF). *Proc Natl Acad Sci USA,* 79: 3527–3531, 1982.
27. Boylon J F, Jackson J, Steiner M, Shih T Y, Duigou G J, Roszman T, Fisher P B & Zimmer S G. Role of Ha-ras (ras$^H$) oncogene in mediating progression of the tumor cell phenotype (review). *Anticancer Res,* 10: 717–724, 1990.
28. Boylon J F, Shih T Y, Fisher P B & Zimmer S G. Induction and progression of the transformed phenotype in cloned rat embryo fibroblast cells: studies employing type 5 adenovirus and wild-type and mutant Ha-ras oncogenes. *Mol Carcinog,* 3: 309–318, 1992.
29. Su Z-z, Austin V N, Zimmer S G & Fisher P B. Defining the critical gene expression changes associated with expression and suppression of the tumorigenic and metastatic phenotype in Ha-ras-transformed cloned rat embryo fibroblast cells. *Oncogene,* 8: 1211–1219, 1993.
30. Su Z-z, Yemul S, Estabrook A, Friedman R M, Zimmer S G & Fisher P B. Transcriptional switching model for the regulation of tumorigenesis and metastasis by the Ha-ras oncogene: transcriptional changes in the Ha-ras tumor suppressor gene lysyl oxidase. *Intl J Oncol.* 7: 1279–1284, 1995.
31. Su Z-z, Zhang N, Wang M-N, Goldstein N I & Fisher P B. Expression of progression elevated gene-3 promotes angiogenesis and regulates cancer cell progression in vivo in nude mice. Manuscript in preparation, 1997.
32. Jiang H, Waxman S & Fisher P B. Regulation of c-fos, c-jun and jun-B gene expression in human melanoma cells induced to terminally differentiate. *Mol Cell Different,* 1 (2): 197–214, 1993.
33. Sambrook J, Fritsch E F & Maniatis T. In: *Molecular Cloning: A Laboratory Manual,* 2nd edition, Cold Spring Harbor Laboratories Press, Cold Spring Harbor, N.Y., 1989.
34. Johansen F-E & Prywes R. Two pathways for serum regulation of the c-fos serum response element require specific sequence elements and a minimal domain of serum response factor. *Mol Cell Biol* 14: 5920–5928, 1994.
35. Albanese C, Johnson J, Watanabe G, Eklund D, Vu D, Arnold A & Pestell R G. Transforming p21ras mutants and c-Ets-2 activate the cyclin D1 promoter through distinguishable regions. *J Biol Chem* 270: 23589–23597, 1995.
36. Jiang H, Lin J J, Su Z-z, Goldstein N I & Fisher P B. Subtraction hybridization identifies a novel melanoma differentiation associated gene, mda-7, modulated during human melanoma differentiation, growth and progression. *Oncogene,* 11: 2477–2486, 1995.
37. Babiss L E, Fisher P B & Ginsberg H S. Deletion and insertion mutations in early region 1a of type 5 adenovirus producing cold-sensitive or defective phenotypes for transformation. *J Virol,* 49: 731–740, 1984.
38. Babiss L E, Fisher P B & Ginsberg H S. Effect on transformation of mutations in the E1b-encoded 21 kd and 55 kd proteins of type 5 adenovirus. *J Virol,* 52: 389–395, 1984.
39. Herbst R S, Hermo H Jr, Fisher P B & Babiss L E. Regulation of adenovirus and cellular gene expression and cellular transformation by the E1B-encoded 175R protein. *J Virol,* 62: 4634–4643, 1988.
40. Su Z-z, Shen R, Young C S H & Fisher P B. Genetic analysis of carcinogen enhancement of type 5 adenovirus transformation oc cloned Fischer rat embryo fibroblast cells. *Mol Carcinog,* 8: 155–166, 1993.
41. Lin J, Su Z-z, Grunberger D, Zimmer S G & Fisher P B. Expression of the transformed phenotype induced by diverse acting viral oncogenes mediates sensitivity to growth suppression induced by caffeic acid phenethyl ester (CAPE). *Intl J Oncol,* 5: 5–15, 1994.
42. Su Z-z, Lin J, Prewett M, Goldstein N I & Fisher P B. Apoptosis mediates the selective toxicity of caffeic acid phenethyl ester (CAPE) toward oncogene-transformed rat embryo fibroblast cells. *Anticancer Res,* 15: 1841–1848, 1995.
43. Gorospe M, Martindale J L, Sheikh M S, Fornace A J Jr & Holbrook N J. Regulation of $p_{21}^{CIP1/WAF1}$ expression by cellular stress: p53-dependent and p53-independent mechanisms. *Mol Cell Different,* 4 (1): 47–65, 1996.
44. Maniatis T, Goodbourn S & Fischer A. Regulation of inducible and tissue-specific gene expression. *Science,* 236: 1237–1244, 1987.
45. Ptashne M. How eukaryotic transcriptional activators work. *Nature,* 335: 683–689, 1988.
46. Su Z-z, Yemul S, Stein C A & Fisher P B. c-fos is a positive regulator of carcinogen enhancement of adenovirus transformation. *Oncogene,* 10: 2037–2049, 1995.
47. Jiang H, Lin J, Young S-m, Goldstein N I, Waxman S, Davila V, Chellappan S P & Fisher P B. Cell cycle gene expression and E2F transcription factor complexes in human melanoma cells induced to terminally differentiate. *Oncogene,* 11: 1179–1189, 1995.
48. Thanos D & Maniatis T. The high mobility group protein HMGI(Y) is required for NF-κB dependent virus induction of the human IFN-b gene. *Cell,* 71: 777–789, 1992.
49. Weber J A & Gilmour D S. Genomic footprinting of the hsp70 and histone H3 promoters in Drosophila embryos reveal novel protein-DNA interactions. *Nucleic Acids Res,* 23: 3327–3334, 1995.
50. Kamat J P, Basu K, Satyamoorthy L, Showe L & Howe C C. IPEB transcription factor regulating intracisternal A particle during F9 cell differentiation is expressed at sites of lymphoid development. *Mol Rep Dev,* 41: 8–15, 1995.
51. Basu A, Dong B, Krainer A R & Howe C C. The intracisternal A-particle proximal enhancer-binding protein activates transcription and iss identical to the RNA- and DNA-binding protein p54$^{nrb}$/NonO. *Mol Cell Biol,* 17: 677–686, 1997.
52. Aebersold R H, Leavitt R A, Saavedra R A, Hood L E & Kent S B H. Internal amino acid sequence analysis of proteins separated by one- or two-dimensional gel electrophoresis after in situ protease digestion on nitrocellulose. *Proc Natl Acad Sci USA,* 84: 6970–6974, 1987.
53. Lin J J, Jiang H & Fisher P B. Characterization of a novel melanoma differentiation associated gene, mda-9, that is down-regulated during terminal cell differentiation. *Mol Cell Different,* 4 (4): 317–333, 1996.
54. Lin J J, Jiang H & Fisher P B. Melanoma differentiation associated gene-9, mda-9, is a human gamma interferon responsive gene. *Gene, in press,* 1997.
55. Shen R, Goswami S K, Mascareno E, Kumar A & Siddiqui M A Q. Tissue-specific transcription of the cardiac myosin light-chain 2 gene is regulated by an upstream repressor element. *Mol Cell Biol,* 11: 1676–1685, 1991.
56. Fisher A L, Ohsako S & Caudy M. The WRPW motif of the hairy-related basic helix-loop-helix repressor proteins acts as a 4-amino-acid transcription repression and protein-protein interaction domain. *Mol Cell Biol,* 16: 2670–2677, 1996.
57. Bischoff J R, Kirn D H, Williams A, Heise C, Horn S, Muna M, Ng L, Nye J A, Sampson-Johannes A, Fattaey A & McCormick F. An adenovirus mutant that replicates selectively in p53-deficient human tumor cells. *Science,* 274: 373–376, 1996.
58. Heise C, Sampson-Johannes A, Williams A, McCormick F, von Hoff D D & Kirn D H. ONYX-015, an E1B gene-attenuated adenovirus, causes tumor-specific cytoloysis and antitumoral efficacy that can be augmented by standard chemotherapeutic agents. *Nature Med,* 3: 639–645, 1997.
59. Rodriguez R, Schuur E R, Lim H Y, Henderson G A, Simons J W & Henderson D R. Prostate attenuated replication competent adenovirus (ARCA) CN706: a selective cytotoxic for prostate-specific antigen-positive prostate cancer cells. *Cancer Res,* 57: 2559–2563, 1977.
60. Borrelli E, Heyman R, Hsi M & Evans R M. Targeting of an inducible toxic phenotype in animal cells. *Proc Natl Acad Sci USA,* 85: 7572–7576, 1988.
61. Culver K W, Ran Z, Wallbridge I H, Oldfield E H & Balese R M. In vivo gene transfer with retroviral vector-producing cells for treatment of experimental brain tumors. *Science,* 256: 1550–1552, 1992.
62. Moolten F L & Wells J M. Curability of tumors bearing herpes thymidine kinase genes transferred by retroviral vectors. *J Natl Cancer Inst,* 82: 297–300, 1990.
63. Smythe W R, Hwang H C, Amin K M, Eck S L, Davidson B L, Wilson J M, Kaiser L R & Albelda S M. Use of recombinant adenovirus to transfer the herpes simplex virus thymidine kinase (HSV-TK) gene to thoracic neoplasms: an effective in vitro drug sensitization system. *Cancer Res,* 54: 2055–2059, 1994.
64. Kinzler K W & Vogelstein B. Cancer therapy meets p53. *N Engl J Med,* 331: 49–50, 1994.
65. Greenblatt M S, Bennett W P, Hollstein M & Harris C C. Mutations in the p53 tumor suppressor gene: clues to cancer etiology and molecular pathogenesis. *Cancer Res,* 54: 4855–4878, 1994.
66. Jiang H, Su Z-z, Lin J J, Goldstein N I, Young C S H & Fisher P B. The melanoma differentiation associated gene mda-7 suppresses cancer cell growth. *Proc Natl Acad Sc USA,* 93: 9160–9165, 1996.
67. Su Z-z, Madireddi M T, Lin J J, Young C S H, Kitada S, Reed J C, Goldstein N I & Fisher P B. The cancer growth suppressor gene mda-7 selectively induces apoptosis in human cancer cells and inhibits tumor growth in nude mice. In submission, 1998.
68. Xiong Y, Hannon G J, Zhang H, Casso D, Kobayashi R & Beach D. p21 is a universal inhibitor of cyclin kinases. *Nature,* 366: 701–704, 1993.
69. Chellappan S P, Giordano A & Fisher P B. Role of cyclin-dependent kinases and their inhibitors in cellular differentiation and development. *Curr Topics Microbiol Immunol,* 227: 57–103, 1997.
70. Yang Z-Y, Perkins N D, Ohno O, Nabel E G & Nabel G J. The p21 cyclin-dependent kinase inhibitor suppresses tumorigenicity in vivo. *Nature Med,* 1: 1052–1056, 1995.
71. Hitt M M & Graham F L. Adenovirus E1A under the control of hererologous prmoters: wide variation in E1A expression levels has little effect on virus replication. *Virology,* 179: 667–678, 1990.

What is claimed is:

1. An isolated nucleic acid molecule comprising (i) a first nucleic acid molecule encoding a protein, operatively linked to (ii) a second nucleic acid molecule having a sequence as set forth for nucleotides 1–1754 of the rat PEG-3 promotor (SEQ ID NO:8), wherein the second nucleic acid molecule regulates expression of the protein in mammalian cells.

2. The isolated nucleic acid molecule of claim 1, wherein the protein is a tumor suppressor.

3. The isolated nucleic acid molecule of claim 2, wherein the tumor suppressor is p53.

4. The isolated nucleic acid molecule of claim 2, wherein the tumor suppressor is mda-7.

5. The isolated nucleic acid molecule of claim 2, wherein the tumor suppressor is p21.

6. A vector encoding the isolated nucleic acid molecule of claim 1.

7. The vector of claim 6, wherein the protein is a tumor suppressor.

8. The vector of claim 6, wherein the tumor suppressor is p53.

9. The vector of claim 6, wherein the tumor suppressor is mda-7.

10. The vector of claim 6, wherein the tumor suppressor is p21.

* * * * *